United States Patent
Shipps, Jr. et al.

(10) Patent No.: US 9,242,981 B2
(45) Date of Patent: Jan. 26, 2016

(54) FUSED PYRAZOLE DERIVATIVES AS NOVEL ERK INHIBITORS

(75) Inventors: Gerald W. Shipps, Jr., Stoneham, MA (US); Yongqi Deng, Newton, MA (US); Alan B. Cooper, West Caldwell, NJ (US); Xiaolei Gao, Bridgewater, NJ (US); Binyuam Sun, Chestnut Hill, MA (US); James Wang, Westfield, NJ (US); Liang Zhu, Waltham, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/821,149

(22) PCT Filed: Sep. 12, 2011

(86) PCT No.: PCT/US2011/051149
§ 371 (c)(1),
(2), (4) Date: Mar. 6, 2013

(87) PCT Pub. No.: WO2012/036997
PCT Pub. Date: Mar. 22, 2012

(65) Prior Publication Data
US 2013/0172341 A1   Jul. 4, 2013

Related U.S. Application Data

(60) Provisional application No. 61/383,376, filed on Sep. 16, 2010.

(51) Int. Cl.
| | | |
|---|---|---|
| A61K 31/44 | (2006.01) |
| C07D 471/02 | (2006.01) |
| C07D 491/02 | (2006.01) |
| C07D 498/02 | (2006.01) |
| C07D 513/02 | (2006.01) |
| C07D 515/02 | (2006.01) |
| C07D 471/04 | (2006.01) |
| C07D 401/04 | (2006.01) |
| C07D 401/14 | (2006.01) |
| C07D 405/14 | (2006.01) |
| C07D 409/14 | (2006.01) |
| C07D 417/14 | (2006.01) |
| C07D 519/00 | (2006.01) |
| C07D 405/04 | (2006.01) |

(52) U.S. Cl.
CPC ............ *C07D 471/04* (2013.01); *C07D 401/04* (2013.01); *C07D 401/14* (2013.01); *C07D 405/04* (2013.01); *C07D 405/14* (2013.01); *C07D 409/14* (2013.01); *C07D 417/14* (2013.01); *C07D 519/00* (2013.01)

(58) Field of Classification Search
None
See application file for complete search history.

(56) References Cited

U.S. PATENT DOCUMENTS

| | | | | |
|---|---|---|---|---|
| 4,500,525 A | * | 2/1985 | Winters et al. | 514/210.21 |
| 6,897,208 B2 | * | 5/2005 | Edwards et al. | 514/183 |
| 2006/0014756 A1 | * | 1/2006 | Edwards et al. | 514/254.06 |
| 2006/0235013 A1 | * | 10/2006 | Georges et al. | 514/234.2 |

FOREIGN PATENT DOCUMENTS

| | | |
|---|---|---|
| EP | 0086422 A2 | 8/1983 |
| WO | 03035065 A1 | 5/2003 |
| WO | 2009105500 A1 | 8/2009 |
| WO | WO 2010/060854 A1 * | 6/2010 |

OTHER PUBLICATIONS

Carey, FA. Organic Chemistry 6th Ed. McGraw Hill. 2006, chapter 1, p. 9.*
Patani, KV. et al. Bioisosterism: A Rational Approach in Drug Design. Chem. Rev. 1996, vol. 96, p. 3149.*
Ohori, M. et al., Identification of a selective ERK inhibitor and structural determination of the inhibitor-ERK2 complex, Biochemical and Biophysical Research Communications, 2005, 357-363, 336.

* cited by examiner

*Primary Examiner* — Rita Desai
*Assistant Examiner* — Ben S Michelson
(74) *Attorney, Agent, or Firm* — Richard S. Parr; Laura M. Ginkel

(57) ABSTRACT

Disclosed are the ERK inhibitors of Formula (I): (Formula (I)) and the pharmaceutically acceptable salts thereof. All substitutents are as defined herein. Also disclosed are methods of treating cancer using the compounds of Formula (I).

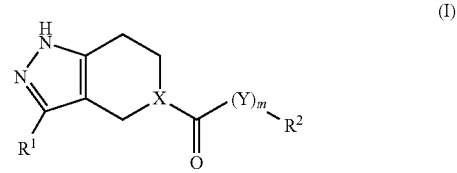

2 Claims, No Drawings

FUSED PYRAZOLE DERIVATIVES AS NOVEL ERK INHIBITORS

REFERENCE TO RELATED APPLICATION

This application claims the benefit of U.S. Provisional Application Ser. No. 61/383,376 filed Sep. 16, 2010.

FIELD OF THE INVENTION

The present invention is directed to fused pyrazole derivatives of Formula I as inhibitors of ERK kinase, compositions comprising at least one fused pyrazole derivative of Formula I, and methods of using the fused pyrazole derivatives of Formula I for treating cancer and other disorders where ERK kinase is deregulated.

BACKGROUND

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumours.

Therefore, a welcome contribution to the art would be small-molecules (i.e., compounds) that inhibit ERK activity (i.e., ERK1 and ERK2 activity), which small-molecules would be useful for treating a broad spectrum of cancers, such as, for example, melanoma, pancreatic cancer, thyroid cancer, colorectal cancer, lung cancer, breast cancer, and ovarian cancer. Such a contribution is provided by this invention.

SUMMARY OF THE INVENTION

This invention provides compounds that inhibit the activity of ERK1 and/or the activity of ERK2.

The compounds of this invention also inhibit the phosphorylation of ERK1 and ERK2.

Thus, this invention provides compounds that are ERK inhibitors (i.e., ERK1 inhibitors and/or ERK2 inhibitors), said compounds being of the Formula I:

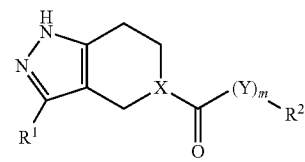

or the pharmaceutically acceptable salts thereof, wherein all substituents are independently selected and are as defined below.

This invention also provides pharmaceutically acceptable salts of the compounds of Formula I.

This invention also provides solvates of the compounds of Formula I.

This invention includes the compound of Formula I in all its isolated forms. The compound of Formula I is intended to encompass all forms of the compound such as, for example, any solvates, hydrates, stereoisomers, tautomers etc.

This invention also provides a pharmaceutical composition comprising an effective amount of at least one compound of Formula I, and a pharmaceutically acceptable carrier.

This invention also provides a pharmaceutical composition comprising an effective amount of at least one compound of Formula I, and an effective amount of at least one other pharmaceutically active ingredient (such as, for example, a chemotherapeutic agent), and a pharmaceutically acceptable carrier.

This invention also provides a method of inhibiting ERK (i.e., inhibiting the activity of ERK), such as ERK1 and/or ERK2 in a patient in need of such treatment comprising administering to said patient an effective amount of at least one compound of Formula I.

This invention also provides a method for treating cancer in a patient in need of such treatment, said method comprising administering to said patient an effective amount of at least one compound of Formula I.

This invention also provides a method for treating cancer in a patient in need of such treatment, said method comprising administering to said patient an effective amount of at least one compound of Formula I, in combination with an effective amount of at least one chemotherapeutic agent.

The methods of treating cancers described herein can optionally include the administration of an effective amount of radiation (i.e., the methods of treating cancers described herein optionally include the administration of radiation therapy).

DETAILED DESCRIPTION OF THE INVENTION

This invention provides a compound of Formula I:

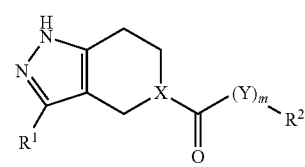

or a pharmaceutically acceptable salt, solvate, hydrate, ester, prodrug or stereoisomer thereof, wherein:

X is selected from the group consisting of: (1) —C($R^6$)—, and (2) —N—;

Y is selected from the group consisting of (1) —C(R⁷R⁸)—, (2) —O—, (3) —N(R⁶)—, and (4) —N(R⁶)C(R⁷R⁸)CH₂—;

R¹ is selected from the group consisting of (1) aryl, and (2) heteroaryl,
wherein said aryl and heteroaryl groups are unsubstituted or substituted by one to three R¹⁴ groups, or alternatively two R¹⁴ can optionally be taken together with the carbon atoms to which they are attached to form a five- or six-membered cycloalkyl, cycloalkenyl, heterocyclyl, heterocyclenyl, aryl or heteroaryl;

R² is selected from the group consisting of:

(1) cycloalkyl, (2) aryl, (3) heteroaryl, (4) 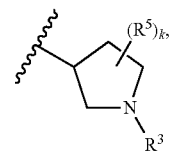

(5) 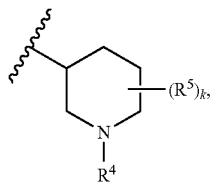

(6) 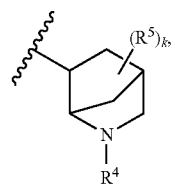

(7) 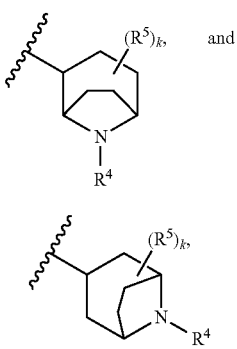 and (8)

wherein said cycloalkyl, aryl and heteroaryl groups are unsubstituted or substituted by one to three R¹¹ groups, or alternatively two R¹¹ groups can optionally be taken together with the carbon atoms to which they are attached to form a five- or six-membered cycloalkyl, cycloalkenyl, heterocyclyl, heterocyclenyl, aryl or heteroaryl;

R³ is selected from the group consisting of: (1) hydrogen, (2) alkyl, (3) haloalkyl, (4) aryl-alkyl-, and (5) heteroaryl-alkyl-, wherein said aryl and heteroaryl groups are unsubstituted or substituted by one to three R¹² groups;

R⁴ is selected from the group consisting of: (1) hydrogen, (2) alkyl, (3) haloalkyl, (4) carboxyl, (5) alkoxycarbonyl, (6) alkylsulfonyl-, (7) aryl-alkyl-, (8) heterocyclyl-alkyl-, (9) heteroaryl-alkyl-, (10) heterocyclyl-aryl-alkyl-, (11) aryl-heteroaryl-alkyl-, (12) aryl-aryl-alkyl-, and (13) heteroaryl-aryl-alkyl-, wherein said aryl, heterocyclyl and heteroaryl groups are unsubstituted or substituted by one to three R¹³ groups, or alternatively two R¹³ can optionally be taken together with the carbon atoms to which they are attached to form a five- or six-membered cycloalkyl, cycloalkenyl, heterocyclyl, heterocyclenyl, aryl or heteroaryl;

each R⁵ is independently selected from the group consisting of: (1) hydrogen, (2) alkyl, (3) haloalkyl, (4) hydroxyalkyl-, (5) halo, (6) hydroxy, (7) carboxyl, (8) alkoxycarbonyl, and (9) aryl, wherein said aryl is unsubstituted or substituted by one to three substituents each independently selected from halo, alkyl, haloalkyl or phenyl;

R⁶ is selected from the group consisting of: (1) hydrogen, and (2) alkyl;

R⁷ and R⁸ independently are selected from the group consisting of (1) hydrogen, (2) alkyl, (3) haloalkyl-, (4) hydroxyalkyl-, and (5) alkoxyalkyl-, or
alternatively R⁷ and R⁸ together with the carbon atom to which they are attached form a cycloalkyl ring;

R⁹ and R¹⁰ independently are selected from the group consisting of: (1) hydrogen, and (2) alkyl;

each R¹¹ is independently selected from the group consisting of: (1) alkyl-, (2) haloalkyl-, (3) aryl-alkyl-, (4) halo, (5) cyano, (6) hydroxy, (7) alkoxy, (8) haloalkoxy, (9) aryloxy, (10) heteroaryloxy, (11) arylthio, (12))N(R⁹R¹⁰)-alkoxy-, (13) heterocycyl-alkoxy-, (14) aryl-alkyloxy-, (15) heteroaryl-alkoxy-, (16) aryl, (17) heteroaryl, (18) carboxy, (19) NR⁹R¹⁰, and (20) alkylsulfonyl-, wherein said aryl, heteroaryl, heterocyclyl is unsubstituted or substituted by one to three substituents each independently selected from alkyl, haloalkyl, halo, alkoxy, haloalkoxy, acyl, alkoxycarbonyl, heterocyclyl, heteroaryl and aryl;

each R¹² is independently selected from the group consisting of: (1) alkyl, (2) haloalkyl, and (3) halo;

each R¹³ is independently selected from the group consisting of: (1) alkyl, (2) halo, (3) haloalkyl, (4) hydroxy, (5) alkoxy, (6) cyano, (7) NO₂, (8) alkoxycarbonyl-, (9) acyl, (10) aryl, (11) heterocyclyl, and (12) —NR⁹R¹⁰;

each R¹⁴ is independently selected from the group consisting of: (1) alkyl, (2) halo, (3) haloalkyl, (4) hydroxy, (5) alkoxyl, (6) aryl;

k is 1, 2, 3 or 4; and
m is 0 or 1.

In one embodiment of this invention is a compound of Formula I wherein X is selected from the group consisting of —C(R⁶)—, and —N—. In one class of this embodiment, X is selected from the group consisting of —C(H)—, —C(CH₃)—, and —N—. In another class of this embodiment, X is —C(R⁶)—. In another class of this embodiment, X is —C(H)—. In another class of this embodiment, X is —C(CH₃)—. In yet another embodiment, X is —N—.

In another embodiment of this invention is a compound of Formula I wherein Y is selected from the group consisting of —C(R⁷R⁸)—, —O—, —N(R⁶)—, and —N(R⁶)C(R⁷R⁸)CH₂—. In one embodiment, Y is —C(R⁷R⁸)—. In another class of this embodiment, Y is —O—. In another class of this embodiment Y is —N(R⁶)—. In another class of this embodiment Y is N(R⁶)C(R⁷R⁸)CH₂—.

In another class of this embodiment, Y is selected from the group consisting of:

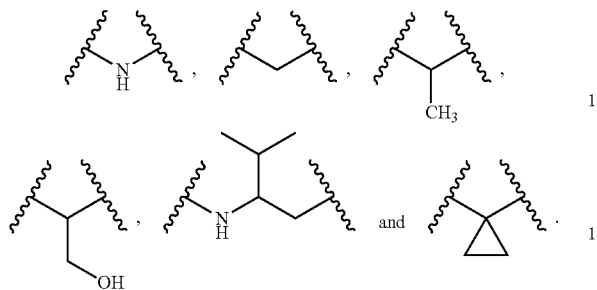

In another class of this embodiment, Y is

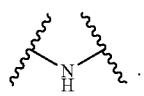

In another class of this embodiment, Y is

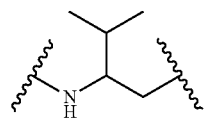

In another class of this embodiment, Y is selected from the group consisting of

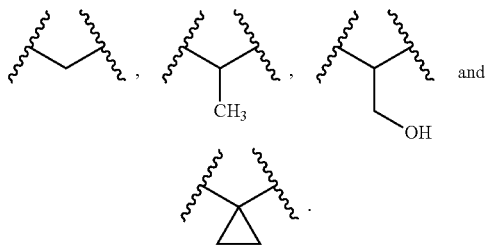

In another class of this embodiment, Y is

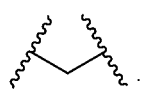

In another class of this embodiment, Y is

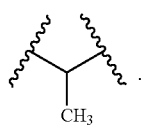

In another class of this embodiment, Y is

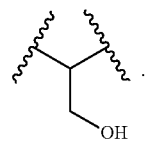 [SMILES: *C(*)CO ; "."]

In another class of this embodiment, Y is

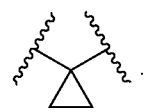 [SMILES: *C1(*)CC1 ; "."]

In one embodiment of this invention is a compound of Formula I wherein:

$R^1$ is selected from the group consisting of aryl, and heteroaryl, wherein said aryl, and heteroaryl groups are unsubstituted or substituted by one to three $R^{14}$ groups; or alternatively two $R^{14}$ can optionally be taken together with the carbon atoms to which they are attached to form a five- or six-membered cycloalkyl, cycloalkenyl, heterocyclyl, heterocyclenyl, aryl or heteroaryl. In one class of this embodiment, $R^1$ is heteroaryl, wherein said heteroaryl group is unsubstituted or substituted by one to three $R^{14}$ groups, alternatively two $R^{14}$ can optionally be taken together with the carbon atoms to which they are attached to form a five- or six-membered cycloalkyl, cycloalkenyl, heterocyclyl, heterocyclenyl, aryl or heteroaryl. In another class of this embodiment, $R^1$ is aryl, wherein said aryl group is unsubstituted or substituted by one to three $R^{14}$ groups, alternatively two $R^{14}$ can optionally be taken together with the carbon atoms to which they are attached to form a five- or six-membered cycloalkyl, cycloalkenyl, heterocyclyl, heterocyclenyl, aryl or heteroaryl.

In another class of this embodiment, $R^1$ is selected from the group consisting of:

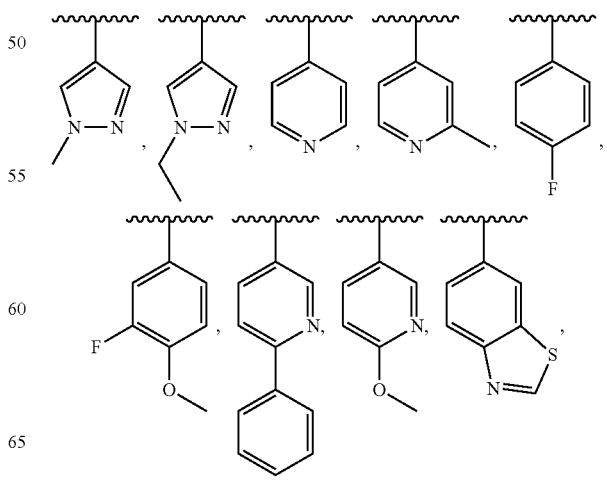

-continued
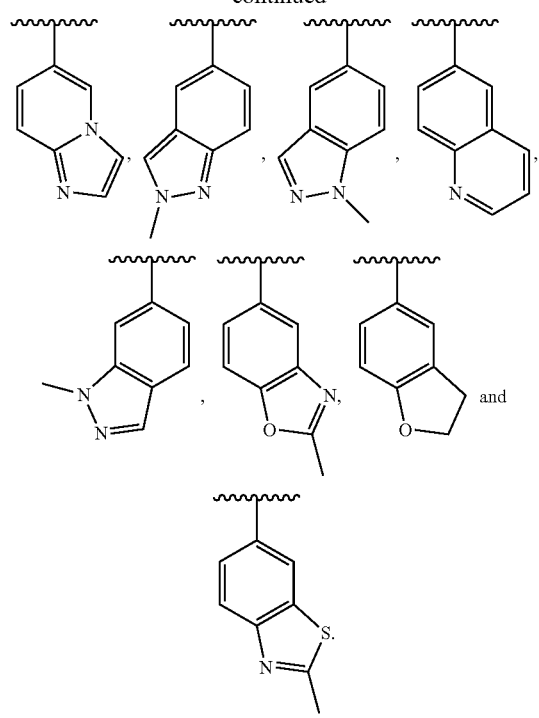
In another class of this embodiment, $R^1$ is
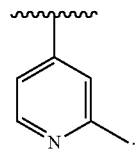 [SMILES: *c1ccnc(C)c1]
In another class of this embodiment, $R^1$ is
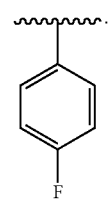 [SMILES: *c1ccc(F)cc1]
In another class of this embodiment, $R^1$ is
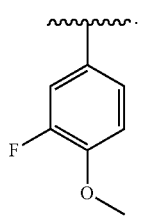
In another class of this embodiment, $R^1$ is
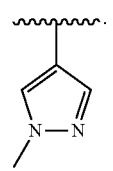
In another class of this embodiment, $R^1$ is
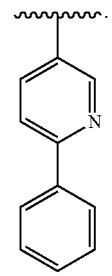 [SMILES: *c1ccc(-c2ccccc2)nc1]
In another class of this embodiment, $R^1$ is
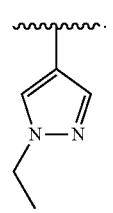
In another class of this embodiment, $R^1$ is
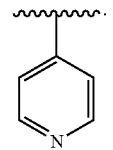
In another class of this embodiment, $R^1$ is
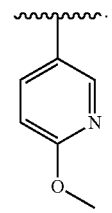 [SMILES: *c1ccc(OC)nc1]

In another class of this embodiment, R¹ is

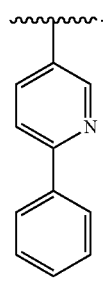

In another class of this embodiment, R¹ is

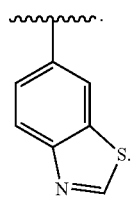 [SMILES: *c1ccc2ncsc2c1]

In another class of this embodiment, R¹ is

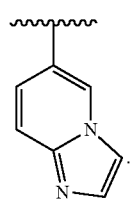

In another class of this embodiment, R¹ is

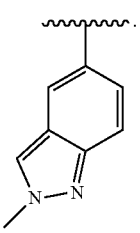 [SMILES: *c1ccc2nn(C)cc2c1]

In another class of this embodiment, R¹ is

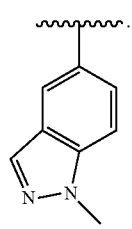

In another class of this embodiment, R¹ is

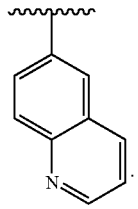 [SMILES: *c1ccc2ncccc2c1]

In another class of this embodiment, R¹ is

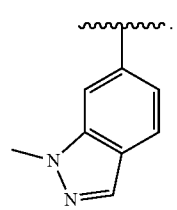 [SMILES: *c1ccc2cnn(C)c2c1]

In another class of this embodiment, R¹ is

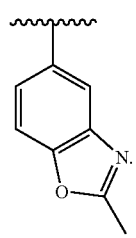 [SMILES: *c1ccc2oc(C)nc2c1]

In another class of this embodiment, R¹ is

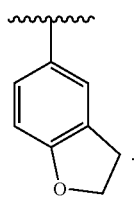 [SMILES: *c1ccc2c(c1)CCO2 ; "."]

In another class of this embodiment, R¹ is

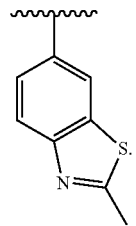 [SMILES: *c1ccc2nc(C)sc2c1]

In one embodiment of this invention is a compound of Formula I wherein: R² is selected from the group consisting of cycloalkyl, aryl, heteroaryl,

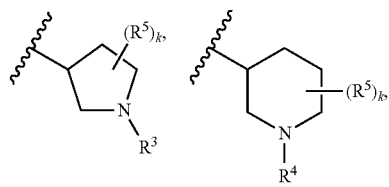

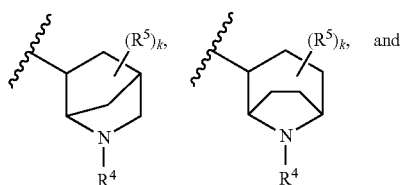

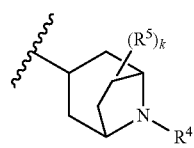

wherein said cycloalkyl, aryl and heteroaryl groups are unsubstituted or substituted one to three $R^{11}$ groups, or alternatively two $R^{11}$ groups can optionally be taken together with the carbon atoms to which they are attached to form a five- or six-membered cycloalkyl, cycloalkenyl, heterocyclyl, heterocyclenyl, aryl or heteroaryl.

In another class of this embodiment, $R^2$ is cycloalkyl, wherein said cycloalkyl group is unsubstituted or substituted by at one to three $R^{11}$ groups, or alternatively two $R^{11}$ groups can optionally be taken together with the carbon atoms to which they are attached to form a five- or six-membered cycloalkyl, cycloalkenyl, heterocyclyl, heterocyclenyl, aryl or heteroaryl. In another class of this embodiment, $R^2$ is aryl, wherein said aryl group is unsubstituted or substituted by at one to three $R^{11}$ groups, or alternatively two $R^{11}$ groups can optionally be taken together with the carbon atoms to which they are attached to form a five- or six-membered cycloalkyl, cycloalkenyl, heterocyclyl, heterocyclenyl, aryl or heteroaryl. In another class of this embodiment, $R^2$ is heteroaryl, wherein said heteroaryl group is unsubstituted or substituted by one to three $R^{11}$ groups, or alternatively two $R^{11}$ groups can optionally be taken together with the carbon atoms to which they are attached to form a five- or six-membered cycloalkyl, cycloalkenyl, heterocyclyl, heterocyclenyl, aryl or heteroaryl.

In another class of this embodiment, $R^2$ is

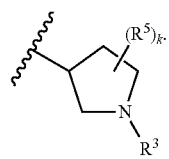

In another class of this embodiment, $R^2$ is

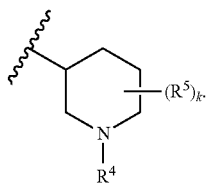

In another class of this embodiment, $R^2$ is

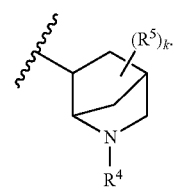

In another class of this embodiment, $R^2$ is

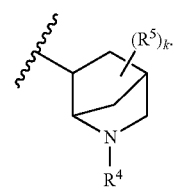

In another class of this embodiment, $R^2$ is

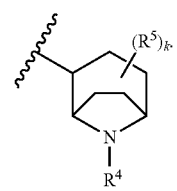

In another class of this embodiment, $R^2$ is

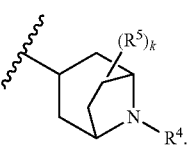

In another class of this embodiment, $R^2$ is selected from the group consisting of:

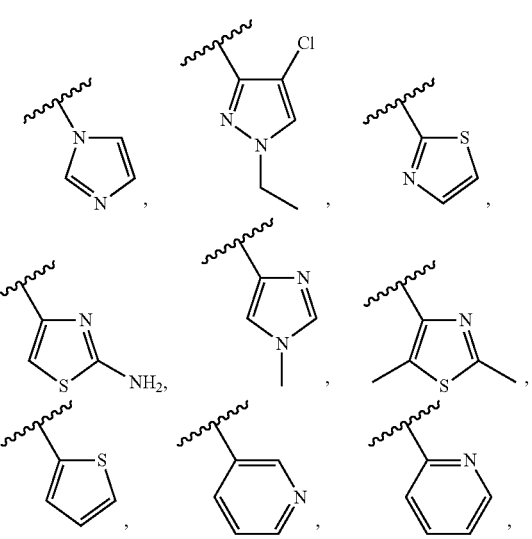

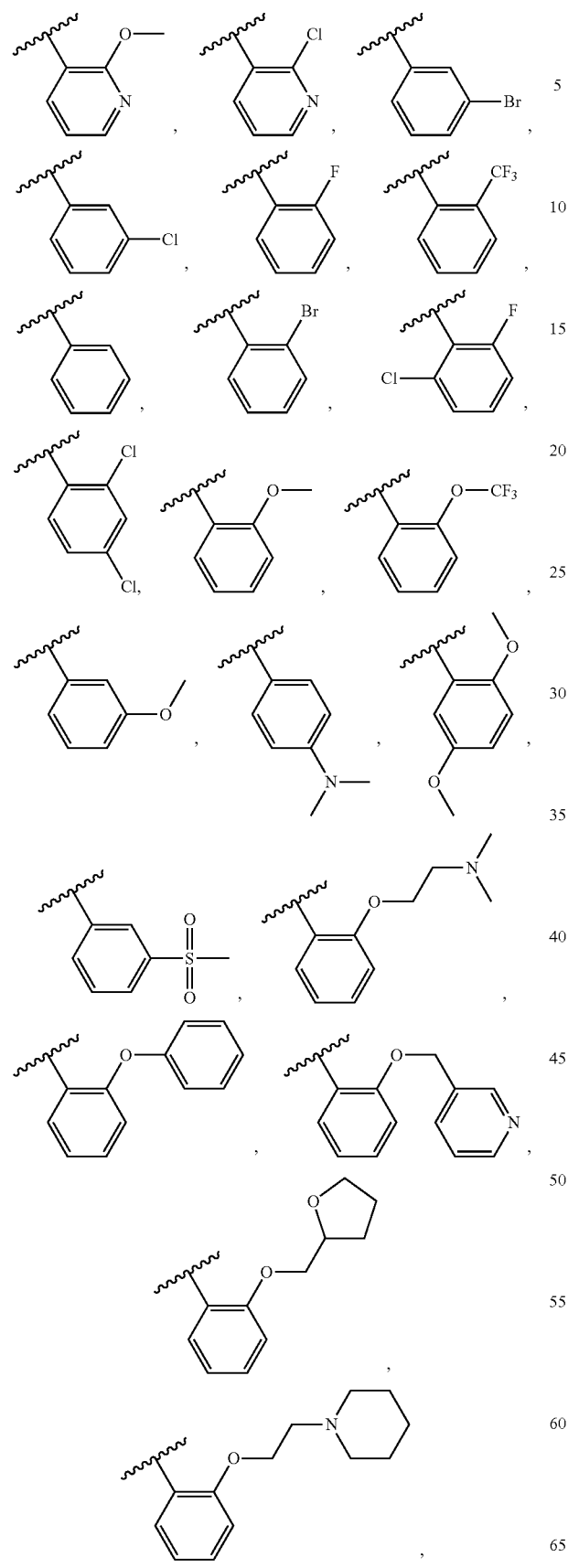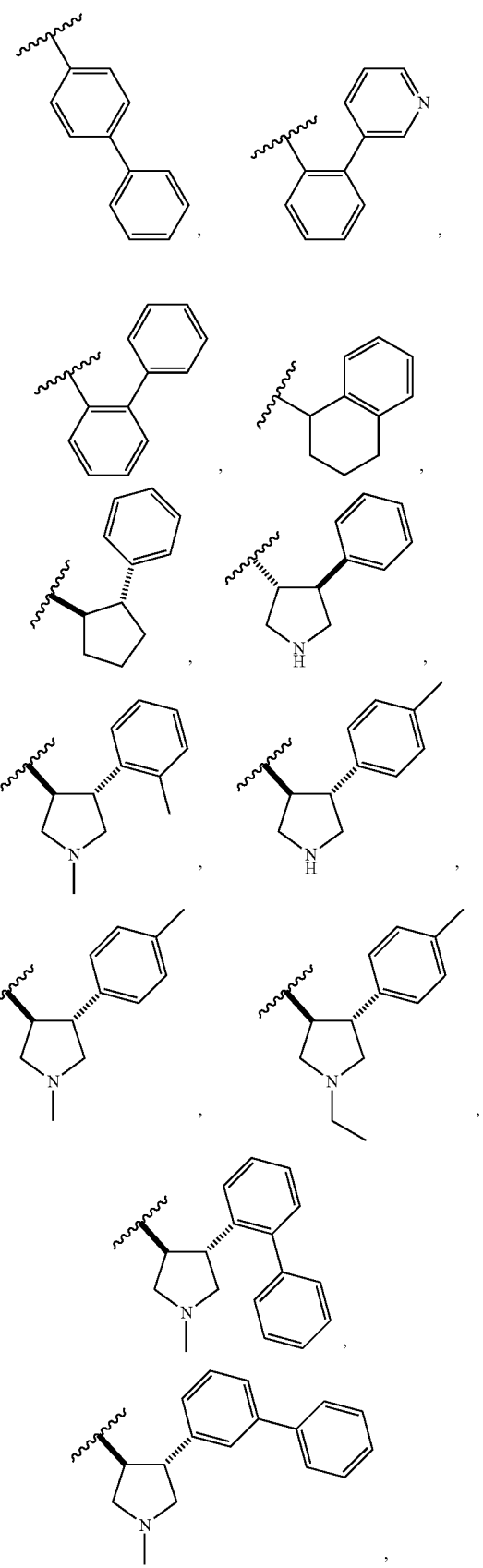

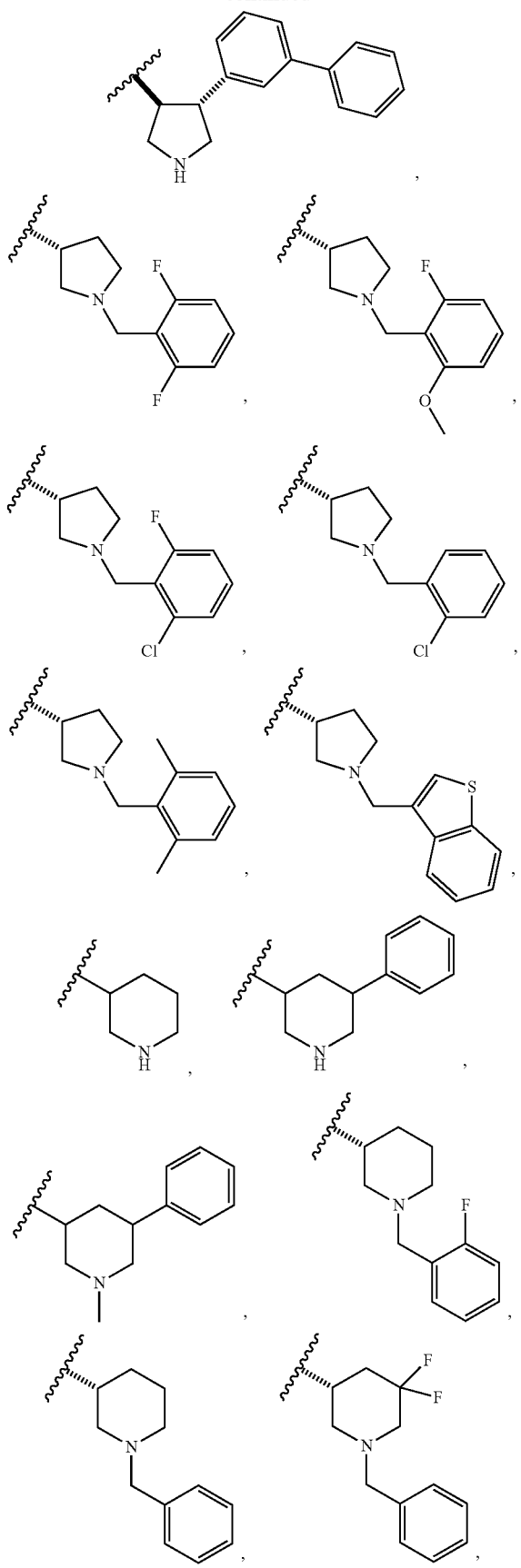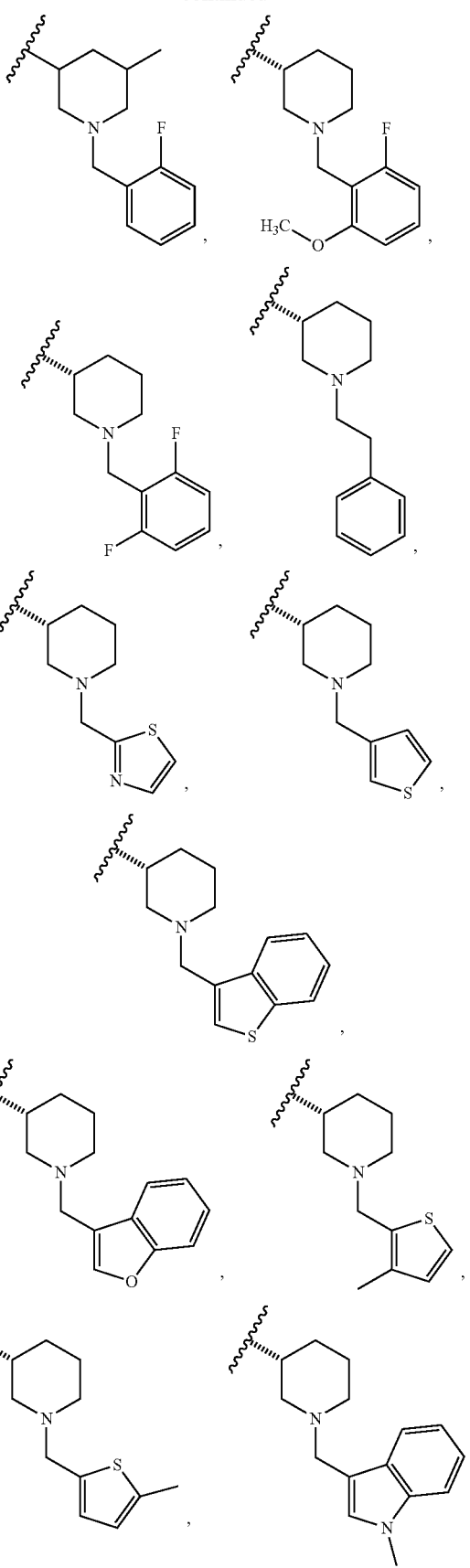

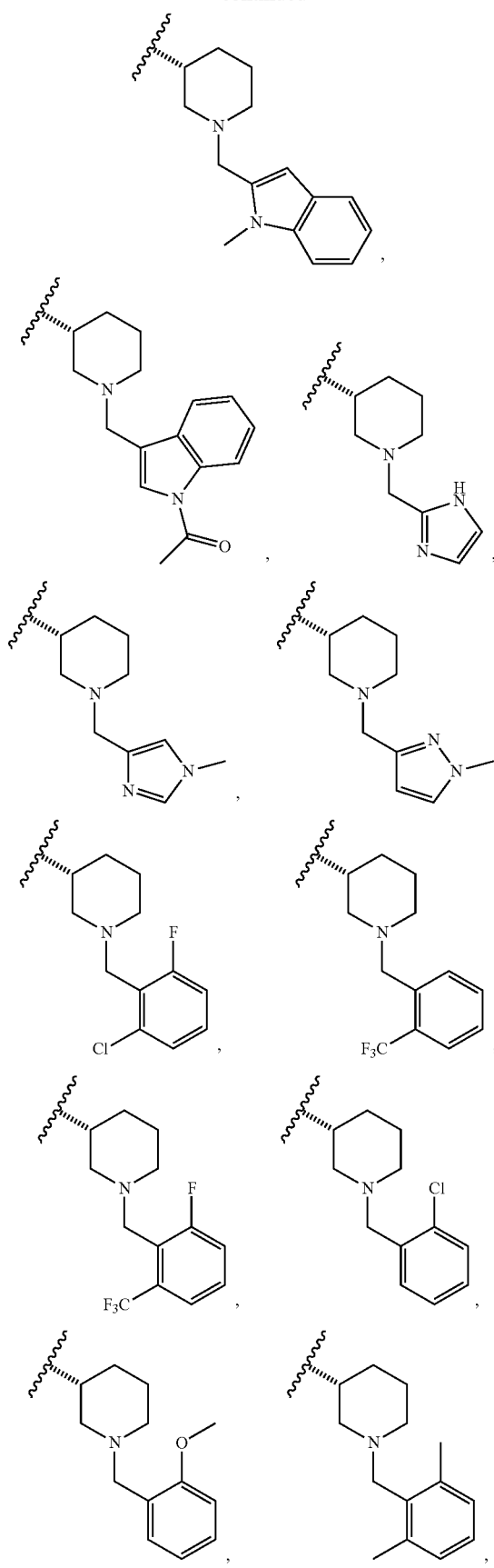
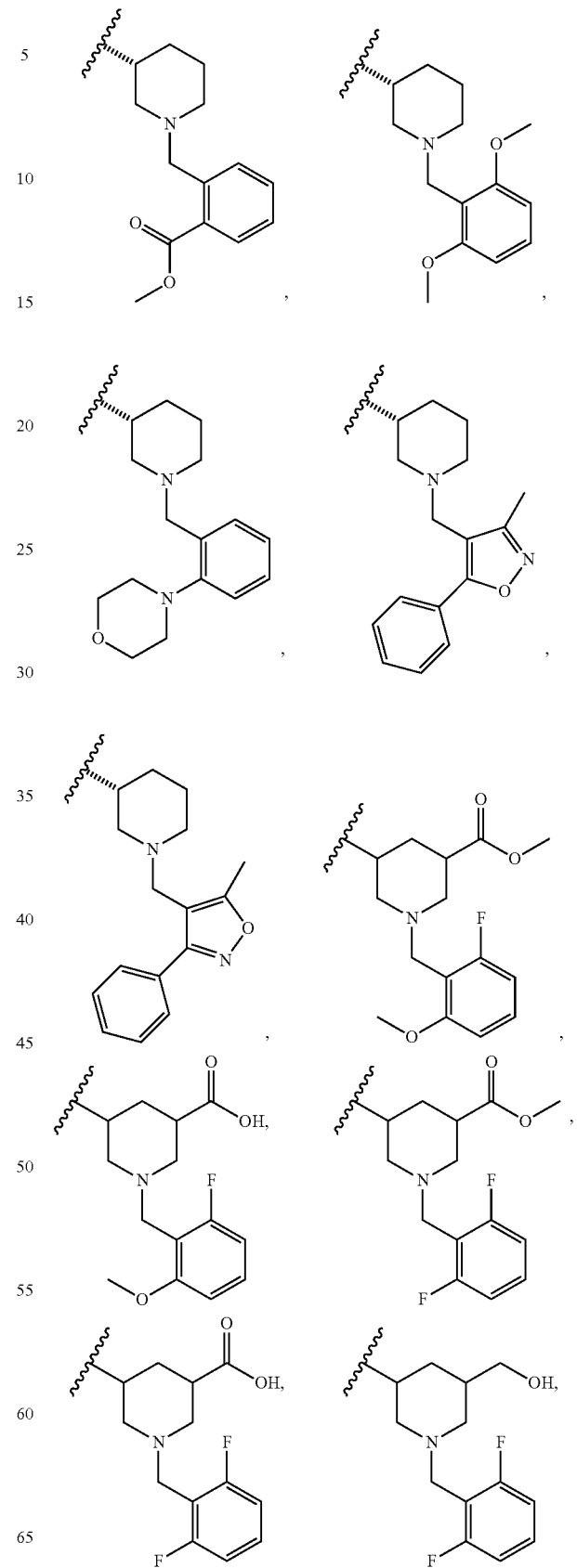

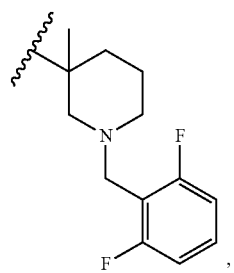 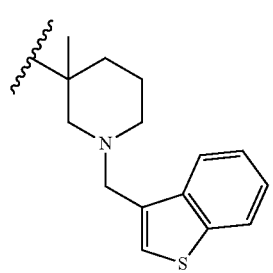 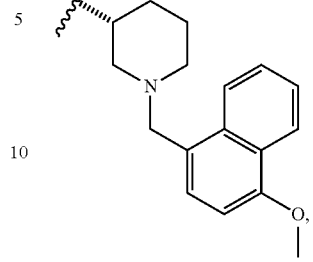 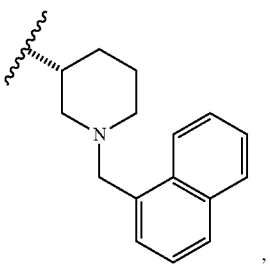
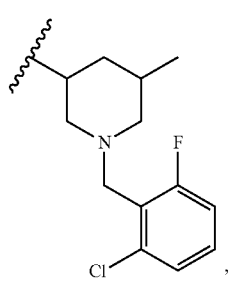 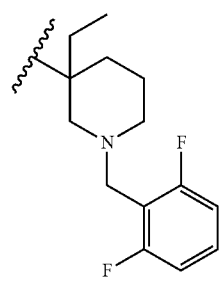 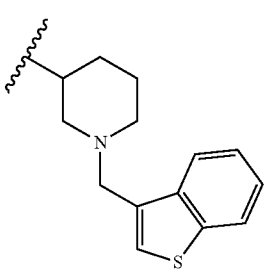 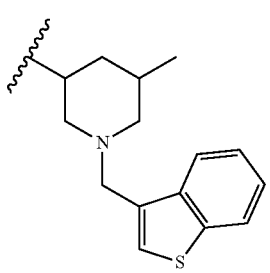
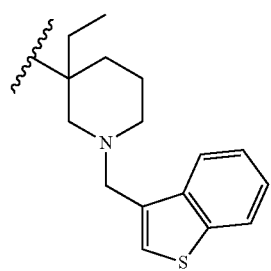 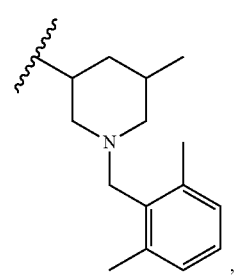 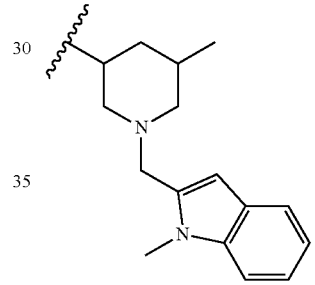 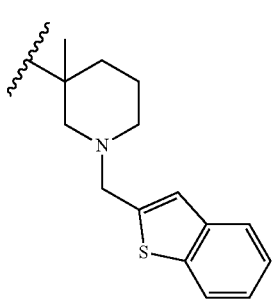
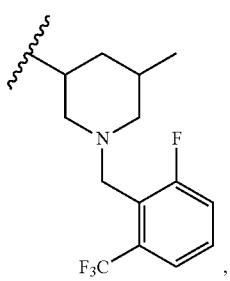 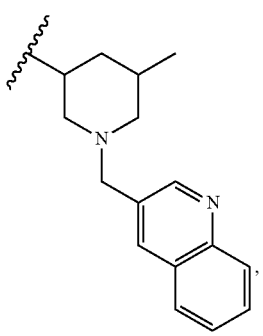 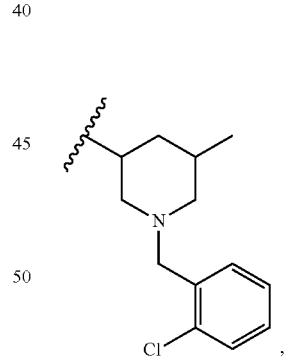 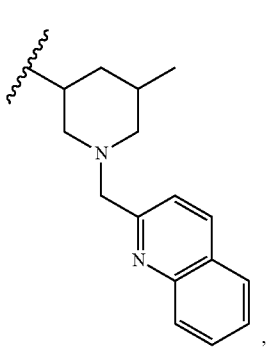
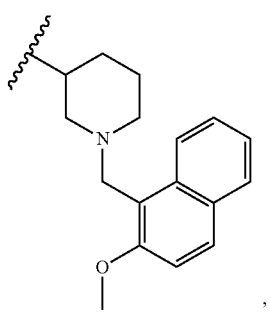 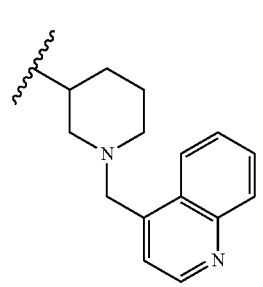 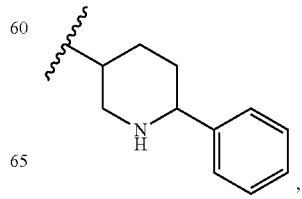 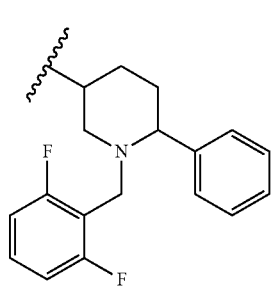

-continued
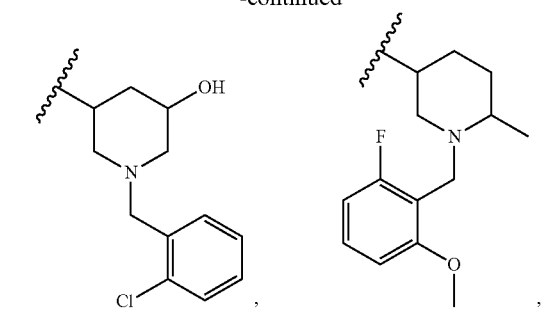
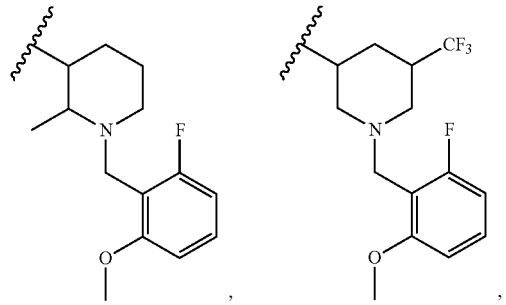
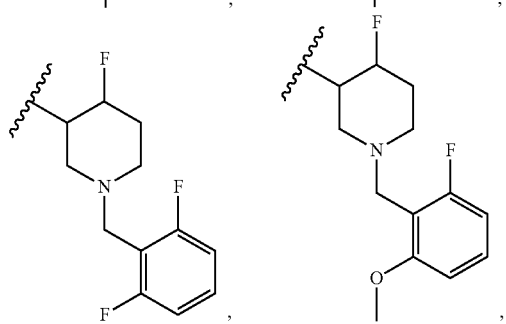
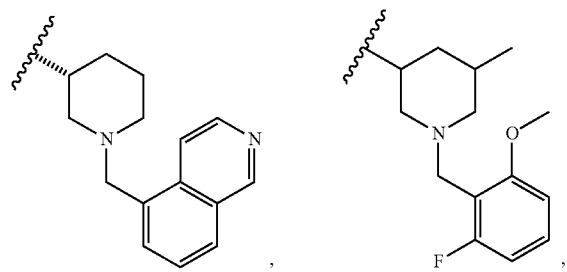
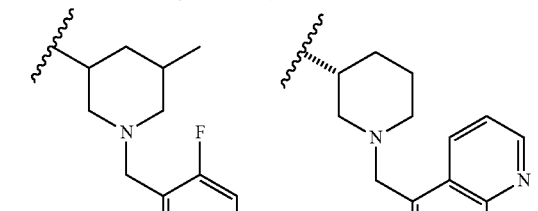
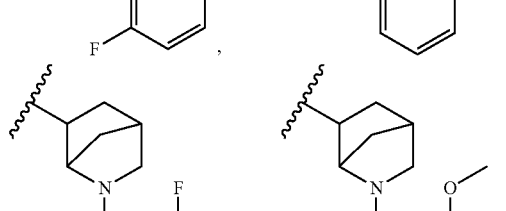
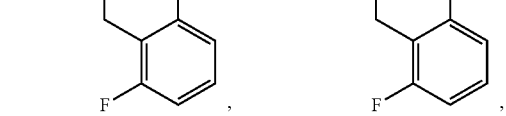
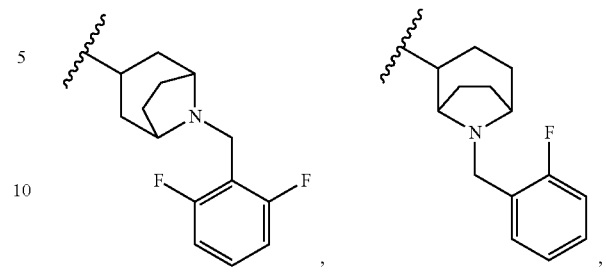
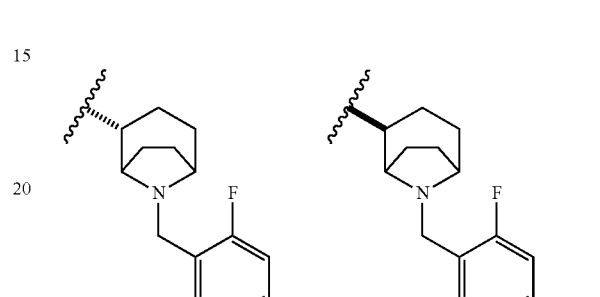
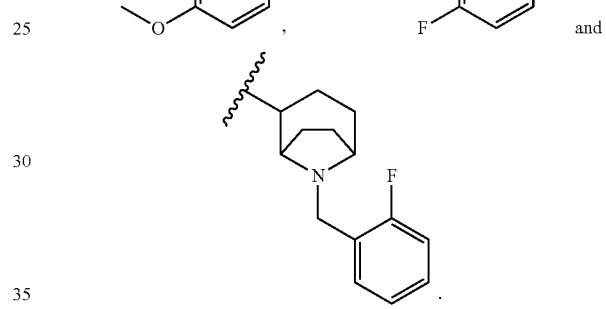
In another class of this embodiment, $R^2$ is
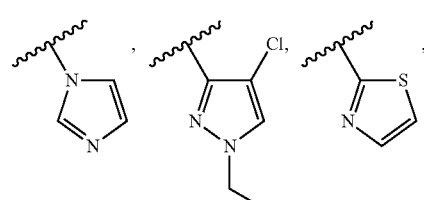
In another class of this embodiment, $R^2$ is selected from the group consisting of:
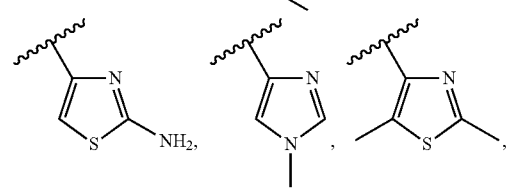

-continued
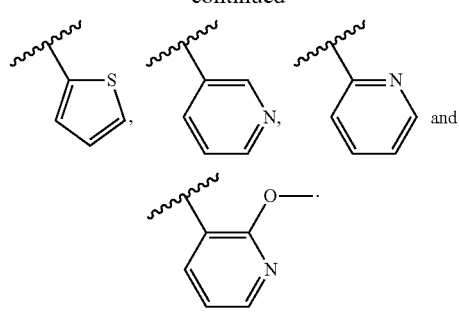
In another class of this embodiment, $R^2$ is selected from the group consisting of:
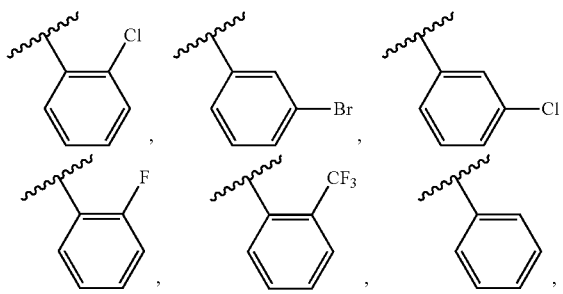
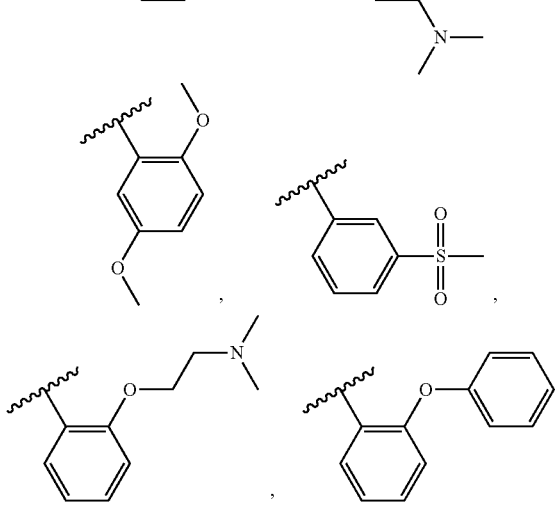
-continued
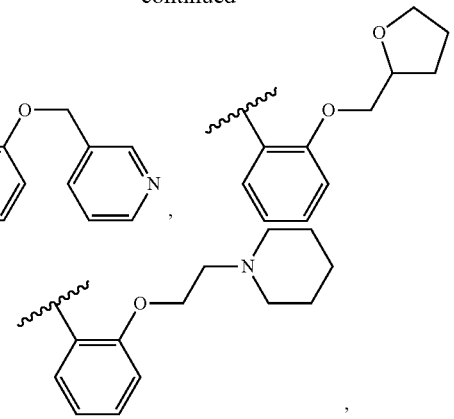
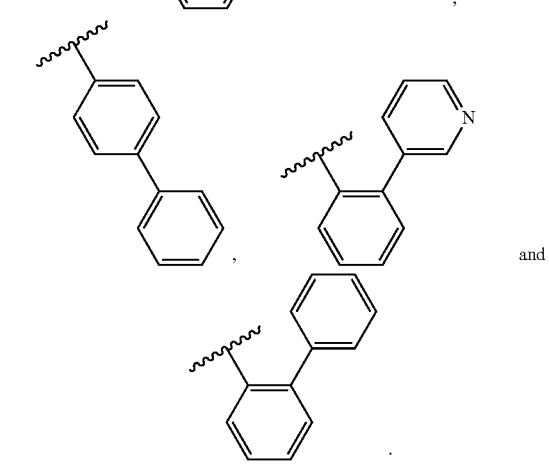
In another class of this embodiment, $R^2$ is selected from the group consisting of:
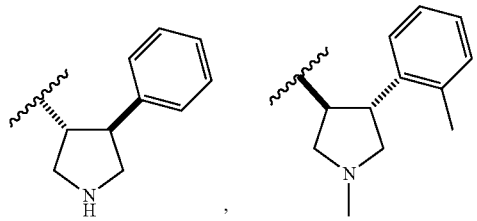
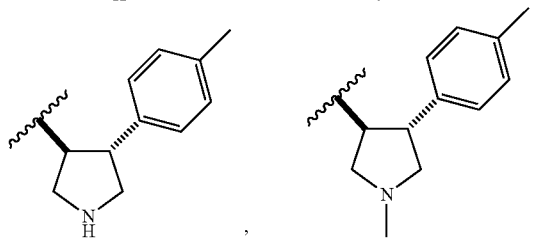
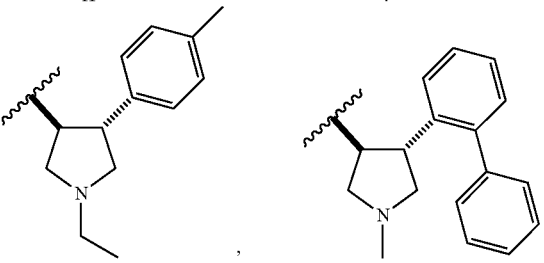

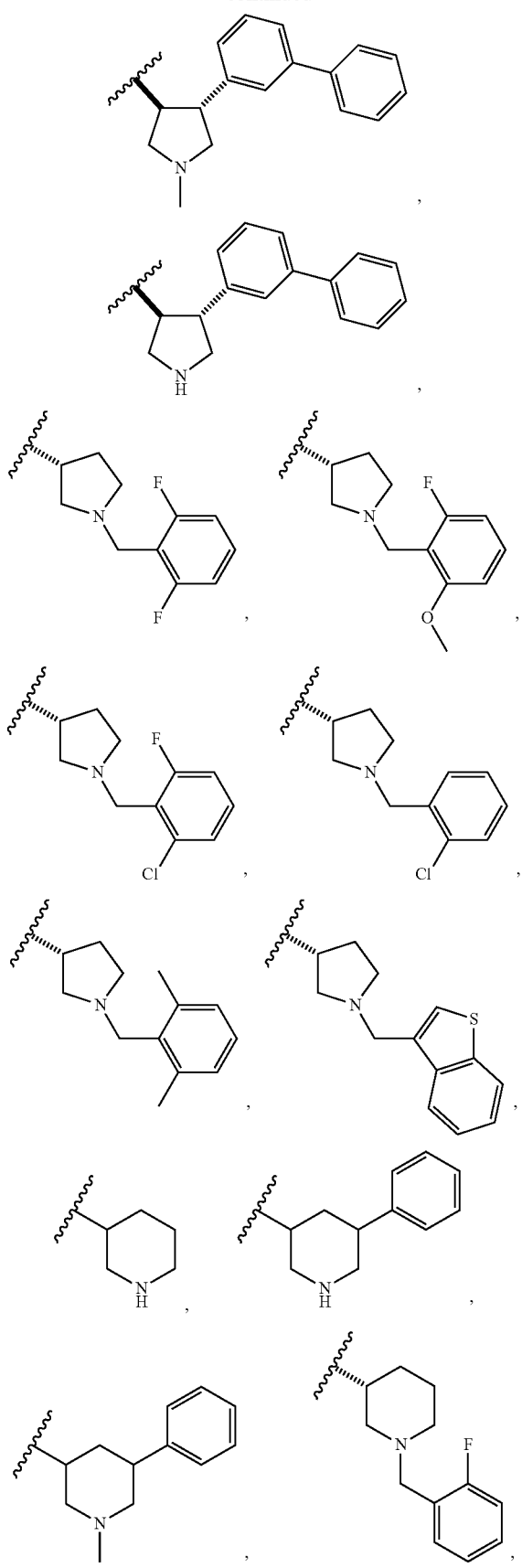
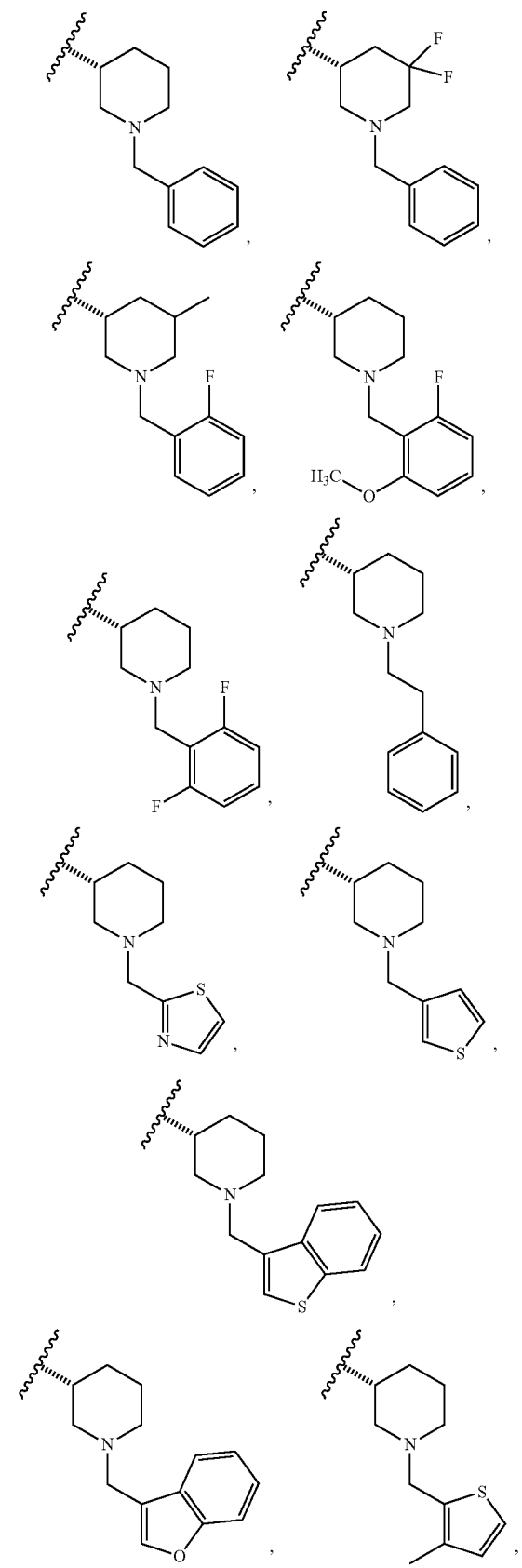

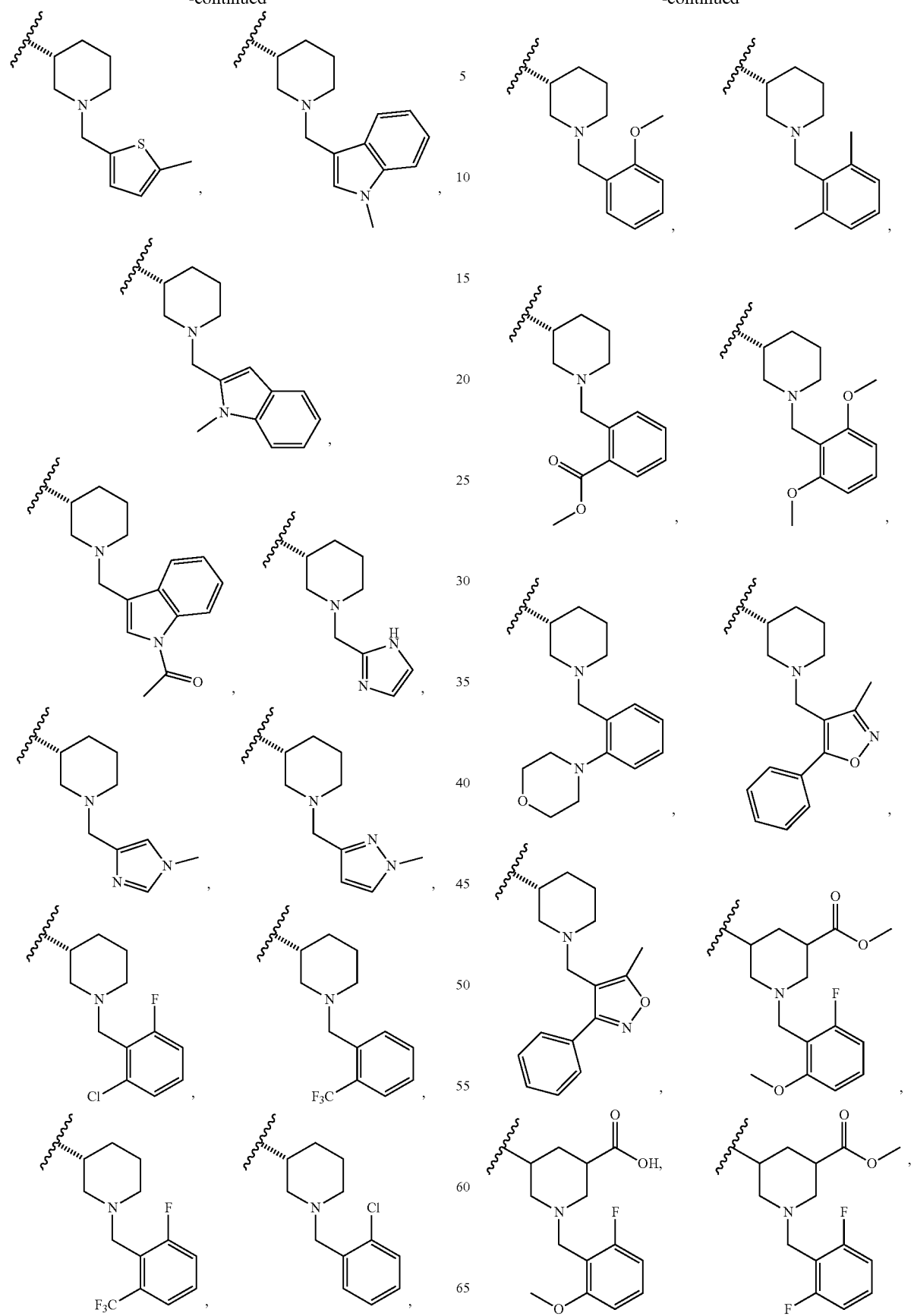

-continued
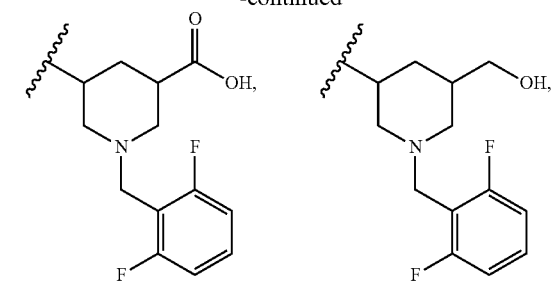
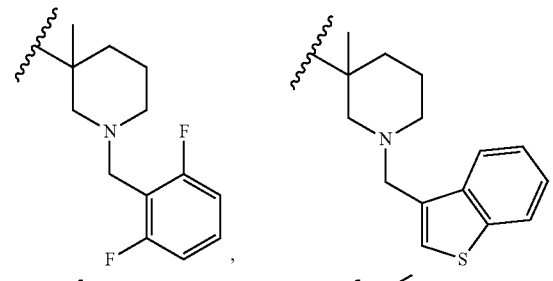
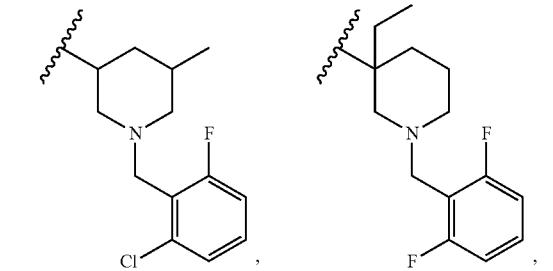
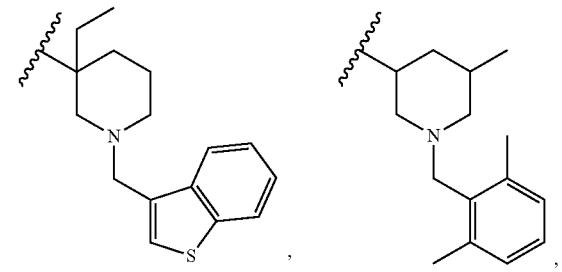
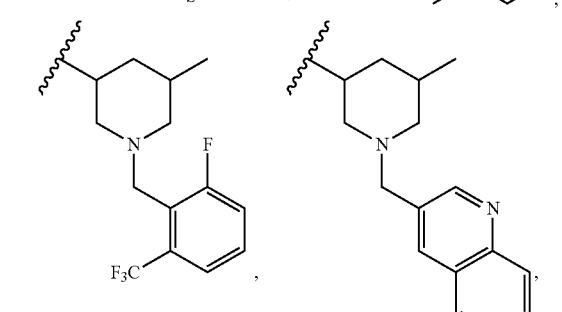
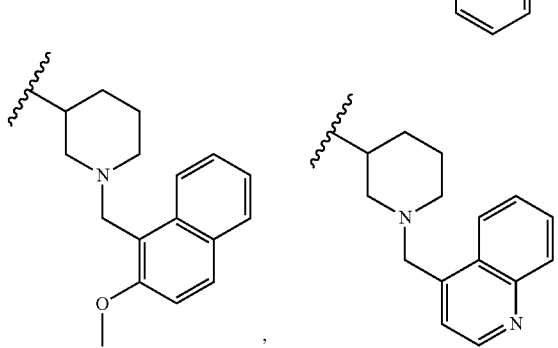
-continued
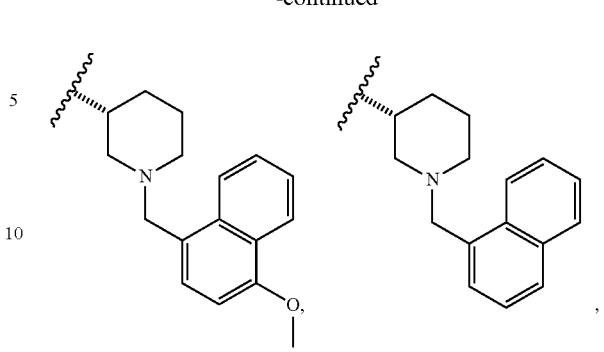
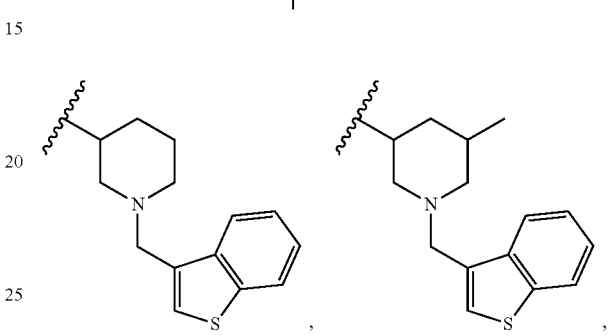
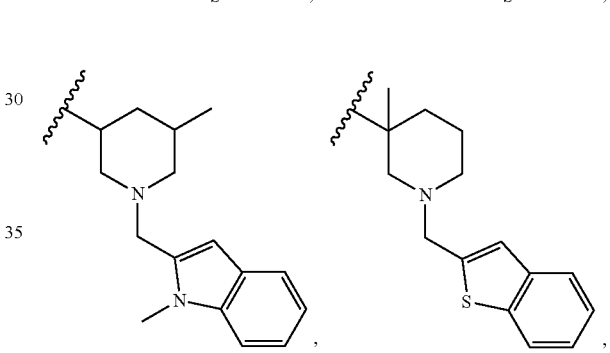
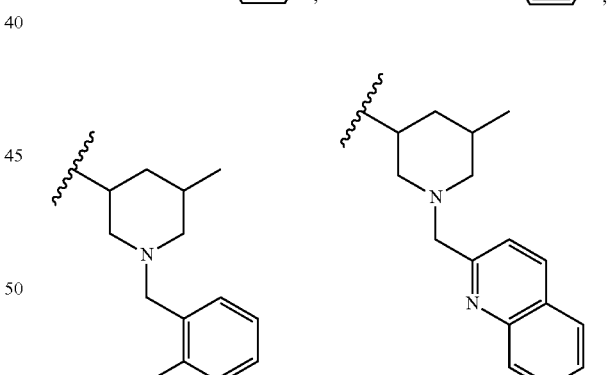
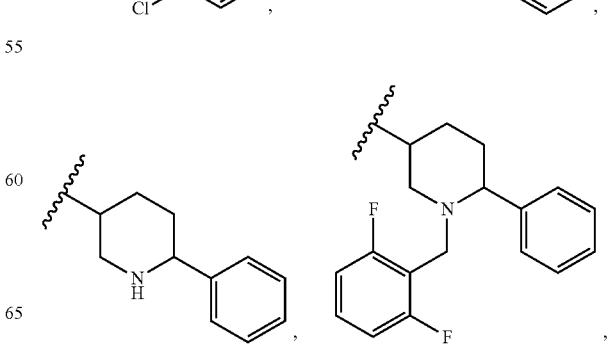

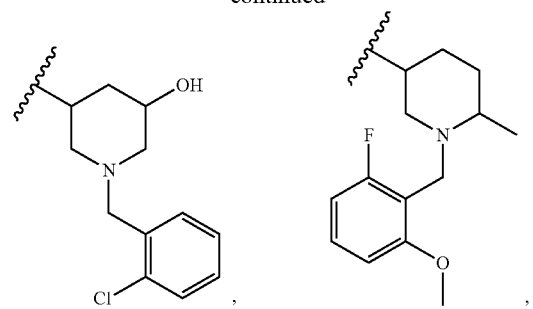
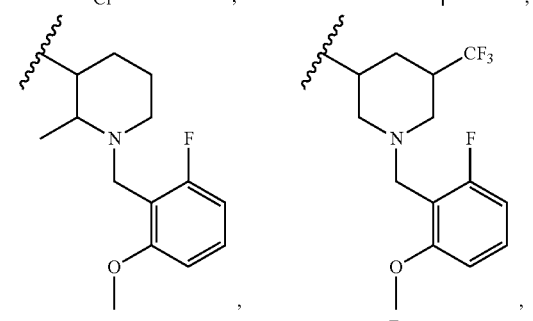
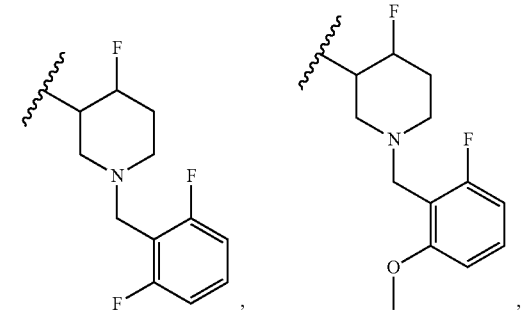
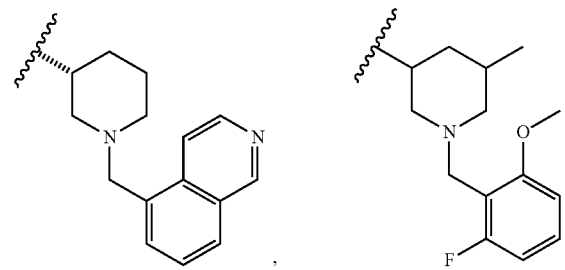
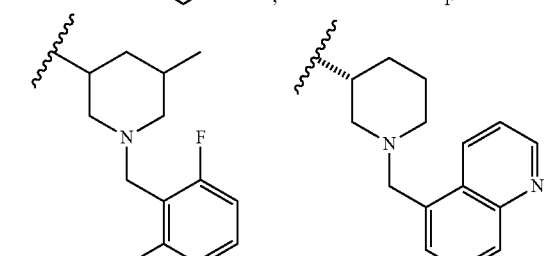
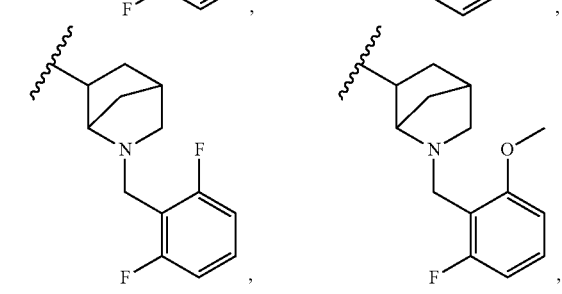
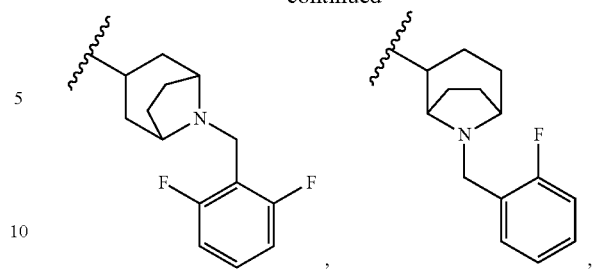
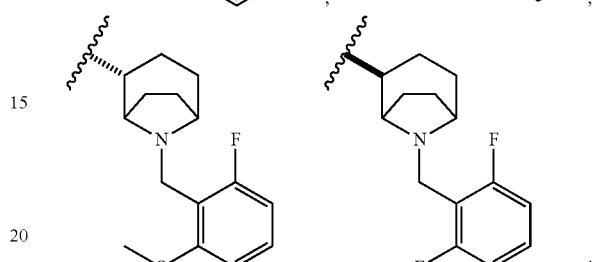
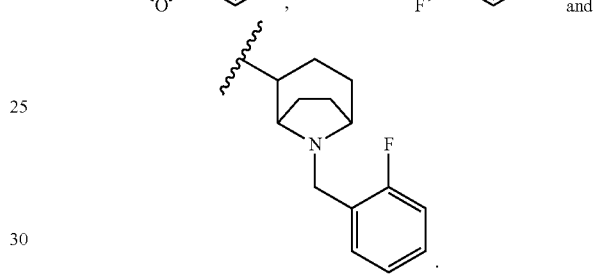
In another class of this embodiment, $R^2$ is selected from the group consisting of:
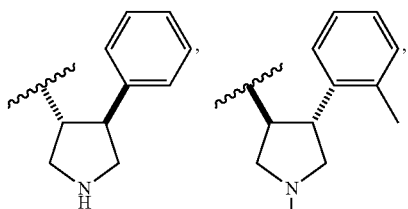
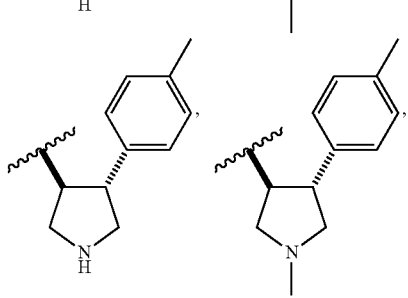
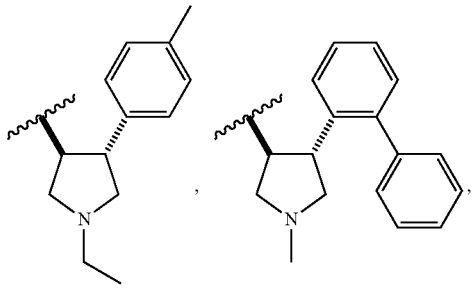

-continued

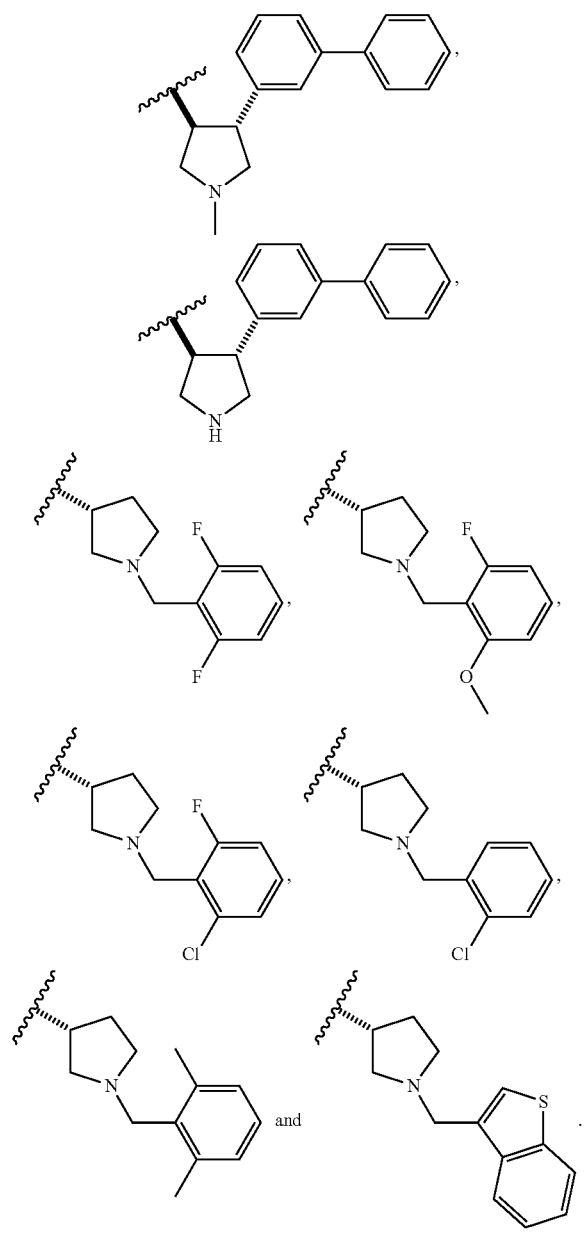

In another class of this embodiment, R² is selected from the group consisting of:

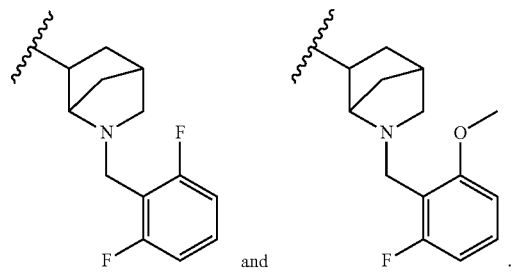 [SMILES: *C1CC2CC1N(Cc1c(F)cccc1F)C2 ; "and" ; *C1CC2CC1N(Cc1c(F)cccc1OC)C2 ; "."]

In another class of this embodiment, R² is selected from the group consisting of:

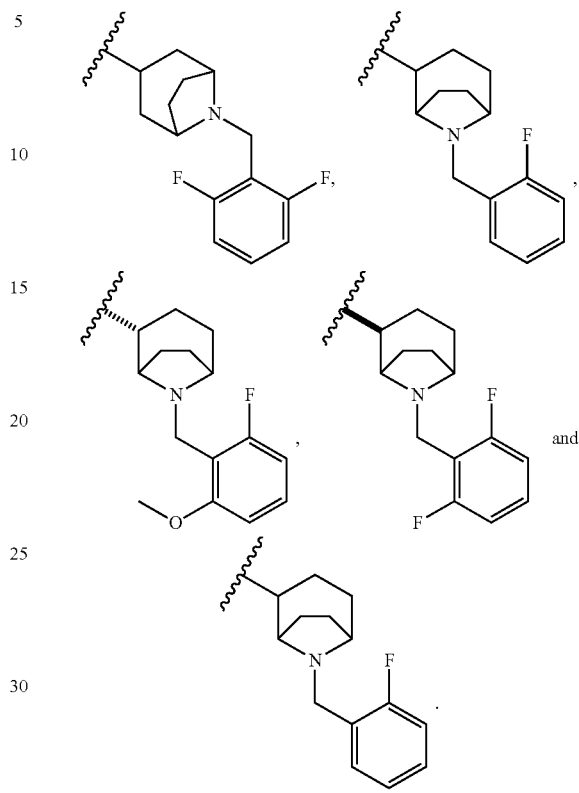

In another embodiment of this invention is a compound of Formula I wherein $R^1$ is heteroaryl, wherein said heteroaryl group is unsubstituted or substituted by at one to three $R^{14}$ groups; and $R^2$ is cycloalkyl, wherein said cycloalkyl group is unsubstituted or substituted by one to three $R^{11}$ groups, or alternatively two $R^{11}$ groups can optionally be taken together with the carbon atoms to which they are attached to form a five- or six-membered cycloalkyl, cycloalkenyl, heterocyclyl, heterocyclenyl, aryl or heteroaryl. In another embodiment of this invention is a compound of Formula I wherein $R^1$ is aryl, wherein said aryl group is unsubstituted or substituted by one to three $R^{14}$ groups; and $R^2$ is cycloalkyl, wherein said cycloalkyl group is unsubstituted or substituted by one to three $R^{11}$ groups, or alternatively two $R^{11}$ groups can optionally be taken together with the carbon atoms to which they are attached to form a five- or six-membered cycloalkyl, cycloalkenyl, heterocyclyl, heterocyclenyl, aryl or heteroaryl. In another embodiment of this invention is a compound of Formula I wherein $R^1$ is heteroaryl, wherein said heteroaryl group is unsubstituted or substituted by one to three $R^{14}$ groups; and $R^2$ is aryl, wherein said aryl group is unsubstituted or substituted by one to three $R^{11}$ groups, or alternatively two $R^{11}$ groups can optionally be taken together with the carbon atoms to which they are attached to form a five- or six-membered cycloalkyl, cycloalkenyl, heterocyclyl, heterocyclenyl, aryl or heteroaryl. In another embodiment of this invention is a compound of Formula I wherein $R^1$ is aryl, wherein said aryl group is unsubstituted or substituted by one to three $R^{14}$ groups; and $R^2$ is aryl, wherein said aryl group is unsubstituted or substituted by one to three $R^{11}$ groups, or alternatively two $R^{11}$ groups can optionally be taken together with the carbon atoms to which they are attached to form a five- or six-membered cycloalkyl, cycloalkenyl, heterocyclyl, heterocyclenyl, aryl or heteroaryl. In another embodiment of this invention is a compound of Formula I wherein $R^1$ is heteroaryl, wherein said heteroaryl group is unsubstituted or substituted by one to three $R^{14}$ groups; and $R^2$ is heteroaryl, wherein said heteroaryl group is unsubstituted or substituted by one to three $R^{11}$ groups, or alternatively two $R^{11}$ groups can optionally be taken together with the carbon atoms to which they are attached to form a five- or six-membered cycloalkyl, cycloalkenyl, heterocyclyl, heterocyclenyl, aryl or heteroaryl. In another embodiment of this invention is a compound of Formula I wherein $R^1$ is aryl, wherein said aryl group is unsubstituted or substituted by one to three $R^{14}$ groups; and $R^2$ is heteroaryl, wherein said heteroaryl group is unsubstituted or substituted by one to three $R^{11}$ groups, or alternatively two $R^{11}$ groups can optionally be taken together with the carbon atoms to which they are attached to form a five- or six-membered cycloalkyl, cycloalkenyl, heterocyclyl, heterocyclenyl, aryl or heteroaryl.

In another embodiment of this invention is a compound of Formula I wherein $R^1$ is heteroaryl, wherein said heteroaryl group is unsubstituted or substituted by one to three $R^{14}$ groups; and $R^2$ is

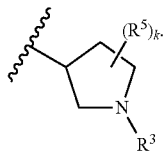

In another embodiment of this invention is a compound of Formula I wherein $R^1$ aryl, wherein said aryl group is unsubstituted or substituted by one to three $R^{14}$ groups; and $R^2$ is

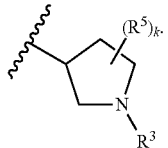

In another embodiment of this invention is a compound of Formula I wherein $R^1$ is heteroaryl, wherein said heteroaryl group is unsubstituted or substituted by one to three $R^{14}$ groups; and $R^2$ is

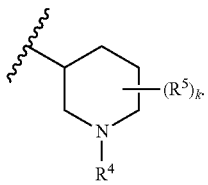

In another embodiment of this invention is a compound of Formula I wherein $R^1$ aryl, wherein said aryl group is unsubstituted or substituted by one to three $R^{14}$ groups; and $R^2$ is

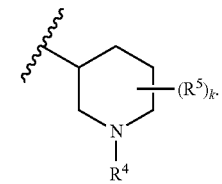

In another embodiment of this invention is a compound of Formula I wherein $R^1$ is heteroaryl, wherein said heteroaryl group is unsubstituted or substituted by one to three $R^{14}$ groups; and $R^2$ is

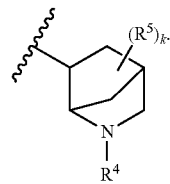

In another embodiment of this invention is a compound of Formula I wherein $R^1$ aryl, wherein said aryl group is unsubstituted or substituted by one to three $R^{14}$ groups; and $R^2$ is

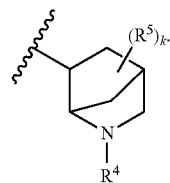

In another embodiment of this invention is a compound of Formula I wherein $R^1$ is heteroaryl, wherein said heteroaryl group is unsubstituted or substituted by one to three $R^{14}$ groups; and $R^2$ is

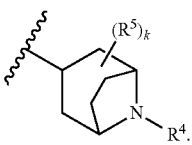

In another embodiment of this invention is a compound of Formula I wherein $R^1$ is aryl, wherein said aryl group is unsubstituted or substituted by one to three $R^{14}$ groups; and $R^2$ is

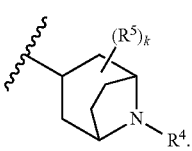

In another embodiment of this invention is a compound of Formula I wherein $R^1$ is heteroaryl, wherein said heteroaryl group is unsubstituted or substituted by one to three $R^{14}$ groups; and $R^2$ is

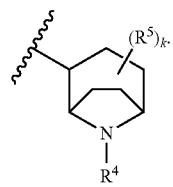

In another embodiment of this invention is a compound of Formula I wherein R¹ aryl, wherein said aryl group is unsubstituted or substituted by one to three R¹⁴ groups; and R² is

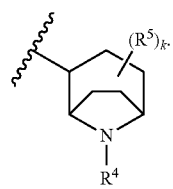

In another embodiment of this invention is a compound of Formula I wherein X is selected from the group consisting of —C(R⁶)—; and —N—; Y is selected from the group consisting of —C(R⁷R⁸)—, —O—, —N(R⁶)—, and —N(R⁶)C(R⁷R⁸)CH₂—; and m is 1. In class of this embodiment, X is —C(R⁶)—; and Y is —N(R⁶)—. In class of this embodiment, X is —C(R⁶)—; and Y is —C(R⁷R⁸)—. In class of this embodiment, X is —C(R⁶)—; and Y is —O—. In class of this embodiment, X is —C(R⁶)—; and Y is —N(R⁶)C(R⁷R⁸)CH₂—. In class of this embodiment, X is —N—; and Y is —N(R⁶)—. In class of this embodiment, X is —N—; and Y is —C(R⁷R⁸)—. In class of this embodiment, X is —N—; and Y is —O—. In class of this embodiment, X is —N—; and Y is —N(R⁶)C(R⁷R⁸)CH₂—.

In class of this embodiment, X is selected from the group consisting of —CH—, —C(CH₃)—, and —N—; Y is selected from the group consisting of

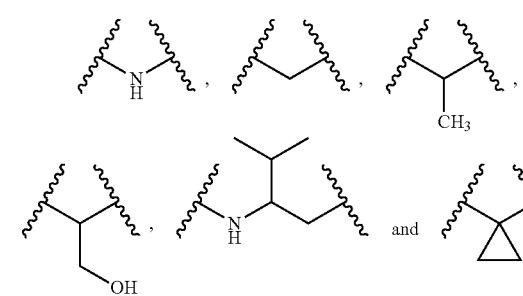

In class of this embodiment, X is selected from the group consisting of —CH—, and —C(CH₃)—. In class of this embodiment, X is selected from the group consisting of —CH—, and —C(CH₃)—; and Y is

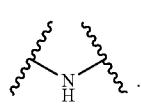

In class of this embodiment, X is selected from the group consisting of —CH—, and —C(CH₃)—; and Y is

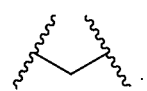

In class of this embodiment, X is —N—. In class of this embodiment, X is —N—; and Y is

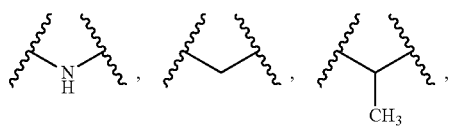

In class of this embodiment, X is —N—; and Y is

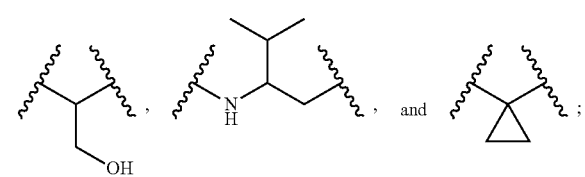

In another embodiment of this invention is a compound of Formula I wherein X is selected from the group consisting of —CH—, —C(CH₃)—, and Y is selected from the group consisting of

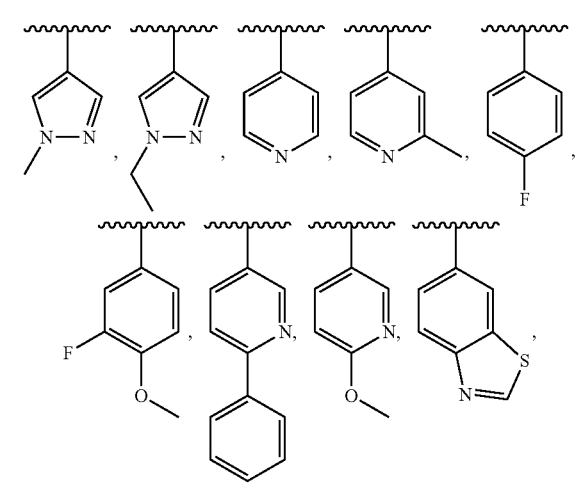

R¹ is selected from the group consisting of

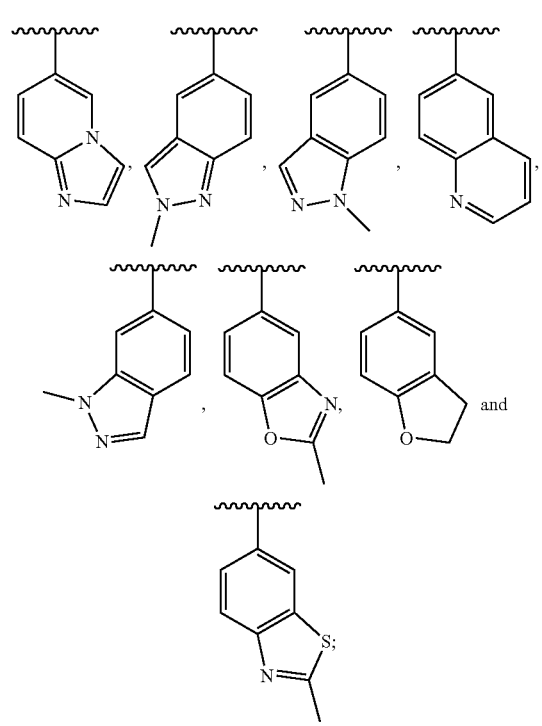
and m is 1.
In class of this embodiment, X is selected from the group consisting of —CH—, and —C(CH$_3$)—. In class of this embodiment, X is N—.
In class of this embodiment, R$^2$ is selected from the group consisting of:
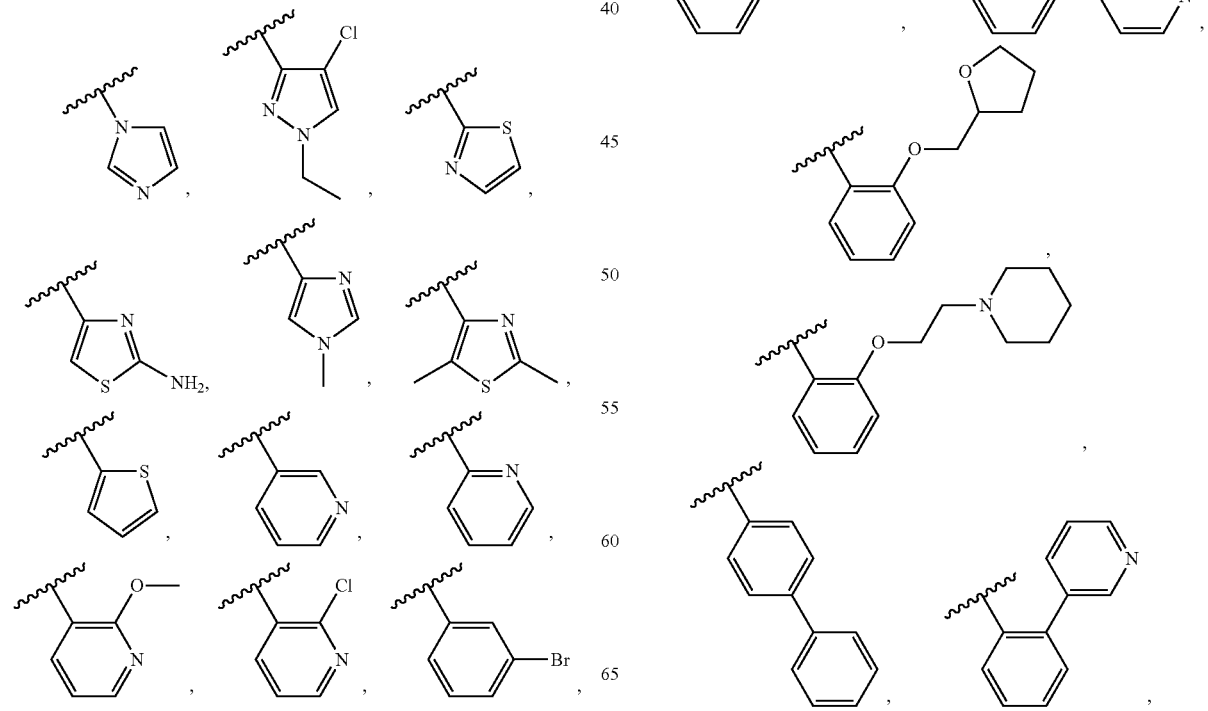
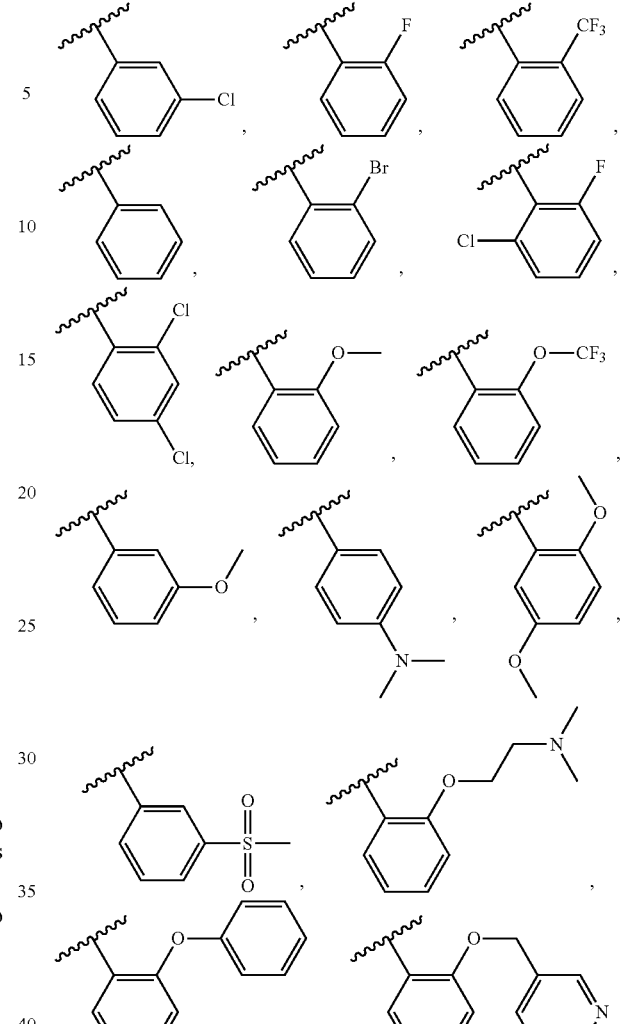

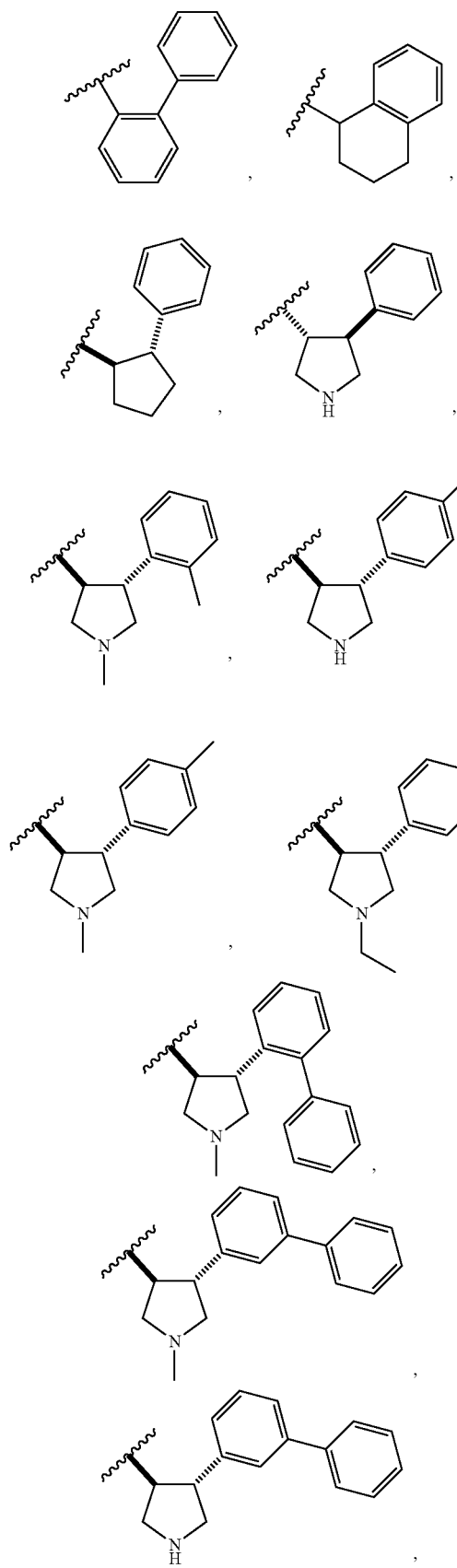
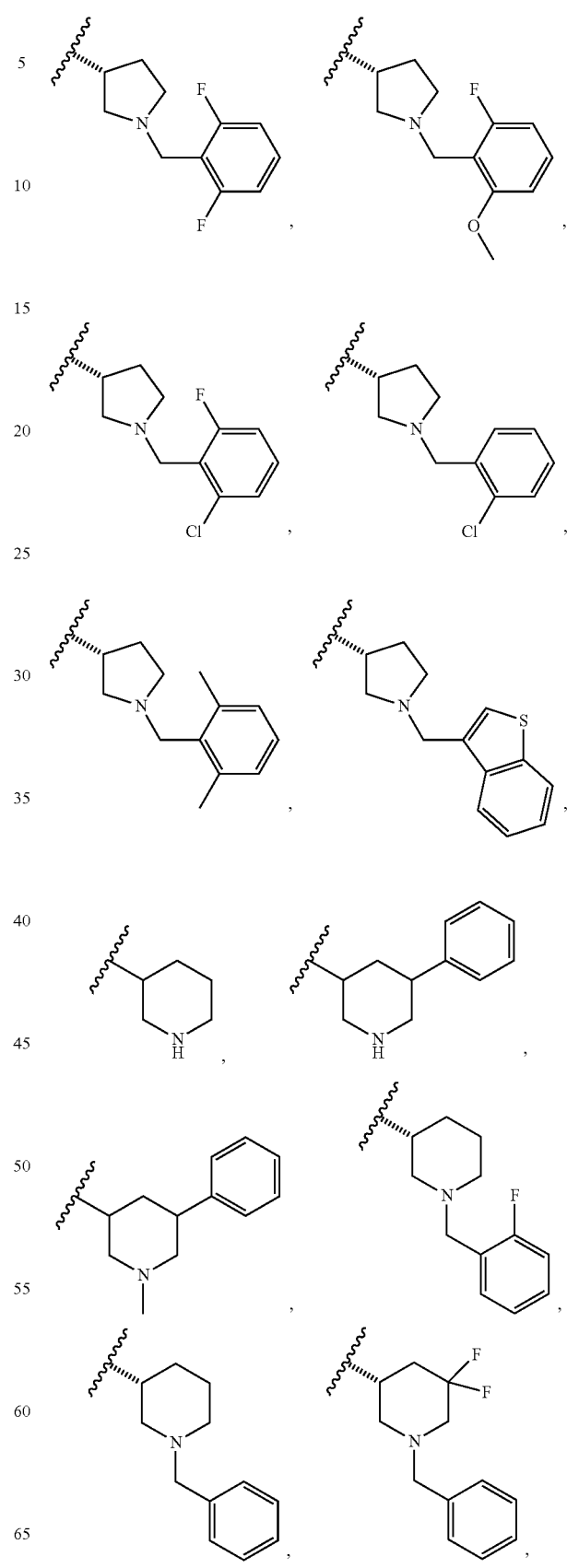

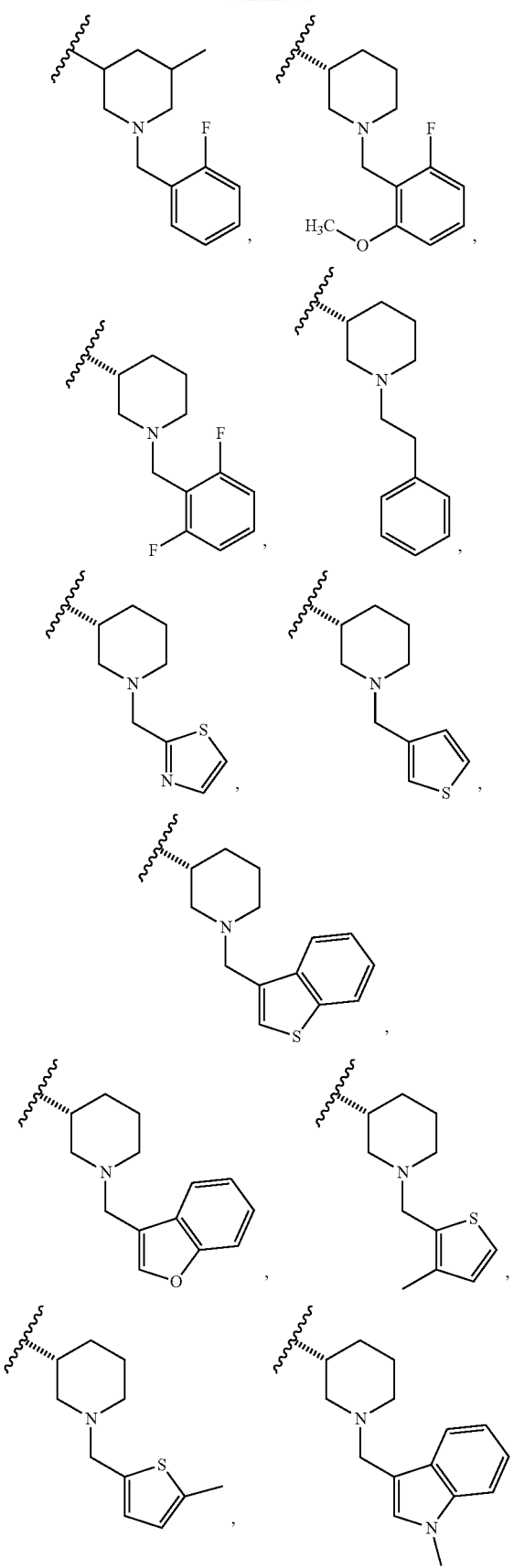
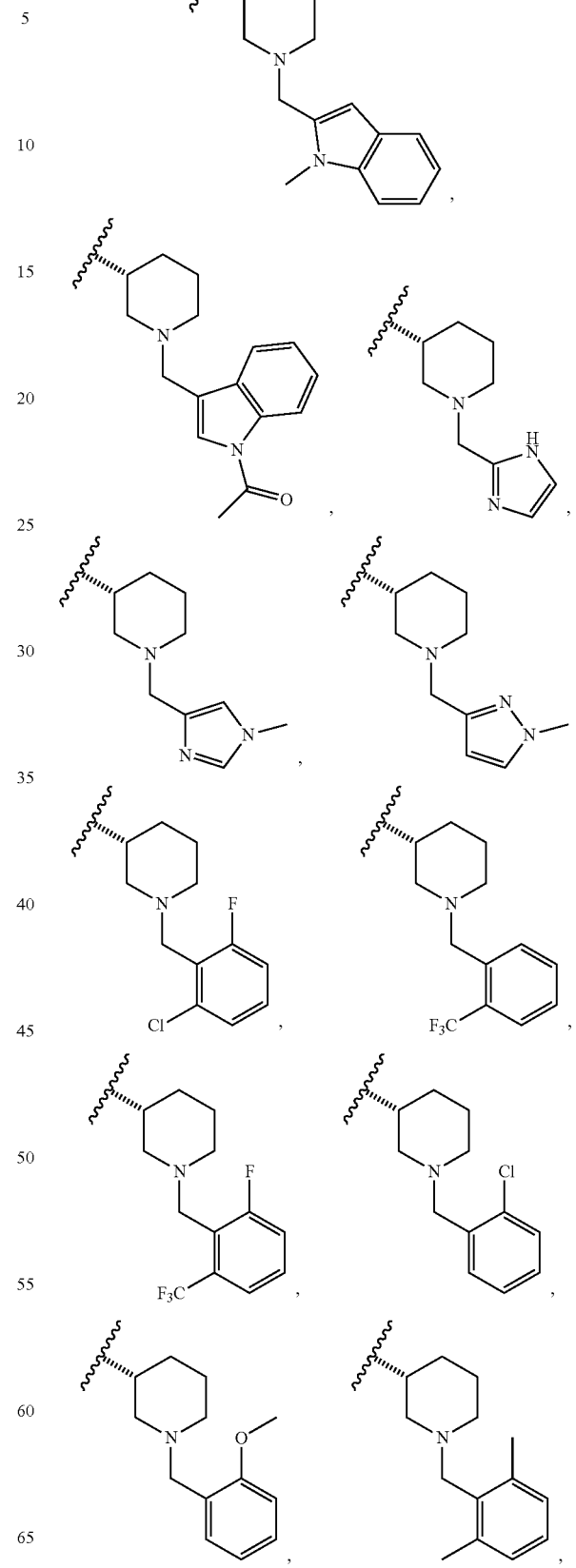

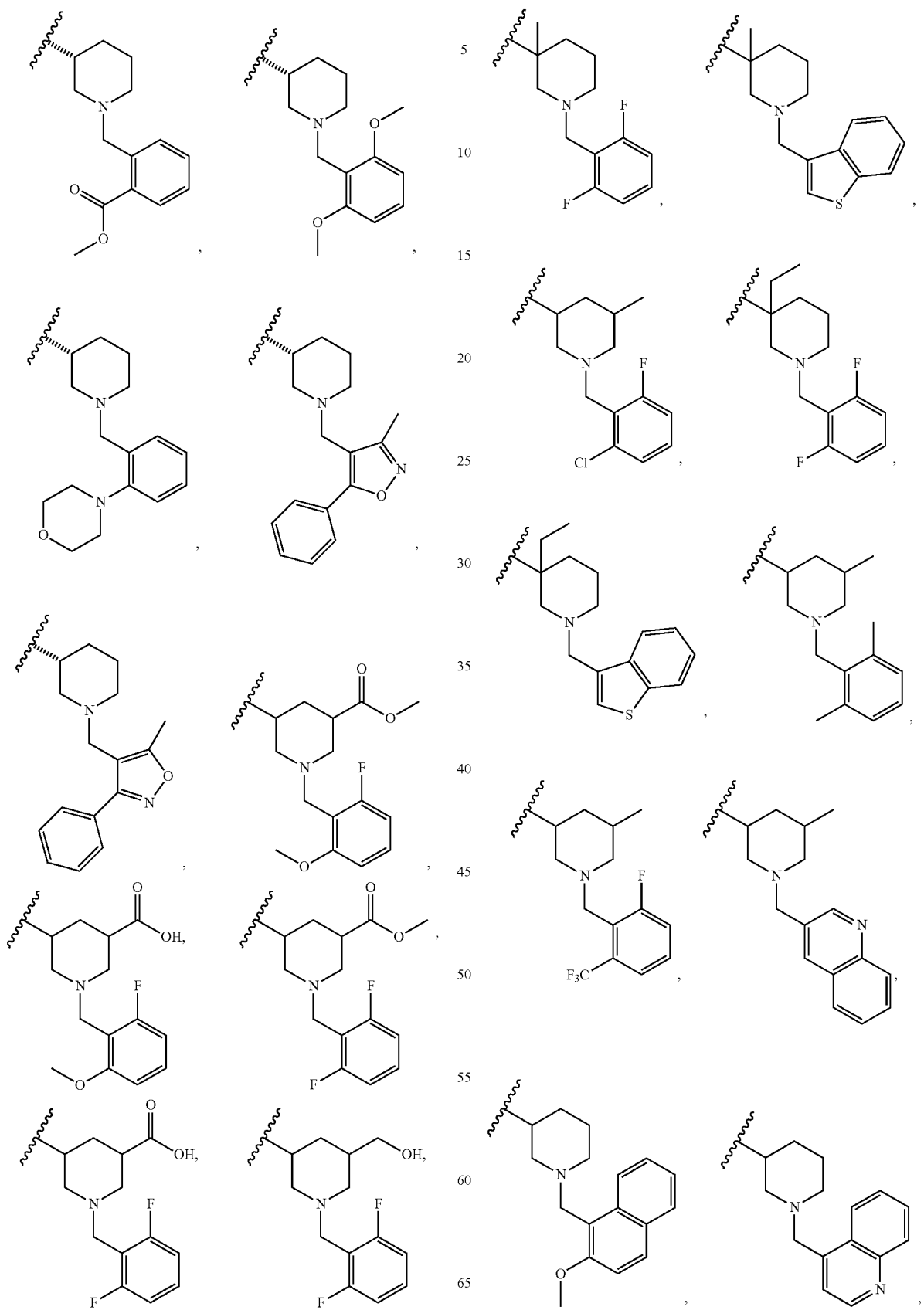

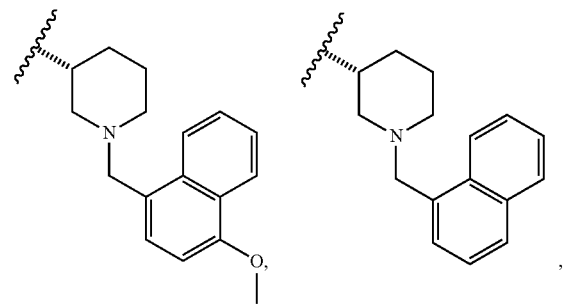
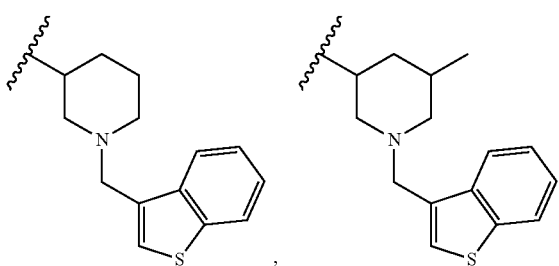
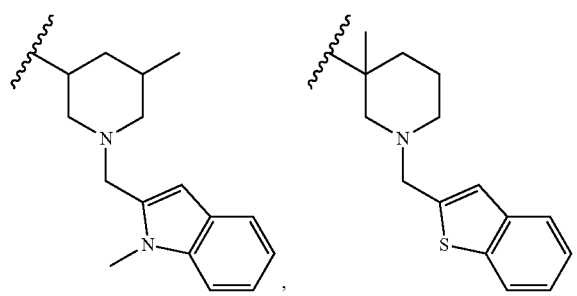
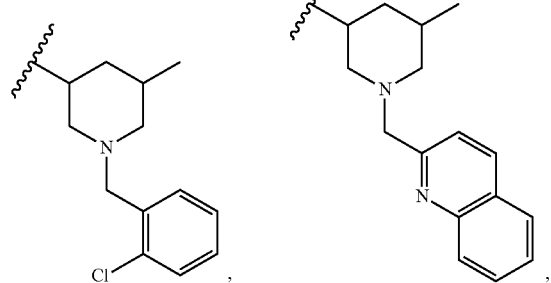
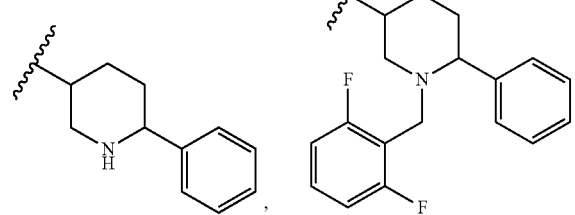
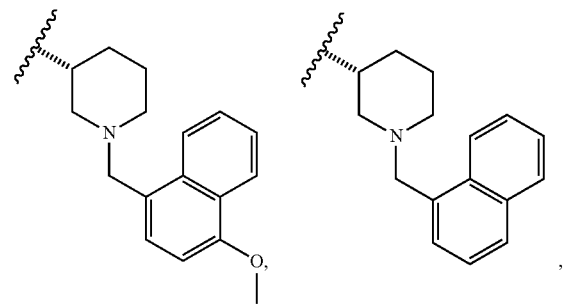
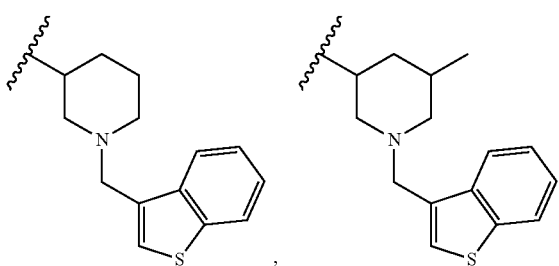
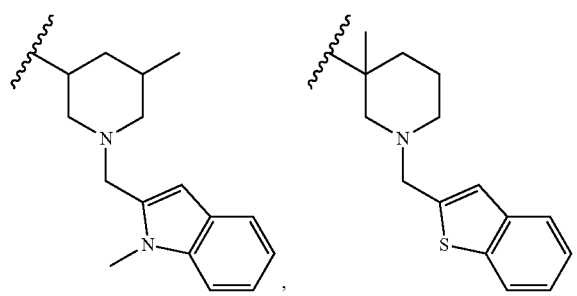
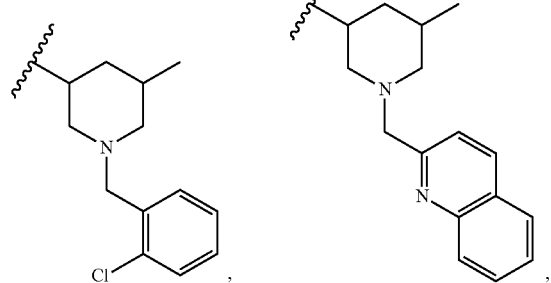
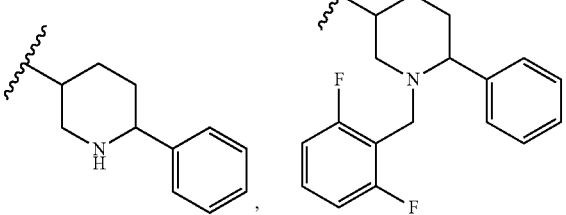
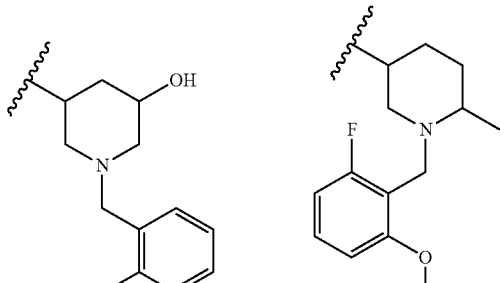
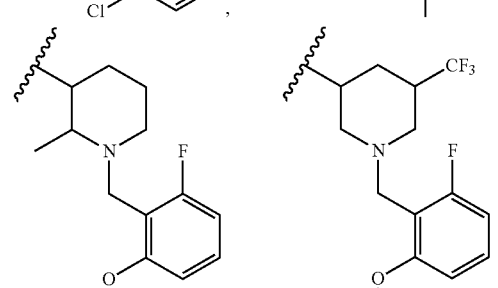
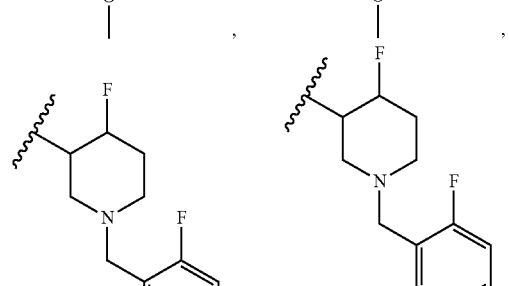
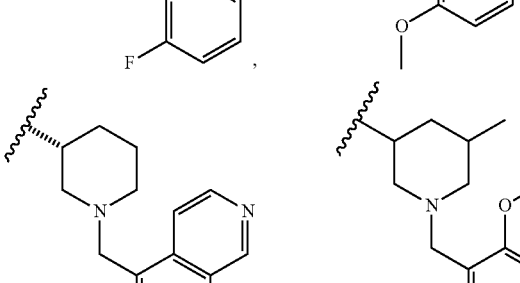
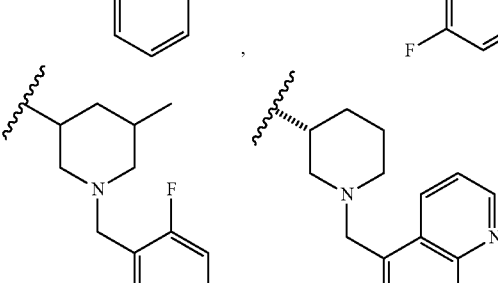
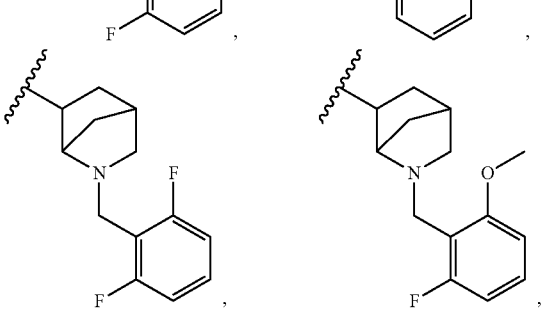

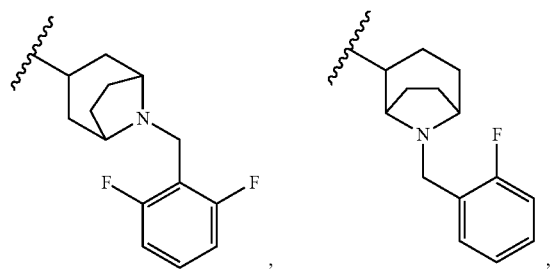

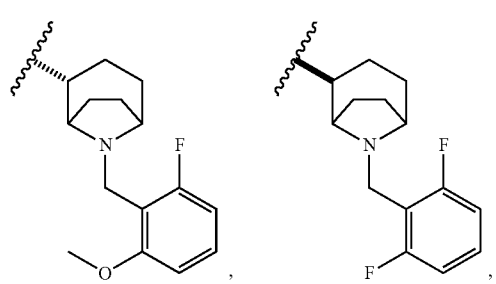

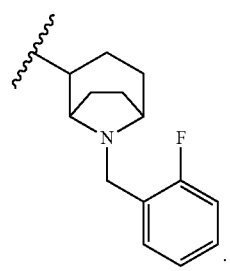

In another embodiment, the present invention provides compounds which are represented by structural formulas I-a-I-h or a pharmaceutically acceptable salt, solvate or ester thereof, wherein the various moieties are as described above:

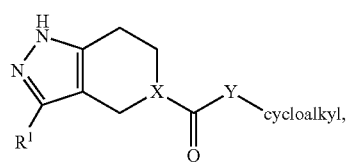

I-a

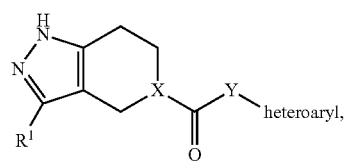

I-b

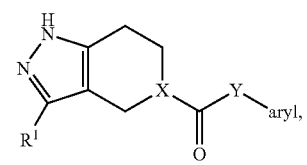

I-c

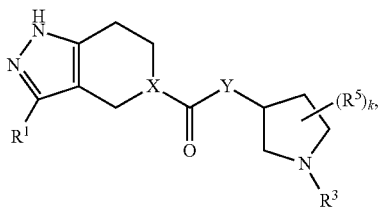

I-d

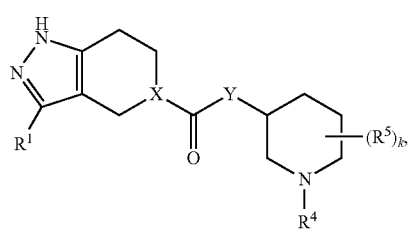

I-e

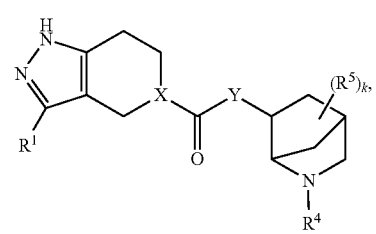

I-f

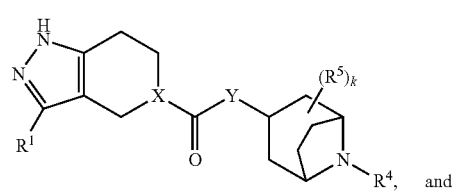

I-g, and

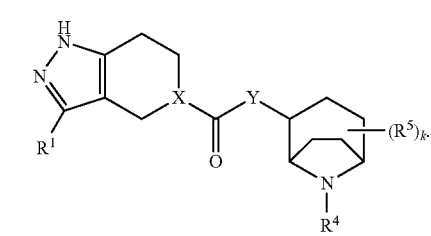

I-h

In another embodiment, the present invention provides compounds which are represented by structural Formula I-a or a pharmaceutically acceptable salt, solvate or ester thereof, wherein the various moieties are as described above:

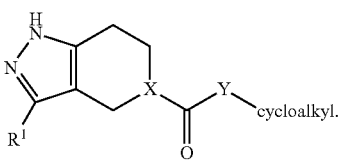

I-a

In another embodiment, the present invention discloses compounds which are represented by structural Formula I-b or a pharmaceutically acceptable salt, solvate or ester thereof, wherein the various moieties are as described above:

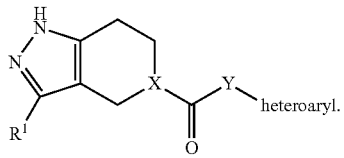

I-b

In another embodiment, the present invention discloses compounds which are represented by structural Formula I-c or a pharmaceutically acceptable salt, solvate or ester thereof, wherein the various moieties are as described above:

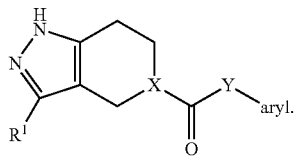

I-c

In another embodiment, the present invention discloses compounds which are represented by structural Formula I-d or a pharmaceutically acceptable salt, solvate or ester thereof, wherein the various moieties are as described above:

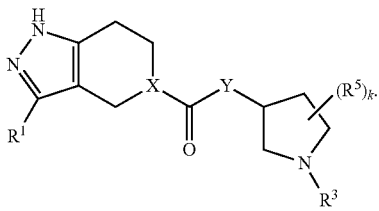

I-d

In another embodiment, the present invention discloses compounds which are represented by structural Formula I-e or a pharmaceutically acceptable salt, solvate or ester thereof, wherein the various moieties are as described above:

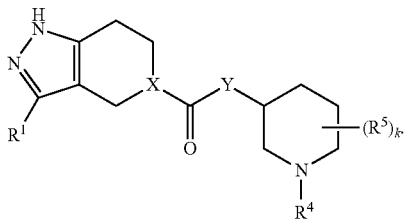

I-e

In another embodiment, the present invention discloses compounds which are represented by structural Formula I-f or a pharmaceutically acceptable salt, solvate or ester thereof, wherein the various moieties are as described above:

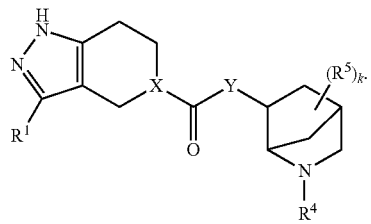

I-f

In another embodiment, the present invention discloses compounds which are represented by structural Formula I-g or a pharmaceutically acceptable salt, solvate or ester thereof, wherein the various moieties are as described above:

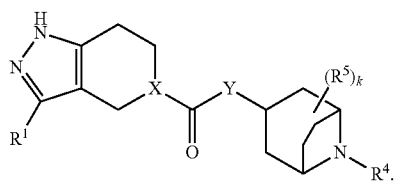

I-g

In another embodiment, the present invention discloses compounds which are represented by structural Formula I-h or a pharmaceutically acceptable salt, solvate or ester thereof, wherein the various moieties are as described above:

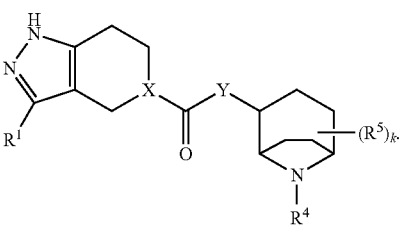

I-h

Representative compounds of the present invention include those presented in the Examples and pharmaceutically salts and individual stereoisomers thereof.

Other embodiments of this invention are directed to any one of the embodiments above wherein one or more hydrogen atoms are deuterium.

Another embodiment of this invention is directed to the compounds of Formula I in pure and isolated form.

Another embodiment of this invention is directed to the compounds of Formula I in pure form.

Another embodiment of this invention is directed to the compounds of Formula I in isolated form.

Included in the instant invention is the free form of compounds of Formula I, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.,* 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

UTILITY

The compounds of the instant invention are inhibitors of the activity of ERK (i.e., ERK1 and ERK2 activity) and are thus useful in the treatment of cancer, in particular cancers associated with irregularities in the activity of ERK and downstream cellular targets of ERK. Such cancers include, but are not limited to, melanoma, pancreatic cancer, thyroid cancer, colorectal cancer, lung cancer, breast cancer, and ovarian cancer.

The compounds, compositions and methods provided herein are particularly deemed useful for the treatment of cancer including solid tumors such as skin, breast, brain, cervical carcinomas, testicular carcinomas, etc. More particularly, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibro sarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In a one embodiment, the instant compound is selected from the group of a selective inhibitor of ERK1, a selective inhibitor of ERK2 and a selective inhibitor of both ERK1 and ERK2.

The present invention is further directed to a method of inhibiting ERK activity which comprises administering to a mammal in need thereof a pharmaceutically effective amount of the instant compound.

The compounds of this invention may be administered to mammals, including humans, either alone or, in combination with pharmaceutically acceptable carriers, excipients' or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium croscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisole or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.) The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

In an embodiment, a suitable amount of an inhibitor of ERK is administered to a mammal undergoing treatment for cancer. Administration occurs in an amount of inhibitor of between about 0.1 mg/kg of body weight to about 60 mg/kg of body weight per day, or between 0.5 mg/kg of body weight to about 40 mg/kg of body weight per day. Another therapeutic dosage that comprises the instant composition includes from about 0.01 mg to about 1000 mg of inhibitor of ERK. In another embodiment, the dosage comprises from about 1 mg to about 1000 mg of inhibitor of ERK.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors, angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs), agents that interfere with cell cycle checkpoints, and other ERK inhibitors. The instant compounds are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors, angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs), agents that interfere with cell cycle checkpoints, and other ERK inhibitors.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors and ubiquitin ligase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diariziclinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184-476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are top otecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H, 15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',':6,7)naphtho(2,3-d)-1,3-dioxol-6-one, 2,3-(methylenedioxy)-5-methyl-7-hydroxy-8-methoxybenzo[c]-phenanthradinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthene-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768 and WO 01/98278, and pending U.S. Ser. Nos. 60/338,779 (filed Dec. 6, 2001), 60/338,344 (filed Dec. 6, 2001), 60/338,383 (filed Dec. 6, 2001), 60/338, 380 (filed Dec. 6, 2001), 60/338,379 (filed Dec. 6, 2001) and 60/344,453 (filed Nov. 7, 2001). In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. J. Med. Chem. 46(24):5097-5116 (2003). "Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1'-diazatetracyclo(7.4.1.0-0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-$\alpha$, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Int. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin H antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chest La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140 and WO 02/083138), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633, 272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2, 5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\beta_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_2$, $\alpha_5\beta_1$, $\alpha_6\beta_1$, and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylindenyl]indolin-2-one, 17-(allylamino)-17-demethoxygeldanamycin, 4-(3-chloro-4-fluorophenylamino)-7-methoxy-643-(4-morpholinyl)propoxyl]quinazoline, N-(3-ethynylphenyl)-6,7-bis (2-methoxyethoxy)-4-quinazolinamine, BIBX1382,2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD 121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-11039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-G-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (*Cancer Medicine,* 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, C11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

A compound of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention, are also useful in combination with potassium salts, magnesium salts, beta-blockers (such as atenolol) and endothelin-a (ETa)antagonists with the goal of maintaining cardiovascular homeostasis.

A compound of the instant invention, are also useful in combination with insulin, insulin secretagogues, PPAR-gamma agonists, metformin, somatostatin receptor agonists such as octreotide, DPP4 inhibitors, sulfonylureas and alpha-glucosidase inhibitors with the goal of maintaining glucose homeostasis.

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®), cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa) and vorinostat (Zolinza®).

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, and an agent that interferes with a cell cycle checkpoint.

The compounds of this invention can be combined with MTOR inhibitors.

Thus, any of the methods of this invention can optionally include the administration of an effective amount of one or more (e.g., 1, 2 or 3, or 1 or 2, or 1) MTOR inhibitors. The MTOR inhibitors can be administered currently or sequentially with the compounds of the invention and with the optional chemotherapeutic agents.

Examples of mTOR inhibitors include but are not limited to: those disclosed in: US 2007/0112005 (which describes fused bicyclic mTOR inhibitors useful in treatment of cancer), WO 2007/087395 (which describes unsaturated mTOR inhibitors useful in treatment of cancer), WO 2006/090169 (which describes 2,4-diamineo-pyrido-pyrmidine derivatives and their use as mTOR inhibitors), WO 2007/066099 (which describes pyrimidine derivatives useful as mTOR kinase inhibitors for anticancer), US 2005/0222171 (which describes pyrazolo[1,5 a]pyrimidin-7-yl amine derivatives to treat protein kinase dependent diseases), WO 2005/070431 (which describes pyrazolo[1,5 a]pyrimidin-7-yl amine derivatives to treat protein kinase dependent diseases), WO 2007/0570431 (which describes pyrazolo[1,5 a]pyrimidin-7-yl amine derivatives to treat protein kinase dependent diseases), WO 2007/009773 (which describes pyrazolo[1,5 a]pyrimidin-7-yl amine derivatives to treat protein kinase dependent diseases), and US 2002/0041880 (which describes pyrazolo[1,5 a]pyrimidin-7-yl derivatives to inhibit kinase insert domain-containing receptor to block angiogenesis).

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blacker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an EV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, and an agent that interferes with a cell cycle checkpoint.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, and an agent that interferes with a cell cycle checkpoint.

All patents, publications and pending patent applications identified are hereby incorporated by reference.

The following abbreviations have the following meanings unless defined otherwise: ACN=Acetonitrile; AcOH=Acetic acid; DAST=(diethylamino)sulfur trifluoride; DCC=Dicyclohexylcarbodiimide; DCU=Dicyclohexylurea; DCM=Dichloromethane; DI=Deionized water; DIAD=Diisopropylazodicarboxylate; DIEA=Diisopropylethylamine; DMAP-4-Dimethylaminopyridine; DME=Dimethoxyethane; DMF=Dimethylformamide; DMFDMA=N,N-Dimethylfounamide dimethylacetal; DMSO=Dimethyl sulfoxide; DTT=Dithiothreitol; EDCI=1-(3-dimethylamino-propyl)-3-ethylcarbodiimide hydrochloride; EtOAc=Ethyl acetate; EtOH=Ethanol; HATU=N,N,N,N'-Tetramethyl-O-(7-Azabenzotriazol-1-yl)Uronium Hexafluorophosphate; Hex=hexanes; HOBt=1-Hydroxylbenzotriazole; HPLC=High pressure liquid chromatography; LCMS=Liquid chromatography mass spectrometry; LDA=Lithium diisopropylamide; mCPBA=meta-Chloroperoxybenzoic acid; MeOH=Methanol; MTT=(3-[4,5-dimethyl-thiazol-2-yl]-2,5-diphenyltetrazolium bromide, Thiazolyl blue); NMR=Nuclear magnetic resonance; PFP=Pentafluorophenol; PMB=p-methoxybenzyl; Pyr=Pyridine; Rb=Round bottom flask; Rbt=Round bottom flask; RT=Room temperature; SEMCl=2-(Trimethylsily) ethoxy methyl chloride; TEA=Triethylamine; Tr=Triphenyl methane; Trt=Triphenyl methane; TrCl=Triphenyl methane chloride; TFA=Trifluoroacetic acid; THF=Tetrahydrofuran; TLC=Thin layer chromatography; TMS=Trimethylsilyl.

As used herein, unless otherwise specified, the following terms have the following meanings:

"anti-cancer agent" means a drug (medicament or pharmaceutically active ingredient) for treating cancer;

"antineoplastic agent" means a drug (medicament or pharmaceutically active ingredient) for treating cancer (i.e., a chemotherapeutic agent);

"at least one", as used in reference to the number of compounds of this invention means for example 1-6, generally 1-4, more generally 1, 2 or 3, and usually one or two, and more usually one;

"at least one", as used in reference to the number of chemotherapeutic agents used, means for example 1-6, generally 1-4, more generally 1, 2 or 3, and usually one or two, or one;

"chemotherapeutic agent" means a drug (medicament or pharmaceutically active ingredient) for treating cancer (i.e., and antineeoplastic agent);

"compound" with reference to the antineoplastic agents, includes the agents that are antibodies;

"concurrently" means (1) simultaneously in time (e.g., at the same time); or (2) at different times during the course of a common treatment schedule;

"consecutively" means one following the other;

"different" as used in the phrase "different antineoplastic agents" means that the agents are not the same compound or structure; preferably, "different" as used in the phrase "different antineoplastic agents" means not from the same class of antineoplastic agents; for example, one antineoplastic agent is a taxane, and another antineoplastic agent is a platinum coordinator compound;

"effective amount" or "therapeutically effective amount" is meant to describe an amount of compound or a composition of the present invention, or an amount of radiation, effective in treating or inhibiting the diseases or conditions described herein, and thus producing the desired therapeutic, ameliorative, inhibitory or preventative effect; thus, for example, in the methods of treating cancer described herein "effective amount" (or "therapeutically effective amount") means, for example, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor; for example, in the treatment of lung cancer (e.g., non small cell lung cancer) a therapeutically effective amount is that amount that alleviates or eliminates cough, shortness of breath and/or pain; also, for example, an effective amount, or a therapeutically effective amount of the ERK inhibitor (i.e., a compound of this invention) is that amount which results in the reduction in ERK (ERK1 and/or ERK2) activity and phosphorylation; the reduction in ERK activity may be determined by the analysis of pharmacodynamic markers such as phosphorylated RSK1,2 and phosphorylated ERK1,2, using techniques well known in the art;

"Ex" in the tables represents "Example";

"one or more" has the same meaning as "at least one";

"patient" means an animal, such as a mammal (e.g., a human being, and preferably a human being);

"prodrug" means compounds that are rapidly transformed, for example, by hydrolysis in blood, in vivo to the parent compound, i.e., to the compounds of Formula I or to a salt and/or to a solvate thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes Prodrugs of the novel compounds of this invention;

sequentially-represents (1) administration of one component of the method ((a) compound of the invention, or (b) chemotherapeutic agent, signal transduction inhibitor and/or radiation therapy) followed by administration of the other component or components; after administration of one component, the next component can be administered substantially immediately after the first component, or the next component can be administered after an effective time period after the first component; the effective time period is the amount of time given for realization of maximum benefit from the administration of the first component; and "solvate" means a physical association of a compound of this invention with one or more solvent molecules; this physical association involves varying degrees of ionic and covalent bonding, including hydrogen bonding; in certain instances the solvate will be capable of isolation, for example when one or more solvent molecules are incorporated in the crystal lattice of the crystalline solid; "solvate" encompasses both solution-phase and isolatable solvates; non-limiting examples of suitable solvates include ethanolates, methanolates, and the like; "hydrate" is a solvate wherein the solvent molecule is $H_2O$.

As used herein, unless otherwise specified, the following terms have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl, and the like):

"acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as defined below (and as defined below, the alkyl, alkenyl, alkynyl, cycloalkyl, cycloalkenyl and cycloalkynyl moieties can be substituted); the bond to the parent moiety is through the carbonyl; preferred acyls contain a lower alkyl; Non-limiting examples of suitable acyl groups include formyl, acetyl, propanoyl, 2-methylpropanoyl, butanoyl and cyclohexanoyl;

"alkenyl" means an aliphatic hydrocarbon group (chain) comprising at least one carbon to carbon double bond, wherein the chain can be straight or branched, and wherein said group comprises about 2 to about 15 carbon atoms; Preferred alkenyl groups comprise about 2 to about 12 carbon atoms in the chain; and more preferably about 2 to about 6 carbon atoms in the chain; branched means that one or more lower alkyl groups, such as methyl, ethyl or propyl, or alkenyl groups are attached to a linear alkenyl chain; "lower alkenyl" means an alkenyl group comprising about 2 to about 6 carbon atoms in the chain, and the chain can be straight or branched; the term "substituted alkenyl" means that the alkenyl group is substituted by one or more independently selected substituents, and each substituent is independently selected from the group consisting of: halo, alkyl, aryl, cycloalkyl, cyano, alkoxy and —S(alkyl); non-limiting examples of suitable alkenyl groups include ethenyl, propenyl, n-butenyl, 3-methylbut-2-enyl, n-pentenyl, octenyl and decenyl;

"alkoxy" means alkyl-O— (i.e., the bond to the parent moiety is through the oxygen group);

"alkoxyalkyl" (or alkoxylalkyl) means alkoxy-alkyl- or alkyl-O-alkyl- group (i.e., the bond to the parent moiety is through the alkyl group) wherein the alkyl or alkoxy groups are unsubstituted or substituted as defined above;

"alkoxycarbonyl" means an alkyl-O—CO— group (i.e., the bond to the parent moiety is through the carbonyl) wherein the alkyl group is unsubstituted or substituted as previously defined; non-limiting examples of suitable alkoxycarbonyl groups include methoxycarbonyl and ethoxycarbonyl;

"alkyl" (including the alkyl portions of other moieties, such as trifluoroalkyl and alkyloxy) means an aliphatic hydrocarbon group (chain) that can be straight or branched wherein said group comprises about 1 to about 20 carbon atoms in the chain; preferred alkyl groups comprise about 1 to about 12 carbon atoms in the chain; more preferred alkyl groups comprise about 1 to about 6 carbon atoms in the chain; branched means that one or more lower alkyl groups, such as methyl, ethyl or propyl, are attached to a linear alkyl chain; "lower alkyl" means a group comprising about 1 to about 6 carbon atoms in the chain, and said chain can be straight or branched; the term "substituted alkyl" means that the alkyl group is substituted by one or more independently selected substituents, and wherein each substituent is independently selected from the group consisting of: halo, aryl, cycloalkyl, cyano, hydroxy, alkoxy, alkylthio, amino, —NH(alkyl), —NH(cycloalkyl), —N(alkyl)$_2$, carboxy, —C(O)O-alkyl and —S(alkyl); non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl;

"alkylaryl" (or alkaryl) means an alkyl-aryl- group (i.e., the bond to the parent moiety is through the aryl group) wherein the alkyl group is unsubstituted or substituted as defined above, and the aryl group is unsubstituted or substituted as defined below; preferred alkylaryls comprise a lower alkyl group; non-limiting examples of suitable alkylaryl groups include o-tolyl, p-tolyl and xylyl;

"alkylheteroaryl" means an alkyl-heteroaryl- group (i.e., the bond to the parent moiety is through the heteroaryl group) wherein the alkyl is unsubstituted or substituted as defined above and the heteroaryl group is unsubstituted or substituted as defined below;

"alkylsulfinyl" means an alkyl-S(O)— group (i.e., the bond to the parent moiety is through the sulfinyl) wherein the alkyl group is unsubstituted or substituted as previously defined; preferred groups are those in which the alkyl group is lower alkyl;

"alkylsulfonyl" means an alkyl-S(O$_2$)— group (i.e., the bond to the parent moiety is through the sulfonyl) wherein the alkyl group is unsubstituted or substituted as previously defined; preferred groups are those in which the alkyl group is lower alkyl;

"alkylthio" means an alkyl-S— group (i.e., the bond to the parent moiety is through the sulfur) wherein the alkyl group is unsubstituted or substituted as previously described; non-limiting examples of suitable alkylthio groups include methylthio, ethylthio, i-propylthio and heptylthio;

"alkynyl" means an aliphatic hydrocarbon group (chain) comprising at least one carbon to carbon triple bond, wherein the chain can be straight or branched, and wherein the group comprises about 2 to about 15 carbon atoms in the; preferred alkynyl groups comprise about 2 to about 12 carbon atoms in the chain; and more preferably about 2 to about 4 carbon atoms in the chain; Branched means that one or more lower alkyl groups, such as methyl, ethyl or propyl, are attached to a linear alkynyl chain; "lower alkynyl" means an alkynyl group comprising about 2 to about 6 carbon atoms in the chain, and the chain can be straight or branched; non-limiting examples of suitable alkynyl groups include ethynyl, propynyl, 2-butynyl, 3-methylbutynyl, n-pentynyl, and decynyl; the term "substituted alkynyl" means that the alkynyl group is substituted by one or more independently selected, and each substituent is independently selected from the group consisting of alkyl; aryl and cycloalkyl;

"amino means a —NH$_2$ group;

"aralkenyl" (or arylalkenyl) means an aryl-alkenyl- group (i.e., the bond to the parent moiety is through the alkenyl group) wherein the aryl group is unsubstituted or substituted as defined below, and the alkenyl group is unsubstituted or substituted as defined above; preferred aralkenyls contain a lower alkenyl group; non-limiting examples of suitable aralkenyl groups include 2-phenethenyl and 2-naphthylethenyl;

"aralkyloxy" (or arylalkyloxy) means an aralkyl-O— group (i.e., the bond to the parent moiety is through the ether oxygen) wherein the aralkyl group is unsubstituted or substituted as previously described; non-limiting examples of suitable aralkyloxy groups include benzyloxy and 1- or 2-naphthalenemethoxy;

"aralkoxycarbonyl" means an aralkyl-O—C(O)— group (i.e., the bond to the parent moiety is through the carbonyl) wherein the aralkyl group is unsubstituted or substituted as previously defined; a non-limiting example of a suitable aralkoxycarbonyl group is benzyloxycarbonyl;

"aralkylthio" means an aralkyl-S— group (i.e., the bond to the parent moiety is through the sulfur) wherein the aralkyl group is unsubstituted or substituted as previously described; a non-limiting example of a suitable aralkylthio group is benzylthio;

"aralkyl" (or arylalkyl) means an aryl-alkyl- group (i.e., the bond to the parent moiety is through the alkyl group) wherein the aryl is unsubstituted or substituted as defined below and the alkyl is unsubstituted or substituted as defined above; preferred aralkyls comprise a lower alkyl group; non-limiting examples of suitable aralkyl groups include benzyl, 2-phenethyl and naphthalenylmethyl;

"aroyl" means an aryl-C(O)— group (i.e., the bond to the parent moiety is through the carbonyl) wherein the aryl group is unsubstituted or substituted as defined below; non-limiting examples of suitable groups include benzoyl and 1- and 2-naphthoyl;

"aryl" (sometimes abbreviated "ar") means an aromatic monocyclic or multicyclic ring system comprising about 6 to about 14 carbon atoms, preferably about 6 to about 10 carbon atoms; the aryl group can be optionally substituted with one or more independently selected "ring system substituents" (defined below). Non-limiting examples of suitable aryl groups include phenyl and naphthyl;

"arylalkynyl" means an aryl-alkynyl- group (i.e., the bond to the parent moiety is through the alkynyl group) wherein the aryl group is unsubstituted or substituted as defined above, and the alkynyl group is unsubstituted or substituted as defined above;

"arylaminoheteroaryl" means an aryl-amino-heteroaryl group (i.e., the bond to the parent moiety is through the heteroaryl group) wherein the aryl group is unsubstituted or substituted as defined above, the amino group is as defined above (i.e., a —NH— here), and the heteroaryl group is unsubstituted or substituted as defined below;

"arylheteroaryl" means an aryl-heteroarylgroup- (i.e., the bond to the parent moiety is through the heteroaryl group) wherein the aryl group is unsubstituted or substituted as defined above, and the heteroaryl group is unsubstituted or substituted as defined below;

"aryloxy" means an aryl-O— group (i.e., the bond to the parent moiety is through the ether oxygen) wherein the aryl group is unsubstituted or substituted as defined above; non-limiting examples of suitable aryloxy groups include phenoxy and naphthoxy;

"aryloxycarbonyl" means an aryl-O—C(O)— group (i.e., the bond to the parent moiety is through the carbonyl) wherein the aryl group is unsubstituted or substituted as previously defined; non-limiting examples of suitable aryloxycarbonyl groups include phenoxycarbonyl and naphthoxycarbonyl;

"arylsulfinyl" means an aryl-S(O)— group (i.e., the bond to the parent moiety is through the sulfonyl) wherein aryl is unsubstituted or substituted as previously defined;

"arylsulfonyl" means an aryl-S($O_2$)— group (i.e., the bond to the parent moiety is through the sulfonyl) wherein aryl is unsubstituted or substituted as previously defined;

"arylthio" means an aryl-S— group (i.e., the bond to the parent moiety is through the sulfur) wherein the aryl group is unsubstituted or substituted as previously described; non-limiting examples of suitable arylthio groups include phenylthio and naphthylthio;

"carboxyl" (or carboxy) means —$CO_2H$;

"cyano" means NC— or CN— (i.e., the bond to the parent moiety is through the carbon group);

"cycloalkyl" means a non-aromatic mono- or multicyclic ring system comprising about 3 to about 7 carbon atoms, preferably about 3 to about 6 carbon atoms; the cycloalkyl can be optionally substituted with one or more independently selected "ring system substituents" (defined below); non-limiting examples of suitable monocyclic cycloalkyls include cyclopropyl, cyclopentyl, cyclohexyl, cycloheptyl and the like; non-limiting examples of suitable multicyclic cycloalkyls include 1-decalin, norbornyl, adamantyl and the like;

"cycloalkenyl" means a non-aromatic mono or multicyclic ring system comprising about 3 to about 10 carbon atoms, preferably about 5 to about 10 carbon atoms that contains at least one carbon-carbon double bond; preferred cycloalkenyl rings contain about 5 to about 7 ring atoms; the cycloalkenyl can be optionally substituted with one or more independently selected "ring system substituents" (defined below); Non-limiting examples of suitable monocyclic cycloalkenyls include cyclopentenyl, cyclohexenyl, cycloheptenyl, and the like; a non-limiting example of a suitable multicyclic cycloalkenyl is norbornylenyl;

"cycloalkylalkyl" means a cycloalkyl-alkyl-group (i.e., the bond to the parent moiety is through the alkyl group) wherein the cycloalkyl moiety is unsubstituted or substituted as defined above, and the alkyl moiety is unsubstituted or substituted as defined above;

"halo" means fluoro, chloro, bromo, or iodo groups; preferred halos are fluoro, chloro or bromo, and more preferred are fluoro and chloro;

"halogen" means fluorine, chlorine, bromine, or iodine; preferred halogens are fluorine, chlorine and bromine;

"haloalkoxy" means an alkoxy group, wherein one or more hydrogen atoms on the alkyl is replaced by a halo group, as defined above;

"haloalkyl" means an alkyl, as defined above, wherein one or more hydrogen atoms on the alkyl is replaced by a halo group, as defined above;

"haloalkoxy" means haloalkyl-O— (i.e., the bond to the parent moiety is through the oxygen group) wherein halolalkyl- is defined below;

"heteroaralkenyl" means a heteroaryl-alkenyl- group (i.e., the bond to the parent moiety is through the alkenyl group) wherein the heteroaryl group is unsubstituted or substituted as defined below, and the alkenyl group is unsubstituted or substituted as defined above;

"heteroaralkyl" (or heteroarylalkyl) means a heteroaryl-alkyl- group (i.e., the bond to the parent moiety is through the alkyl group) in which the heteroaryl is unsubstituted or substituted as defined below, and the alkyl group is unsubstituted or substituted as defined above; preferred heteroaralkyls comprise an alkyl group that is a lower alkyl group; non-limiting examples of suitable aralkyl groups include pyridylmethyl, 2-(furan-3-yl)ethyl and quinolin-3-ylmethyl;

"heteroaralkylthio" means a heteroaralkyl-S— group wherein the heteroaralkyl group is unsubstituted or substituted as defined above;

"heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; preferred heteroaryls comprise about 5 to about 6 ring atoms; the "heteroaryl" can be optionally substituted by one or more independently selected "ring system substituents" (defined below); the prefix aza, oxa or thia before the heteroaryl root name means that at least a nitrogen, oxygen or sulfur atom, respectively, is present as a ring atom; a nitrogen atom of a heteroaryl can be optionally oxidized to the corresponding N-oxide; non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine and the like;

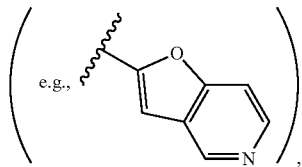

"heteroarylalkynyl" (or heteroaralkynyl) means a heteroaryl-alkynyl- group (i.e., the bond to the parent moiety is through the alkynyl group) wherein the heteroaryl group is unsubstituted or substituted as defined above, and the alkynyl group is unsubstituted or substituted as defined above;

"heteroarylaryl" (or heteroararyl) means a heteroaryl-aryl- group (i.e., the bond to the parent moiety is through the aryl group) wherein the heteroaryl group is unsubstituted or substituted as defined above, and the aryl group is unsubstituted or substituted as defined above;

"heteroarylheteroarylaryl" means a heteroaryl-heteroaryl- group (i.e., the bond to the parent moiety is through the last heteroaryl group) wherein each heteroaryl group is independently unsubstituted or substituted as defined above;

"heteroaryloxy" means a heteroaryl-O group wherein the heteroaryl group is unsubstituted or substituted as defined above;

"heteroarylsulfinyl" means a heteroaryl-SO— group wherein the heteroaryl group is unsubstituted or substituted as defined above;

"heteroarylsulfonyl" means a heteroaryl-SO$_2$— group wherein the heteroaryl group is unsubstituted or substituted as defined above;

"heteroarylthio" means a heteroaryl-S— group wherein the heteroaryl group is unsubstituted or substituted as defined above;

"heteroaryl-alkoxy" (or heteroarylalkoxy) means a heteroaryl-alkyl-O— group (i.e., the bond to the parent moiety is through the alkyl group) wherein the heteroaryl group is unsubstituted or substituted as defined above, and the alkyl group is unsubstituted or substituted as defined above;

"heterocyclenyl" (or heterocycloalkenyl) means a non-aromatic monocyclic or multicyclic ring system comprising about 3 to about 10 ring atoms, preferably about 5 to about 10 ring atoms, in which one or more of the atoms in the ring system is an element other than carbon (for example one or more heteroatoms independently selected from the group consisting of nitrogen, oxygen and sulfur atom), and which contains at least one carbon-carbon double bond or carbon-nitrogen double bond; there are no adjacent oxygen and/or sulfur atoms present in the ring system; Preferred heterocyclenyl rings contain about 5 to about 6 ring atoms; the prefix aza, oxa or thia before the heterocyclenyl root name means that at least a nitrogen, oxygen or sulfur atom, respectively, is present as a ring atom; the heterocyclenyl can be optionally substituted by one or more independently selected "Ring system substituents" (defined below); the nitrogen or sulfur atom of the heterocyclenyl can be optionally oxidized to the corresponding N-oxide, S-oxide or S,S-dioxide; non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like; Non-limiting examples of suitable oxaheterocyclenyl groups include 3,4-dihydro-2H-pyran, dihydrofuranyl, fluorodihydrofuranyl, and the like; A non-limiting example of a suitable multicyclic oxaheterocyclenyl group is 7-oxabicyclo[2.2.1]heptenyl;

examples of suitable monocyclic thiaheterocyclenyl rings include dihydrothiophenyl, dihydrothiopyranyl, and the like;

"heterocycloalkylalkyl" (or heterocyclylalkyl) means a heterocycloalkyl-alkyl- or heterocyclyl-alkyl- group (i.e., the bond to the parent moiety is through the alkyl group) wherein the heterocycloalkyl group (i.e., the heterocyclyl group) is unsubstituted or substituted as defined below, and the alkyl group is unsubstituted or substituted as defined above;

"heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination; there are no adjacent oxygen and/or sulfur atoms present in the ring system; preferred heterocyclyls contain about 5 to about 6 ring atoms; the prefix aza, oxa or thia before the heterocyclyl root name means that at least a nitrogen, oxygen or sulfur atom respectively is present as a ring atom; the heterocyclyl can be optionally substituted by one or more independently selected "ring system substituents" (defined below); the nitrogen or sulfur atom of the heterocyclyl can be optionally oxidized to the corresponding N-oxide, S-oxide or S,S-dioxide; non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like;

"heterocyclylarylalkyl" means a heterocyclyl-aryl-alkyl- group (i.e., the bond to the parent moiety is through the alkyl group) wherein the heterocyclyl group (i.e., heterocycloalkyl group) is unsubstituted or substituted as defined below, and the alkyl group is unsubstituted or substituted as defined above;

"hydroxyl" (or hydroxy) means a HO— group (i.e., the bond to the parent moiety is through the oxygen group).

"hydroxyalkyl" means a HO-alkyl- group wherein the alkyl group is substituted or unsubstituted as defined above; preferred hydroxyalkyls comprise a lower alkyl; Non-limiting examples of suitable hydroxyalkyl groups include hydroxymethyl and 2-hydroxyethyl; and "ring system substituent" means a substituent attached to an aromatic or non-aromatic ring system that, for example, replaces an available hydrogen on the ring system; ring system substituents are each independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfonyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N$—, $R^{60}R^{65}N$-alkyl-, $R^{60}R^{65}NC(O)$— and $R^{60}R^{65}NSO_2$—, wherein $R^{60}$ and $R^{65}$ are each independently selected from the group consisting of: hydrogen, alkyl, aryl, and aralkyl; "Ring system substituent" also means a cyclic ring of 3 to 7 ring atoms, wherein 1-2 ring atoms can be heteroatoms, attached to an aryl, heteroaryl, heterocyclyl or heterocyclenyl ring by simultaneously substituting two ring hydrogen atoms on said aryl, heteroaryl, heterocyclyl or heterocyclenyl ring; Non-limiting examples include:

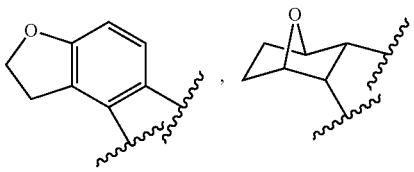 [SMILES: *c1ccc2c(c1*)CCO2 ; *C1C2CCC(O2)C1*]

and the like

Lines drawn into a ring mean that the indicated bond may be attached to any of the substitutable ring carbon atoms.

Any carbon or heteroatom with unsatisfied valences in the text, schemes, examples, structural formulae, and any Tables herein is assumed to have the hydrogen atom or atoms to satisfy the valences.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hem isolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, capsules, pills and the like. Similarly, the herein-described methods of treating a patient by administering a pharmaceutical composition of the present invention is also intended to encompass the administration of the afore-said bulk composition and individual dosage units.

Prodrugs of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of Formula I, or a pharmaceutically acceptable salt, hydrate or solvate of the compound, contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxy-methyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxy-carbonyl)amino) ethyl having from 4 to 10 carbon atoms, 3-phthalidyl, 4-crotonolactonyl, gamma-butyrolacton-4-yl, di-N,N—($C_1$-$C_2$) alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino ($C_2$-$C_3$)alkyl, and the like.

Similarly, if a compound of Formula I contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyl-oxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula I incorporates an amine functional group, a prodrug can be formed by the replacement of a hydrogen atom in the amine group with a group such as, for example, $R^{70}$-carbonyl, $R^{70}$O-carbonyl, $NR^{70}R^{75}$-carbonyl where $R^{70}$ and $R^{75}$ are each independently ($C_1$-$C_{10}$)alkyl, ($C_3$-$C_7$) cycloalkyl, benzyl, or $R^{70}$-carbonyl is a natural α-aminoacyl or natural α-aminoacyl, C(OH)C(O)OY$^{80}$ wherein Y$^{80}$ is H, ($C_1$-$C_6$)alkyl or benzyl, —C(OY$^{82}$)Y$^{84}$ wherein Y$^{82}$ is ($C_1$-$C_4$) alkyl and Y$^{84}$ is ($C_1$-$C_6$)alkyl, carboxy ($C_1$-$C_6$)alkyl, amino($C_1$-$C_4$)alkyl or mono-N— or di-N,N—($C_1$-$C_6$)alkylaminoalkyl, —C(Y$^{86}$)Y$^{88}$ wherein Y$^{86}$ is H or methyl and Y$^{88}$ is mono-N— or di-N,N—($C_1$-$C_6$)alkylamino morpholino, piperidin-1-yl or pyrrolidin-1-yl, and the like.

This invention also includes the compounds of this invention in isolated and purified form.

Polymorphic forms of the compounds of Formula I, and of the salts, solvates and prodrugs of the compounds of Formula I, are intended to be included in the present invention.

Certain compounds of the invention may exist in different isomeric (e.g., enantiomers, diastereoisomers, atropisomers) forms. The invention contemplates all such isomers both in pure form and in admixture, including racemic mixtures. Enol forms are also included.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974

Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

The compounds of Formula I form salts that are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable salts) are preferred. Salts of the compounds of the Formula I may be formed, for example, by reacting a compound of Formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Ina Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, as an amide or imino ether). All such tautomeric forms are contemplated herein as part of the present invention.

In hetero-atom containing ring systems of this invention, there are no hydroxyl groups on carbon atoms adjacent to a N, O or S, and there are no N or S groups on carbon adjacent to another heteroatom. Thus, for example, in the ring:

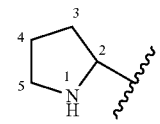

there is no —OH attached directly to carbons marked 2 and 5.

The compounds of Formula I may exist in different tautomeric forms, and all such forms are embraced within the scope of the invention. Also, for example, all keto-enol and imine-enamine forms of the compounds are included in the invention.

Tautomeric forms such as, for example, the moieties:

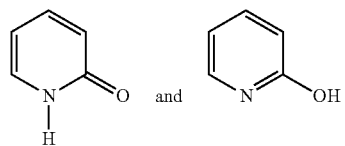 [SMILES: O=c1cccc[nH]1 ; Oc1ccccn1]

are considered equivalent in certain embodiments of this invention.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified faint" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^3$, etc.) occurs more than one time in any moiety or in any compound of Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labelled reagent for a non-isotopically labelled reagent.

General Scheme:

The compounds of this invention can be made according to the processes described below.

Scheme 1: General Synthetic Scheme for Fuse-Piperidinyl Series

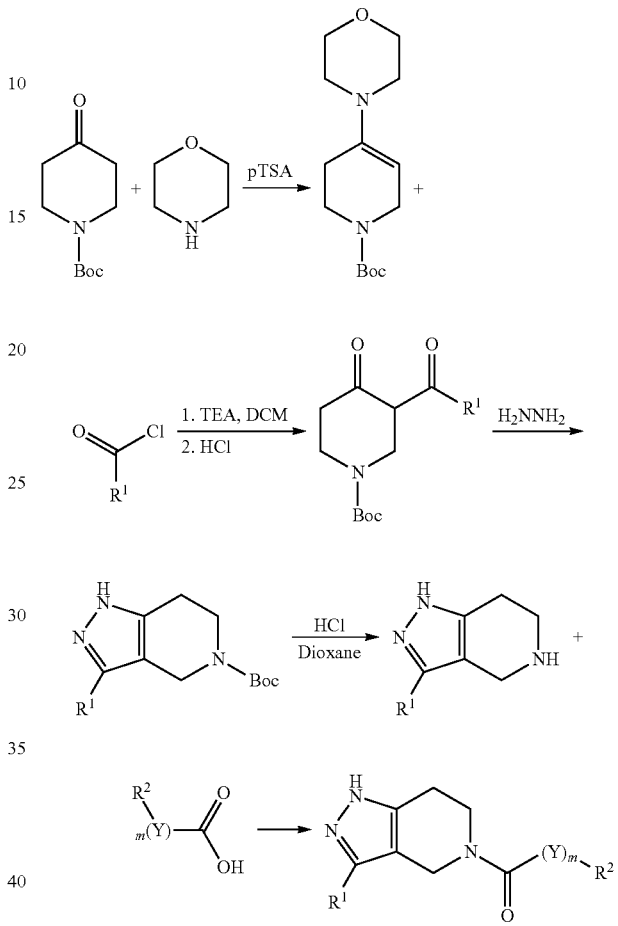

Synthesis of tert-butyl 4-morpholino-5,6-dihydropyridine-1(2H)-carboxylate

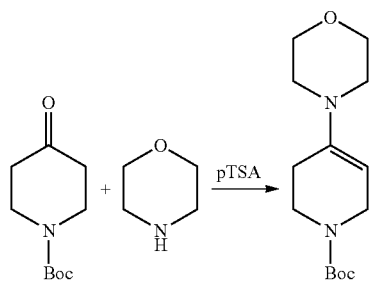

In a round-bottom flask equipped with a Dean-Starke trap, 20 g of tert-butyl 4-oxopiperidine-1-carboxylate, 0.1 mol), morpholine (9.63 mL, 0.11 mol) and p-toluenesulfonic acid (5 mg) in benzene (42.3 mL) was heated up to reflux. Water was removed and the reaction was continued at reflux for 8 hours. The reaction mixture was then cooled to room temperature and concentrated in vacuo to give crude product as a yellow oil (27 g), which was used for next step without further purification.

Synthesis of tert-butyl 3-isonicotinoyl-4-oxopiperidine-1-carboxylate

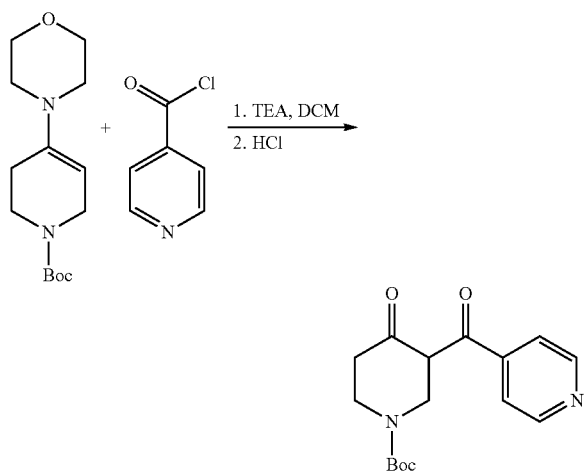

To a solution of tert-butyl 4-morpholino-5,6-dihydropyridine-1(2H)-carboxylate (10 g, 37.3 mmol) and TEA (3.2 ml) in DCM (45 ml) at 0° C., isonicotinoyl chloride (5.78 g, 41 mmol) was added in several portions. The reaction mixture was gradually warmed up to room temperature and was left stirring for overnight.

The reaction mixture was cooled to 0° C. and 1N HCl was added to adjust pH to be around 1. The reaction mixture was then stirred at room temperature for 2 hours. The organic layer was collected and was concentrated to give the desired product, which was used directly in the next step without further purification. LC-MS found 305.14 (M+H)

Synthesis of tert-butyl 3-(pyridin-4-yl)-6,7-dihydro-1H-pyrazolo[4,3-c]pyridine-5(4H)-carboxylate

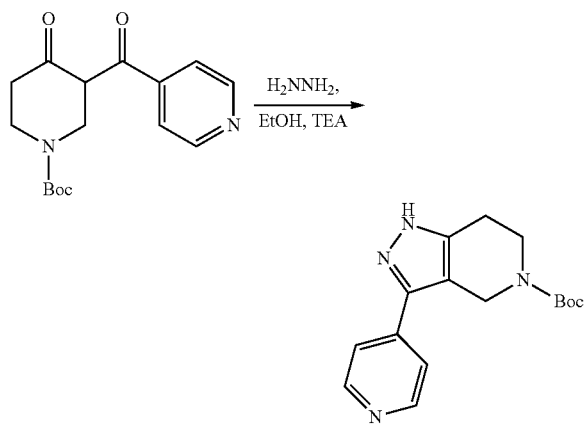

To a mixture of tert-butyl 3-isonicotinoyl-4-oxopiperidine-1-carboxylate (7.4 g, 24.3 mmol) and TEA (10.15 ml) in ethanol was added hydrazine (3.65 ml, 73 mmol). The reaction mixture was stirred at room temperature for overnight. The solvent was removed under vacuum and DCM (50 ml) was added, followed by water (50 ml). The organic layer was collected, washed with brine and dried over sodium sulfate. Removal of solvent gave the desired product (7 g). LC-MS found 301.2 (M+H)

Synthesis of 3-(pyridin-4-yl)-4,5,6,7-tetrahydro-1H-pyrazolo[4,3-c]pyridine hydrochloride

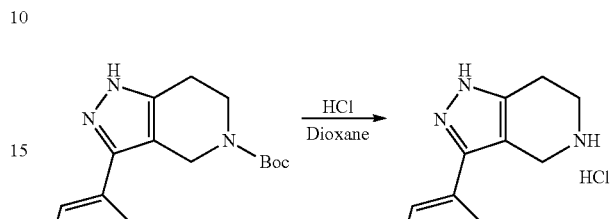

To tert-butyl 3-(pyridin-4-yl)-6,7-dihydro-1H-pyrazolo[4,3-c]pyridine-5(4H)-carboxylate (3 g, 10 mmol) in a round-bottom flask was added HCl in dioxane (4 N, 8 ml) and the reaction was stirred at room temperature for overnight. After removal of the solvent, ethyl ether was added and the desired product was obtained by filtration as a light yellow solid (2.2 g). LC-MS found 201 (M+H)

Synthesis of 2-(2-chlorophenyl)-1-(3-(pyridin-4-yl)-6,7-dihydro-1H-pyrazolo pyridin-5(4H)-yl)ethanone

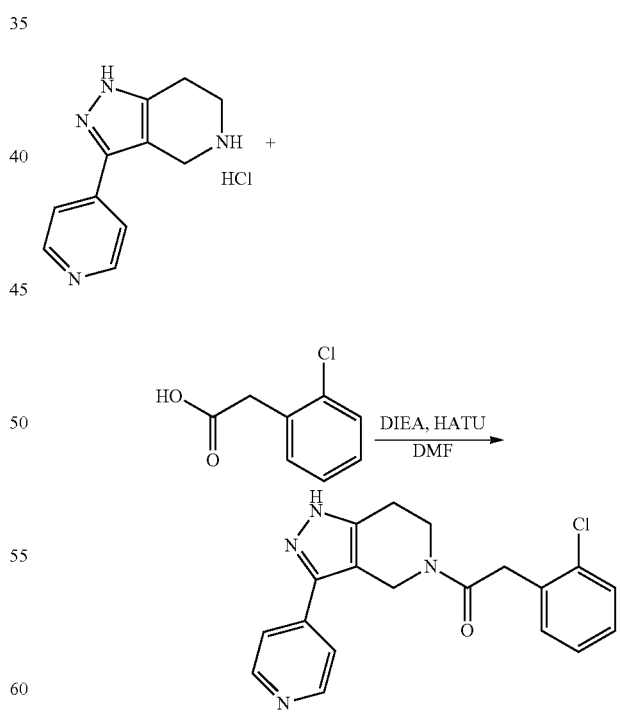

To a mixture of 2-(2-chlorophenyl)acetic acid (34 mg, 0.2 mmol) and DIEA (89 µA, 0.6 mmol) in DMF (1 ml) at 0° C., was added HATU (91 mg, 0.24 mmol). After stirring for 30 min, (3-(pyridin-4-yl)-4,5,6,7-tetrahydro-1H-pyrazolo[4,3-c]pyridine hydrochloride was added. The reaction mixture was warmed to room temperature and continued stirring for 2 hour. Water was added and the reaction mixture was extracted with ethyl acetate (10 ml). The organic component was washed with water (5 ml) and brine (5 ml). After dry over sodium sulfate, solvent was removed under vacuum and the residue was purified using prep-HPLC to give the desired compound as white solid (20 mg). LC-MS found 353.22 (M+H).

The following compounds were prepared using a similar method:

| Cmpd ID No. | Chemical Name | Structure | LC-MS (M + H) |
|---|---|---|---|
| 5 | 5-[(2-amino-4-thiazolyl)-acetyl]-4,5,6,7-tetrahydro-3-(4-pyridinyl)-1H-pyrazolo[4,3-c]pyridine | 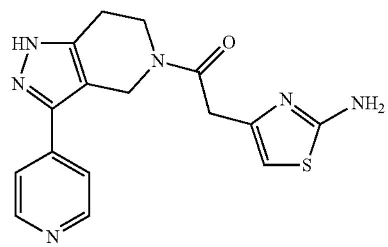 [SMILES: Nc1nc(CC(=O)N2CCc3[nH]nc(-c4ccncc4)c3C2)cs1] | 341.1 found, 341.1 required. |
| 6 | 4,5,6,7-tetrahydro-5-[(1-methyl-1H-imidazol-4-yl)acetyl]-3-(4-pyridinyl)-1H-pyrazolo[4,3-c]pyridine | 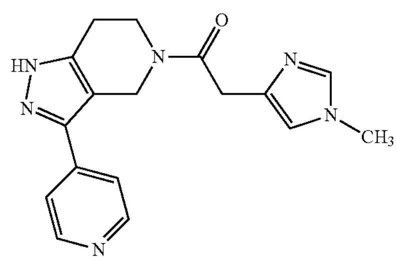 [SMILES: Cn1cnc(CC(=O)N2CCc3[nH]nc(-c4ccncc4)c3C2)c1] | 323.3 found, 323.2 required. |
| 7 | 4,5,6,7-tetrahydro-3-(4-pyridinyl)-5-(2-thienylacetyl)-1H-pyrazolo[4,3-c]pyridine | 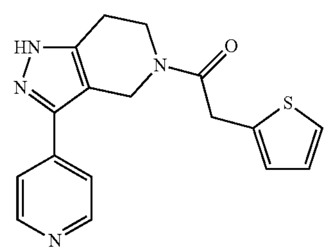 [SMILES: O=C(Cc1cccs1)N1CCc2[nH]nc(-c3ccncc3)c2C1] | 325.2 found, 325.1 required. |
| 8 | 5-[(2-chlorophenyl)acetyl]-4,5,6,7-tetrahydro-3-(4-pyridinyl)-1H-pyrazolo[4,3-c]pyridine | 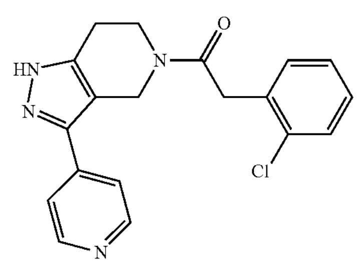 [SMILES: O=C(Cc1ccccc1Cl)N1CCc2[nH]nc(-c3ccncc3)c2C1] | 353.2 found, 353.1 required. |
| 9 | 5-[(3-bromophenyl)acetyl]-4,5,6,7-tetrahydro-3-(4-pyridinyl)-1H-pyrazolo[4,3-c]pyridine | 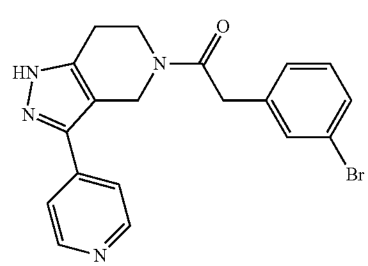 [SMILES: O=C(Cc1cccc(Br)c1)N1CCc2[nH]nc(-c3ccncc3)c2C1] | 397.1 found, 397.1 required. |

-continued

| Cmpd ID No. | Chemical Name | Structure | LC-MS (M + H) |
|---|---|---|---|
| 10 | 4,5,6,7-tetrahydro-5-[(2-methoxyphenyl)acetyl]-3-(4-pyridinyl)-1H-pyrazolo[4,3-c]pyridine | 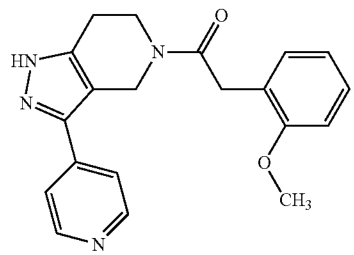 [SMILES: COc1ccccc1CC(=O)N1CCc2[nH]nc(-c3ccncc3)c2C1] | 349.3 found, 349.2 required. |
| 11 | 5-[(2,5-dimethyl-4-thiazolyl)acetyl]-4,5,6,7-tetrahydro-3-(4-pyridinyl)-1H-pyrazolo[4,3-c]pyridine | 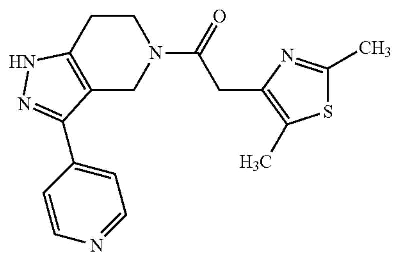 [SMILES: Cc1nc(CC(=O)N2CCc3[nH]nc(-c4ccncc4)c3C2)c(C)s1] | 354.3 found, 354.1 required. |
| 3 | 4,5,6,7-tetrahydro-5-[(3-methoxyphenyl)acetyl]-3-(4-pyridinyl)-1H-pyrazolo[4,3-c]pyridine | 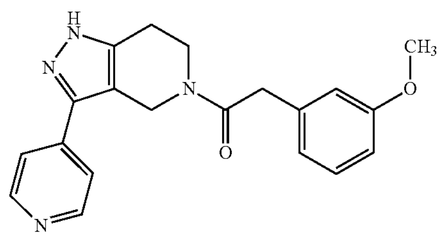 [SMILES: COc1cccc(CC(=O)N2CCc3[nH]nc(-c4ccncc4)c3C2)c1] | 349.3 found, 349.2 required. |
| 22 | 5[[4-(dimethylamino)-phenyl]acetyl]-4,5,6,7-tetrahydro-3-(4-pyridinyl)-1H-pyrazolo[4,3-c]pyridine | 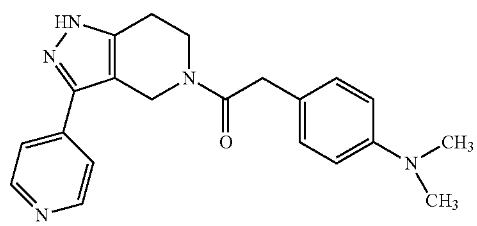 [SMILES: CN(C)c1ccc(CC(=O)N2CCc3[nH]nc(-c4ccncc4)c3C2)cc1] | 362.3 found, 362.2 required. |
| 23 | 5-[(2,5-dimethoxyphenyl)-acetyl]-4,5,6,7-tetrahydro-3-(4-pyridinyl)-1H-pyrazolo[4,3-c]pyridine | 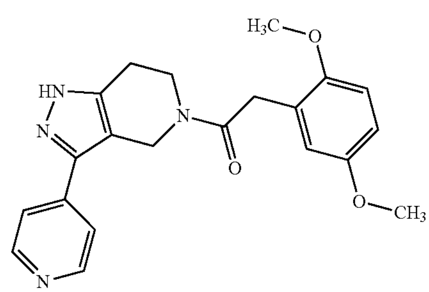 [SMILES: COc1ccc(OC)c(CC(=O)N2CCc3[nH]nc(-c4ccncc4)c3C2)c1] | 379.5 found, 379.2 required. |
| 24 | 5-[(2-fluorophenyl)acetyl]-4,5,6,7-tetrahydro-3-(4-pyridinyl)-1H-pyrazolo[4,3-c]pyridine | 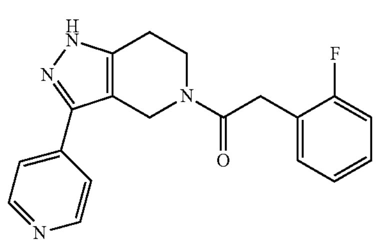 [SMILES: O=C(Cc1ccccc1F)N1CCc2[nH]nc(-c3ccncc3)c2C1] | 337.2 found, 337.1 required. |

-continued

| Cmpd ID No. | Chemical Name | Structure | LC-MS (M + H) |
|---|---|---|---|
| 25 | 4,5,6,7-tetrahydro-3-(4-pyridinyl)-5-(3-pyridinylacetyl)-1H-pyrazolo[4,3-c]pyridine | 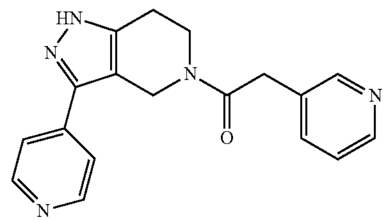 [SMILES: O=C(Cc1cccnc1)N1CCc2[nH]nc(-c3ccncc3)c2C1] | 320.3 found, 320.1 required. |
| 26 | 4,5,6,7-tetrahydro-3-(4-pyridinyl)-5-[[2-(trifluoromethyl)phenyl]-acetyl-1H-pyrazolo[4,3-c]pyridine | 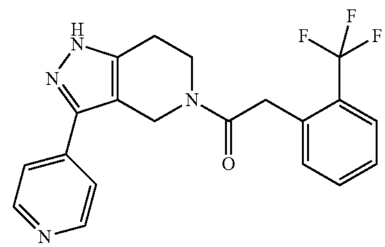 [SMILES: O=C(Cc1ccccc1C(F)(F)F)N1CCc2[nH]nc(-c3ccncc3)c2C1] | 387.2 found, 387.1 required. |
| 27 | 5-[(2-chloro-6-fluorophenyl)acetyl]-4,5,6,7-tetrahydro-3-(4-pyridinyl)-1H-pyrazolo[4,3-c]pyridine | 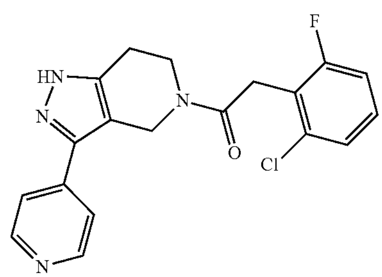 [SMILES: O=C(Cc1c(F)cccc1Cl)N1CCc2[nH]nc(-c3ccncc3)c2C1] | 371.2 found, 371.1 required. |
| 28 | 5-[[1-(2,4-dichlorophenyl)-cylcopropyl]carbonyl]-4,5,6,7-tetrahydro-3-(4-pyridinyl)-1H-pyrazolo[4,3-c]pyridine | 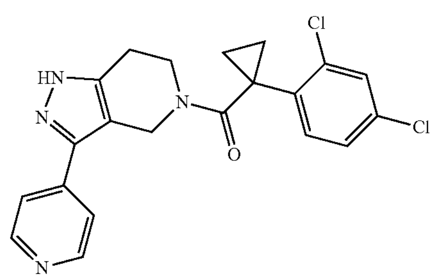 [SMILES: O=C(N1CCc2[nH]nc(-c3ccncc3)c2C1)C1(c2ccc(Cl)cc2Cl)CC1] | 413.1 found, 413.1 required. |
| 29 | 4,5,6,7-tetrahydro-5-[(2-phenoxyphenyl)acetyl]-3-(4-pyridinyl)-1H-pyrazol[4,3-c]pyridine | 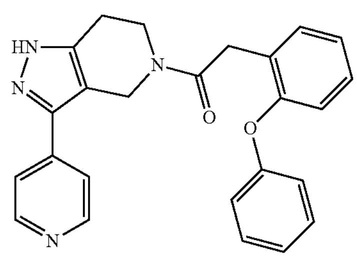 [SMILES: O=C(Cc1ccccc1Oc1ccccc1)N1CCc2[nH]nc(-c3ccncc3)c2C1] | 411.3 found, 411.2 required. |
| 30 | 4,5,6,7-tetrahydro-3-(4-pyridinyl)-5-(2-pyridinylacetyl)-1H-pyrazolo[4,3-c]pyridine | 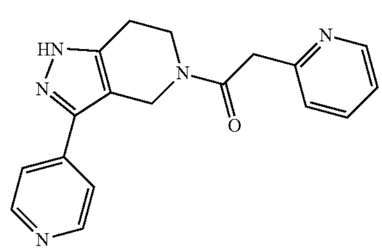 [SMILES: O=C(Cc1ccccn1)N1CCc2[nH]nc(-c3ccncc3)c2C1] | 320.3 found, 320.1 required. |

| Cmpd ID No. | Chemical Name | Structure | LC-MS (M + H) |
|---|---|---|---|
| 31 | 4,5,6,7-tetrahydro-5[[3-(methylsulfonyl)phenyl-[acetyl]-3-(4-pyridinyl)-1H-pyrazolo[4,3-c]pyridine | 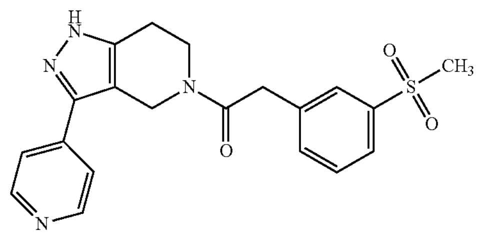 [SMILES: CS(=O)(=O)c1cccc(CC(=O)N2CCc3[nH]nc(-c4ccncc4)c3C2)c1] | 397.2 found, 397.1 required, |
| 32 | 5-([1,1'-biphenyl]-4-ylacetyl)-4,5,6,7-tetrahydro-3-(4-pyridinyl)-1H-pyrazolo[4,3-c]pyridine | 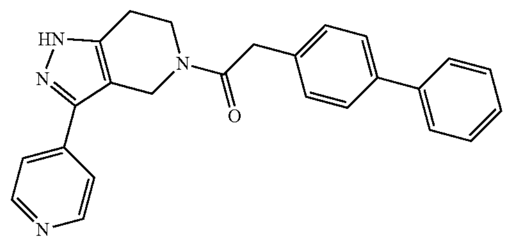 [SMILES: O=C(Cc1ccc(-c2ccccc2)cc1)N1CCc2[nH]nc(-c3ccncc3)c2C1] | 395.2 found, 395.2 required. |
| 33 | 4,5,6,7-tetrahydro-3-(4-pyridinyl)-5-[[2-(3-pyridinyl)phenyl]acetyl]-1H-pyrazolo[4,3-c]pyridine | 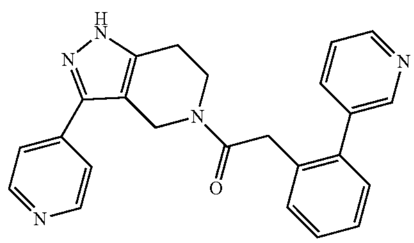 [SMILES: O=C(Cc1ccccc1-c1cccnc1)N1CCc2[nH]nc(-c3ccncc3)c2C1] | 395.4 found, 396.2 required. |
| 34 | 5-[(3-chlorophenyl)acetyl]-4,5,6,7-tetrahydro-3-(4-pyridinyl)-1H-pyrazolo[4,3-c]pyridine | 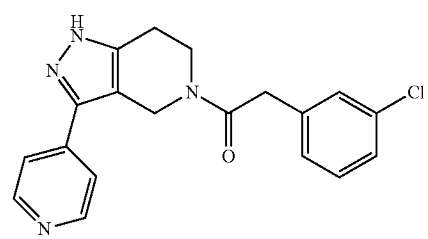 [SMILES: O=C(Cc1cccc(Cl)c1)N1CCc2[nH]nc(-c3ccncc3)c2C1] | 353.2 found, 353.1 required. |
| 35 | 5-([1,1'-biphenyl]-2-ylacetyl)-4,5,6,7-tetrahydro-3-(4-pyridinyl)-1H-pyrazolo[4,3-c]pyridine | 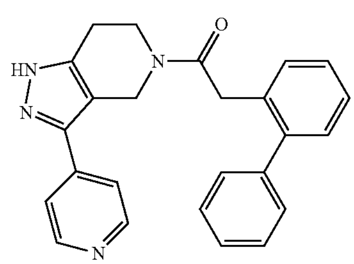 [SMILES: O=C(Cc1ccccc1-c1ccccc1)N1CCc2[nH]nc(-c3ccncc3)c2C1] | 395.1 found, 395.2 required. |
| 36 | 5-[(2-bromophenyl)acetyl]-4,5,6,7-tetrahydro-3-(4-pyridinyl)-1H-pyrazolo[4,3-c]pyridine | 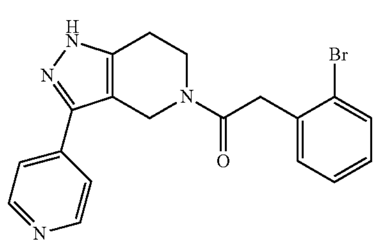 [SMILES: O=C(Cc1ccccc1Br)N1CCc2[nH]nc(-c3ccncc3)c2C1] | 397.1 found, 397.1 required. |

-continued

| Cmpd ID No. | Chemical Name | Structure | LC-MS (M + H) |
|---|---|---|---|
| 37 | 1,4,6,7-tetrahydro-N-(trans-4-phenyl-3-pyrrolidinyl)-3-(4-pyridinyl)-5H-pyrazolo[4,3-c]pyridine-5-carboxamide (racemic) | 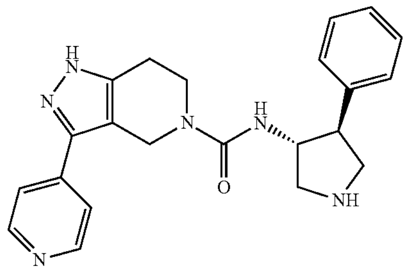 [SMILES: O=C(N[C@H]1CNC[C@@H]1c1ccccc1)N1CCc2[nH]nc(-c3ccncc3)c2C1] | 389.3 found, 389.2 required. |
| 38 | 1,4,6,7-tetrahydro-gamma-oxo-beta-phenyl-3-(4-pyridinyl)-5H-pyrazolo[4,3-c]pyridine-5-propanol | 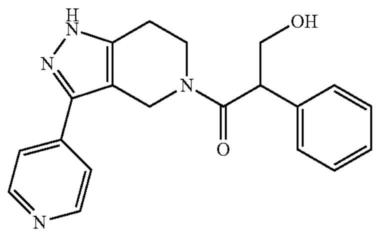 [SMILES: O=C(C(CO)c1ccccc1)N1CCc2[nH]nc(-c3ccncc3)c2C1] | 349.3 found, 349.2 required. |
| 51 | 4,5,6,7-tetrahydro-5-(3-piperidinylacetyl)-3-(4-pyridinyl)-1H-pyrazolo[4,3-c]pyridine | 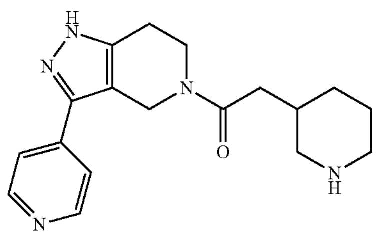 [SMILES: O=C(CC1CCCNC1)N1CCc2[nH]nc(-c3ccncc3)c2C1] | 327.2 found, 326.2 required. |
| 39 | 4,5,6,7-tetrahydro-3-(4-pyridinyl)-5-[(1,2,3,4-tetrahydro-1-naphthalenyl)carbonyl]-1H-pyrazolo[4,3-c]pyridine | 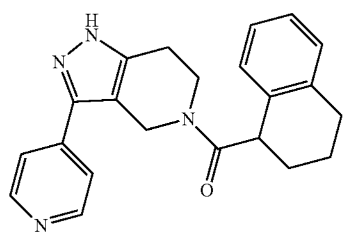 [SMILES: O=C(C1CCCc2ccccc21)N1CCc2[nH]nc(-c3ccncc3)c2C1] | 359.3 found, 359.2 required. |
| 40 | 4,5,6,7-tetrahydro-5-(1-oxo-2-phenylpropyl)-3-(4-pyridinyl)-1H-pyrazolo[4,3-c]pyridine | 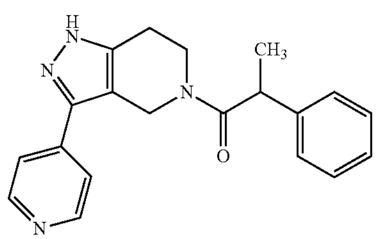 [SMILES: CC(C(=O)N1CCc2[nH]nc(-c3ccncc3)c2C1)c1ccccc1] | 333.3 found, 333.2 required. |
| 41 | 5-[2-(2-chlorophenyl)-1-oxopropyl]-4,5,6,7-tetrahydro-3-(4-pyridinyl)-1H-pyrazolo[4,3-c]pyridine | 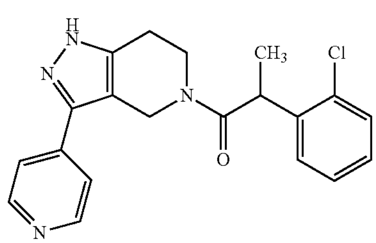 [SMILES: CC(C(=O)N1CCc2[nH]nc(-c3ccncc3)c2C1)c1ccccc1Cl] | 367.2 found, 367.1 required. |

Synthesis of (R)-tert-butyl 3-((prop-1-en-2-yloxy)carbonylamino)piperidine-1-carboxylate

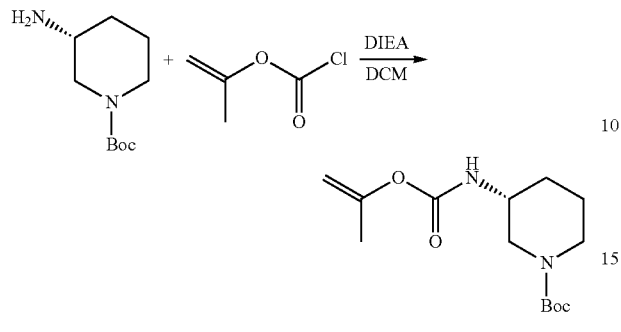

To a solution of (R)-tert-butyl 3-aminopiperidine-1-carboxylate (1 g, 5 mmol) and DIEA (1.76 ml) in DCM (10 ml) at 0° C. was added isopropenyl chloroformate dropwise. After the addition, the reaction mixture was allowed to warm up to room temperature and was stirred for 30 minutes. Saturated sodium bicarbonate solution (10 ml) was added and the organic layer was collected, washed with water and dried over sodium sulfate. After removal of solvent, the crude product (1.8 g) was used directly for the next step reaction.

Synthesis of tert-butyl 3-(3-(pyridin-4-yl)-4,5,6,7-tetrahydro-1H-pyrazolo[4,3-c]pyridine-5-carboxamido)piperidine-1-carboxylate

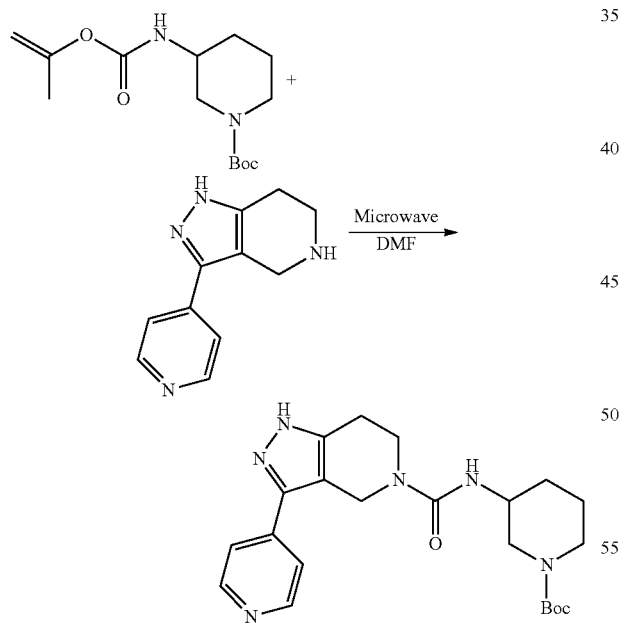

The crude product from previous step was dissolved in DMF (20 ml) and was transferred to a micro-wave tube. To this solution was added DIEA (1.76 ml) and 3-(pyridin-4-yl)-4,5,6,7-tetrahydro-1H-pyrazolo[4,3-c]pyridine hydrochloride (1 g, 4.2 mmol). The micro-wave tube containing the reaction mixture was heated under microwave at 140° C. for 20 minutes. After cooling to room temperature, water (40 ml) was added and the mixture was extracted with ethyl acetate (20 ml×3). The combined organic layer was washed with water (30 ml×2) and brine (20 ml). After the solvent was removed, the residual was purified using a flash column chromatography (10% methanol in DCM) to give 800 mg of titled compound. LC-MS found 427.2 (M+H)

Synthesis of N-(piperidin-3-yl)-3-(pyridin-4-yl)-6,7-dihydro-1H-pyrazolo[4,3-c]pyridine-5(4H)-carboxamide trifluoroacetate salt

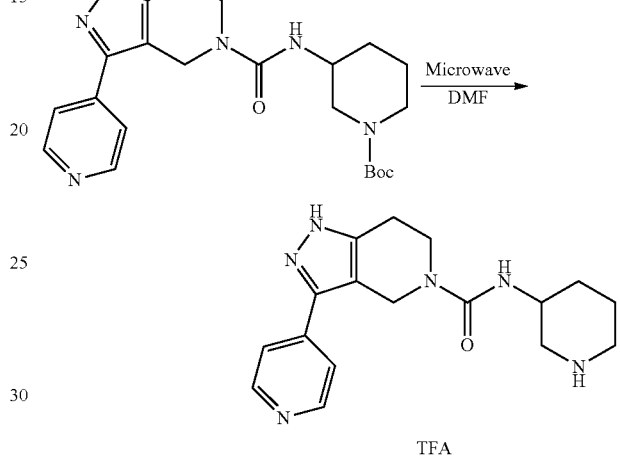

To tert-butyl 3-(3-(pyridin-4-yl)-4,5,6,7-tetrahydro-1H-pyrazolo[4,3-c]pyridine-5-carboxamido)piperidine-1-carboxylate (800 mg, 1.87 mmol) obtained from previous step, was added trifluoroacetic acid (10 ml). After stirring at room temperature for 10 minutes, excess TFA was removed under vacuum. To the residue, ethyl ether was added and precipitate formed. The desired product was collected by filtration as light yellow solid (750 mg). LC-MS found 327.1 (M+H)

Synthesis of N-(1-(2-fluorobenzyl)piperidin-3-yl)-3-(pyridin-4-yl)-6,7-dihydro-1H-pyrazolo[4,3-c]pyridine-5(4H)-carboxamide

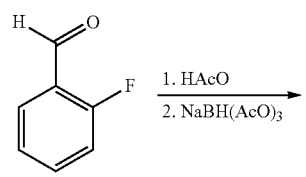

-continued

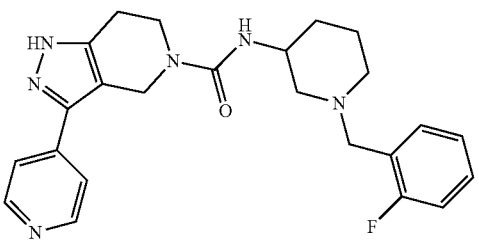

In a flask, dichloromethane (0.295 mL) and acetic acid (2 drops) was added to N-(piperidin-3-yl)-3-(pyridin-4-yl)-6,7-dihydro-1H-pyrazolo[4,3-c]pyridine-5(4H)-carboxamide trifluoroacetate salt (0.021 g, 0.05 mmol) and 2-fluorobenzaldehyde (0.0124 g, 0.1 mmol). The reaction was sonicated for 1 hr. Sodium triacetoxyborohydride (0.050 g, 0.25 mmol) was added in one portion. The reaction was stirred for an additional 16 hours. Saturated sodium bicarbonate (1 mL) was added. The reaction was stirred for an additional 5 minutes and was extracted with dichloromethane (3×1 mL). The extracts were combined, dried with anhydrous sodium sulfate, filtered, and concentrated in vacuo. The resulting crude product was purified by prep LC/MS. LC-MS: 435.68 [M+H]. LC/MS RT=1.82 min.

The following compounds were prepared using a similar method:

| Cmpd ID No | Compound Name | Structure | LC-MS (M + H) |
|---|---|---|---|
| 45 | 1,4,6,7-tetrahydro-3(4-pyridinyl)-N-(2-thiazolyl)-5H-pyrazolo[4,3-c]pyridine-5-carboxamide | 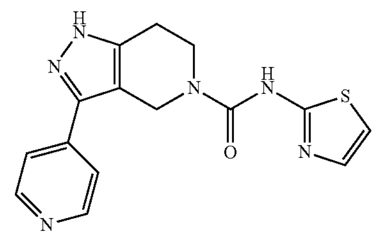 [SMILES: O=C(Nc1nccs1)N1CCc2[nH]nc(-c3ccncc3)c2C1] | 327.1 found, 327.1 required. |
| 46 | 1,4,6,7-tetrahydro-N-[1-methyl-4(R)-(2-methylphenyl)-3(S)-pyrrolidinyl]-3-(4-pyridinyl)-5H-pyrazolo[4,3-c]pyridine-5-carboxamide | 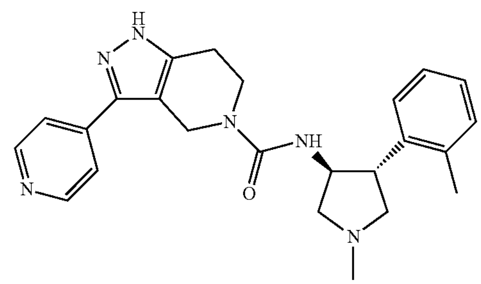 [SMILES: Cc1ccccc1[C@@H]1CN(C)C[C@H]1NC(=O)N1CCc2[nH]nc(-c3ccncc3)c2C1] | 417.7 found, 417.2 required. |
| 47 | 1,4,6,7-tetrahydro-N-(5-phenyl-3-piperidinyl)-3-(4-pyridinyl)-5H-pyrazolo[4,3-c]pyridine-5-carboxamide | 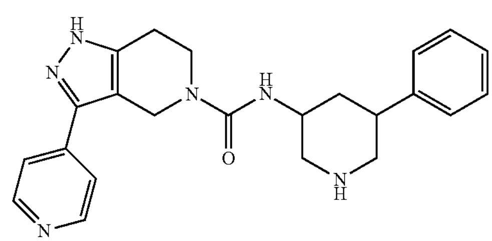 [SMILES: O=C(NC1CNCC(c2ccccc2)C1)N1CCc2[nH]nc(-c3ccncc3)c2C1] | 403.7 found, 403.2 required. |
| 48 | N-[1-[(2-fluorophenyl)methyl]-3(R)-piperidinyl]-1,4,6,7-tetrahydro-3-(4-pyridinyl)-5H-pyrazolo[4,3-c]pyridine-5-carboxamide | 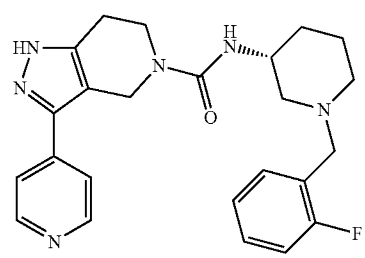 [SMILES: O=C(N[C@@H]1CCCN(Cc2ccccc2F)C1)N1CCc2[nH]nc(-c3ccncc3)c2C1] | 435.7 found, 435.2 required. |

-continued

| Cmpd ID No | Compound Name | Structure | LC-MS (M + H) |
|---|---|---|---|
| 49 | 1,4,6,7-tetrahydro-N-(1-methyl-5-phenyl-3-piperidinyl)-3-(4-pyridinyl)-5H-pyrazolo[4,3-c]pyridine-5-carboxamide | 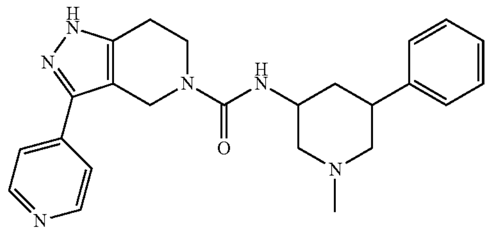 [SMILES: CN1CC(NC(=O)N2CCc3[nH]nc(-c4ccncc4)c3C2)CC(c2ccccc2)C1] | 417.7 found, 417.2 required. |
| 53 | N-[1-[(2-fluoro-6-methoxyphenyl)methyl]-3(R)-piperidinyl]-1,4,6,7-tetrahydro-3-(4-pyridinyl)-5H-pyrazolo[4,3-c]pyridine-5-carboxamide | 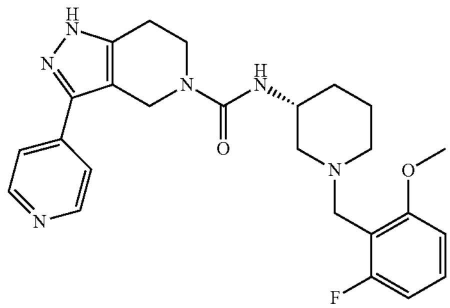 [SMILES: COc1cccc(F)c1CN1CCC[C@@H](NC(=O)N2CCc3[nH]nc(-c4ccncc4)c3C2)C1] | 465.7 found, 465.2 required. |
| 54 | N-[1-[(2,6-difluorophenyl)methyl]-3(R)-piperidinyl]-1,4,6,7-tetrahydro-3-(4-pyridinyl)-5H-pyrazolo[4,3-c]pyridine-5-carboxamide, | 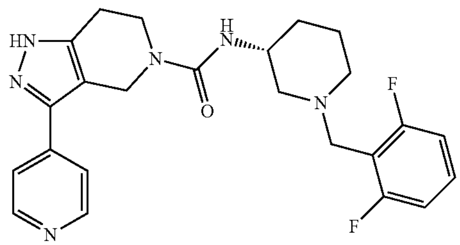 [SMILES: O=C(N[C@@H]1CCCN(Cc2c(F)cccc2F)C1)N1CCc2[nH]nc(-c3ccncc3)c2C1] | 453.7 found, 453.2 required. |
| 55 | 1,4,6,7-tetrahydro-3-(4-pyridinyl)-N-[1-(2-thiazolylmethyl)-3(R)-piperidinyl]-5H-pyrazolo[4,3-c]pyridine-5-carboxamide | 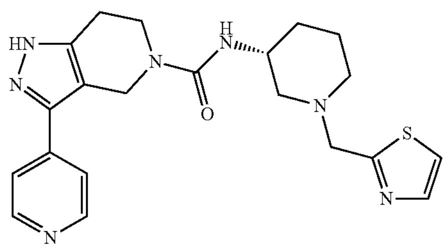 [SMILES: O=C(N[C@@H]1CCCN(Cc2nccs2)C1)N1CCc2[nH]nc(-c3ccncc3)c2C1] | 424.7 found, 424.2 required. |
| 56 | 1,4,6,7-tetrahydro-3-(4-pyridinyl)-N-[1-(3-thienylmethyl)-3(R)-piperidinyl]-5H-pyrazolo[4,3-c]pyridine-5-carboxamide | 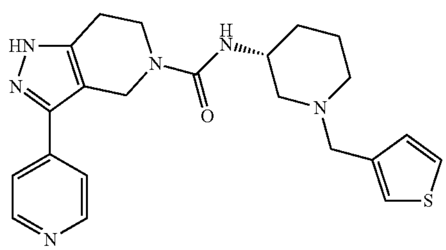 [SMILES: O=C(N[C@@H]1CCCN(Cc2ccsc2)C1)N1CCc2[nH]nc(-c3ccncc3)c2C1] | 423.7 found, 423.2 required. |
| 57 | N-[1-(benzo[b]thien-3-ylmethyl)-3(R)-piperidinyl]-1,4,6,7-tetrahydro-3-(4-pyridinyl)-5H-pyrazolo[4,3-c]pyridine-5-carboxamide | 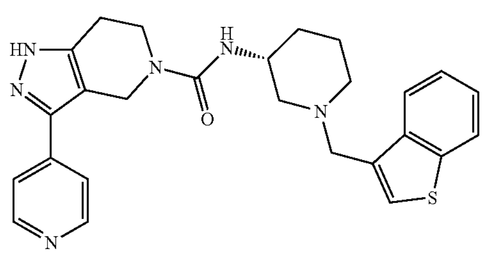 [SMILES: O=C(N[C@@H]1CCCN(Cc2csc3ccccc23)C1)N1CCc2[nH]nc(-c3ccncc3)c2C1] | 473.7 found, 473.2 required. |

-continued

| Cmpd ID No | Compound Name | Structure | LC-MS (M + H) |
|---|---|---|---|
| 58 | 1,4,6,7-tetrahydro-N-[1-[(3-methyl-2-thienyl)methyl]-3(R)-piperidinyl]-3-(4-pyridinyl)-5H-pyrazolo[4,3-c]pyridine-5-carboxamide | 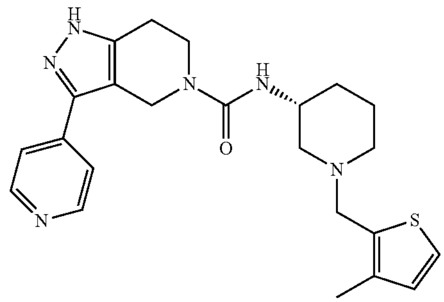 [SMILES: Cc1ccsc1CN1CCC[C@@H](NC(=O)N2CCc3[nH]nc(-c4ccncc4)c3C2)C1] | 437.7 found, 437.2 required. |
| 59 | 1,4,6,7-tetrahydro-N-[1-[(5-methyl-2-thienyl)methyl]-3(R)-piperidinyl]-3-(4-pyridinyl)-5H-pyrazolo[4,3-c]pyridine-5-carboxamide | 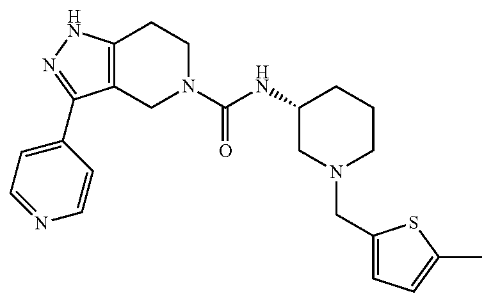 [SMILES: Cc1ccc(CN2CCC[C@@H](NC(=O)N3CCc4[nH]nc(-c5ccncc5)c4C3)C2)s1] | 437.7 found, 437.2 required. |
| 60 | 1,4,6,7-tetrahydro-N-[1-[(1-methyl-1H-indol-3-yl)methyl]-3(R)-piperidinyl]-3-(4-pyridinyl)-5H-pyrazolo[4,3-c]pyridine-5-carboxamide | 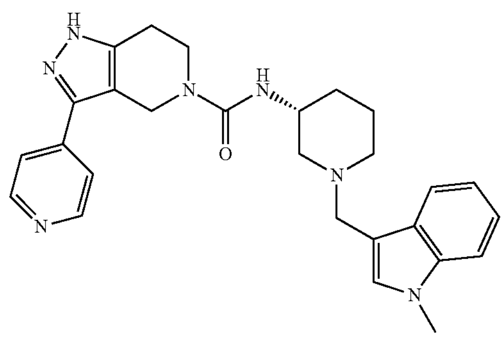 [SMILES: Cn1cc(CN2CCC[C@@H](NC(=O)N3CCc4[nH]nc(-c5ccncc5)c4C3)C2)c2ccccc21] | 470.7 found, 470.3 required. |
| 61 | 1,4,6,7-tetrahydro-N-[1-[(1-methyl-1H-indol-2-yl)methyl]-3(R)-piperidinyl]-3-(4-pyridinyl)-5H-pyrazolo[4,3-c]pyridine-5-carboxamide | 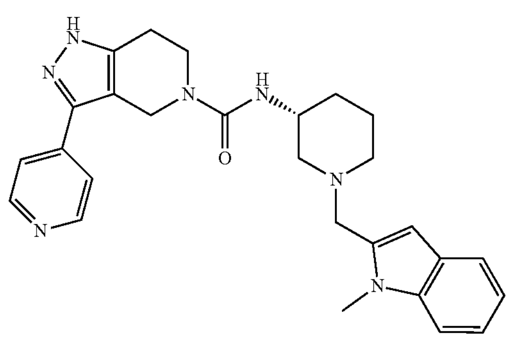 [SMILES: Cn1c(CN2CCC[C@@H](NC(=O)N3CCc4[nH]nc(-c5ccncc5)c4C3)C2)cc2ccccc21] | 470.7 found, 470.3 required. |

-continued

| Cmpd ID No | Compound Name | Structure | LC-MS (M + H) |
|---|---|---|---|
| 62 | N-[1-[(1-acetyl-1H-indol-3-yl)methyl]-3(R)-piperidinyl]-1,4,6,7-tetrahydro-3-(4-pyridinyl)-5H-pyrazolo[4,3-c]pyridine-5-carboxamide | 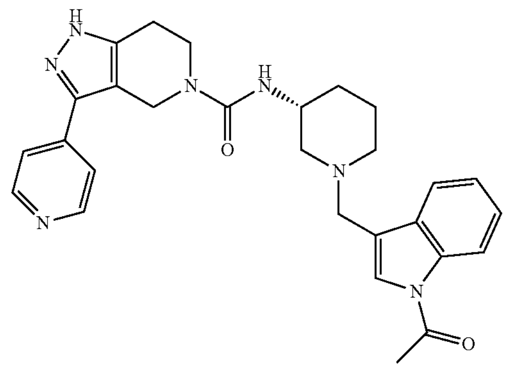 [SMILES: CC(=O)n1cc(CN2CCC[C@@H](NC(=O)N3CCc4[nH]nc(-c5ccncc5)c4C3)C2)c2ccccc21] | 498.8 found, 498.3 required. |
| 63 | 1,4,6,7-tetrahydro-N-[1-(1H-imidazoL-2-ylmethyl)-3(R)-piperidinyl]-3-(4-pyridinyl)-5H-pyrazolo[4,3-c]pyridine-5-carboxamide | 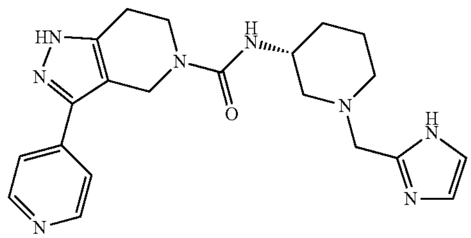 [SMILES: O=C(N[C@@H]1CCCN(Cc2ncc[nH]2)C1)N1CCc2[nH]nc(-c3ccncc3)c2C1] | 407.7 found, 407.2 required. |
| 64 | 1,4,6,7-tetrahydro-N-[1-[(1-methyl-1H-imidazoL-4-yl)methyl]-3(R)-piperidinyl]-3-(4-pyridinyl)-5H-pyrazolo[4,3-c]pyridine-5-carboxamide | 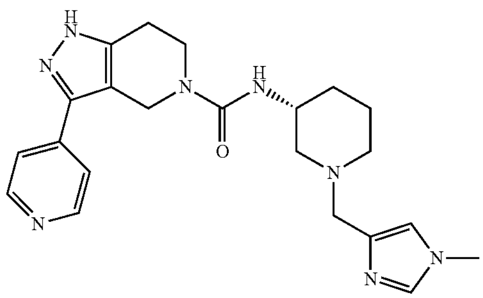 [SMILES: Cn1cnc(CN2CCC[C@@H](NC(=O)N3CCc4[nH]nc(-c5ccncc5)c4C3)C2)c1] | 421.7 found, 421.2 required. |
| 65 | 1,4,6,7-tetrahydro-N-[1-[(1-methyl-1H-pyrazol-3-yl)methyl]-3(R)-piperidinyl]-3-(4-pyridinyl)-5H-pyrazolo[4,3-c]pyridine-5-carboxamide | 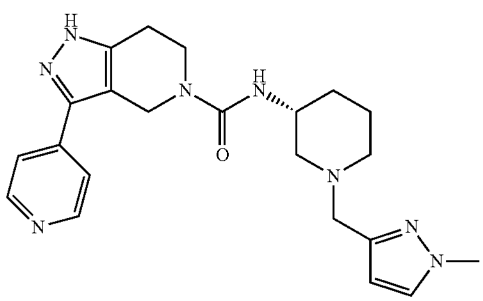 | 421.7 found, 421.2 required. |
| 66 | N-[1-[(2-chloro-6-fluorophenyl)methyl]-3(R)-piperidinyl]-1,4,6,7-tetrahydro-3-(4-pyridinyl)-5H-pyrazolo[4,3-c]pyridine-5-carboxamide | 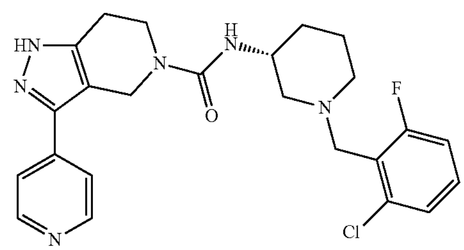 [SMILES: O=C(N[C@@H]1CCCN(Cc2c(F)cccc2Cl)C1)N1CCc2[nH]nc(-c3ccncc3)c2C1] | 469.6 found, 469.2 required. |

| Cmpd ID No | Compound Name | Structure | LC-MS (M + H) |
|---|---|---|---|
| 67 | 1,4,6,7-tetrahydro-3-(4-pyridinyl)-N-[1-[[2-(trifluoromethyl)phenyl]methyl]-3(R)-piperidinyl]-5H-pyrazolo[4,3-c]pyridine-5-carboxamide | 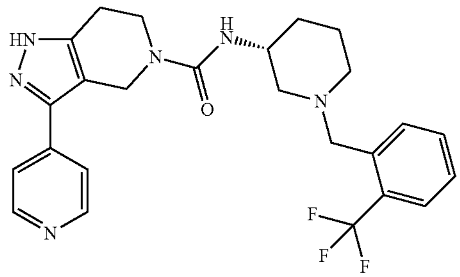 [SMILES: O=C(N[C@@H]1CCCN(Cc2ccccc2C(F)(F)F)C1)N1CCc2[nH]nc(-c3ccncc3)c2C1] | 485.7 found, 485.2 required. |
| 68 | N-[1-[[2-fluoro-6-(trifluoromethyl)phenyl]methyl]-3(R)-piperidinyl]-1,4,6,7-tetrahydro-3-(4-pyridinyl)-5H-pyrazolo[4,3-c]pyridine-5-carboxamide | 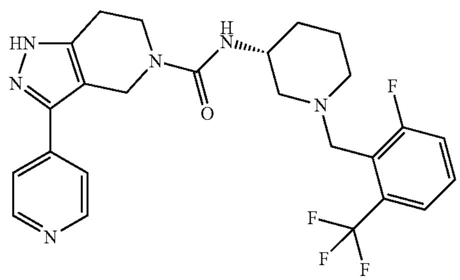 [SMILES: O=C(N[C@@H]1CCCN(Cc2c(F)cccc2C(F)(F)F)C1)N1CCc2[nH]nc(-c3ccncc3)c2C1] | 503.7 found, 503.2 required. |
| 69 | N-[1-[(2-chlorophenyl)methyl]-3(R)-piperidinyl]-1,4,6,7-tetrahydro-3-(4-pyridinyl)-5H-pyrazolo[4,3-c]pyridine-5-carboxamide | 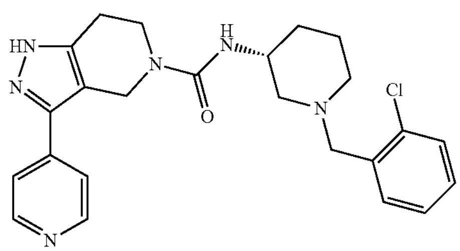 [SMILES: O=C(N[C@@H]1CCCN(Cc2ccccc2Cl)C1)N1CCc2[nH]nc(-c3ccncc3)c2C1] | 451.7 found, 451.2 required. |
| 70 | 1,4,6,7-tetrahydro-N-[1-[(2-methoxyphenyl)methyl]-3(R)-piperidinyl]-3-(4-pyridinyl)-5H-pyrazolo[4,3-c]pyridine-5-carboxamide | 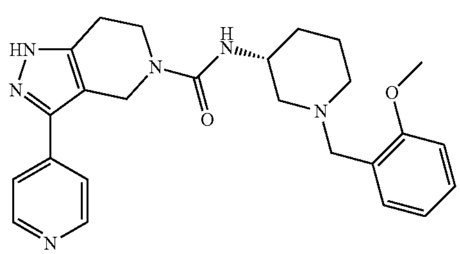 [SMILES: COc1ccccc1CN1CCC[C@@H](NC(=O)N2CCc3[nH]nc(-c4ccncc4)c3C2)C1] | 447.7 found, 447.2 required. |
| 71 | N-[1-[(2,6-dimethylphenyl)methyl]-3(R)-piperidinyl]-1,4,6,7-tetrahydro-3-(4-pyridinyl)-5H-pyrazolo[4,3-c]pyridine-5-carboxamide | 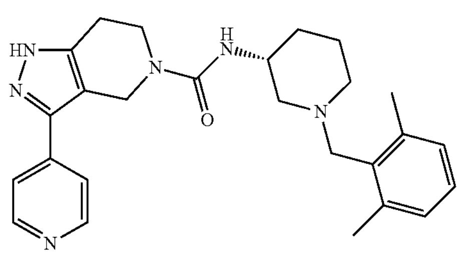 [SMILES: Cc1cccc(C)c1CN1CCC[C@@H](NC(=O)N2CCc3[nH]nc(-c4ccncc4)c3C2)C1] | 445.8 found, 445.3 required. |

| Cmpd ID No | Compound Name | Structure | LC-MS (M + H) |
|---|---|---|---|
| 72 | methyl 2-[[3(R)-[[[1,4,6,7-tetrahydro-3-(4-pyridinyl)-5H-pyrazolo[4,3-c]pyridin-5-yl]carbonyl]amino]-1-piperidinyl]methyl]benzoate | 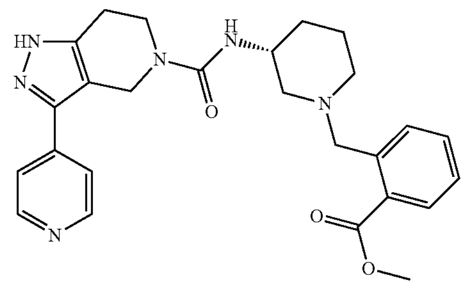 [SMILES: COC(=O)c1ccccc1CN1CCC[C@@H](NC(=O)N2CCc3[nH]nc(-c4ccncc4)c3C2)C1] | 475.7 found, 475.2 required. |
| 73 | N-[1-[(2,6-dimethoxyphenylmethyl]-3(R)-piperidinyl]-1,4,6,7-tetrahydro-3-(4-pyridinyl)-5H-pyrazolo[4,3-c]pyridine-5-carboxamide | 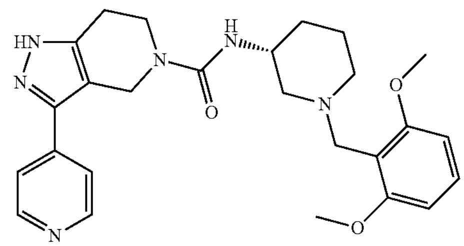 [SMILES: COc1cccc(OC)c1CN1CCC[C@@H](NC(=O)N2CCc3[nH]nc(-c4ccncc4)c3C2)C1] | 477.8 found, 477.3 required. |
| 74 | 1,4,6,7-tetrahydro-N-[1-[[2-(4-morpholinyl)phenyl]methyl]-3(R)-piperidinyl]-3-(4-pyridinyl)-5H-pyrazolo[4,3-c]pyridine-5-carboxamide | 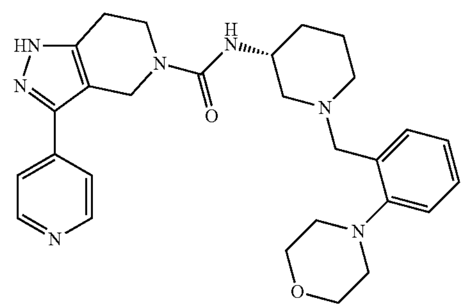 [SMILES: O=C(N[C@@H]1CCCN(Cc2ccccc2N2CCOCC2)C1)N1CCc2[nH]nc(-c3ccncc3)c2C1] | 502.7 found, 502.3 required. |
| 75 | 1,4,6,7-tetrahydro-N-[1-[(3-methyl-5-phenyl-4-isoxazolyl)methyl]-3(R)-piperidinyl]-3-(4-pyridinyl)-5H-pyrazolo[4,3-c]pyridine-5-carboxamide | 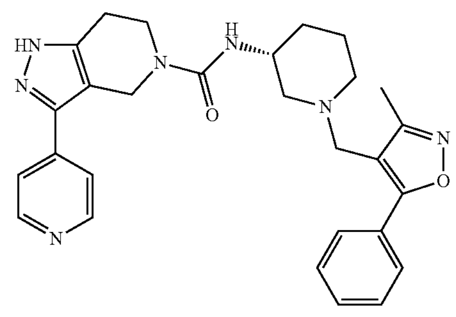 [SMILES: Cc1noc(-c2ccccc2)c1CN1CCC[C@@H](NC(=O)N2CCc3[nH]nc(-c4ccncc4)c3C2)C1] | 498.7 found, 498.3 required. |
| 76 | 1,4,6,7-tetrahydro-N-[1-[(5-methyl-3-phenyl-4-isoxazolyl)methyl]-3(R)-piperidinyl]-3-(4-pyridinyl)-5H-pyrazolo[4,3-c]pyridine-5-carboxamide | 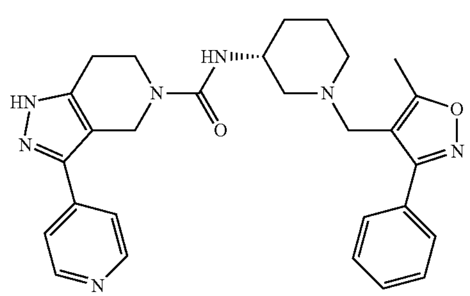 [SMILES: Cc1onc(-c2ccccc2)c1CN1CCC[C@@H](NC(=O)N2CCc3[nH]nc(-c4ccncc4)c3C2)C1] | 498.7 found, 498.3 required. |

| Cmpd ID No | Compound Name | Structure | LC-MS (M + H) |
|---|---|---|---|
| 42 | N-(4-chloro-1-ethyl-1H-pyrazol-3-yl)-1,4,6,7-tetrahydro-3-(4-pyridinyl)-5H-pyrazolo[4,3-c]pyridine-5-carboxamide | 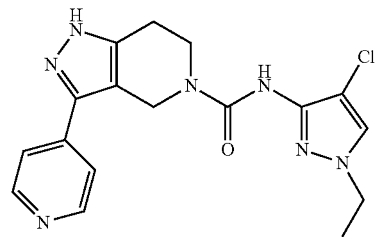 [SMILES: CCn1cc(Cl)c(NC(=O)N2CCc3[nH]nc(-c4ccncc4)c3C2)n1] | 372.2 found, 372.1 required. |
| 81 | N-[1-[(2,6-difluorophenyl)methyl]-3(R)-piperidinyl]-1,4,6,7-tetrahydro-3-(2-methyl-4-pyridinyl)-5H-pyrazolo[4,3-c]pyridine-5-carboxamide | 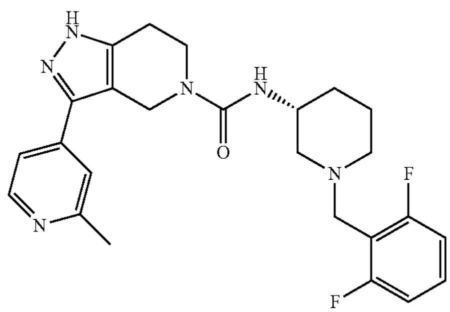 [SMILES: Cc1cc(-c2n[nH]c3c2CN(C(=O)N[C@@H]2CCCN(Cc4c(F)cccc4F)C2)CC3)ccn1] | 467.1 found, 467.2 required. |
| 82 | methyl 1-[(2,6-difluorophenyl)methyl]-5-[[[1,4,6,7-tetrahydro-3-(2-methyl-4-pyridinyl)-5H-pyrazolo[4,3-c]pyridin-5-yl]carbonyl]amino]-3-piperidinecarboxylate | 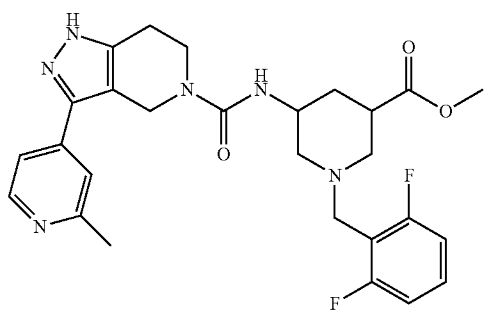 [SMILES: COC(=O)C1CC(NC(=O)N2CCc3[nH]nc(-c4ccnc(C)c4)c3C2)CN(Cc2c(F)cccc2F)C1] | 525.2 found, 525.2 required. |
| 83 | 1-[(2,6-difluorophenyl)methyl]-5-[[[1,4,6,7-tetrahydro-3-(2-methyl-4-pyridinyl)-5H-pyrazolo[4,3-c]pyridin-5-yl]carbonyl]amino]-3-piperidinecarboxylic acid | 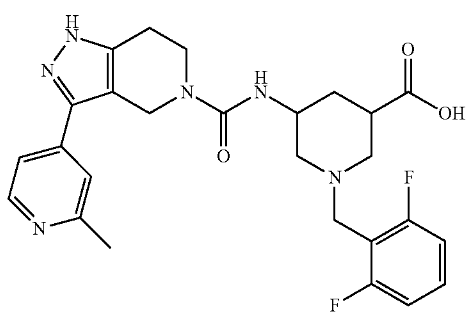 [SMILES: Cc1cc(-c2n[nH]c3c2CN(C(=O)NC2CC(C(=O)O)CN(Cc4c(F)cccc4F)C2)CC3)ccn1] | 551.2 found, 551.1 required. |
| 84 | N-[1-[(2,6-dimethylphenyl)methyl]-3-piperidinyl]-1,4,6,7-tetrahydro-3-(2-methyl-4-pyridinyl)-5H-pyrazolo[4,3-c]pyridine-5-carboxamide | 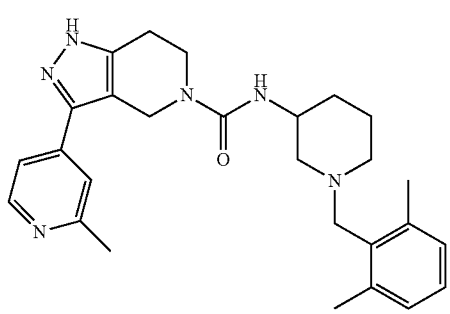 [SMILES: Cc1cc(-c2n[nH]c3c2CN(C(=O)NC2CCCN(Cc4c(C)cccc4C)C2)CC3)ccn1] | 459.2 found, 459.3 required. |

-continued

| Cmpd ID No | Compound Name | Structure | LC-MS (M + H) |
|---|---|---|---|
| 85 | N-[1-[(2-chloro-6-fluorophenyl)methyl]-3-piperidinyl]-1,4,6,7-tetrahydro-3-(2-methyl-4-pyridinyl)-5H-pyrazolo[4,3-c]pyridine-5-carboxamide | 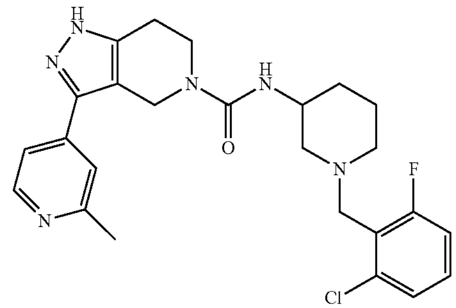 [SMILES: Cc1cc(-c2n[nH]c3c2CN(C(=O)NC2CCCN(Cc4c(F)cccc4Cl)C2)CC3)ccn1] | 483.1 found, 483.2 required. |
| 86 | N-[1-[(2,6-difluorophenyl)-methyl]-5-(hydroxymethyl)-3-piperidinyl]-1,4,6,7-tetrahydro-3-(2-methyl-4-pyridinyl)-5H-pyrazolo[4,3-c]pyridine-5-carboxamide | 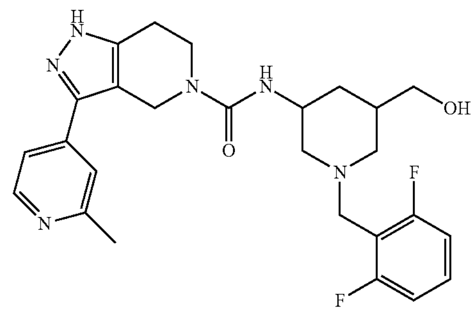 [SMILES: Cc1cc(-c2n[nH]c3c2CN(C(=O)NC2CC(CO)CN(Cc4c(F)cccc4F)C2)CC3)ccn1] | 497.2 found, 497.2 required. |
| 97 | 1,4,6,7-tetrahydro-N-[1-[(2-Methoxy-1-naphthalenyl)-methyl]-3(R)-piperidinyl]-3-(2-methyl-4-pyridinyl)-5H-pyrazolo[4,3-c]pyridine-5-carboxamide | 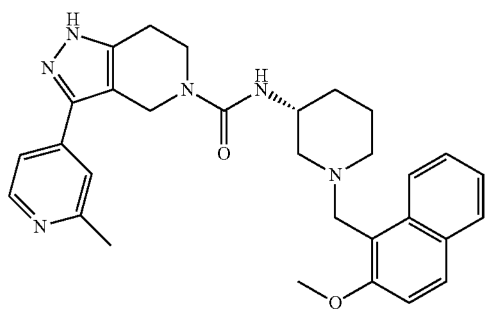 [SMILES: COc1ccc2ccccc2c1CN1CCC[C@@H](NC(=O)N2CCc3[nH]nc(-c4ccnc(C)c4)c3C2)C1] | 511.0 found, 511.3 required. |
| 98 | 1,4,6,7-tetrahydro-3-(2-methyl-4-pyridinyl)-N-[1-(4-quinolinyl]methyl]-3(R)-piperidinyl]-5H-pyrazolo[4,3-c]pyridine-5-carboxamide | 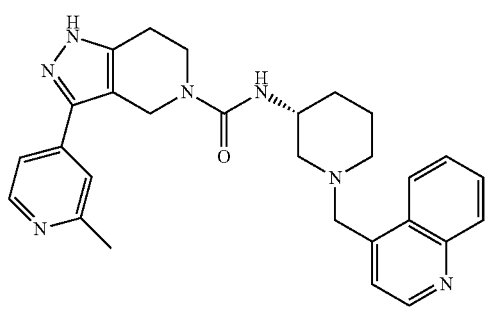 [SMILES: Cc1cc(-c2n[nH]c3c2CN(C(=O)N[C@@H]2CCCN(Cc4ccnc5ccccc45)C2)CC3)ccn1] | 482.0 found, 482.3 required. |
| 99 | 1,4,6,7-tetrahydro-N-[1-[(4-Methoxy-1-naphthalenyl)-methyl]-3(R)-piperidinyl]-3-(2-methyl-4-pyridinyl)-5H-pyrazolo[4,3-c]pyridine-5-carboxamide | 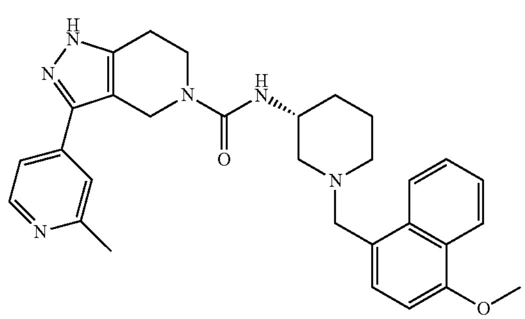 [SMILES: COc1ccc(CN2CCC[C@@H](NC(=O)N3CCc4[nH]nc(-c5ccnc(C)c5)c4C3)C2)c2ccccc12] | 511.0 found, 511.3 required. |

-continued

| Cmpd ID No | Compound Name | Structure | LC-MS (M + H) |
|---|---|---|---|
| 100 | 1,4,6,7-tetrahydro-3-(2-methyl-4-pyridinyl)-N-[1-(1-naphthalenylmethyl)-3(R)-piperidinyl]-5H-pyrazolo[4,3-c]pyridine-5-carboxamide | 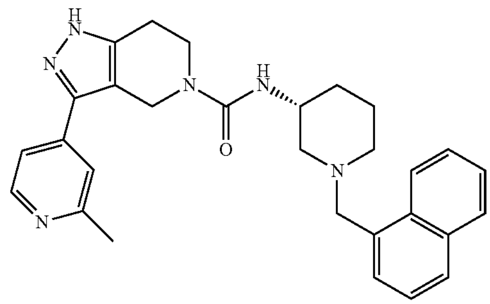 | 481.0 found, 481.3 required. |
| 87 | N-[1-[(2,6-difluorophenyl)-methyl]-3-methyl-3-piperidinyl]-1,4,6,7-tetrahydro-3-(2-methyl-4-pyridinyl)-5H-pyrazolo[4,3-c]pyridine-5-carboxamide | 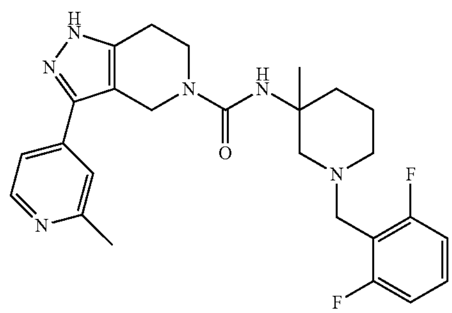 [SMILES: Cc1cc(-c2n[nH]c3c2CN(C(=O)NC2(C)CCCN(Cc4c(F)cccc4F)C2)CC3)ccn1] | 481.2 found, 481.2 required. |
| 88 | N-[1-(benzo[b]thien-3-ylmethyl)-3-methyl-3-piperidinyl]-1,4,6,7-tetrahydro-3-(2-methyl-4-pyridinyl)-5H-pyrazolo[4,3-c]pyridine-5-carboxamide | 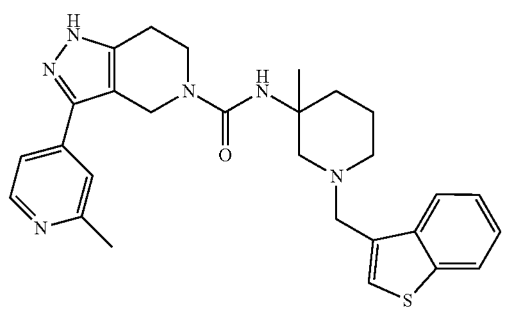 [SMILES: Cc1cc(-c2n[nH]c3c2CN(C(=O)NC2(C)CCCN(Cc4csc5ccccc45)C2)CC3)ccn1] | 501.2 found, 501.2 required. |
| 92 | N-[1-[(2,6-difluorophenyl)-methyl]-3-ethyl-3-piperidinyl]-1,4,6,7-tetrahydro-3-(2-methyl-4-pyridinyl)-5H-pyrazolo[4,3-c]pyridine-5-carboxamide | 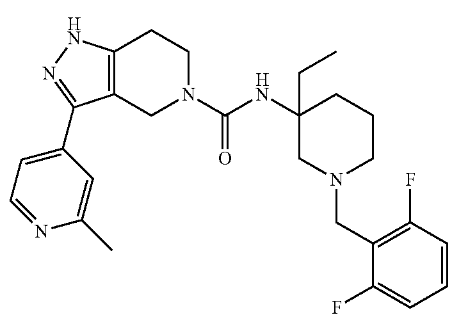 [SMILES: CCC1(NC(=O)N2CCc3[nH]nc(-c4ccnc(C)c4)c3C2)CCCN(Cc2c(F)cccc2F)C1] | 495.2 found, 495.3 required. |
| 93 | N-[1-(benzo[b]thien-3-ylmethyl)-3-ethyl-3-piperidinyl]-1,4,6,7-tetrahydro-3-(2-methyl-4-pyridinyl)-5H-pyrazolo[4,3-c]pyridine-5-carboxamide | 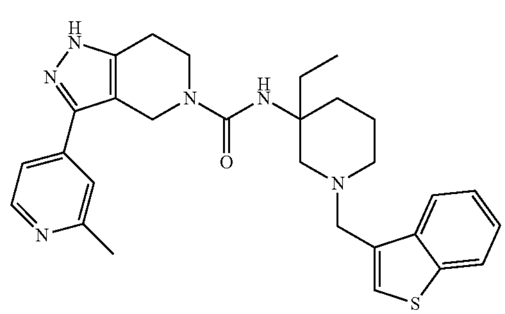 [SMILES: CCC1(NC(=O)N2CCc3[nH]nc(-c4ccnc(C)c4)c3C2)CCCN(Cc2csc3ccccc23)C1] | 515.2 found, 515.2 required. |

-continued

| Cmpd ID No | Compound Name | Structure | LC-MS (M + H) |
|---|---|---|---|
| 105 | 1,4,6,7-tetrahydro-3-(2-methyl-4-pyridinyl)-N-(6-phenyl-3-piperidinyl)-5H-pyrazolo[4,3-c]pyridine-5-carboxamide | 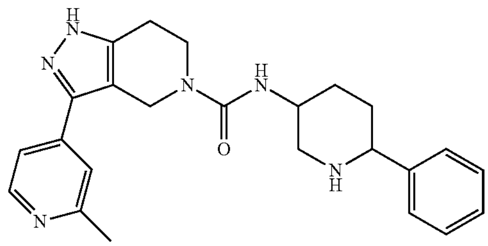 [SMILES: Cc1cc(-c2n[nH]c3c2CN(C(=O)NC2CCC(c4ccccc4)NC2)CC3)ccn1] | 417.2 found, 417.2 required. |
| 106 | N-[1-[(2,6-difluorophenyl)-methyl]-6-phenyl-3-piperidinyl]-1,4,6,7-tetrahydro-3-(2-methyl-4-pyridinyl)-5H-pyrazolo[4,3-c]pyridine-5-carboxamide | 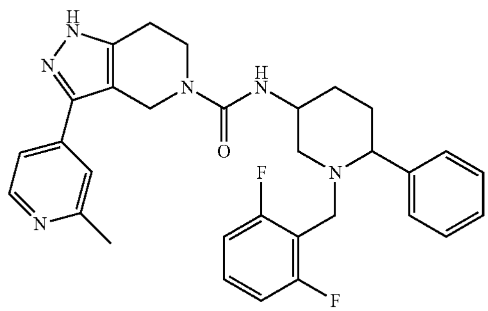 [SMILES: Cc1cc(-c2n[nH]c3c2CN(C(=O)NC2CCC(c4ccccc4)N(Cc4c(F)cccc4F)C2)CC3)ccn1] | 543.3 found, 543.3 required. |
| 107 | N-[2-[(2,6-difluorophenyl)-methyl]-2-azabicyclo[2.2.1]-hept-6-yl]-1,4,6,7-tetrahydro-3-(4-pyridinyl)-5H-pyrazolo[4,3-c]pyridine-5-carboxamide | 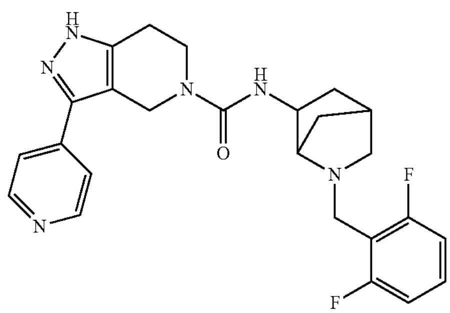 [SMILES: O=C(NC1CC2CC1N(Cc1c(F)cccc1F)C2)N1CCc2[nH]nc(-c3ccncc3)c2C1] | 465.2 found, 465.2 required. |
| 108 | N-[2-[(2-fluoro-6-methoxyphenyl)methyl]-2-azabicyclo[2.2.1]hept-6-yl]-1,4,6,7-tetrahydro-3-(4-pyridinyl)-5H-pyrazolo[4,3-c]pyridine-5-carboxamide | 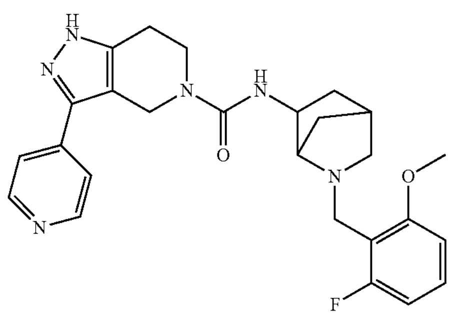 [SMILES: COc1cccc(F)c1CN1CC2CC(NC(=O)N3CCc4[nH]nc(-c5ccncc5)c4C3)C1C2] | 477.2 found, 477.2 required. |
| 109 | N-[1-(benzo[b]thien-3-ylmethyl)-3(R)-piperidinyl]-1,4,6,7-tetrahydro-3-(imidazo[1,2-a]pyridin-6-yl)-5H-pyrazolo[4,3-c]pyridine-5-carboxamide | 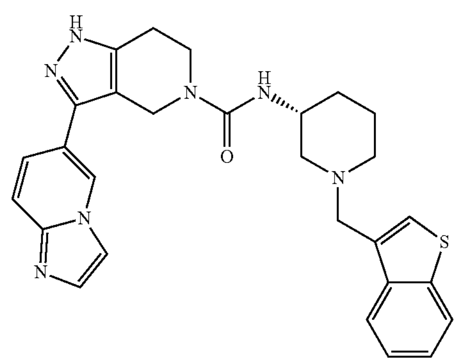 [SMILES: O=C(N[C@@H]1CCCN(Cc2csc3ccccc23)C1)N1CCc2[nH]nc(-c3ccc4nccn4c3)c2C1] | 512.4 found, 512.2 required. |

-continued

| Cmpd ID No | Compound Name | Structure | LC-MS (M + H) |
|---|---|---|---|
| 110 | N-[1-[(2,6-dimethylphenyl)-methyl-3(R)-piperidinyl]-1,4,6,7-tetrahydro-3-(imidazo[1,2-a]pyridin-6-yl)-5H-pyrazolo[4,3-c]pyridine-5-carboxamide | 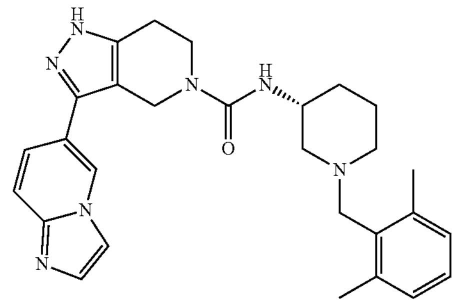 [SMILES: Cc1cccc(C)c1CN1CCC[C@@H](NC(=O)N2CCc3[nH]nc(-c4ccc5nccn5c4)c3C2)C1] | 483.9 found, 484.3 required. |
| 111 | N-[1-[(2,6-difluorophenyl)-methyl]-3(R)-piperidinyl]-1,4,6,7-tetrahydro-3-(imidazo[1,2-a]pyridin-6-yl)-5H-pyrazolo[4,3-c]pyridine-5-carboxamide | 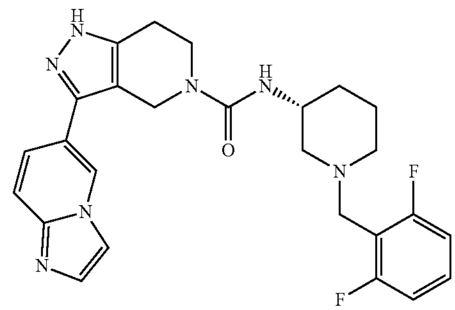 [SMILES: O=C(N[C@@H]1CCCN(Cc2c(F)cccc2F)C1)N1CCc2[nH]nc(-c3ccc4nccn4c3)c2C1] | 492.3 found, 492.2 required. |
| 112 | 1,4,6,7-tetrahydro-3-imidazo[1,2-a]pyridin-6-yl-N-[1-(1-naphthalenylmethyl)-3(R)-piperidinyl]-5H-pyrazolo[4,3-c]pyridine-5-carboxamide | 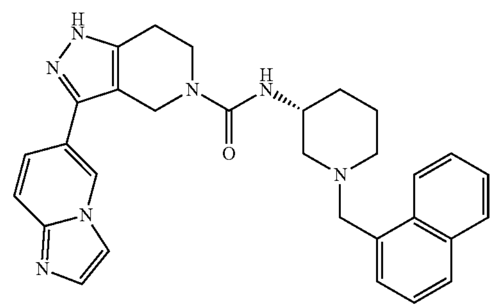 [SMILES: O=C(N[C@@H]1CCCN(Cc2cccc3ccccc23)C1)N1CCc2[nH]nc(-c3ccc4nccn4c3)c2C1] | 506.3 found, 506.3 required. |
| 113 | N-[1-[(2-fluoro-6-methoxyphenyl)methyl]-3(R)-piperidinyl]-1,4,6,7-tetrahydro-3-(imidazo[1,2-a]pyridin-6-yl)-5H-pyrazolo[4,3-c]pyridine-5-carboxamide | 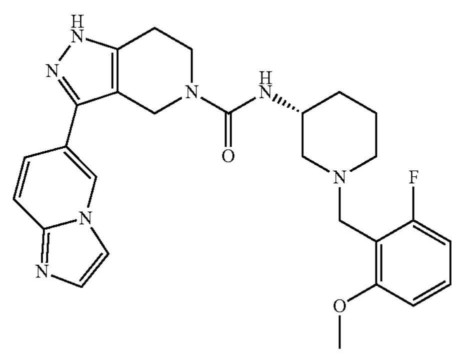 [SMILES: COc1cccc(F)c1CN1CCC[C@@H](NC(=O)N2CCc3[nH]nc(-c4ccc5nccn5c4)c3C2)C1] | 504.2 found, 504.2 required. |
| 114 | N-[1-[(2-chlorophenyl)-methyl]-5-hydroxy-3-piperidinyl]-1,4,6,7-tetrahydro-3-(4-pyridinyl)-5H-pyrazolo[4,3-c]pyridine-5-carboxamide | 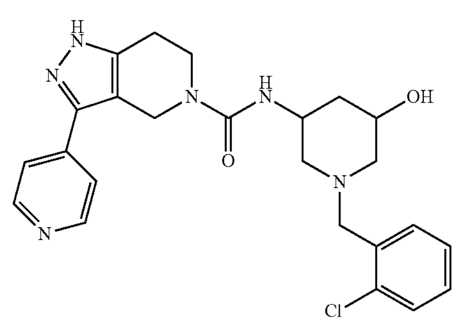 [SMILES: O=C(NC1CC(O)CN(Cc2ccccc2Cl)C1)N1CCc2[nH]nc(-c3ccncc3)c2C1] | 467.2 found, 467.2 required. |

| Cmpd ID No | Compound Name | Structure | LC-MS (M + H) |
|---|---|---|---|
| 115 | N-[1-[(2,6-difluorophenyl)-methyl]-3(R)-pyrrolidinyl]-1,4,6,7-tetrahydro-3-(2-methyl-4-pyridinyl)-5H-pyrazolo[4,3-c]pyridine-5-carboxamide | 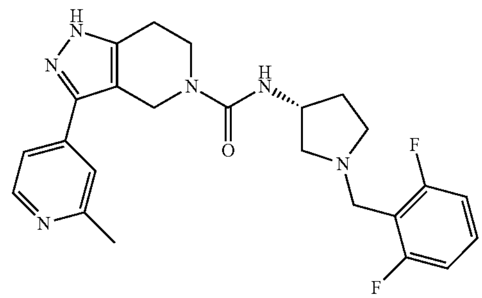 [SMILES: Cc1cc(-c2n[nH]c3c2CN(C(=O)N[C@@H]2CCN(Cc4c(F)cccc4F)C2)CC3)ccn1] | 453.0 found, 453.2 required. |
| 116 | N-[1-[(2-fluoro-6-methoxyphenyl)methyl]-3(R)-pyrrolidinyl]-1,4,6,7-tetrahydro-3-(2-methyl-4-pyridinyl)-5H-pyrazolo[4,3-c]pyridine-5-carboxamide | 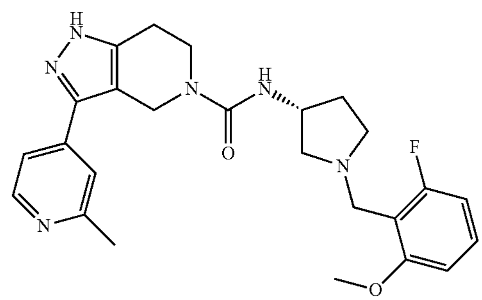 [SMILES: COc1cccc(F)c1CN1CC[C@@H](NC(=O)N2CCc3[nH]nc(-c4ccnc(C)c4)c3C2)C1] | 464.9 found, 465.2 required. |
| 117 | N-[1-[(2-chloro-6-fluorophenyl)methyl]-3(R)-pyrrolidinyl]-1,4,6,7-tetrahydro-3-(2-methyl-4-pyridinyl)-5H-pyrazolo[4,3-c]pyridine-5-carboxamide | 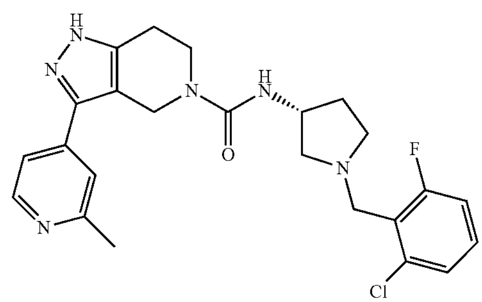 [SMILES: Cc1cc(-c2n[nH]c3c2CN(C(=O)N[C@@H]2CCN(Cc4c(F)cccc4Cl)C2)CC3)ccn1] | 468.9 found, 469.2 required. |
| 118 | N-[1-[(2-chlorophenyl)-methyl]-3(R)-pyrrolidinyl]-1,4,6,7-tetrahydro-3-(2-methyl-4-pyridinyl)-5H-pyrazolo[4,3-c]pyridine-5-carboxamide | 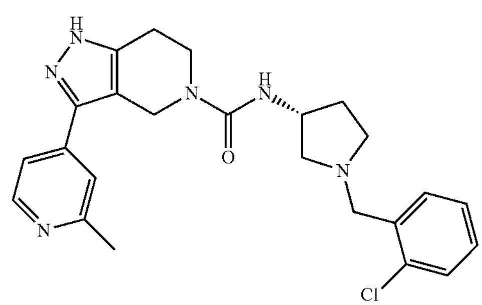 [SMILES: Cc1cc(-c2n[nH]c3c2CN(C(=O)N[C@@H]2CCN(Cc4ccccc4Cl)C2)CC3)ccn1] | 450.9 found, 451.2 required. |
| 119 | N-[1-[(2,6-dimethylphenyl)-methyl]-3(R)-pyrrolidinyl]-1,4,6,7-tetrahydro-3-(2-methyl-4-pyridinyl)-5H-pyrazolo[4,3-c]pyridine-5-carboxamide | 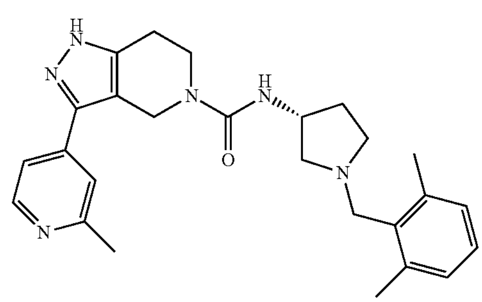 [SMILES: Cc1cc(-c2n[nH]c3c2CN(C(=O)N[C@@H]2CCN(Cc4c(C)cccc4C)C2)CC3)ccn1] | 445.0 found, 445.3 required. |

-continued

| Cmpd ID No | Compound Name | Structure | LC-MS (M + H) |
|---|---|---|---|
| 120 | N-[1-(benzo[b]thien-3-ylmethyl)-3(R)-pyrrolidinyl]-1,4,6,7-tetrahydro-3-(2-methyl-4-pyridinyl)-5H-pyrazolo[4,3-c]pyridine-5-carboxamide | 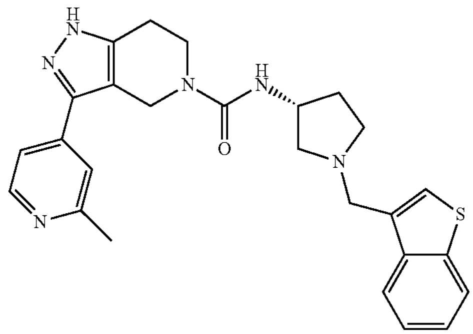 [SMILES: Cc1cc(-c2n[nH]c3c2CN(C(=O)N[C@@H]2CCN(Cc4csc5ccccc45)C2)CC3)ccn1] | 472.9 found, 473.2 required. |
| 121 | N-[1-[(2-fluoro-6-methoxyphenyl)methyl]-6-methyl-3-piperidinyl]-1,4,6,7-tetrahydro-3-(2-methyl-4-pyridinyl)-5H-pyrazolo[4,3-c]pyridine-5-carboxamide | 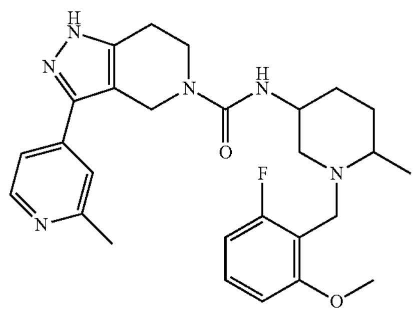 [SMILES: COc1cccc(F)c1CN1CC(NC(=O)N2CCc3[nH]nc(-c4ccnc(C)c4)c3C2)CCC1C] | 493.0 found, 493.3 required. |
| 122 | N-[1-[(2-fluoro-6-methoxyphenyl)methyl]-2-methyl-3-piperidinyl]-1,4,6,7-tetrahydro-3-(2-methyl-4-pyridinyl)-5H-pyrazolo[4,3-c]pyridine-5-carboxamide | 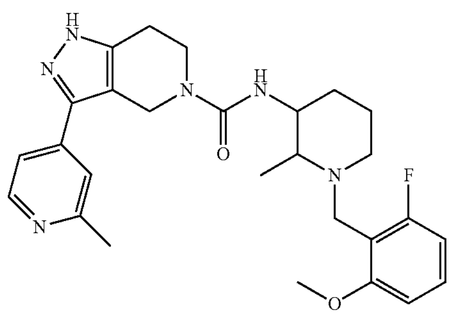 [SMILES: COc1cccc(F)c1CN1CCCC(NC(=O)N2CCc3[nH]nc(-c4ccnc(C)c4)c3C2)C1C] | 493.0 found, 493.3 required. |
| 123 | N-[1-[(2-fluoro-6-methoxyphenyl)methyl]-5-(trifluoromethyl)-3-piperidinyl]-1,4,6,7-tetrahydro-3-(2-methyl-4-pyridinyl)-5H-pyrazolo[4,3-c]pyridine-5-carboxamide | 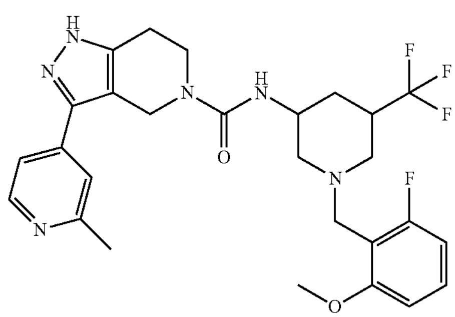 [SMILES: COc1cccc(F)c1CN1CC(NC(=O)N2CCc3[nH]nc(-c4ccnc(C)c4)c3C2)CC(C(F)(F)F)C1] | 547.0 found, 547.2 required. |
| 124 | N-[1-[(2,6-dimethylphenyl)methyl]-3(R)-piperidinyl]-3-(3-fluoro-4-methoxyphenyl)-1,4,6,7-tetrahydro-5H-pyrazolo[4,3-c]pyridine-5-carboxamide | 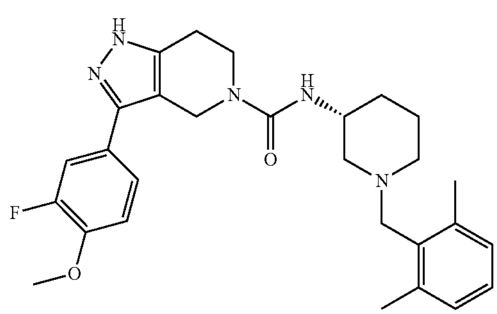 [SMILES: COc1ccc(-c2n[nH]c3c2CN(C(=O)N[C@@H]2CCCN(Cc4c(C)cccc4C)C2)CC3)cc1F] | 492.1 found, 492.3 required. |

| Cmpd ID No | Compound Name | Structure | LC-MS (M + H) |
|---|---|---|---|
| 125 | N-[1-[(2,6-dimethylphenyl)-methyl]-3(R)-piperidinyl]-1,4,6,7-tetrahydro-3-(6-Methoxy-3-pyridinyl)-5H-pyrazolo[4,3-c]pyridine-5-carboxamide | 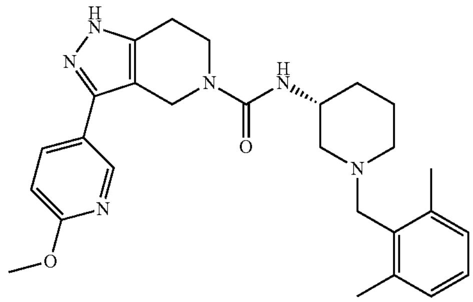 [SMILES: COc1ccc(-c2n[nH]c3c2CN(C(=O)N[C@@H]2CCCN(Cc4c(C)cccc4C)C2)CC3)cn1] | 475.1 found, 475.3 required. |
| 126 | N-[1-[(2,6-dimethylphenyl)-methyl]-3(R)-piperidinyl]-1,4,6,7-tetrahydro-3-(2-methyl-2H-indazol-5-yl)-5H-pyrazolo[4,3-c]pyridine-5-carboxamide | 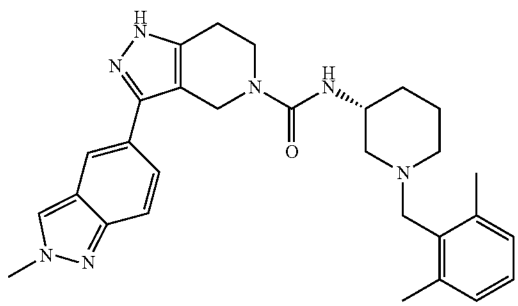 [SMILES: Cc1cccc(C)c1CN1CCC[C@@H](NC(=O)N2CCc3[nH]nc(-c4ccc5nn(C)cc5c4)c3C2)C1] | 498.1 found, 498.3 required. |
| 127 | N-[1-[(2,6-dimethylphenyl)-methyl]-3(R)-piperidinyl]-1,4,6,7-tetrahydro-3-(1-methyl-1H-inclazol-5-yl)-5H-pyrazolo[4,3-c]pyridine-5-carboxamide | 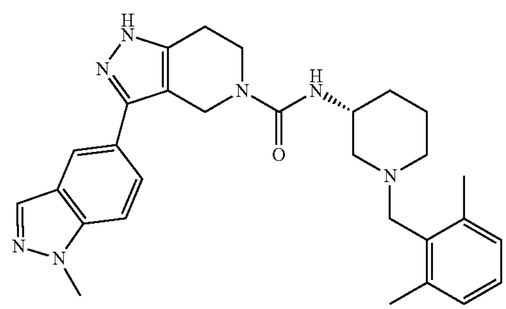 [SMILES: Cc1cccc(C)c1CN1CCC[C@@H](NC(=O)N2CCc3[nH]nc(-c4ccc5c(cnn5C)c4)c3C2)C1] | 498.1 found, 498.3 required. |
| 128 | N-[8-[(2,6-difluorophenyl)-methyl]-8-azabicyclo[3.2.1]-oct-3-yl]-1,4,6,7-tetrahydro-3-(2-methyl-4-pyridinyl)-5H-pyrazolo[4,3-c]pyridine-5-carboxamide | 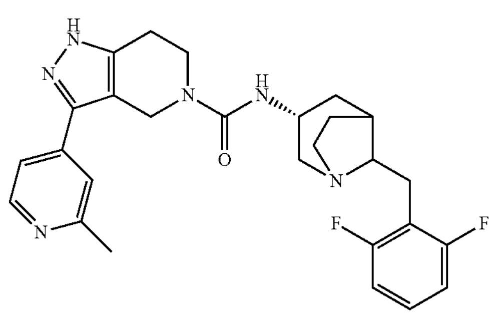 [SMILES: Cc1cc(-c2n[nH]c3c2CN(C(=O)N[C@@H]2CC4CCN(C2)C4Cc2c(F)cccc2F)CC3)ccn1] | 493.0 found, 493.2 required. |

| Cmpd ID No | Compound Name | Structure | LC-MS (M + H) |
|---|---|---|---|
| 129 | N-[1-(benzo[b]thien-3-ylmethyl)-3(R)-pyrrolidinyl]-1,4,6,7-tetrahydro-3-(6-phenyl-3-pyridinyl)-5H-pyrazolo[4,3-c]pyridine-5-carboxamide | 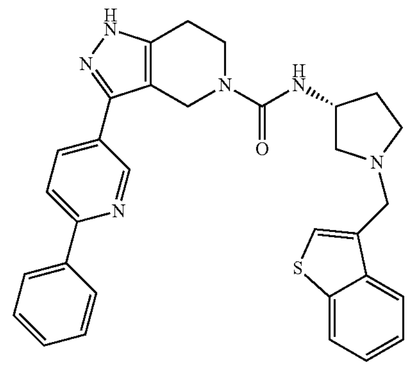 [SMILES: O=C(N[C@@H]1CCN(Cc2csc3ccccc23)C1)N1CCc2[nH]nc(-c3ccc(-c4ccccc4)nc3)c2C1] | 535.0 found, 535.2 required. |
| 130 | N-[1-[(2,6-difluorophenyl)-methyl]-3(R)-piperidinyl]-1,4,6,7-tetrahydro-3-(6-quinolinyl)-5H-pyrazolo[4,3-c]pyridine-5-carboxamide | 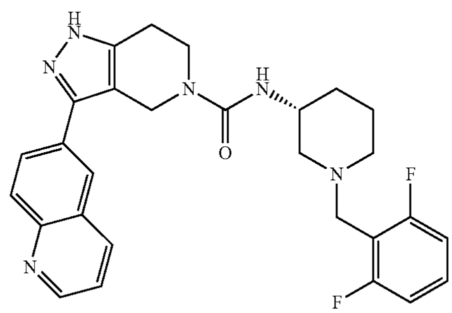 [SMILES: O=C(N[C@@H]1CCCN(Cc2c(F)cccc2F)C1)N1CCc2[nH]nc(-c3ccc4ncccc4c3)c2C1] | 503.0 found, 503.2 required. |
| 131 | N-[1-[(2,6-difluorophenyl)-methyl]-3(R)-piperidinyl]-3-(3-fluoro-4-methoxyphenyl)-1,4,6,7-tetrahydro-5H-pyrazolo[4,3-c]pyridine-5-carboxamide | 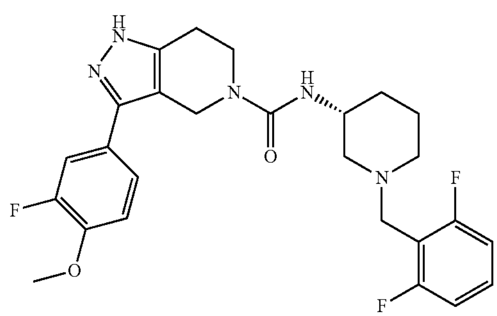 [SMILES: COc1ccc(-c2n[nH]c3c2CN(C(=O)N[C@@H]2CCCN(Cc4c(F)cccc4F)C2)CC3)cc1F] | 499.9 found, 500.2 required. |
| 132 | N-[1-[(2,6-difluorophenyl)-methyl]-3(R)-piperidinyl]-1,4,6,7-tetrahydro-3-(6-Methoxy-3-pyridinyl)-5H-pyrazolo[4,3-c]pyridine-5-carboxamide | 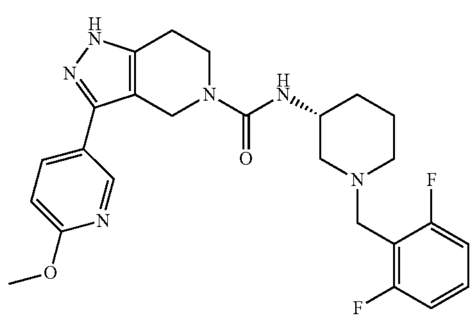 [SMILES: COc1ccc(-c2n[nH]c3c2CN(C(=O)N[C@@H]2CCCN(Cc4c(F)cccc4F)C2)CC3)cn1] | 483.0 found, 483.2 required. |

| Cmpd ID No | Compound Name | Structure | LC-MS (M + H) |
|---|---|---|---|
| 133 | N[1-[(2,6-difluorophenyl)-methyl]-3(R)-piperidinyl]-1,4,6,7-tetrahydro-3-(2-methyl-2H-indazol-5-yl)-5H-pyrazolo[4,3-c]pyridine-5-carboxamide | 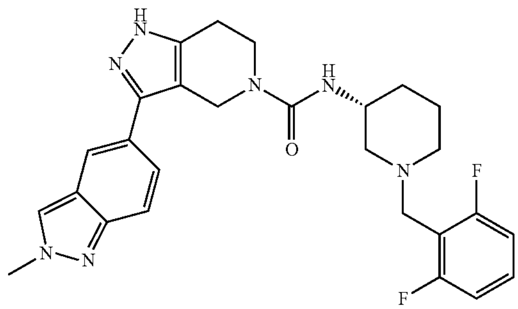 [SMILES: Cn1cc2cc(-c3n[nH]c4c3CN(C(=O)N[C@@H]3CCCN(Cc5c(F)cccc5F)C3)CC4)ccc2n1] | 506.0 found, 506.2 required. |
| 134 | N-[1-[(2,6-difluorophenyl)-methyl]-3(R)-piperidinyl]-1,4,6,7-tetrahydro-3-(1-methyl-1H-indazol-5-yl)-5H-pyrazolo[4,3-c]pyridine-5-carboxamide | 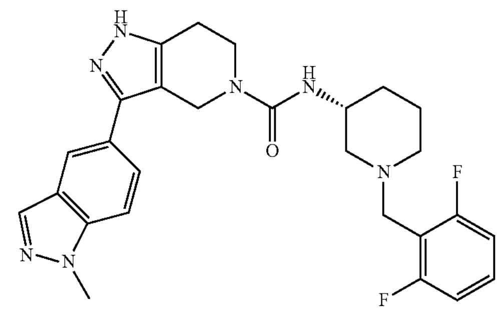 [SMILES: Cn1ncc2cc(-c3n[nH]c4c3CN(C(=O)N[C@@H]3CCCN(Cc5c(F)cccc5F)C3)CC4)ccc21] | 506.4 found, 506.2 required. |
| 135 | N-[4-fluoro-1-[(2-fluoro-6-methoxyphenyl)methyl]-3-piperidinyl]-1,4,6,7-tetrahydro-3-(2-methyl-4-pyridinyl)-5H-pyrazolo[4,3-c]pyridine-5-carboxamide | 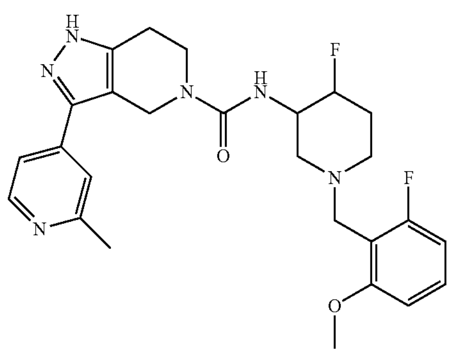 [SMILES: COc1cccc(F)c1CN1CCC(F)C(NC(=O)N2CCc3[nH]nc(-c4ccnc(C)c4)c3C2)C1] | 496.9 found, 497.2 required. |
| 136 | N-[1-(benzo[b]thien-3-ylmethyl)-3(R)-piperidinyl]-1,4,6,7-tetrahydro-3-(6-phenyl-3-pyridinyl)-5H-pyrazolo[4,3-c]pyridine-5-carboxamide | 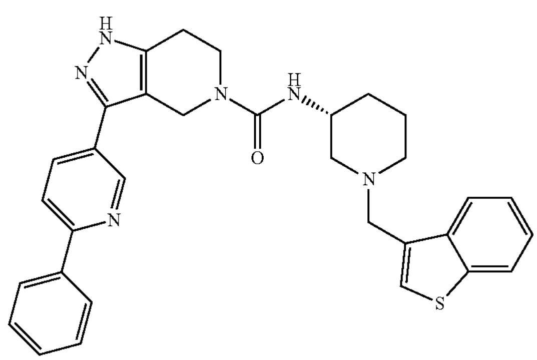 [SMILES: O=C(N[C@@H]1CCCN(Cc2csc3ccccc23)C1)N1CCc2[nH]nc(-c3ccc(-c4ccccc4)nc3)c2C1] | 549.0 found, 549.2 required. |

| Cmpd ID No | Compound Name | Structure | LC-MS (M + H) |
|---|---|---|---|
| 137 | N-[1-[(2,6-difluorophenyl)-methyl]-3(R)-piperidinyl]-1,4,6,7-tetrahydro-3-(6-phenyl-3-pyridinyl)-5H-pyrazolo[4,3-c]pyridine-5-carboxamide | 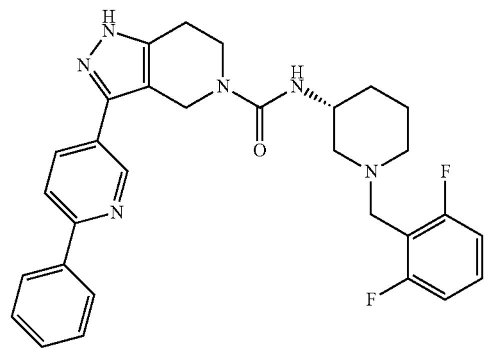 [SMILES: O=C(N[C@@H]1CCCN(Cc2c(F)cccc2F)C1)N1CCc2[nH]nc(-c3ccc(-c4ccccc4)nc3)c2C1] | 529.0 found, 529.3 required. |
| 138 | N-[1-[(2-fluoro-6-methoxyphenyl)methyl]-3(R)-piperidinyl]-1,4,6,7-tetrahydro-3-(6-phenyl-3-pyridinyl)-5H-pyrazolo[4,3-c]pyridine-5-carboxamide | 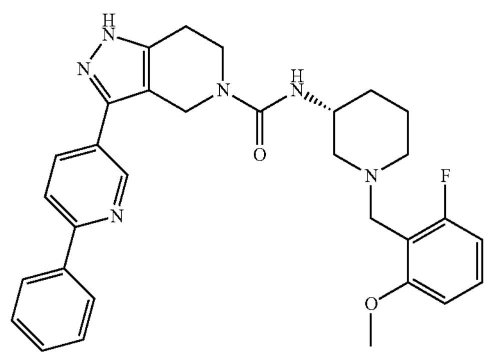 [SMILES: COc1cccc(F)c1CN1CCC[C@@H](NC(=O)N2CCc3[nH]nc(-c4ccc(-c5ccccc5)nc4)c3C2)C1] | 541.0 found, 541.3 required. |
| 139 | N-[1-[(2,6-dimethylphenyl)-methyl]-3(R)-pyrrolidinyl]-1,4,6,7-tetrahydro-3-(6-phenyl-3-pyridinyl)-5H-pyrazolo[4,3-c]pyridine-5-carboxamide | 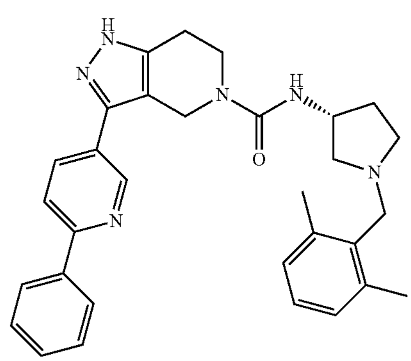 [SMILES: Cc1cccc(C)c1CN1CC[C@@H](NC(=O)N2CCc3[nH]nc(-c4ccc(-c5ccccc5)nc4)c3C2)C1] | 507.0 found, 507.3 required. |
| 171 | 1,4,6,7-tetrahydro-N-(3(R)-piperidinyl)-3-(4-pyridinyl)-5H-pyrazolo[4,3-c]pyridine-5-carboxamide (single isomer) | 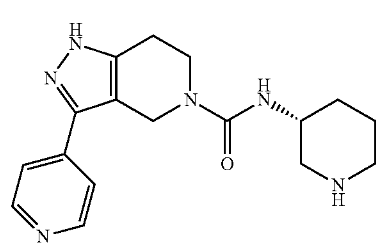 [SMILES: O=C(N[C@@H]1CCCNC1)N1CCc2[nH]nc(-c3ccncc3)c2C1] | 327.0 found, 327.2 required. |

-continued

| Cmpd ID No | Compound Name | Structure | LC-MS (M + H) |
|---|---|---|---|
| 173 | 1,4,6,7-tetrahydro-N-[1-(2-phenylethyl)-3(R)-piperidinyl]-3-(4-pyridinyl)-5H-pyrazolo[4,3-c]pyridine-5-carboxamide (pure isomer) | 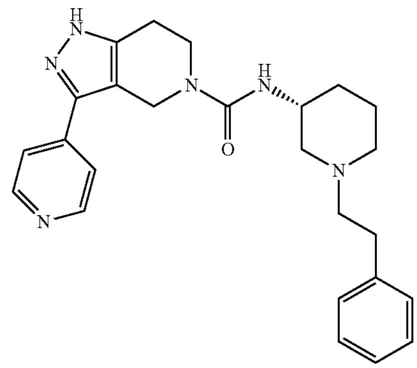 [SMILES: O=C(N[C@@H]1CCCN(CCc2ccccc2)C1)N1CCc2[nH]nc(-c3ccncc3)c2C1] | 431.0 found, 431.2 required. |
| 175 | 1,4,6,7-tetrahydro-N-[1-(phenylmethyl)-3(R)-piperidinyl]-3-(4-pyridinyl)-5H-pyrazolo[4,3-c]pyridine-5-carboxamide (single isomer) | 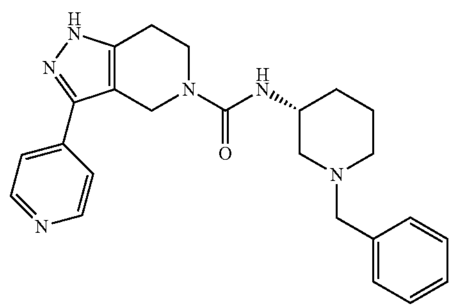 [SMILES: O=C(N[C@@H]1CCCN(Cc2ccccc2)C1)N1CCc2[nH]nc(-c3ccncc3)c2C1] | 417.0 found, 417.2 required. |
| 177 | 3-(2,3-dihydro-5-benzofuranyl)-1,4,6,7-tetrahydro-N-[1-(phenylmethyl)-3(R)-piperidinyl]-5H-pyrazolo[4,3-c]pyridine-5-carboxamide (pure enantiomer) | 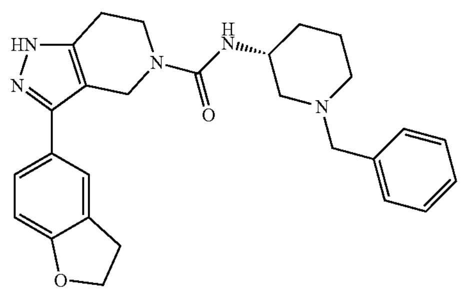 [SMILES: O=C(N[C@@H]1CCCN(Cc2ccccc2)C1)N1CCc2[nH]nc(-c3ccc4c(c3)CCO4)c2C1] | 458.4 found, 458.2 required. |
| 179 | N[1-[(2,6-difluorophenyl)methyl]-3(R)-piperidinyl]-3-(2,3-dihydro-5-benzofuranyl)-1,4,6,7-tetrahydro-5H-pyrazolo[4,3-c]pyridine-5-carboxamide (pure enantiomer) | 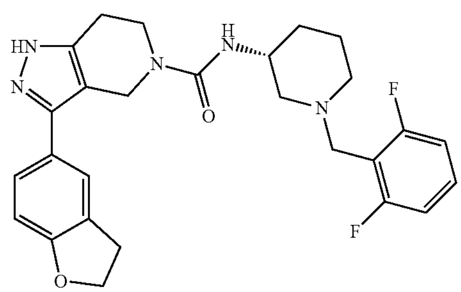 [SMILES: O=C(N[C@@H]1CCCN(Cc2c(F)cccc2F)C1)N1CCc2[nH]nc(-c3ccc4c(c3)CCO4)c2C1] | 494.2 found, 494.2 required. |
| 181 | (R)-3-(2,3-dihydrobenzofuran-5-yl)-N-(1-(2-fluoro-6-methoxybenzyl)piperidin-3-yl)-6,7-dihydro-1H-pyrazolo[4,3-c]pyridine-5(4H)-carboxamide | 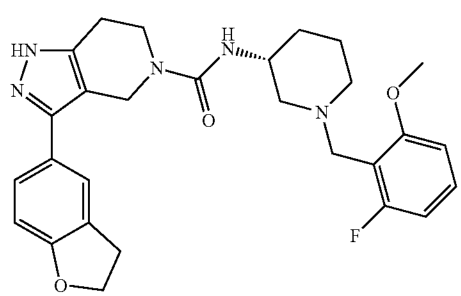 [SMILES: COc1cccc(F)c1CN1CCC[C@@H](NC(=O)N2CCc3[nH]nc(-c4ccc5c(c4)CCO5)c3C2)C1] | 506.2 found, 506.2 required. |

| Cmpd ID No | Compound Name | Structure | LC-MS (M + H) |
|---|---|---|---|
| 183 | N-[1-(benzo[b]thien-3-ylmethyl)-3(R)-piperidinyl]-3-(2,3-dihydro-5-benzofuranyl)-1,4,6,7-tetrahydro-5H-pyrazolo[4,3-c]pyridine-5-carboxamide (pure enantiomer) | 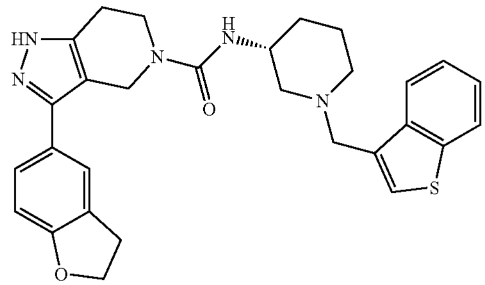 [SMILES: O=C(N[C@@H]1CCCN(Cc2csc3ccccc23)C1)N1CCc2[nH]nc(-c3ccc4c(c3)CCO4)c2C1] | 514.2 found, 514.2 required. |
| 185 | 1,4,6,7-tetrahydro-3-(2-methyl-6-benzoxazolyl)-N-[1-(phenylmethyl)-3(R)-piperidinyl]-5H-pyrazolo[4,3-c]pyridine-5-carboxamide | 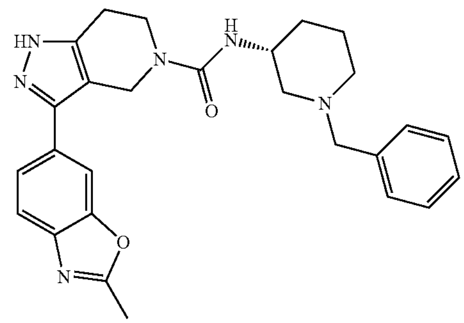 [SMILES: Cc1nc2ccc(-c3n[nH]c4c3CN(C(=O)N[C@@H]3CCCN(Cc5ccccc5)C3)CC4)cc2o1] | 471.3 found, 471.2 required. |
| 187 | N-[1-[(2,6-difluorophenyl)methyl]-3(R)-piperidinyl]-1,4,6,7-tetrahydro-3-(2-methyl-6-benzoxazolyl)-5H-pyrazolo[4,3-c]pyridine-5-carboxamide | 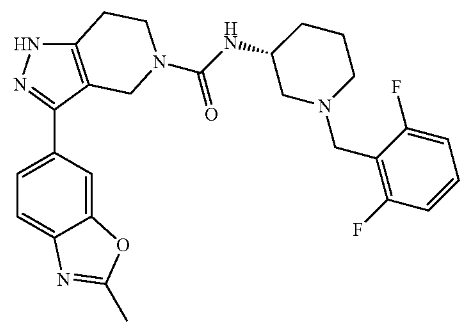 [SMILES: Cc1nc2ccc(-c3n[nH]c4c3CN(C(=O)N[C@@H]3CCCN(Cc5c(F)cccc5F)C3)CC4)cc2o1] | 507.2 found, 507.2 required. |
| 189 | N-[1-(benzo[b]thien-3-ylmethyl)-3(R)-piperidinyl]-1,4,6,7-tetrahydro-3-(2-methyl-6-benzoxazolyl)-5H-pyrazolo[4,3-c]pyridine-5-carboxamide | 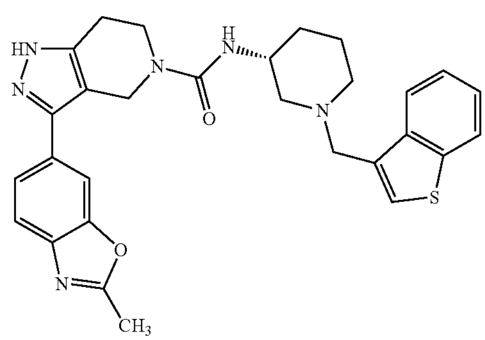 [SMILES: Cc1nc2ccc(-c3n[nH]c4c3CN(C(=O)N[C@@H]3CCCN(Cc5csc6ccccc56)C3)CC4)cc2o1] | 527.2 found, 527.2 required. |

| Cmpd ID No | Compound Name | Structure | LC-MS (M + H) |
|---|---|---|---|
| 191 | N-[1-[(2-fluorophenyl)-methyl]-3(R)-piperidinyl]-1,4,6,7-tetrahydro-3-(2-methyl-6-benzoxazolyl)-5H-pyrazolo[4,3-c]pyridine-5-carboxamide | 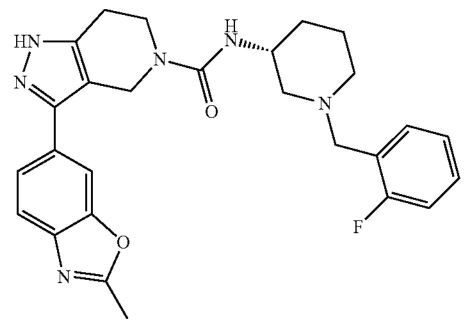 [SMILES: Cc1nc2ccc(-c3n[nH]c4c3CN(C(=O)N[C@@H]3CCCN(Cc5ccccc5F)C3)CC4)cc2o1] | 489.2 found, 489.2 required. |
| 193 | 1,4,6,7-tetrahydro-3-(2-methyl-5-benzoxazolyl)-N-[1-(phenylmethyl)-3(R)-piperidinyl]-5H-pyrazolo[4,3-c]pyridine-5-carboxamide | 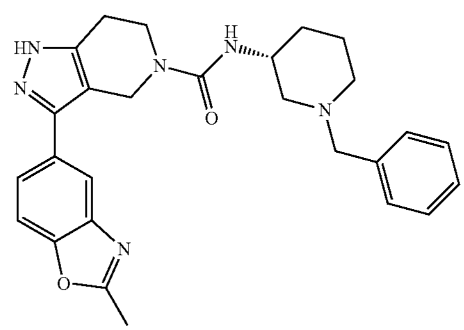 [SMILES: Cc1nc2cc(-c3n[nH]c4c3CN(C(=O)N[C@@H]3CCCN(Cc5ccccc5)C3)CC4)ccc2o1] | 471.3 found, 471.2 required. |
| 195 | N-[1-[(2-fluoro-6-methoxyphenyl)methyl]-3(R)-piperidinyl]-1,4,6,7-tetrahydro-3-(2-methyl-5-benzoxazolyl)-5H-pyrazolo[4,3-c]pyridine-5-carboxamide | 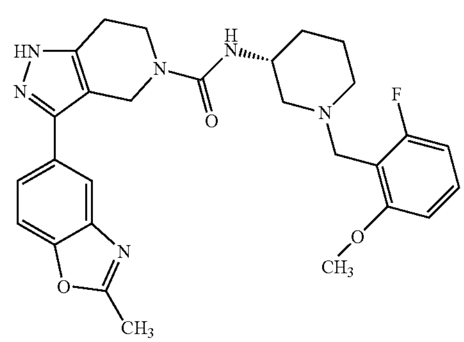 [SMILES: COc1cccc(F)c1CN1CCC[C@@H](NC(=O)N2CCc3[nH]nc(-c4ccc5oc(C)nc5c4)c3C2)C1] | 519.2 found, 519.2 required. |
| 197 | N-[1-[(2,6-difluorophenyl)methyl]-3(R)-piperidinyl]-1,4,6,7-tetrahydro-3-(2-methyl-5-benzoxazolyl)-5H-pyrazolo[4,3-c]pyridine-5-carboxamide | 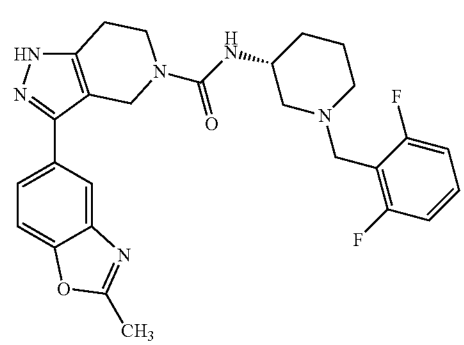 [SMILES: Cc1nc2cc(-c3n[nH]c4c3CN(C(=O)N[C@@H]3CCCN(Cc5c(F)cccc5F)C3)CC4)ccc2o1] | 507.2 found, 507.2 required. |

| Cmpd ID No | Compound Name | Structure | LC-MS (M + H) |
|---|---|---|---|
| 152 | N-[1-(benzo[b]thien-3-ylmethyl)-3(R)-piperidinyl]-1,4,6,7-tetrahydro-3-(2-methyl-5-benzoxazolyl)-5H-pyrazolo[4,3-c]pyridine-5-carboxamide | 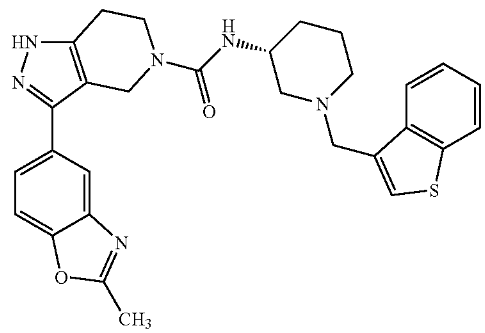 [SMILES: Cc1nc2cc(-c3n[nH]c4c3CN(C(=O)N[C@@H]3CCCN(Cc5csc6ccccc56)C3)CC4)ccc2o1] | 527.2 found, 527.2 required. |
| 142 | 1,4,6,7-tetrahydro-N-[1-(5-isoquinolinylmethyl)-3(R)-pipendinyl]-3-(2-methyl-5-benzoxazolyl)-5H-pyrazolo[4,3-c]pyridine-5-carboxamide | 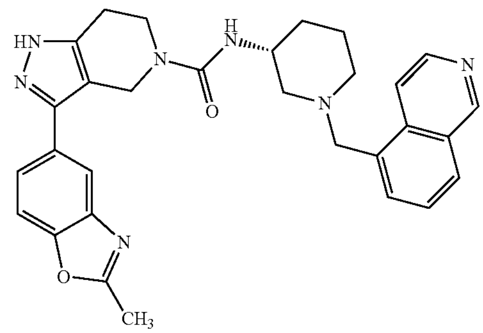 [SMILES: Cc1nc2cc(-c3n[nH]c4c3CN(C(=O)N[C@@H]3CCCN(Cc5cccc6cnccc56)C3)CC4)ccc2o1] | 522.2 found, 522.2 required. |
| 144 | 1,4,6,7-tetrahydro-3-(2-methyl-5-benzoxazolyl)-N-[1-(4-quinolinylmethyl)-3(R)-piperidinyl]-5H-pyrazolo[4,3-c]pyridine-5-carboxamide | 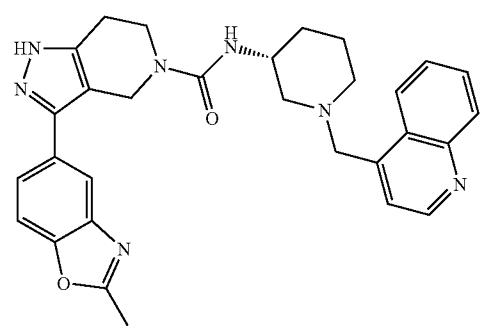 [SMILES: Cc1nc2cc(-c3n[nH]c4c3CN(C(=O)N[C@@H]3CCCN(Cc5ccnc6ccccc56)C3)CC4)ccc2o1] | 522.4 found, 522.2 required. |
| 146 | 1,4,6,7-tetrahydro-3-(2-methyl-5-benzoxazolyl)-N-[1-(5-quinolinylmethyl)-3(R)-piperidinyl]-5H-pyrazolo[4,3-c]pyridine-5-carboxamide | 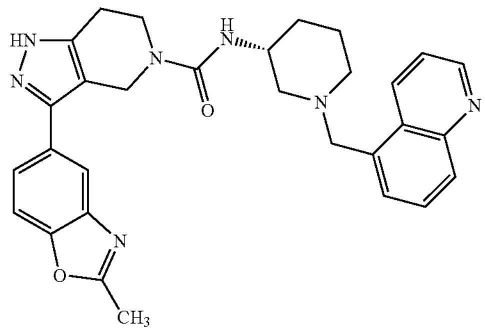 [SMILES: Cc1nc2cc(-c3n[nH]c4c3CN(C(=O)N[C@@H]3CCCN(Cc5cccc6ncccc56)C3)CC4)ccc2o1] | 522.3 found, 522.2 required. |

-continued

| Cmpd ID No | Compound Name | Structure | LC-MS (M + H) |
|---|---|---|---|
| 148 | 1,4,6,7-tetrahydro-3-(2-methyl-5-benzoxazolyl)-N-[1-[(1-methyl-1H-indol-3-yl)methyl]-3(R)-piperidinyl]-5H-pyrazolo[4,3-c]pyridine-5-carboxamide | 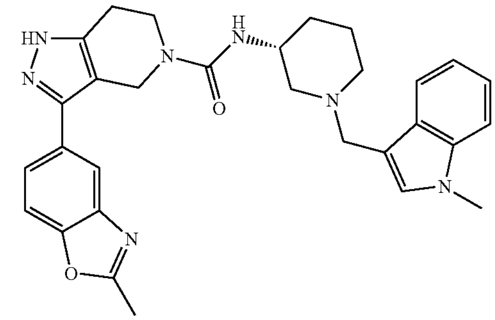 [SMILES: Cc1nc2cc(-c3n[nH]c4c3CN(C(=O)N[C@@H]3CCCN(Cc5cn(C)c6ccccc56)C3)CC4)ccc2o1] | 524.3 found, 524.3 required. |
| 150 | N-[4-fluoro-1-[(2-fluoro-6-methoxyphenyl)methyl]-3-piperidinyl]-1,4,6,7-tetrahydro-3-imidazo[1,2-a]pyridin-6-yl-5H-pyrazolo[4,3-c]pyridine-5-carboxamide | 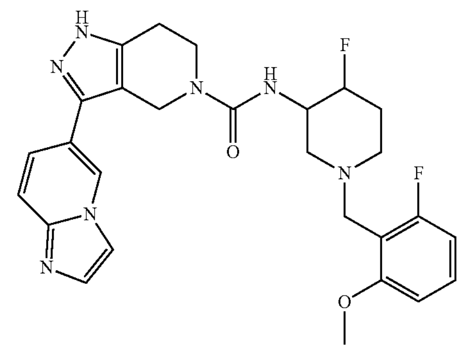 [SMILES: COc1cccc(F)c1CN1CCC(F)C(NC(=O)N2CCc3[nH]nc(-c4ccc5nccn5c4)c3C2)C1] | 522.3 found, 522.2 required. |
| 154 | 1,4,6,7-tetrahydro-3-(2-methyl-5-benzoxazolyl)-N-[1-(2-naphthalenylmethyl)-3(R)-piperidinyl]-5H-pyrazolo[4,3-c]pyridine-5-carboxamide | 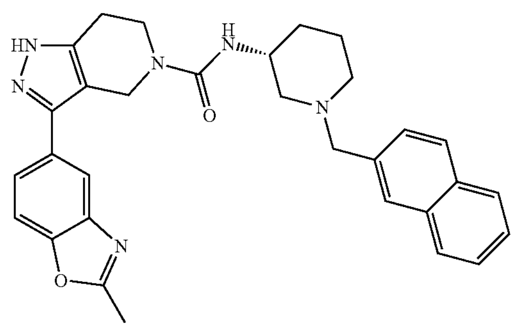 [SMILES: Cc1nc2cc(-c3n[nH]c4c3CN(C(=O)N[C@@H]3CCCN(Cc5ccc6ccccc6c5)C3)CC4)ccc2o1] | 521.3 found, 521.3 required. |
| 156 | N-[cis/trans-1-[(2,6-difluorophenyl)methyl]-4-fluoro-3-piperidinyl]-1,4,6,7-tetrahydro-3-imidazo[1,2-a]pyridin-6-yl-5H-pyrazolo[4,3-c]pyridine-5-carboxamide | 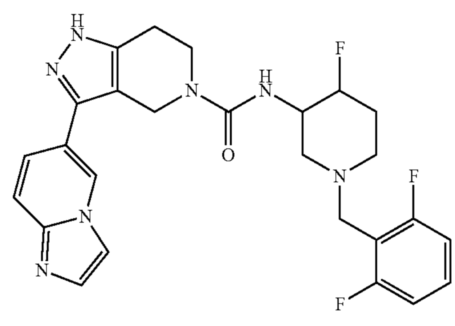 [SMILES: O=C(NC1CN(Cc2c(F)cccc2F)CCC1F)N1CCc2[nH]nc(-c3ccc4nccn4c3)c2C1] | 510.0 found, 510.2 required. |

-continued

| Cmpd ID No | Compound Name | Structure | LC-MS (M + H) |
|---|---|---|---|
| 158 | N-[cis/trans-1-[(2,6-difluorophenyl)methyl]-4-fluoro-3-piperidinyl]-1,4,6,7-tetrahydro-3-(2-methyl-4-pyridinyl)-5H-pyrazolo[4,3-c]pyridine-5-carboxamide | 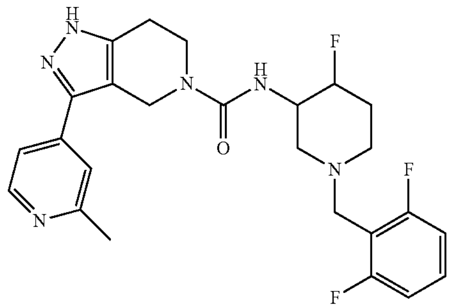 [SMILES: Cc1cc(-c2n[nH]c3c2CN(C(=O)NC2CN(Cc4c(F)cccc4F)CCC2F)CC3)ccn1] | 481.0 found, 485.2 required. |
| 170 | N-[1-[(2-fluoro-6-methoxyphenyl)methyl]-3(R)-piperidinyl]-1,4,6,7-tetrahydro-3-(2-methyl-6-benzothiazolyl)-5H-pyrazolo[4,3-c]pyridine-5-carboxamide | 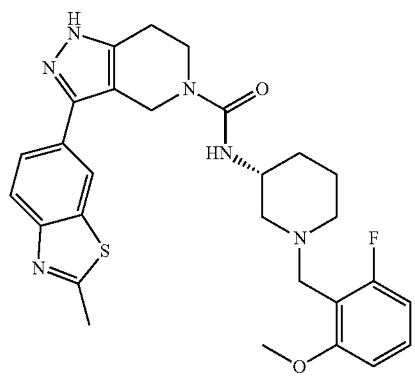 [SMILES: COc1cccc(F)c1CN1CCC[C@@H](NC(=O)N2CCc3[nH]nc(-c4ccc5nc(C)sc5c4)c3C2)C1] | 535.0 found, 535.2 required. |
| 172 | N-[1-[(2,6-difluorophenyl)methyl]-3(R)-piperidinyl]-1,4,6,7-tetrahydro-3-(2-methyl-6-benzothiazolyl)-5H-pyrazolo[4,3-c]pyridine-5-carboxamide | 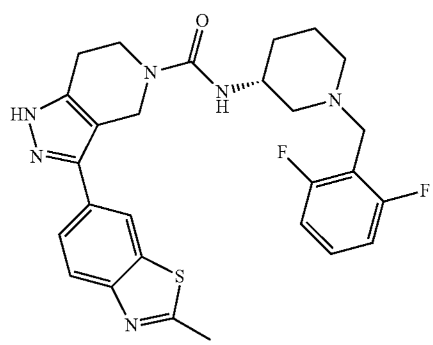 [SMILES: Cc1nc2ccc(-c3n[nH]c4c3CN(C(=O)N[C@@H]3CCCN(Cc5c(F)cccc5F)C3)CC4)cc2s1] | 523.0 found, 523.2 required. |
| 174 | N-[1-(benzo[b]thien-3-ylmethyl)-3(R)-piperidinyl]-1,4,6,7-tetrahydro-3-(2-methyl-6-benzothiazolyl)-5H-pyrazolo[4,3-c]pyridine-5-carboxamide | 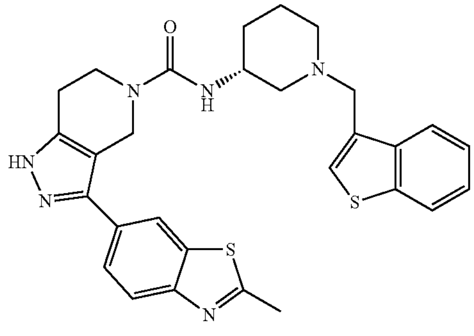 [SMILES: Cc1nc2ccc(-c3n[nH]c4c3CN(C(=O)N[C@@H]3CCCN(Cc5csc6ccccc56)C3)CC4)cc2s1] | 543.0 found, 543.2 required. |

-continued

| Cmpd ID No | Compound Name | Structure | LC-MS (M + H) |
|---|---|---|---|
| 176 | N-[1-(3-benzofuranylmethyl)-3(R)-piperidinyl]-1,4,6,7-tetrahydro-3-(2-methyl-6-benzothiazolyl)-5H-pyrazolo[4,3-c]pyridine-5-carboxamide | 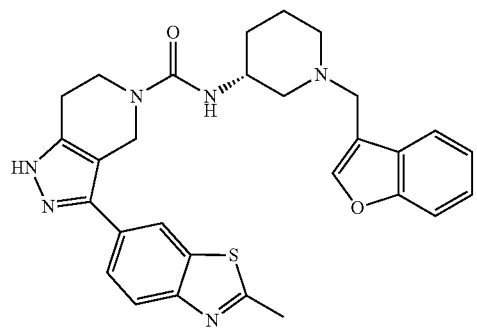 [SMILES: Cc1nc2ccc(-c3n[nH]c4c3CN(C(=O)N[C@@H]3CCCN(Cc5coc6ccccc56)C3)CC4)cc2s1] | 527.0 found, 527.2 required. |
| 180 | N-[1-[(2,6-difluorophenyl)methyl]-5,5-difluoro-3(R)-piperidinyl]-1,4,6,7-tetrahydro-3-(2-methyl-4-pyridinyl)-5H-pyrazolo[4,3-c]pyridine-5-carboxamide | 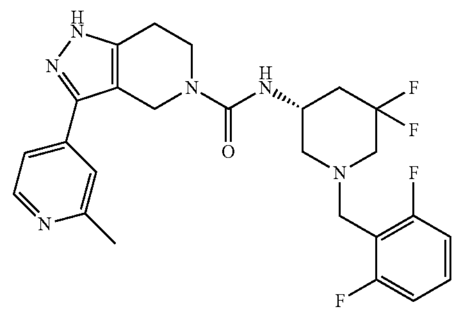 [SMILES: Cc1cc(-c2n[nH]c3c2CN(C(=O)N[C@H]2CN(Cc4c(F)cccc4F)CC(F)(F)C2)CC3)ccn1] | 503.2 found, 503.2 required. |
| 184 | N-[1-[(2,6-dimethylphenyl)methyl]-3(R)-piperidinyl]-1,4,6,7-tetrahydro-3-(2-methyl-5-benzothiazolyl)-5H-pyrazolo[4,3-c]pyridine-5-carboxamide | 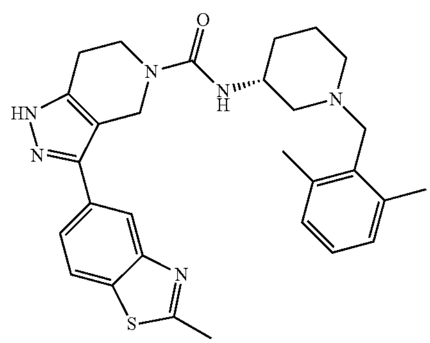 [SMILES: Cc1nc2cc(-c3n[nH]c4c3CN(C(=O)N[C@@H]3CCCN(Cc5c(C)cccc5C)C3)CC4)ccc2s1] | 515.0 found, 515.2 required. |
| 186 | (R)-N-(1-(2-fluoro-6-methoxybenzyl)piperidin-3-yl)-3-(2-methylbenzo[d]thiazol-5-yl)-6,7-dihydro-1H-pyrazolo[4,3-c]pyridine-5(4H)-carboxamide | 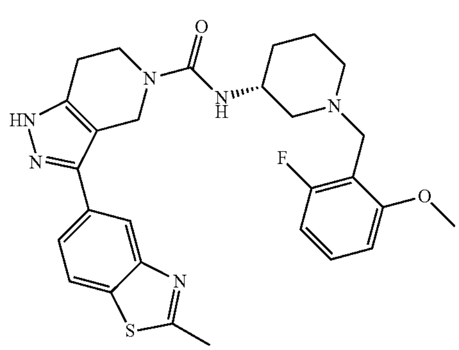 [SMILES: COc1cccc(F)c1CN1CCC[C@@H](NC(=O)N2CCc3[nH]nc(-c4ccc5sc(C)nc5c4)c3C2)C1] | 535.0 found, 535.2 required. |

-continued

| Cmpd ID No | Compound Name | Structure | LC-MS (M + H) |
|---|---|---|---|
| 188 | N-[1-[(2,6-difluorophenyl)methyl]-3(R)-piperidinyl]-1,4,6,7-tetrahydro-3-(2-methyl-5-benzothiazolyl)-5H-pyrazolo[4,3-c]pyridine-5-carboxamide | 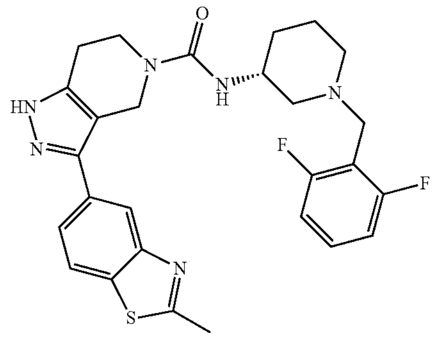 [SMILES: Cc1nc2cc(-c3n[nH]c4c3CN(C(=O)N[C@@H]3CCCN(Cc5c(F)cccc5F)C3)CC4)ccc2s1] | 523.0 found, 523.2 required. |
| 190 | 1,4,6,7-tetrahydro-3-(2-methyl-5-benzothiazolyl)-N-[1-(phenylmethyl)-3(R)-piperidinyl]-5H-pyrazolo[4,3-c]pyridine-5-carboxamide | 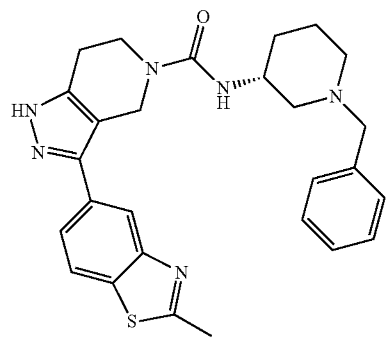 [SMILES: Cc1nc2cc(-c3n[nH]c4c3CN(C(=O)N[C@@H]3CCCN(Cc5ccccc5)C3)CC4)ccc2s1] | 487.0 found, 487.2 required. |
| 192 | 1,4,6,7-tetrahydro-3-(2-methyl-5-benzothiazolyl)-N-[1-(2-naphthalenylmethyl)-3(R)-piperidinyl]-5H-pyrazolo[4,3-c]pyridine-5-carboxamide | 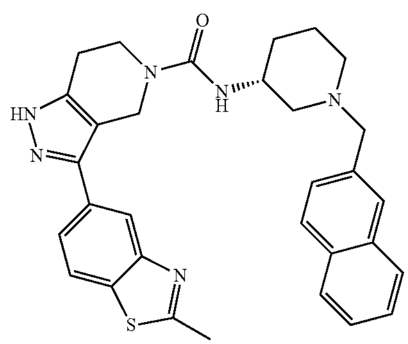 [SMILES: Cc1nc2cc(-c3n[nH]c4c3CN(C(=O)N[C@@H]3CCCN(Cc5ccc6ccccc6c5)C3)CC4)ccc2s1] | 537.0 found, 537.2 required. |
| 194 | N-[cis-1-[(2-fluoro-6-methoxyphenyl)methyl]-5-(trifluoromethyl)-3-piperidinyl]-1,4,6,7-tetrahydro-3-(2-methyl-4-pyridinyl)-5H-pyrazolo[4,3-c]pyridine-5-carboxamide | 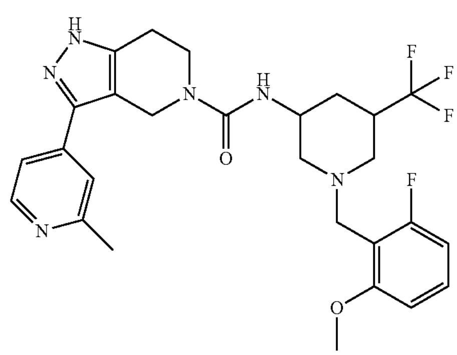 [SMILES: COc1cccc(F)c1CN1CC(NC(=O)N2CCc3[nH]nc(-c4ccnc(C)c4)c3C2)CC(C(F)(F)F)C1] | 547.2 found, 547.2 required. |

-continued

| Cmpd ID No | Compound Name | Structure | LC-MS (M + H) |
|---|---|---|---|
| 196 | N-[cis-1-[(2-fluoro-6-methoxyphenyl)methyl]-5-(trifluoromethyl)-3-piperidinyl]-1,4,6,7-tetrahydro-3-(2-methyl-4-pyridinyl)-5H-pyrazolo[4,3-c]pyridine-5-carboxamide | 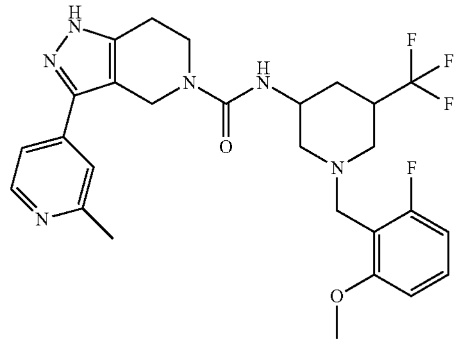 [SMILES: COc1cccc(F)c1CN1CC(NC(=O)N2CCc3[nH]nc(-c4ccnc(C)c4)c3C2)CC(C(F)(F)F)C1] | 547.2 found, 547.2 required. |

Synthesis of methyl 5-methylpiperidine-3-carboxylate

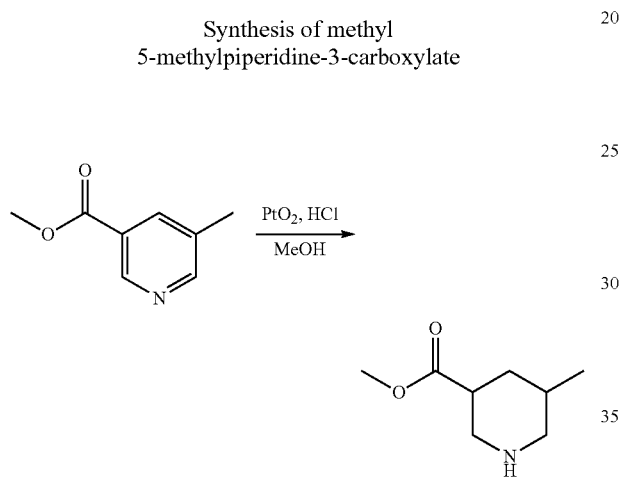

To methyl 5-methylnicotinate (2 g), PtO$_2$ (100 mg) was added. The reaction flask was put under vacuum, and 125 N HCl in methanol (15 mL) was added. The reaction was put under 40 psi hydrogen gas and shaked overnight. The reaction mixture was filtered through celite and concentrated under vacuo. The crude product was progressed to the next step without further purification.

Synthesis of methyl 1-(2-fluorobenzyl)-5-methylpiperidine-3-carboxylate

-continued

In a flask, dichloromethane (8 mL) and acetic acid (8 drops) was added to methyl 5-methylpiperidine-3-carboxylate (300 mg, 1.9 mmol) and 2-fluorobenzaldehyde (3.8 mmol). The reaction was stirred for 15 minutes. Sodium triacetoxyborohydride (1.6 g, 7.6 mmol) was added in one portion. The reaction was stirred overnight. The reaction was concentrated in vacuo and purified using prep LC/MS.

Synthesis of 1-(2-fluorobenzyl)-5-methylpiperidine-3-carboxylic acid

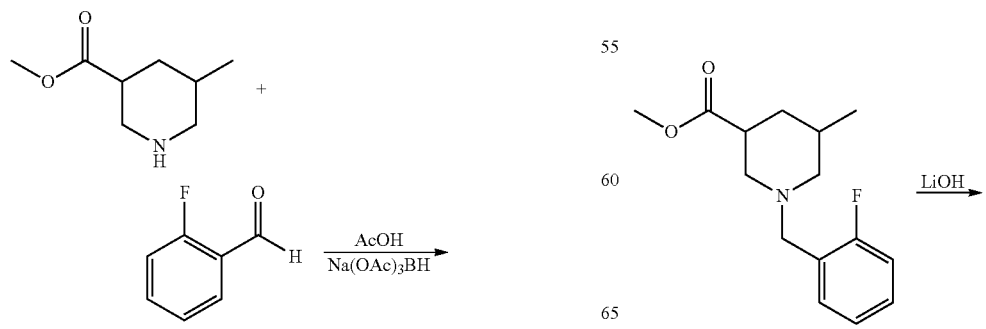

-continued

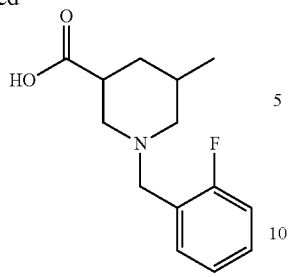

To methyl 1-(2-fluorobenzyl)-5-methylpiperidine-3-carboxylate (0.5 mmol), LiOH (1 mmol) in 2 ml THF/H₂O (1:1) was added. The reaction was stirred overnight. The solvent was removed under vacuo. The crude product was progressed to the next step without further purification.

Synthesis of N-(1-(2-fluorobenzyl)-5-methylpiperidin-3-yl)-3-(pyridin-4-yl)-6,7-dihydro-1H-pyrazolo[4,3-c]pyridine-5(4H)-carboxamide

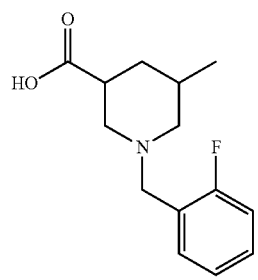

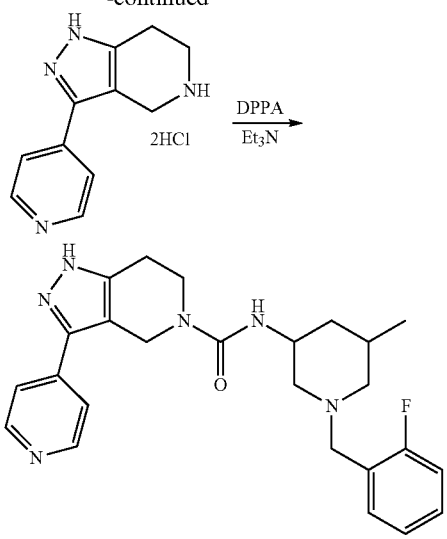

To 1-(2-fluorobenzyl)-5-methylpiperidine-3-carboxylic acid (1.6 mmol) in 5 ml ACN, DPPA (2.4 mmol) and Et₃N (4.8 mmol) were added. The reaction was stirred at 80° C. for 2 h, then 3-(pyridin-4-yl)-4,5,6,7-tetrahydro-1H-pyrazolo[4,3-c]pyridine HCl salt (1.6 mmol) was added. The reaction was stirred at 80° C. for another 2 h. The reaction mixture was filtered through celite and concentrated under vacuo. The crude product was purified using prep LC/MS.

The following compounds were prepared using a similar method:

| Cmpd ID No. | Compound Name | Structure | LC-MS (M + H) |
|---|---|---|---|
| 52 | N-[1-[(2-fluorophenyl)methyl]-5-methyl-3-piperidinyl]-1,4,6,7-tetrahydro-3-(4-pyridinyl)-5H-pyrazolo[4,3-c]pyridine-5-carboxamide | 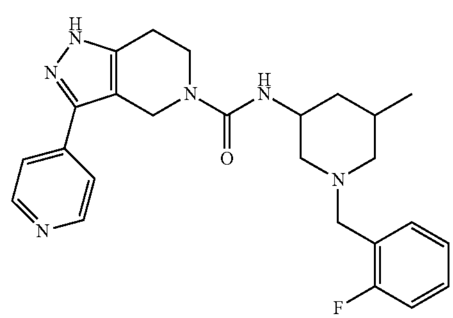 [SMILES: CC1CC(NC(=O)N2CCc3[nH]nc(-c4ccncc4)c3C2)CN(Cc2ccccc2F)C1] | 449.2 found, 449.2 required. |
| 89 | N-[1-[(2,6-difluorophenyl)methyl]-5-methyl-3-piperidinyl]-1,4,6,7-tetrahydro-3-(2-methyl-4-pyridinyl)-5H-pyrazolo[4,3-c]pyridine-5-carboxamide | 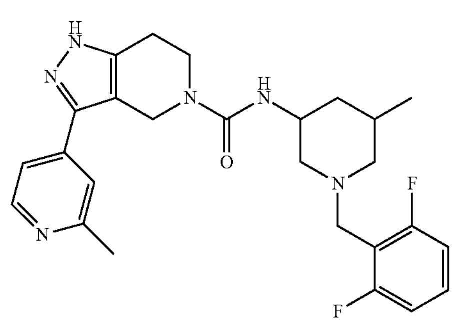 | 481.3 found, 481.3 required. |

-continued

| Cmpd ID No. | Compound Name | Structure | LC-MS (M + H) |
|---|---|---|---|
| 90 | N-[1-[(2-fluoro-6-methoxyphenyl)methyl]-5-methyl-3-piperidinyl]-1,4,6,7-tetrahydro-3-(2-methyl-4-pyridinyl)-5H-pyrazolo[4,3-c]pyridine-5-carboxamide | 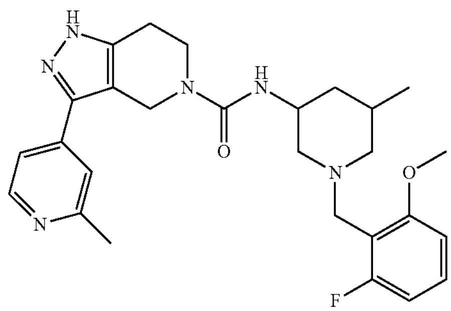 [SMILES: COc1cccc(F)c1CN1CC(C)CC(NC(=O)N2CCc3[nH]nc(-c4ccnc(C)c4)c3C2)C1] | 493.3 found, 493.3 required. |
| 91 | N-[1-[(2-chloro-6-fluorophenyl)methyl]-5-methyl-3-piperidinyl]-1,4,6,7-tetrahydro-3-(2-methyl-4-pyridinyl)-5H-pyrazolo[4,3-c]pyridine-5-carboxamide | 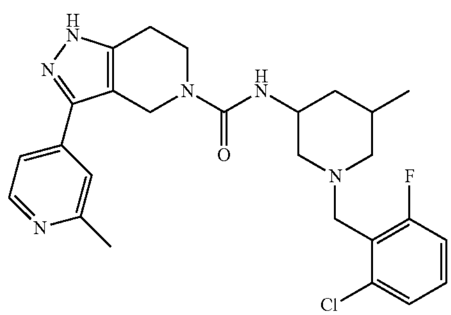 [SMILES: Cc1cc(-c2n[nH]c3c2CN(C(=O)NC2CC(C)CN(Cc4c(F)cccc4Cl)C2)CC3)ccn1] | 497.2 found, 497.2 required. |
| 94 | N-[1-[(2,6-dimethylphenyl)methyl]-5-methyl-3-piperidinyl]-1,4,6,7-tetrahydro-3-(2-methyl-4-pyridinyl)-5H-pyrazolo[4,3-c]pyridine-5-carboxamide | 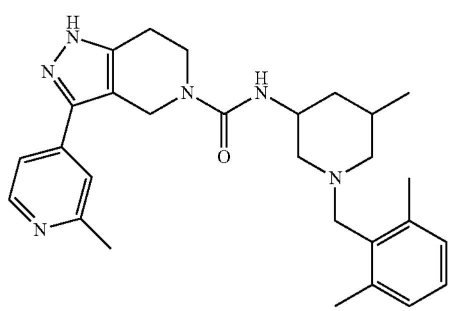 [SMILES: Cc1cc(-c2n[nH]c3c2CN(C(=O)NC2CC(C)CN(Cc4c(C)cccc4C)C2)CC3)ccn1] | 473.3 found, 473.3 |
| 95 | N-[1-[[2-fluoro-6-(trifluoromethyl)phenyl]methyl]-5-methyl-3-piperidinyl]-1,4,6,7-tetrahydro-3-(2-methyl-4-pyridinyl)-5H-pyrazolo[4,3-c]pyridine-5-carboxamide | 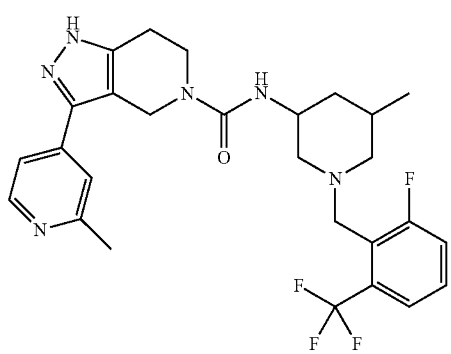 [SMILES: Cc1cc(-c2n[nH]c3c2CN(C(=O)NC2CC(C)CN(Cc4c(F)cccc4C(F)(F)F)C2)CC3)ccn1] | 531.2 found, 531.2 required. |

| Cmpd ID No. | Compound Name | Structure | LC-MS (M + H) |
|---|---|---|---|
| 96 | 1,4,6,7-tetrahydro-3-(2-methyl-4-pyridinyl)-N-[5-methyl-1-(3-quinolinylmethyl)-3-piperidinyl]-5H-pyrazolo[4,3-c]pyridine-5-carboxamide | 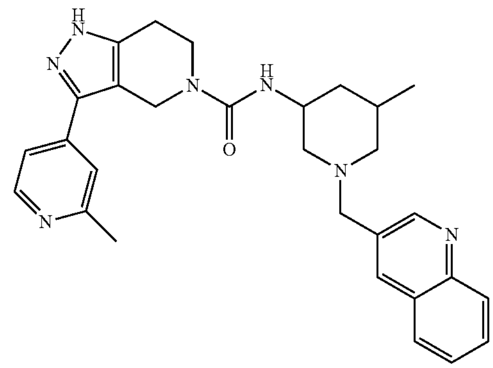 [SMILES: Cc1cc(-c2n[nH]c3c2CN(C(=O)NC2CC(C)CN(Cc4cnc5ccccc5c4)C2)CC3)ccn1] | 496.3 found, 496.3 required. |
| 101 | N-[1-(benzo[b]thien-3-ylmethyl)-5-methyl-3-piperidinyl]-1,4,6,7-tetrahydro-3-(2-methyl-4-pyridinyl)-5H-pyrazolo[4,3-c]pyridine-5-carboxamide | 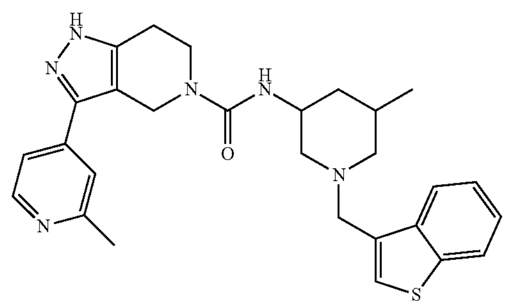 [SMILES: Cc1cc(-c2n[nH]c3c2CN(C(=O)NC2CC(C)CN(Cc4csc5ccccc45)C2)CC3)ccn1] | 501.2 found, 501.2 required. |
| 102 | 1,4,6,7-tetrahydro-N-[5-methyl-1-[(1-methyl-1H-indol-2-yl)methyl]-3-piperidinyl]-3-(2-methyl-4-pyridinyl)-5H-pyrazolo[4,3-c]pyridine-5-carboxamide | 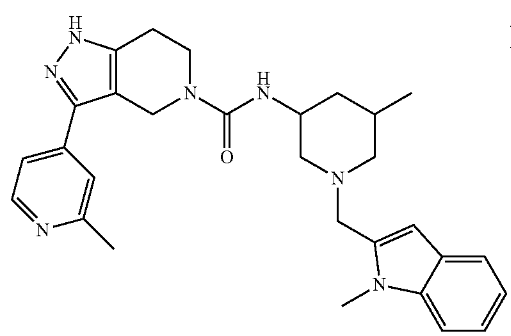 [SMILES: Cc1cc(-c2n[nH]c3c2CN(C(=O)NC2CC(C)CN(Cc4cc5ccccc5n4C)C2)CC3)ccn1] | 498.3 found, 498.3 required. |
| 103 | N-[1-[(2-chlorophenyl)methyl]-5-methyl-3-piperidinyl]-1,4,6,7-tetrahydro-3-(2-methyl-4-pyridinyl)-5H-pyrazolo[4,3-c]pyridine-5-carboxamide | 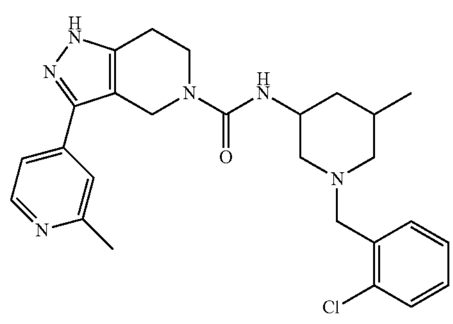 [SMILES: Cc1cc(-c2n[nH]c3c2CN(C(=O)NC2CC(C)CN(Cc4ccccc4Cl)C2)CC3)ccn1] | 479.2 found, 479.2 required. |

| Cmpd ID No. | Compound Name | Structure | LC-MS (M + H) |
|---|---|---|---|
| 104 | 1,4,6,7-tetrahydro-3-(2-methyl-4-pyridinyl)-N-[5-methyl-1-(2-quinolinylmethyl)-3-piperidinyl]-5H-pyrazolo[4,3-c]pyridine-5-carboxamide | 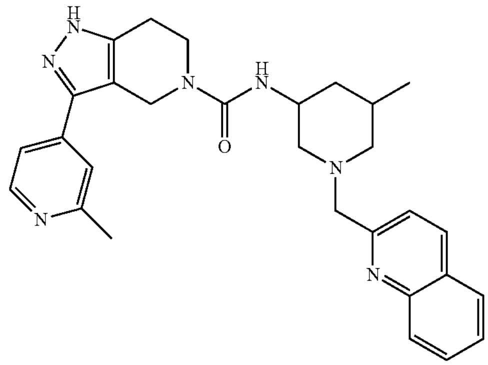 [SMILES: Cc1cc(-c2n[nH]c3c2CN(C(=O)NC2CC(C)CN(Cc4ccc5ccccc5n4)C2)CC3)ccn1] | 496.3 found, 496.3 required. |

Synthesis of 1-methyl-2-(2-nitrovinyl)benzene

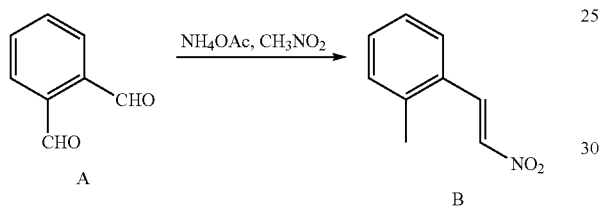

A mixture of A (10 ml, 86.5 mmol), NH$_4$OAc (4.26 g, 55.3 mmol, 0.64 equiv.) in 200 mL of CH$_3$NO$_2$ was stirred at 90° C. for 2 h and concentrated. The residue was diluted with CH$_2$Cl$_2$, washed with 1 N HCl, H$_2$O, brine, dried (MgSO$_4$) and concentrated. Chromatograph on silica gel (hexanes/EtOAc, 100/1) gave product B (14 g, 100% yield) as a yellow oil.

Synthesis of 1-methyl-3-nitro-4-o-tolylpyrrolidine

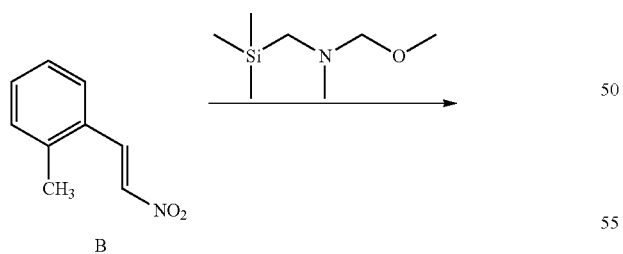

Into a round bottom flask containing B (4.80 g, 29.4 mmol), toluene (30 mL) and trifluoroacetic acid (0.25 mL, 3.3 mmol) heated at 33° C. was added 1-methoxy-N-methyl-N-((trimethylsilyl)methyl)methanamine (8.90 g, 44.1 mmol) dropwise, the rxn was stirred under an atmosphere of Nitrogen for 10 min and concentrated. Chromatograph on silica gel (hexanes/EtOAc, 1/1) gave product C (3.7 g, 57% yield).

Synthesis of 1-methyl-4-o-tolylpyrrolidin-3-amine

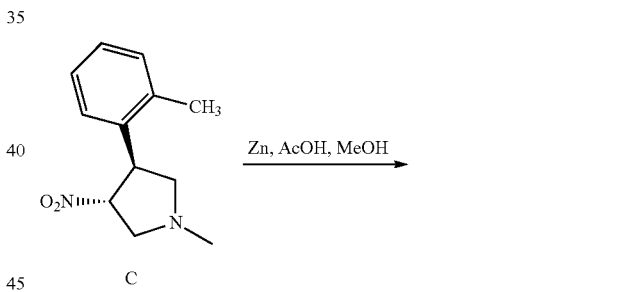

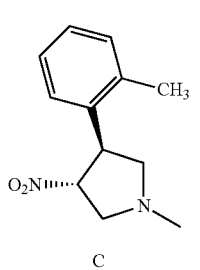

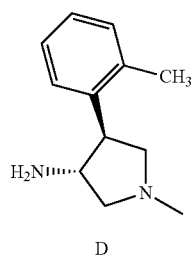

To a stirred solution of C (3.7 g, 17 mmol) in methanol (50 mL) was added Zinc (11.0 g, 168 mmol) and acetic acid (50 mL) The rxn was stirred for one day and concentrated. Chromatograph on silica gel (CH$_2$Cl$_2$/2 N ammonium in MeOH, 9/1) gave product D (3.17 g; 99% yield).

The following compounds were prepared using similar intermediates and methods:

| Cmpd ID No. | Compound Number | Structure | LC-MS (M + H) |
|---|---|---|---|
| 141 | 3-(4-fluorophenyl)-1,4,6,7-tetrahydro-N-[trans-1-methyl-4-(2-methylphenyl)-3-pyrrolidinyl]-5H-pyrazolo[4,3-c]pyridine-5-carboxamide (racemic) | 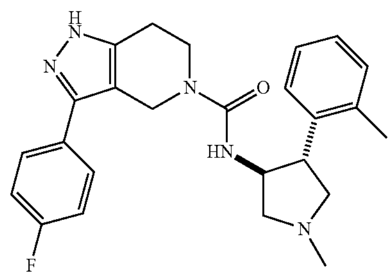 | 434.2 found, 434.2 required. |
| 143 | 1,4,6,7-tetrahydro-N-[trans-2-phenylcyclopentyl]-3-(4-pyridinyl)-5H-pyrazolo[4,3-c]pyridine-5-carboxamide (racemic) | 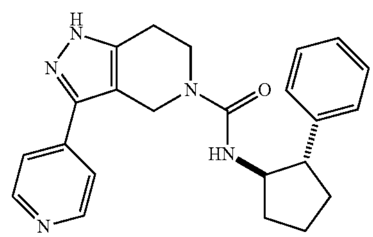 | 388.2 found, 388.2 required. |
| 145 | 3-(2,3-dihydro-5-benzofuranyl)-1,4,6,7-tetrahydro-N-[trans-1-methyl-4-(2-methylphenyl)-3-pyrrolidinyl]-5H-pyrazolo[4,3-c]pyridine-5-carboxamide (racemic) | 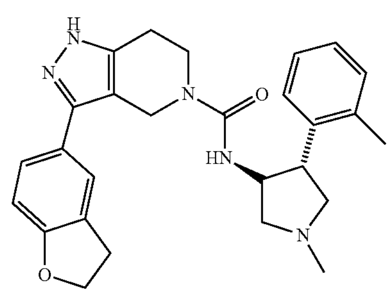 | 458.2 found, 458.2 required. |
| 147 | 3-(1-ethyl-1H-pyrazol-4-yl)-1,4,6,7-tetrahydro-N-ttrans-1-methyl-4-(2-methylphenyl)-3-pyrrolidinyl]-5H-pyrazolo[4,3-c]pyridine-5-carboxamide (racemic) | 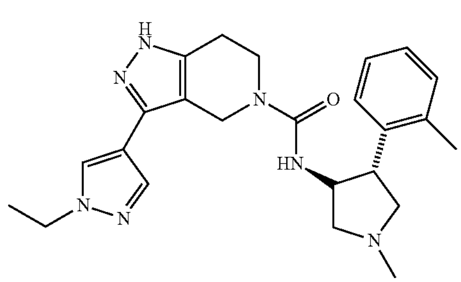 | 434.3 found, 434.3 required. |
| 149 | 1,4,6,7-tetrahydro-N-[trans-1-methyl-4-[2-(trifluoromethyl)phenyl]-3-pyrrolidinyl]-3-(4-pyridinyl)-5H-pyrazolo[4,3-c]pyridine-5-carboxamide (racemic) | 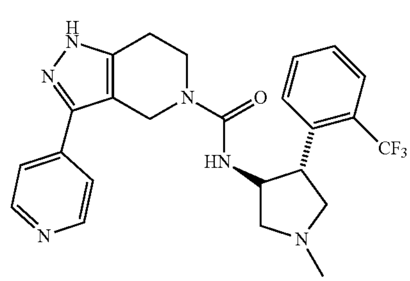 | 471.2 found, 471.2 required. |

| Cmpd ID No. | Compound Number | Structure | LC-MS (M + H) |
|---|---|---|---|
| 151 | 3-(4-fluorophenyl)-1,4,6,7-tetrahydro-N-[trans-1-methyl-4-[2-(trifluoromethyl)phenyl]-3-pyrrolidinyl]-5H-pyrazolo[4,3-c]pyridine-5-carboxamide (racemic) | 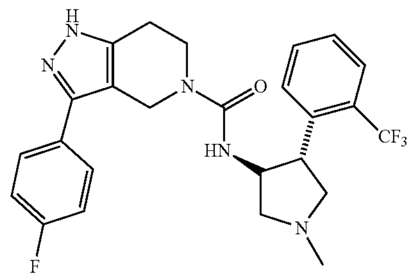 | 488.2 found, 488.2 required. |
| 153 | 3-(2,3-dihydro-5-benzofuranyl)-1,4,6,7-tetrahydro-N-[trans-1-methyl-4-[2-(trifluoromethyl)phenyl]-3-pyrrolidinyl]-5H-pyrazolo[4,3-c]pyridine-5-carboxamide (racemic) | 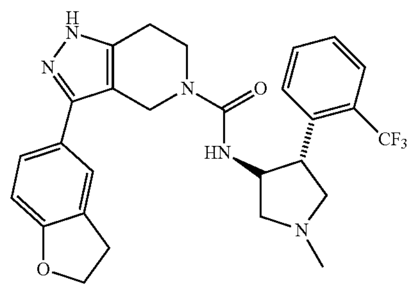 | 512.2 found, 512.2 required. |
| 155 | 3-(1-ethyl-1H-pyrazol-4-yl)-1,4,6,7-tetrahydro-N-[trans1-methyl-4-[2-(trifluoromethyl)phenyl]-3-pyrrolidinyl]-5H-pyrazolo[4,3-c]pyridine-5-carboxamide (racemic) | 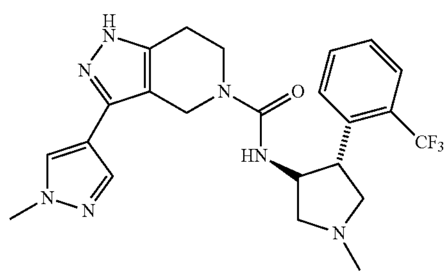 | 488.2 found, 488.2 required |
| 157 | 1,4,6,7-tetrahydro-N-[trans-4-(4-methylphenyl)-3-pyrrolidinyl]-3-(4-pyridinyl)-5H-pyrazolo[4,3-c]pyridine-5-carboxamide (racemic) | 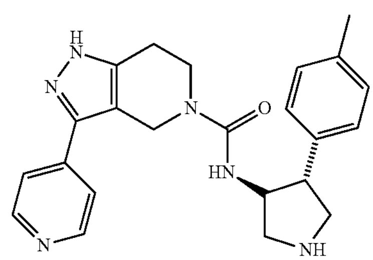 | 403.2 found, 403.2 required. |
| 159 | 1,4,6,7-tetrahydro-N-[trans-1-methyl-4-(4-methylphenyl)-3-pyrrolidinyl]-3-(4-pyridinyl)-5H-pyrazolo[4,3-c]pyridine-5-carboxamide (racemic) | 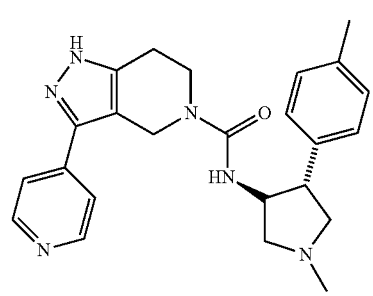 | 417.2 found, 417.2 required. |

| Cmpd ID No. | Compound Number | Structure | LC-MS (M + H) |
|---|---|---|---|
| 161 | N-[trans-1-ethyl-4-(4-methylphenyl)-3-pyrrolidinyl]-1,4,6,7-tetrahydro-3-(4-pyridinyl)-5H-pyrazolo[4,3-c]pyridine-5-carboxamide (racemic) | 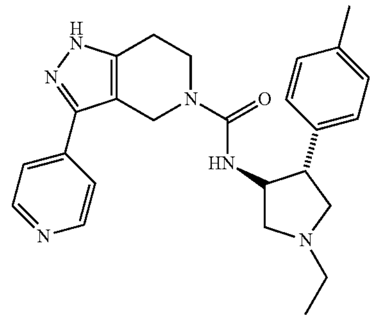 | 431.3 found, 431.2 required. |
| 163 | N-[trans-4-[1,1'-biphenyl]-2-yl-1-methyl-3-pyrrolidinyl]-1,4,6,7-tetrahydro-3-(4-pyridinyl)-5H-pyrazolo[4,3-C]pyridine-5-carboxamide (racemic) | 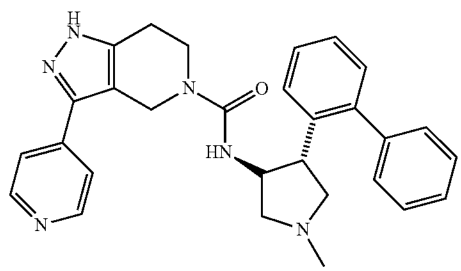 | 479.0 found, 479.2 required. |
| 165 | 1,1-dimethylethyl trans-3-[1,1'-biphenyl]-3-yl-4-[[[1,4,6,7-tetrahydro-3-(4-pyridinyl)-5H-pyrazolo[4,3-c]pyridin-5-yl]carbonyl]amino]-1-pyrrolidinecarboxylate (racemic) | 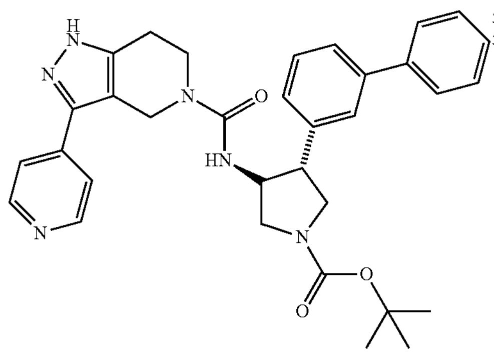 | 565.0 found, 565.3 required. |
| 167 | N-[trans-4-[1,1'-biphenyl]-3-yl-3-pyrrolidinyl]-1,4,6,7-tetrahydro-3-(4-pyridinyl)-5H-pyrazolo[4,3-c]pyridine-5-carboxamide (racemic) | 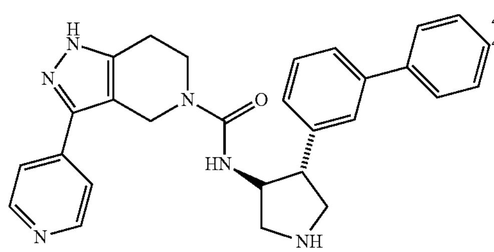 | 465.0 found, 465.2 required. |
| 169 | N-[trans-4-[1,1'-biphenyl]-3-yl-1-methyl-3-pyrrolidinyl]-1,4,6,7-tetrahydro-3-(4-pyridinyl)-5H-pyrazolo[4,3-c]pyridine-5-carboxamide (racemic) | 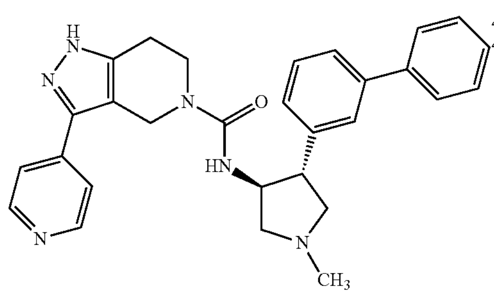 [SMILES: CN1C[C@@H](NC(=O)N2CCc3[nH]nc(-c4ccncc4)c3C2)[C@H](c2cccc(-c3ccccc3)c2)C1] | 479.0 found, 479.2 required. |

Scheme 5: General Synthetic Scheme for Fused-Cyclohexyl Series

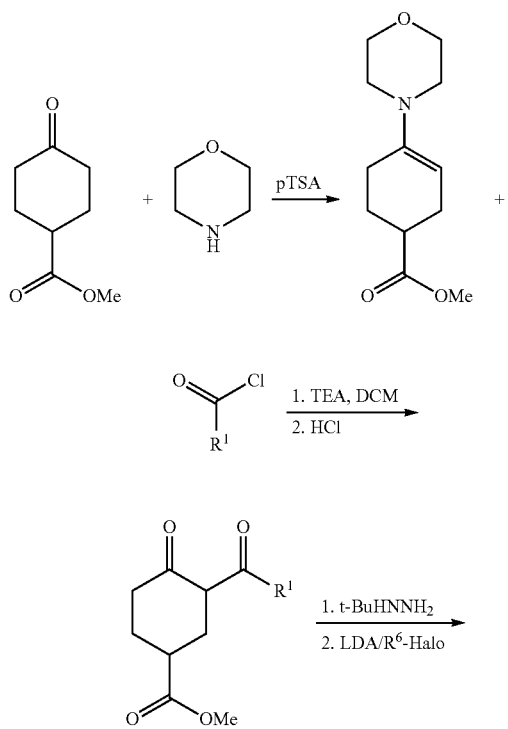

Synthesis of methyl 4-morpholinocyclohex-3-enecarboxylate

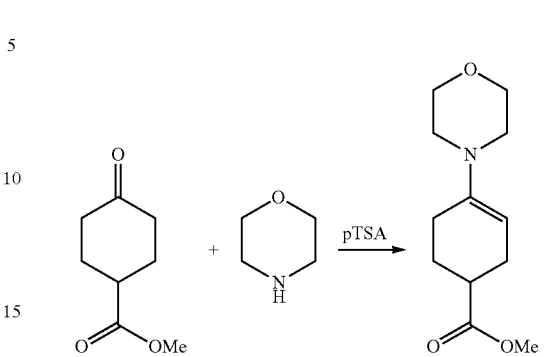

In a round-bottom flask equipped with a Dean-Starke trap, 15.6 g of methyl 4-oxocyclohexanecarboxylate, 0.1 mol), morpholine (9.63 mL, 0.11 mol) and p-toluenesulfonic acid (5 mg) in benzene (42.3 mL) was heated up to reflux. Water was removed and the reaction was continued at reflux for 8 hours. The reaction mixture was then cooled to room temperature and concentrated in vacuo to give crude product as a yellow oil (20 g), which was used for next step without further purification.

Synthesis of methyl 3-isonicotinoyl-4-oxocyclohexanecarboxylate

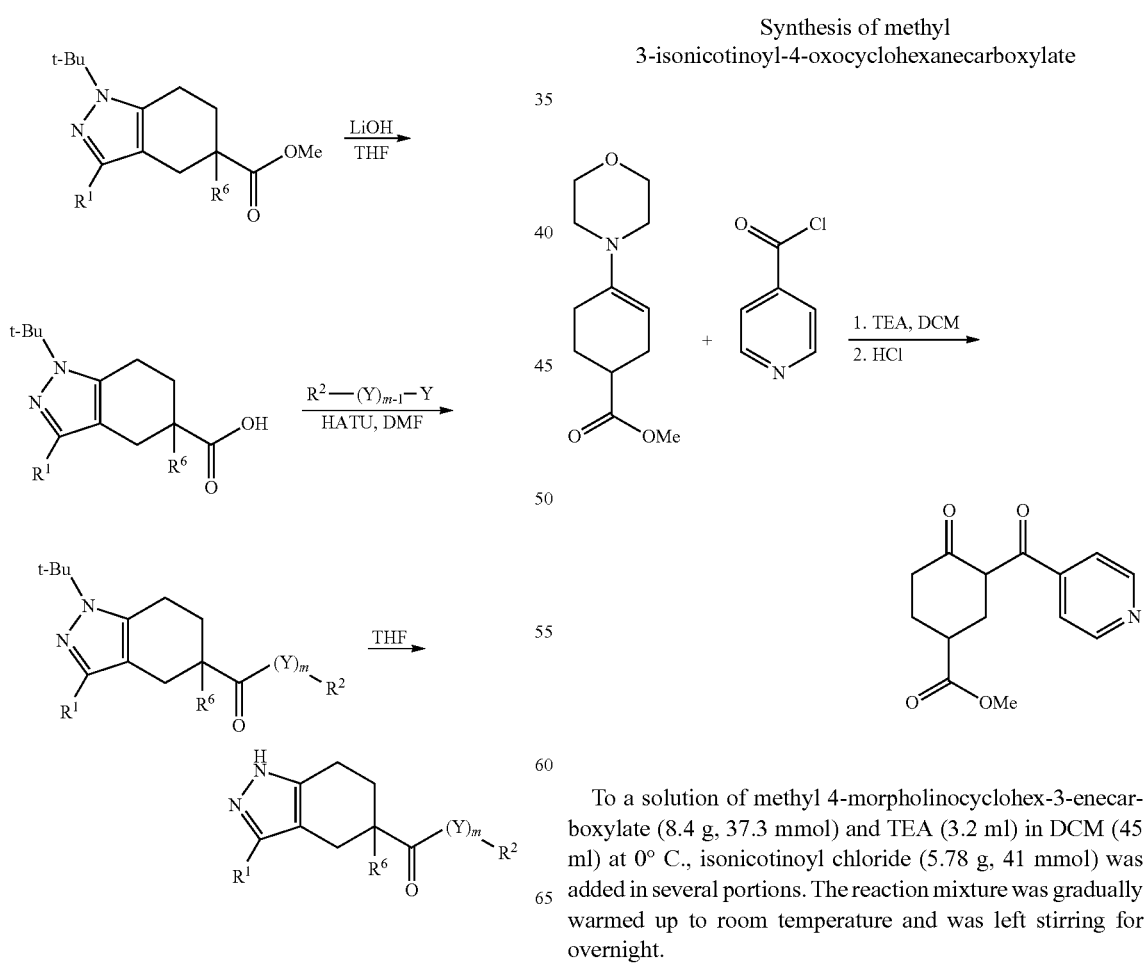

To a solution of methyl 4-morpholinocyclohex-3-enecarboxylate (8.4 g, 37.3 mmol) and TEA (3.2 ml) in DCM (45 ml) at 0° C., isonicotinoyl chloride (5.78 g, 41 mmol) was added in several portions. The reaction mixture was gradually warmed up to room temperature and was left stirring for overnight.

The reaction mixture was cooled to 0° C. and 1N HCl was added to adjust pH to be around 1. The reaction mixture was then stirred at room temperature for 2 hours. The organic layer was collected and was concentrated to give the desired product, which was used directly in the next step without further purification. LC-MS found 262.2 (M+H)

Synthesis of methyl 1-tert-butyl-3-(pyridin-4-yl)-4,5,6,7-tetrahydro-1H-indazole-5-carboxylate

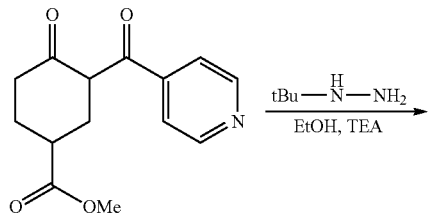

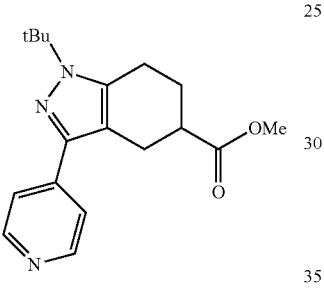

To a mixture of methyl 3-isonicotinoyl-4-oxocyclohexanecarboxylate (6.3 g, 24.3 mmol) and TEA (10.15 ml) in ethanol was added t-Butyl hydrazine (6.4 g, 73 mmol). The reaction mixture was stirred at room temperature for overnight. The solvent was removed under vacuum and DCM (50 ml) was added, followed by water (50 ml). The organic layer was collected, washed with brine and dried over sodium sulfate. Removal of solvent gave the desired product (6.5 g). LC-MS found 314.2 (M+H)

Synthesis of 1-tert-butyl-3-(pyridin-4-yl)-4,5,6,7-tetrahydro-1H-indazole-5-carboxylic acid

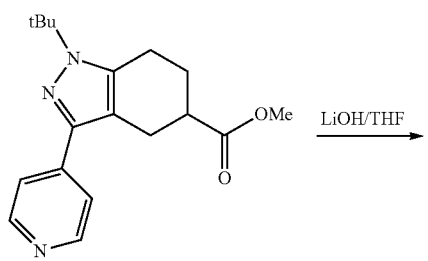

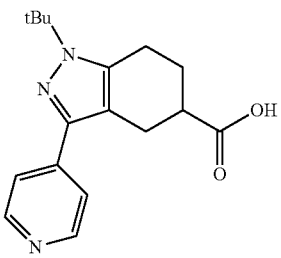

To methyl 1-tert-butyl-3-(pyridin-4-yl)-4,5,6,7-tetrahydro-1H-indazole-5-carboxylate (1.6 g, 5 mmol) in THF (20 mL) was added LiOH (1 M, 10 mL, 10 mmol) and the reaction was stirred at room temperature for overnight. After removal of THF, HCl (1 N) was added until pH 4 to 5. The product precipitated as white solid and was collected by filtration (1.2 g). LC-MS found 300.2 (M+H)

Synthesis of tert-butyl 3-(1-tert-butyl-3-(pyridin-4-yl)-4,5,6,7-tetrahydro-1H-indazole-5-carboxamido)-4-phenylpyrrolidine-1-carboxylate

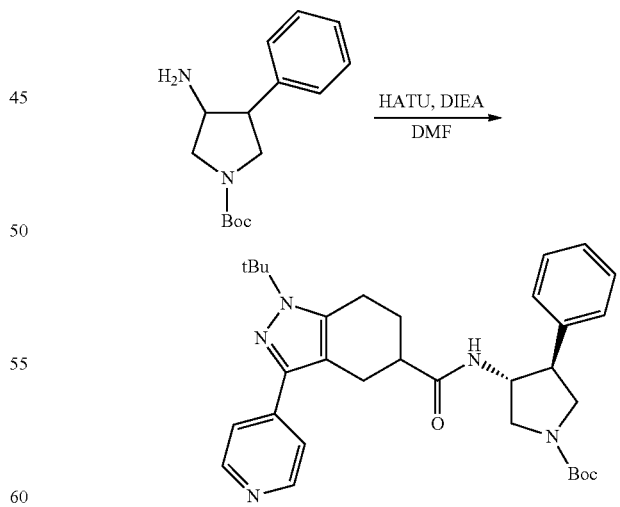

To 1-tert-butyl-3-(pyridin-4-yl)-4,5,6,7-tetrahydro-1H-indazole-5-carboxylic acid (30 mg, 0.1 mmol) in. DMF (1 mL) at 0° C. was added DIEA (35 uL, 0.2 mmol) and HATU (45.6 mg, 0.12 mmol). The reaction mixture was gradually warmed up to room temperature and stirred for overnight. Water was added and the precipitate was collected by filtration. The crude product was used directly in the next step. LC-MS found 544.3 (M+H)

Synthesis of N-((3R,4S)-4-phenylpyrrolidin-3-yl)-3-(pyridin-4-yl)-4,5,6,7-tetrahydro-1H-indazole-5-carboxamide

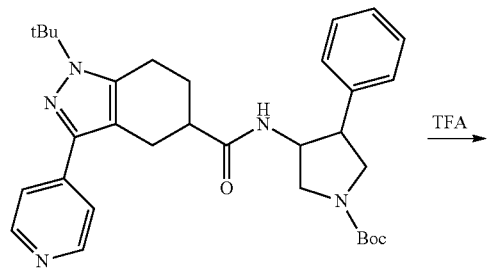

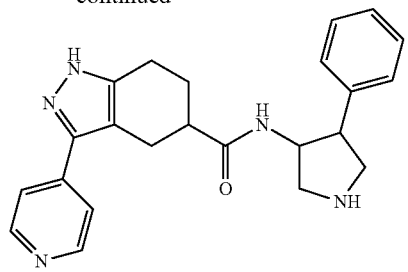

To the product from previous step, was added TFA (1 mL) and the reaction mixture was heated to 80 for 1 hour. After removal of the excess TFA, the crude material was purified using prep HPLC to give the two compounds with identical mass, presumably two diastereomers. LC-MS found 388.2 (M+H)

The following compounds were prepared using similar methods:

| Cmpd ID No. | Compound Name | Structure | LC-MS (M + H) |
|---|---|---|---|
| 2 | N-(4-chloro-1-ethyl-1H-pyrazol-3-yl)-4,5,6,7-tetrahydro-3-(4-pyridinyl)-1H-indazole-5-carboxamide | 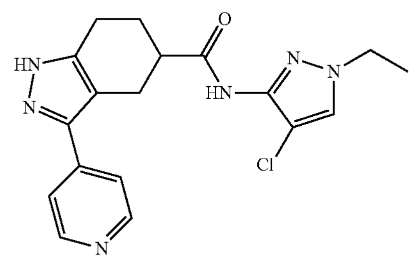 [SMILES: CCn1cc(Cl)c(NC(=O)C2CCc3[nH]nc(-c4ccncc4)c3C2)n1] | 371.4 found, 371.1 required. |
| 12 | 4,5,6,7-tetrahydro-N-(trans-4-phenyl-3-pyrrolidinyl)-3-(4-pyridinyl)-1H-indazole-5(R)-carboxamide (racemic) | 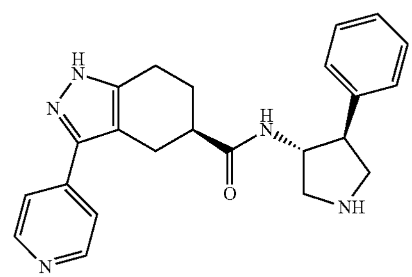 [SMILES: O=C(N[C@H]1CNC[C@@H]1c1ccccc1)[C@@H]1CCc2[nH]nc(-c3ccncc3)c2C1] | 388.3 found, 388.2 required. |
| 13 | 4,5,6,7-tetrahydro-N-(trans-4-phenyl-3-pyrrolidinyl)-3-(4-pyridinyl)-1H-indazole-5(S)-carboxamide (racemic) | 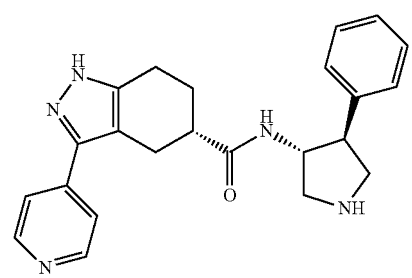 [SMILES: O=C(N[C@H]1CNC[C@@H]1c1ccccc1)[C@H]1CCc2[nH]nc(-c3ccncc3)c2C1] | 388.3 found, 388.2 required. |

| Cmpd ID No. | Compound Name | Structure | LC-MS (M + H) |
|---|---|---|---|
| 43 | 3-(6-benzothiazolyl)-4,5,6,7-tetrahydro-N-(trans-4-phenyl-3-pyrrolidinyl)-1H-indazole-5-carboxamide (racemic) | 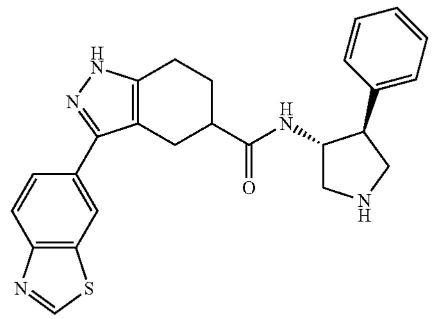 [SMILES: O=C(N[C@H]1CNC[C@@H]1c1ccccc1)C1CCc2[nH]nc(-c3ccc4ncsc4c3)c2C1] | 444.5 found, 444.2 required. |
| 44 | 3-(6-benzothiazolyl)-4,5,6,7-tetrahydro-N-(trans-4-phenyl-3-pyrrolidinyl)-1H-indazole-5(S)-carboxamide (racemic) | 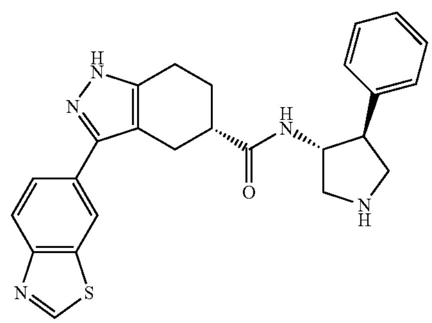 [SMILES: O=C(N[C@H]1CNC[C@@H]1c1ccccc1)[C@H]1CCc2[nH]nc(-c3ccc4ncsc4c3)c2C1] | 444.5 found, 444.2 required. |

Synthesis of methyl 1-tert-butyl-5-methyl-3-(pyridin-4-yl)-4,5,6,7-tetrahydro-1H-indazole-5-carboxylate

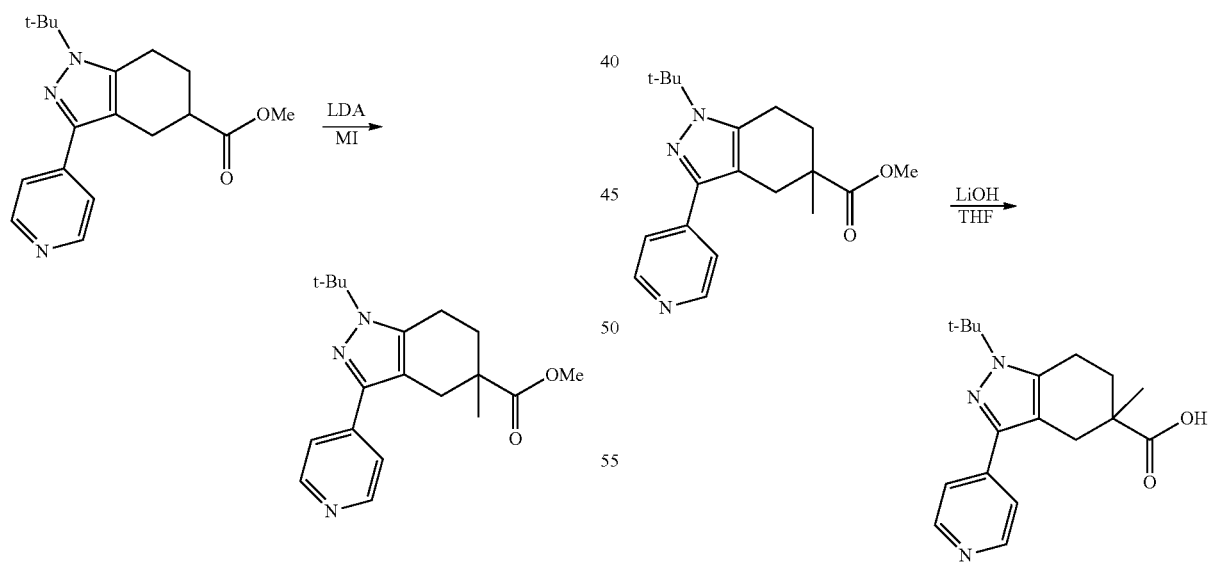

To methyl 1-tert-butyl-3-(pyridin-4-yl)-4,5,6,7-tetrahydro-1H-indazole-5-carboxylate (1.6 g, 5 mmol) in dry THF (20 mL) at −78° C. was added LDA (2 M, 5.5 mmol). The reaction temperature was increase to −25° C. for 1 h and was then cooled down to −78° C., MeI (16 mmol) was added and stood at r.t. for overnight, 20 ml water was added, most of the solvent was removed by distillation and the product was extracted with ethyl acetate, purified using silica chromatography (ethyl acetate/hexane) to give the desired product as yellow solid (1.1 g). LC-MS found 328.2 (M+H)

Synthesis of 1-tert-butyl-5-methyl-3-(pyridin-4-yl)-4,5,6,7-tetrahydro-1H-indazole-5-carboxylic acid To methyl 1-tert-butyl-5-methyl-3-(pyridin-4-yl)-4,5,6,7-tetrahydro-1H-indazole-5-carboxylate (1.1 g, 3.5 mmol) in THF (20 mL) was added LiOH (1 M, 10 mL, 10 mmol) and the reaction was heated at 80° C. for overnight. After removal of THF, HCl (1 N) was added until pH~4 to 5. The product precipitated as white solid and was collected by filtration (1.0 g). LC-MS found 314.19 (M+H)

Synthesis of tert-butyl 3-(1-tert-butyl-5-methyl-3-(pyridin-4-yl)-4,5,6,7-tetrahydro-1H-indazole-5-carboxamido)-4-phenylpyrrolidine-1-carboxylate

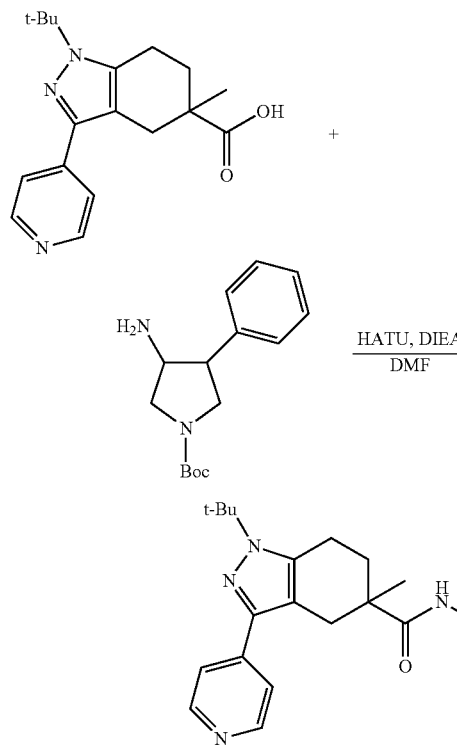

To 1-tert-butyl-5-methyl-3-(pyridin-4-yl)-4,5,6,7-tetrahydro-1H-indazole-5-carboxylic acid (32 mg, 0.1 mmol) in DMF (1 mL) at 0° C. was added DIEA (35 uL, 0.2 mmol) and HATU (45.6 mg, 0.12 mmol). The reaction mixture was gradually warmed up to room temperature and stirred for overnight. Water was added and the precipitate was collected by filtration. The crude product was used directly in the next step. LC-MS found 558.3 (M+H)

Synthesis of 5-methyl-N-(4-phenylpyrrolidin-3-yl)-3-(pyridin-4-yl)-4,5,6,7-tetrahydro-1H-indazole-5-carboxamide

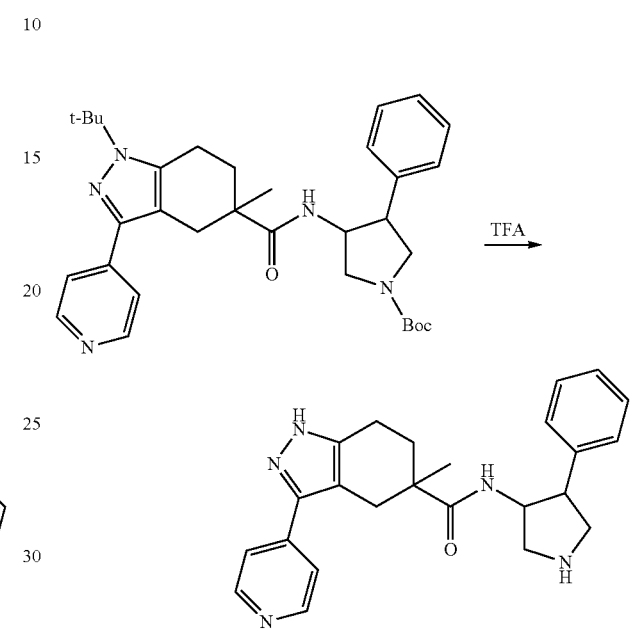

To the product from previous step, was added TFA (1 mL) and the reaction mixture was heated to 80 for 1 hour. After removal of the excess TFA, the crude material was purified using prep HPLC to give the desired product (20 mg). LC-MS found 402.22 (M+H).

The following compounds were prepared using similar methods:

| Cmpd ID No. | Compound Name | Structure | LC-MS (M + H) |
|---|---|---|---|
| 1 | N-(4-chloro-1-ethyl-1H-pyrazol-3-yl)-4,5,6,7-tetrahydro-5-methyl-3-(4-pyridinyl)-1H-indazole-5-carboxamide | 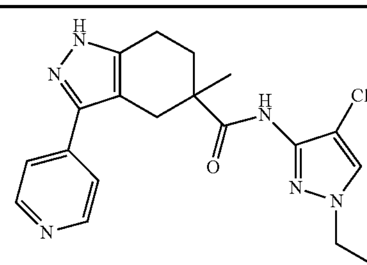 | 385.3 found, 385.1 required. |
| 4 | 4,5,6,7-tetrahydro-5-methyl-N-(trans-4-phenyl-3-pyrrolidinyl)-3-(4-pyridinyl)-1H-indazole-5-carboxamide (racemic) | 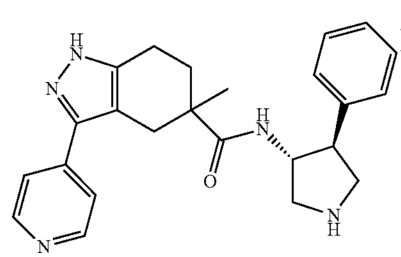 | 402.2 found, 402.2 required. |

-continued

| Cmpd ID No. | Compound Name | Structure | LC-MS (M + H) |
|---|---|---|---|
| 14 | 4,5,6,7-tetrahydro-5-methyl-3-(4-pyridinyl)-N-[2-(3-pyridinylmethoxy)phenyl]-1H-indazole-5-carboxamide | 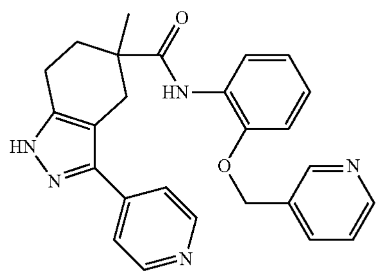 [SMILES: CC1(C(=O)Nc2ccccc2OCc2cccnc2)CCc2[nH]nc(-c3ccncc3)c2C1] | 440.3 found, 440.2 required. |
| 15 | 4,5,6,7-tetrahydro-N-(2-methoxyphenyl)-5-methyl-3-(4-pyridinyl)-1H-indazole-5-carboxamide | 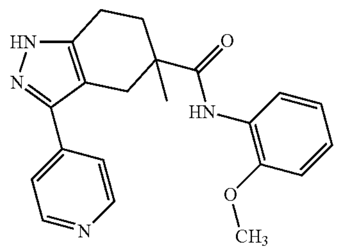 [SMILES: COc1ccccc1NC(=O)C1(C)CCc2[nH]nc(-c3ccncc3)c2C1] | 363.3 found, 363.2 required. |
| 16 | 4,5,6,7-tetrahydro-N-[1-(1H-imidazoL-1-ylmethyl)-2-methylpropyl]-5-methyl-3-(4-pyridinyl)-1H-indazole-5-carboxamide | 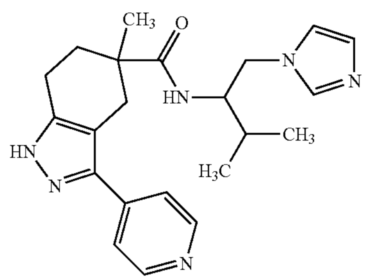 [SMILES: CC(C)C(Cn1ccnc1)NC(=O)C1(C)CCc2[nH]nc(-c3ccncc3)c2C1] | 393.4 found, 393.2 required. |
| 17 | 4,5,6,7-tetrahydro-5-methyl-3-(4-pyridinyl)-N-[2-(trifluoromethoxy)phenyl]-1H-indazole-5-carboxamide | 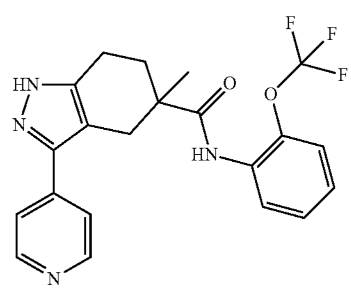 [SMILES: CC1(C(=O)Nc2ccccc2OC(F)(F)F)CCc2[nH]nc(-c3ccncc3)c2C1] | 417.2 found, 417.1 required. |
| 18 | 4,5,6,7-tetrahydro-N-(2-methoxy-3-pyridinyl)-5-methyl-3-(4-pyridinyl)-1H-indazole-5-carboxamide | 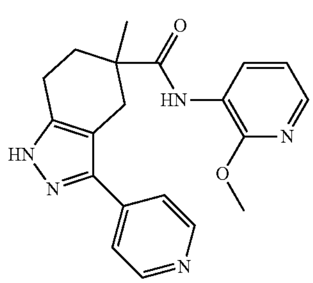 [SMILES: COc1ncccc1NC(=O)C1(C)CCc2[nH]nc(-c3ccncc3)c2C1] | 364.3 found, 364.2 required. |

-continued

| Cmpd ID No. | Compound Name | Structure | LC-MS (M + H) |
|---|---|---|---|
| 19 | N-[2-[2-(dimethylamino)-ethoxy]phenyl]-4,5,6,7-tetrahydro-5-methyl-3-(4-pyridinyl)-1H-indazole-5-carboxamide | 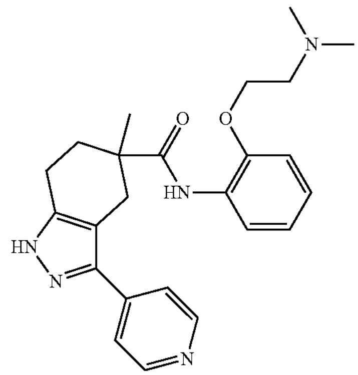 [SMILES: CN(C)CCOc1ccccc1NC(=O)C1(C)CCc2[nH]nc(-c3ccncc3)c2C1] | 420.3 found, 420.2 required. |
| 20 | 4,5,6,7-tetrahydro-5-methyl-3-(4-pyridinyl)-N-[2[(tetrahydro-2-furanyl)-methoxy]phenyl]-1H-indazole-5-carboxamide | 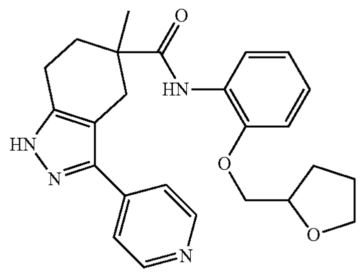 [SMILES: CC1(C(=O)Nc2ccccc2OCC2CCCO2)CCc2[nH]nc(-c3ccncc3)c2C1] | 433.2 found, 433.2 required. |
| 21 | 4,5,6,7-tetrahydro-5-methyl-N-[2-[2-(1-piperidinyl)ethoxy]-phenyl]-3-(4-pyridinyl)-1H-indazole-5-carboxamide | 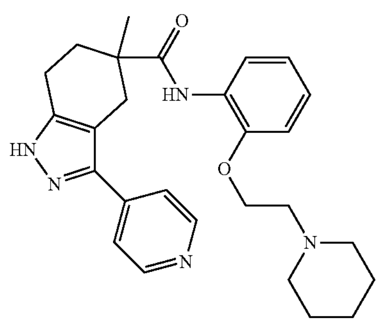 [SMILES: CC1(C(=O)Nc2ccccc2OCCN2CCCCC2)CCc2[nH]nc(-c3ccncc3)c2C1] | 460.3 found, 460.3 required. |

Synthesis of Tert-butyl 3-(imidazo[1,2-a]pyridin-6-yl)-6,7-dihydro-1H-pyrazolo[4,3-c]pyridine-5(4H)-carboxylate

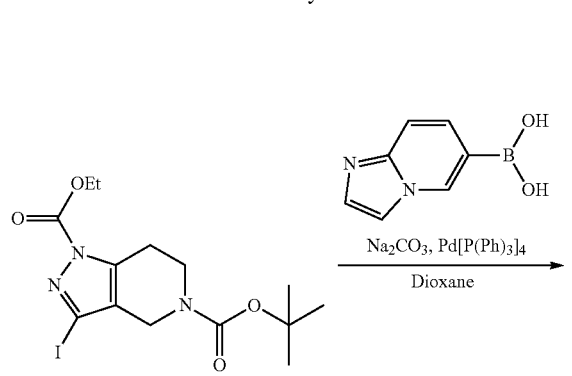

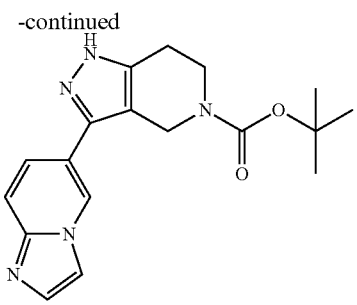

5-Tert-butyl 1-ethyl 3-iodo-6,7-dihydro-1H-pyrazolo[4,3-c]pyridine-1,5(4H)-dicarboxylate (1 g, 0.002 mol), (synthesized from patent procedure: WO 2004014374 A1) was added to a vial containing imidazo[1,2-a]pyridin-6-ylboronic acid (0.577 g, 0.00356 mol) and tetrakis(triphenylphosphine)palladium (0.1372 g, 0.00011 mol). After purging the vial with nitrogen gas, dioxane: ethanol: water solution (7:3:2, 7.125 mL) and 2M sodium carbonate (0.007125 mol) was added to the vial respectively. The reaction mixture was stirred and was heated in the microwave at 160° C. for 20 min. Upon completion, the mixture was concentrated under vacuo. The residue was dissolved in ethyl acetate, and filtered through a fitted reservoir. The ethyl acetate layer was concentrated and columned using flash chromatography (0-100% ethyl acetate in hexane and 0-20% methanol in dichloromethane. The remaining residue that didn't dissolve in ethyl acetate was dissolved in methanol and filtered through a fritted reservoir. The methanol layer was concentrated and submitted for reverse phase prep. Pure product (quantitative yield) was recovered.

Synthesis of 3-(imidazo[1,2-a]pyridin-6-yl)-4,5,6,7-tetrahydro-1H-pyrazolo[4,3-c]pyridine

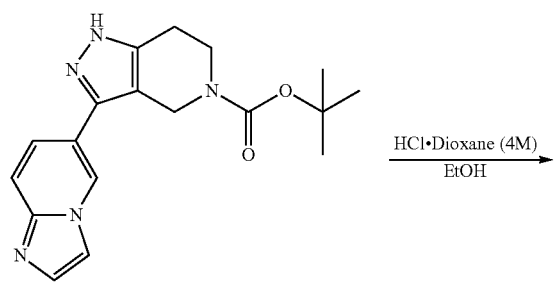

In a flask, ethanol (1 mL) was added to tert-butyl 3-(imidazo[1,2-a]pyridin-6-yl)-6,7-dihydro-1H-pyrazolo[4,3-c]pyridine-5(4H)-carboxylate (0.750 g, 0.0022 mol). Hydrochloric acid in dioxane (4 M, 8 mL) was added to the reaction and was stirred for 30 minutes. Ethanol (5 mL) was added to the reaction, and the resulting solution was concentrated in vacuo. The crude product was progressed to the next step without further purification.

Synthesis of 8-tert-butyl 2-methyl 3-oxo-8-azabicyclo[3.2.1]octane-2,8-dicarboxylate

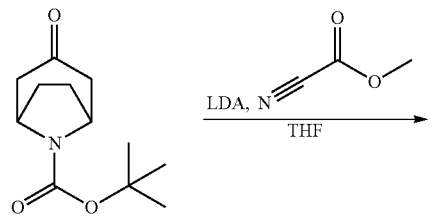

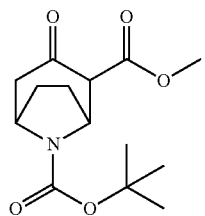

Tetrahydrofuran (55.5 mL) was added to a flask containing tert-butyl 3-oxo-8-azabicyclo[3.2.1]octane-8-carboxylate (10 g, 0.0444 mol). At −78° C., lithium diisopropylamide (24.4 mL, 0.0488 mol) was added dropwise to the reaction. The reaction was allowed to stir for 1 hr, then methyl cyanoformate (4.226 mL, 0.05326 mol) was added dropwise at −78° C. The reaction was let to stir for 5 hrs at room temperature. The reaction was quenched using saturated ammonium chloride solution. Some of the tetrahydrofuran was removed in vacuo. The remaining THF and ammonium chloride mixture was extracted using ethyl acetate three times. The combined ethyl acetate layers were washed with water and dried over sodium sulfate. The solution was filtered, was concentrated, and was purified using flash chromatography (0-100% ethyl acetate in hexane). A yellow oil was recovered (88% yield).

Synthesis of 8-tert-butyl 2-methyl 3-hydroxy-8-azabicyclo[3.2.1]octane-2,8-dicarboxylate

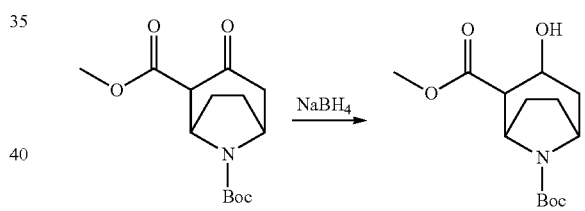

Sodium borohydride (211 mg, 5.56 mmol) was added to a solution of (1R,5S)-8-tort-butyl 2-methyl 3-oxo-8-azabicyclo[3.2.1]octane-2,8-dicarboxylate (1.5 g, 5.29 mmol) in methanol (20 ml) at 0° C. The reaction mixture was warmed to room temperature and stilted for 4 h. EtOAc (100 ml) was added and washed with brine solution (20 ml). The organic layer was separated, and dried over sodium sulfate. The solution was filtered, concentrated, and used in the next step without further purification.

Synthesis of -8-tert-butyl 2-methyl 3-(methylsulfonyloxy)-8-azabicyclo[3.2.1]octane-2,8-dicarboxylate

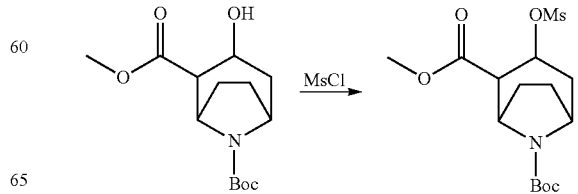

Methanesulfonyl chloride (1.2 g, 10.6 mmol) was added dropwise to a solution of 8-tert-butyl 2-methyl 3-hydroxy-8-azabicyclo[3.2.1]octane-2,8-dicarboxylate (5.29 mmol) and diisopropylethylamine (3.42 g, 26.5 mmol) in dichloromethane (25 ml) at 0° C. The reaction mixture was warmed to room temperature and stirred for 16 h. Dichloromethane (50 ml) was added and washed with saturated sodium bicarbonate solution (50 ml) and brine solution (50 ml). The organic layer was separated, and dried over sodium sulfate. The solution was filtered, concentrated, and used in the next step without further purification.

Synthesis of 8-tert-butyl 2-methyl 8-azabicyclo[3.2.1]oct-2-ene-2,8-dicarboxylate

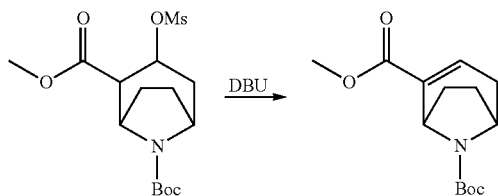

1,8-Diazabicyclo[5.4.0]undec-7-ene (8.05 g, 53 mmol) was added into a solution of 8-tert-butyl 2-methyl 3-(methylsulfonyloxy)-8-azabicyclo[3.2.1]octane-2,8-dicarboxylate (5.29 mmol) in DMF at room temperature and the reaction solution was heated at 100° C. for 16 h. The resulting solution was concentrated and purified using flash chromatography (0-60% ethyl acetate in hexane) to give the titled compound (905 mg, yield 64% for three steps).

Synthesis of 8-tert-butyl 2-methyl 8-azabicyclo[3.2.1]octane-2,8-dicarboxylate

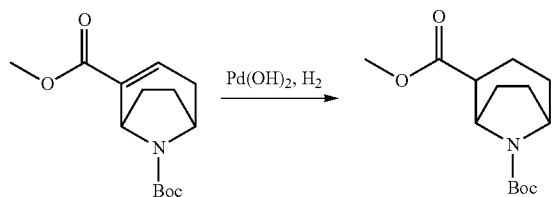 [SMILES: COC(=O)C1=CCC2CCC1N2C(=O)OC(C)(C)C ; COC(=O)C1CCC2CCC1N2C(=O)OC(C)(C)C]

8-tert-butyl 2-methyl 8-azabicyclo[3.2.1]oct-2-ene-2,8-dicarboxylate (880 mg, 3.29 mmol) was dissolved in methanol (15 ml). The reaction flask was flushed with argon and 5% palladium hydroxide on carbon (88 mg) was added. The flask was degassed under vacuum. Hydrogen gas is then added via balloon. The reaction is stirred under hydrogen atmosphere for 16 hours. The reaction was then filtered through celite, and concentrated to give the titled compound (840 mg).

Synthesis of 8-(tert-butoxycarbonyl)-8-azabicyclo[3.2.1]octane-2-carboxylic acid

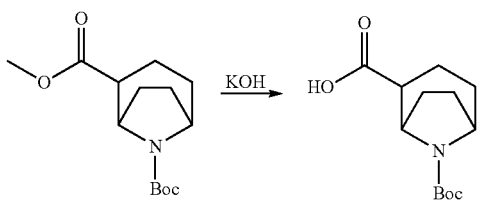

Potassium hydroxide (0.44 g, 7.8 mmol) was added into a solution of 8-tert-butyl 2-methyl 8-azabicyclo[3.2.1]octane-2,8-dicarboxylate (840 mg, 3.12 mmol) in methanol (2 ml) and water (2 ml). The reaction solution was stirred at room temperature for 16 h, and 1.0 N HCl solution was added dropwise to adjust pH to 4. The resulting solution was extracted with EtOAc (50 ml, twice). The combined organic layers were washed with water (10 ml). The organic layer was separated, and dried over sodium sulfate. The solution was filtered, concentrated, and used in the next step without further purification.

Synthesis of tert-butyl 2-isocyanato-8-azabicyclo[3.2.1]octane-8-carboxylate

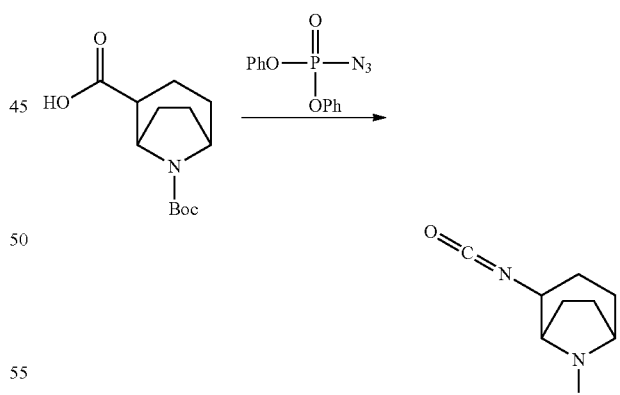

Diphenylphosphoryl azide (890 mg, 3.23 mmol) was added into a solution of 8-(tert-butoxycarbonyl)-8-azabicyclo[3.2.1]octane-2-carboxylic acid (0.75 g, 2.94 mmol) and triethylamine (595 mg, 5.88 mmol) in toluene (10 ml). The reaction solution was heated at 100° C. for 5 h. EtOAc (50 ml) was added and the resulting solution was washed with water (10 ml). The organic layer was separated, and dried over sodium sulfate. The solution was filtered, concentrated, and used in the next step without further purification.

Synthesis of tert-butyl 2-(3-(1-methyl-1H-indazol-5-yl)-4,5,6,7-tetrahydro-1H-pyrazolo[4,3-c]pyridine-5-carboxamido)-8-azabicyclo[3.2.1]octane-8-carboxylate

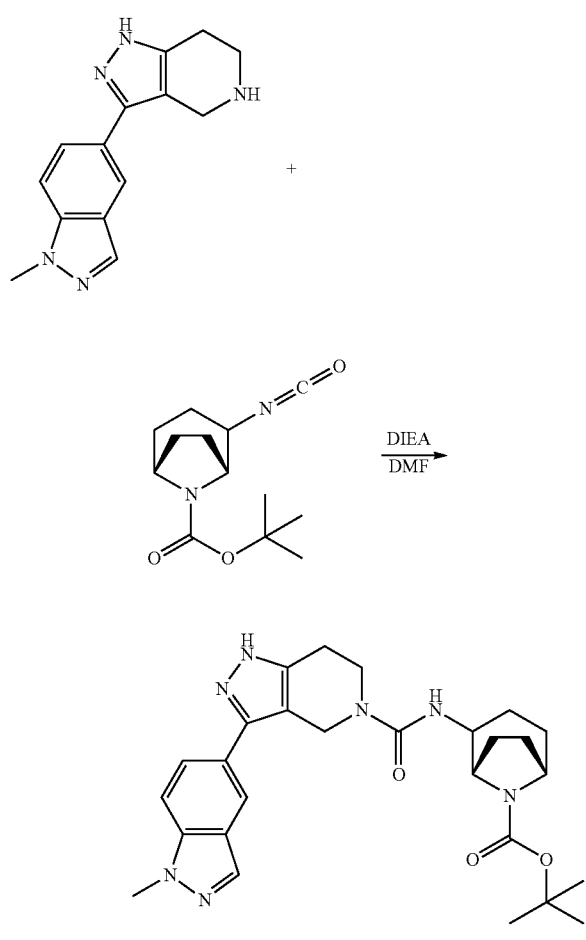

Dimethylformamide (0.7133 mL) was added to a flask containing 3-(1-methyl-1H-indazol-5-yl)-4,5,6,7-tetrahydro-1H-pyrazolo[4,3-c]pyridine (54.2 mg, 0.214 mmol) and tert-butyl 2-isocyanato-8-azabicyclo[3.2.1]octane-8-carboxylate (45 mg, 0.178 mmol). Diisopropylethylamine (0.1474 mL, 0.856 mmoL) was added to the flask, and the reaction was allowed to stir at 70° C. for 16 hrs. The reaction was quenched with water and was extracted using ethyl acetate three times. The ethyl acetate layers were combined, dried over sodium sulfate, filtered, and concentrated. The crude was purified using flash chromatography (methanol in dichloromethane 0-20%).

Synthesis of N-8-azabicyclo[3.2.1]octan-2-yl)-3-(1-methyl-1H-indazol-5-yl)-6,7-dihydro-1H-pyrazolo[4,3-c]pyridine-5(4H)-carboxamide

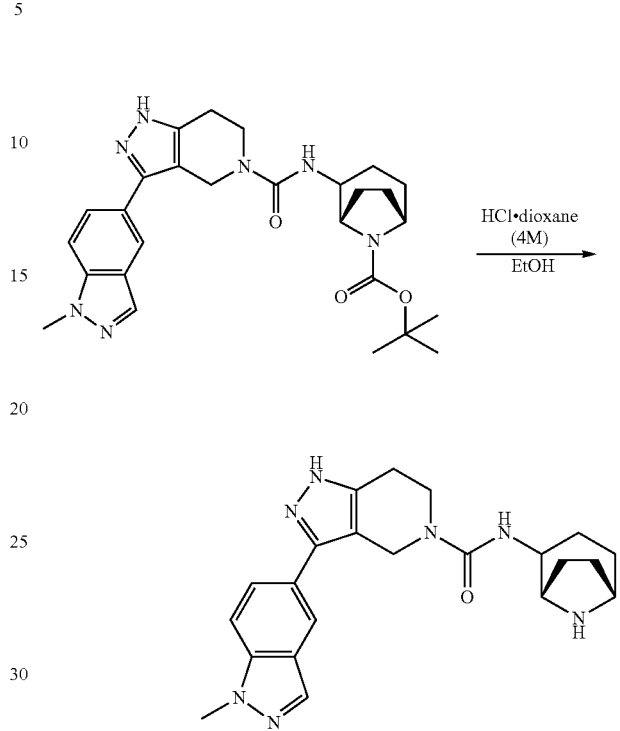

In a flask, ethanol (1 mL) was added to tert-butyl 2-(3-(1-methyl-1H-indazol-5-yl)-4,5,6,7-tetrahydro-1H-pyrazolo[4,3-c]pyridine-5-carboxamido)-8-azabicyclo[3.2.1]octane-8-carboxylate (69.7 mg, 0.138 mmol). Hydrochloric acid in dioxane (4M, 8 mL) was added to the reaction and was stirred for 30 minutes. Ethanol (5 mL) was added to the reaction, and the resulting solution was concentrated in vacuo. The crude product was progressed to the next step without further purification.

Synthesis of N-(8-(2-fluorobenzyl)-8-azabicyclo[3.2.1]octan-2-yl)-3-(1-methyl-1H-indazol-5-yl)-6,7-dihydro-1H-pyrazolo[4,3-c]pyridine-5(4H)-carboxamide

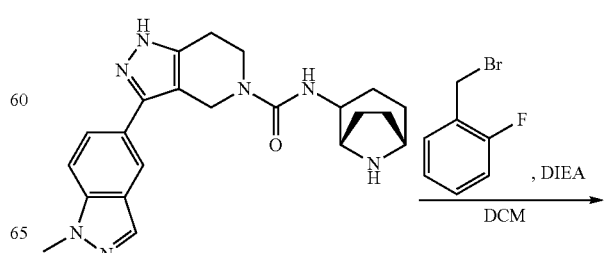

183
-continued

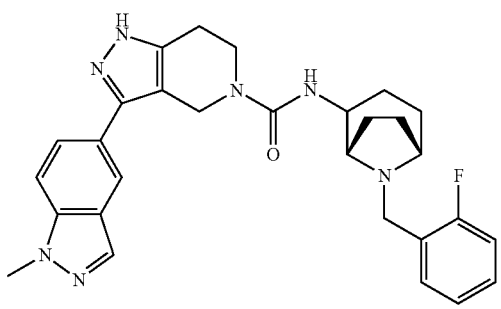

Dichloromethane (1.78 mL) was added to N-((1S,5R)-8-azabicyclo[3.2.1]octan-2-yl)-3-(1-methyl-1H-indazol-5-yl)-6,7-dihydro-1H-pyrazolo[4,3-c]pyridine-5(4H)-carboxamide (72.3 mg, 0.178 mmol) in a flask. 2-Fluorobenzylbromide (0.0214 mL, 0.178 mmol) was added to the reaction. At room temperature, diisopropylethylamine (0.0920 mL, 0.534 mmol) was added dropwise to the reaction. The reaction was allowed to stir at room temperature for 1 hr. The reaction was quenched using water, was extracted three times using dichloromethane. The dichloromethane extractions were combined, dried over sodium sulfate, filtered, and concentrated. The crude was further purified using HPLC. The endo and exo products were separated. LC-MS: 514.3 [M+H]. LC/MS RT=2.17 and 2.238 min.

The following compounds were prepared using similar methods:

| Cmpd ID No. | Compound Name | Structure | LC-MS (M + H) |
|---|---|---|---|
| 160 | N-[endo-8-[(2-fluoro-6-methoxyphenyl)methyl]-8-azabicyclo[3.2.1]oct-2-yl]-1,4,6,7-tetrahydro-3-(2-methyl-4-pyridinyl)-5H-pyrazolo[4,3-c]pyridine-5-carboxamide | 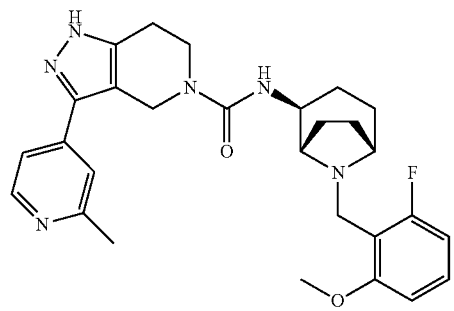 [SMILES: COc1cccc(F)c1CN1[C@H]2CC[C@H](NC(=O)N3CCc4[nH]nc(-c5ccnc(C)c5)c4C3)[C@@H]1CC2] | 505.3 found, 505.3 required. |
| 162 | N-[exo-8-[(2-fluoro-6-methoxyphenyl)methyl]-8-azabicyclo[3.2.1]oct-2-yl]-1,4,6,7-tetrahydro-3-(2-methyl-4-pyridinyl)-5H-pyrazolo[4,3-c]pyridine-5-carboxamide | 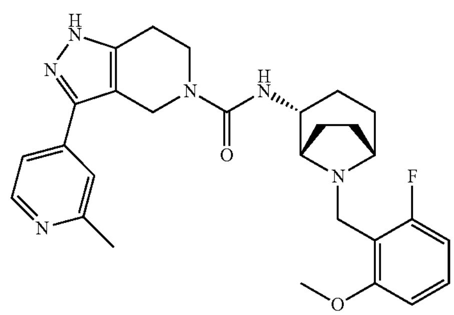 [SMILES: COc1cccc(F)c1CN1[C@H]2CC[C@@H](NC(=O)N3CCc4[nH]nc(-c5ccnc(C)c5)c4C3)[C@@H]1CC2] | 505.3 found, 505.3 required. |
| 164 | N-[endo-8-[(2,6-difluorophenyl)methyl]-8-azabicyclo[3.2.1]oct-2-yl]-1,4,6,7-tetrahydro-3-(2-methyl-4-pyridinyl)-5H-pyrazolo[4,3-c]pyridine-5-carboxamide | 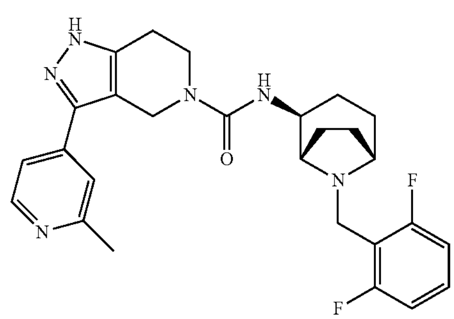 [SMILES: Cc1cc(-c2n[nH]c3c2CN(C(=O)N[C@H]2CC[C@H]4CC[C@@H]2N4Cc2c(F)cccc2F)CC3)ccn1] | 493.2 found, 493.2 required. |

-continued

| Cmpd ID No. | Compound Name | Structure | LC-MS (M + H) |
|---|---|---|---|
| 166 | N-[endo-8-[(2-fluorophenyl)methyl]-8-azabicyclo[3.2.1]oct-2-yl]-1,4,6,7-tetrahydro-3-(2-methyl-4-pyridinyl)-5H-pyrazolo[4,3-c]pyridine-5-carboxamide | 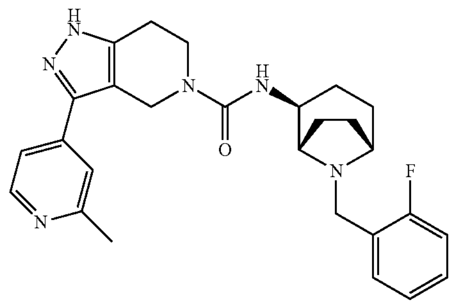 [SMILES: Cc1cc(-c2n[nH]c3c2CN(C(=O)N[C@H]2CC[C@H]4CC[C@@H]2N4Cc2ccccc2F)CC3)ccn1] | 475.3 found, 475.2 required. |
| 168 | N-[exo-8-[(2-fluorophenyl)methyl]-8-azabicyclo[3.2.1]oct-2-yl]-1,4,6,7-tetrahydro-3-(2-methyl-4-pyridinyl)-5H-pyrazolo[4,3-c]pyridine-5-carboxamide | 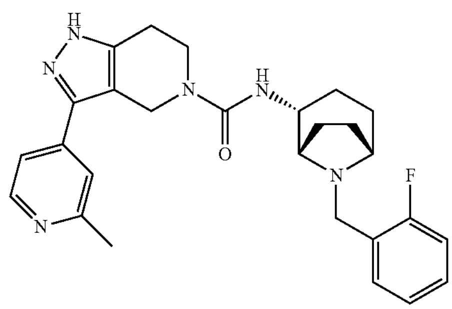 [SMILES: Cc1cc(-c2n[nH]c3c2CN(C(=O)N[C@@H]2CC[C@H]4CC[C@@H]2N4Cc2ccccc2F)CC3)ccn1] | 475.3 found, 475.2 required. |
| 178 | N-[exo-8-[(2,6-difluorophenyl)methyl]-8-azabicyclo[3.2.1]oct-2-yl]-1,4,6,7-tetrahydro-3-(2-methyl-4-pyridinyl)-5H-pyrazolo[4,3-c]pyridine-5-carboxamide | 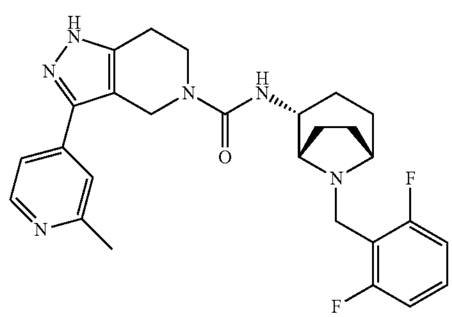 [SMILES: Cc1cc(-c2n[nH]c3c2CN(C(=O)N[C@@H]2CC[C@H]4CC[C@@H]2N4Cc2c(F)cccc2F)CC3)ccn1] | 493.2 found, 493.2 required. |
| 182 | N-[8-[(2,6-difluorophenyl)methyl]-8-azabicyclo[3.2.1]oct-2-yl]-1,4,6,7-tetrahydro-3-imidazo[1,2-a]pyridin-6-yl-5H-pyrazolo[4,3-c]pyridine-5-carboxamide | 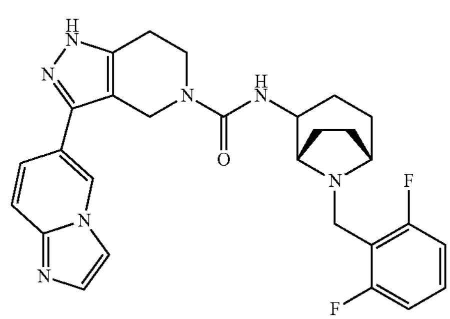 [SMILES: O=C(NC1CC[C@H]2CC[C@@H]1N2Cc1c(F)cccc1F)N1CCc2[nH]nc(-c3ccc4nccn4c3)c2C1] | 518.0 found, 518.2 required. |
| 140 | N-[8-[(2-fluorophenyl)methyl]-8-azabicyclo[3.2.1]oct-2-yl]-1,4,6,7-tetrahydro-3-(1-methyl-1H-indazol-5-yl)-5H-pyrazolo[4,3-c]pyridine-5-carboxamide | 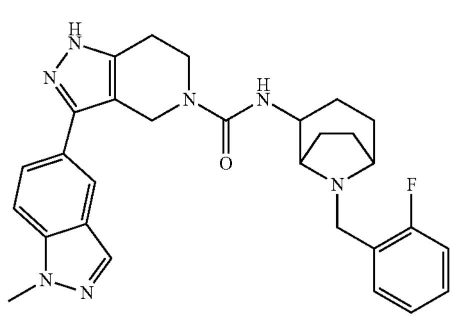 [SMILES: Cn1ncc2cc(-c3n[nH]c4c3CN(C(=O)NC3CCC5CCC3N5Cc3ccccc3F)CC4)ccc21] | 514.2 found, 514.3 required. |

-continued

| Cmpd ID No. | Compound Name | Structure | LC-MS (M + H) |
|---|---|---|---|
| 198 | N-[8-[(2-fluorophenyl)methyl]-8-azabicyclo[3.2.1]oct-2-yl]-1,4,6,7-tetrahydro-3-(1-methyl-1H-indazol-5-yl)-5H-pyrazolo[4,3-c]pyridine-5-carboxamide | 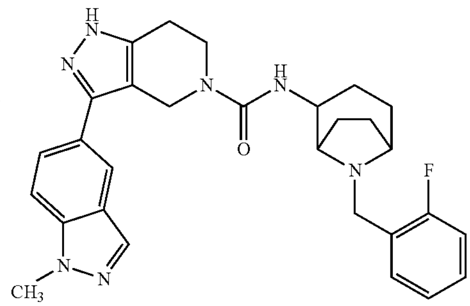 [SMILES: Cn1ncc2cc(-c3n[nH]c4c3CN(C(=O)NC3CCC5CCC3N5Cc3ccccc3F)CC4)ccc21] | 514.2 found, 514.3 required. |

Assays

TdF Assay for ERK

The SAR (Structure Activity Relationship) for ERK ligands covered by this invention was interrogated using the TdF (Temperature Dependence Fluorescence) assay or best known as thermal shift assay. (M. W. Pantoliano, et al., "High-density miniaturized thermal shift assays as a general strategy for drug discovery," *J. Biomol. Screen* 6 (2001) 429-440) The TdF assay was mainly conducted in the 96-well based CHROMO-4 real time fluorescence plate reader (BioRad). The Sypro Orange (Sigma-Aldrich), environmentally sensitive fluorescence dye, was used to monitor the protein folding-unfolding transition. Protein-ligand binding was gauged by the change (or shift) in the unfolding transition temperature ($\Delta T_m$) acquired at protein alone with respect to protein in the presence of ligand of interest.

Compound of interest was first prepared in DMSO stock (typical concentration: 10 mM). Sample of 20 μt was then added into the 96-well PCR plate, where it consisted of 3 μM ERK protein and 15, 50 or 100 μM compound (depending on compound's solubility) in buffer (25 mM HEPES, 150 mM NaCl, pH-7.5 and 1 mM DTT) incorporated with Sypro Orange dye (5× final concentration). Final percentage of DMSO resided in the sample was 2%. The sample plate was heated from 30° C. to 90° C. with thermal ramping rate of 1° C./min. The fluorescence signals were acquired with excitation and emission wavelengths centered at 490 and 560 nm respectively. The instrument thermal stability was ±0.2° C. The melting temperatures ($T_m$) for ERK protein under aforementioned conditions occurred at 61.0±02° C. and 64.8±0.2° C. respectively.

Theoretical Basis for TdF-Based Ligand Binding Affinity Constant

The derivation of TdF-based ligand binding affinity constant ($K_d$) followed closely those previously formulated by Brandts and Lin. (J. F. Brandts, L.-N. Lin, "Study of strong to ultratight protein interactions using differential scanning calorimetry," *Biochemistry* 29 (1990) 6927-6940). In brief, the binding constant of the ligand at the $T_m$ is expressed as below:

$$K_L(T_m) = \frac{\{\exp\{-(\Delta H_u(T_0)/R)(1/T_m - 1/T_0) + (\Delta Cp_u/R)[\ln(T_m/T_0) + (T_0/T_m) - 1]\} - 1\}}{[L_{T_m}]}$$

where $T_0$ is the midpoint of unfolding for unliganded protein and $T_m$ is the midpoint of unfolding in presence of ligand. $[L_{T_m}]$ is free ligand at $T_m$. The $\Delta H_u$ and $\Delta Cp_u$ are the enthalpy of unfolding and heat capacity change of unfolding for the protein respectively. Following algorithm derived by Winsor and coworker, the $T_0$, $\Delta H_u$ and $\Delta Cp_u$ can be determined separately from nonlinear regression fitting the protein alone melting curve:

$$F(T) = \frac{(Y_n + m_n(T)) + (Y_u + m_u(T))\exp\left\{-\left(\frac{\Delta H_u}{RT}\right)\left(1 - \frac{T}{T_0}\right) + \left(\frac{\Delta Cp_u}{RT}\right)\left(T\ln\left(\frac{T}{T_0}\right) + T_0 - T\right)\right\}}{\left(1 + \exp\left\{-\left(\frac{\Delta H_u}{RT}\right)\left(1 - \frac{T}{T_0}\right) + \left(\frac{\Delta Cp_u}{RT}\right)\left(T\ln\left(\frac{T}{T_0}\right) + T_0 - T\right)\right\}\right)}$$

where F(T) is the observed fluorescence intensity at any temperature T, $Y_n$, and $Y_u$ are the predicted fluorescence intensities for fully folded and unfolded protein, respectively; $m_n$ and $m_u$ are slope correction for changes in $Y_n$ and $Y_u$ with respect to changes in temperature (analogously replace $T_0$ with $T_m$ in the above equation for liganded protein to yield $T_m$). (Mayhood, T. W., Windsor, W. T., "Ligand binding affinity determined by temperature-dependent circular dichroism: Cyclin-dependent kinase 2 inhibitors," *Analytical Biochemistry* 345 (2005) 187-197).

Finally, the ligand binding affinity constant at any temperature T (i.e. 25° C.) can be thermodynamically connected to the preceding $K_L(T_m)$ via [2,3]

$$K_L(T) = K_L(T_m)\exp\left\{\left(\frac{-\Delta H_L(T)}{R}\right)\left(\frac{1}{T} - \frac{1}{T_m}\right) + \left(\frac{\Delta Cp_L}{R}\right)\left[\ln\frac{T}{T_m} + 1 - \frac{T}{T_m}\right]\right\}$$

where $\Delta H_L$ (T) is the van't Hoff enthalpy of ligand binding at temperature T and $\Delta Cp_L$ is the heat capacity upon ligand binding. For simplicity, the $\Delta Cp_L$ and $\Delta H_L$ (T) were set to zero and -7 kcal/mol respectively. The uncertainty in the calculated ligand binding affinity constant was estimated to be ±50%.

Coupled ERK2 Assay:

Activity of compounds against inactive ERK2 is tested in a coupled MEK1/ERK2 IMAP assay as follows: Compounds are diluted to 25× final test concentration in 100% DMSO. 14 µl of kinase buffer (10 mM Tris.HCl pH 7.2, 10 mM $MgCl_2$, 0.01% Tween-20, 1 mM DTT) containing 0.4 ng unphosphorylated Mouse ERK2 protein is added to each well of a black 384-well assay plate. 1 µl of 25× compound is added to each well and incubated at room temperature for 30 minutes to allow an opportunity for the compound to bind to the inactive enzyme. DMSO concentration during initial incubation is 6.7%. ERK2 activity is determined to be insensitive to DMSO concentrations up to 20%. ERK2 is then activated and it's kinase activity is measured by the addition of 10 µl kinase buffer with the following components (final concentration per reaction): 2 ng active (phosphorylated) human MEK1 protein and 4 µM (total) ERK2 IMAP substrate peptides (3.9 µM unlabeled IPTTPITTTYFFFK-$CONH_2$ and 100 nM IPTTPITTTYFFFK(5-carboxyfluorescein)-$CONH_2$) and 30 µM ATP. DMSO concentration during ERK activation was 4%. After one hour, reactions are terminated by addition of 60 µl IMAP detections beads in binding buffer (Molecular Devices). Binding is allowed to equilibrate for 30 minutes before reading the plate on an LJL Analyst Fluorescence Polarization plate reader. Compound inhibition is calculated relative to DMSO and fully inhibited standards. Active compounds is reconfirmed in an independent assay.

Active ERK2 Assay:

Activated ERK2 activity was also determined in the IMAP assay format using the procedure outlined above. 1 µl of 25× compound was added to 14 µl of kinase buffer containing 0.25 ng fully phosphorylated, active Mouse ERK2 protein. Following a 30 minute incubation, the reactions were initiated by addition of 10 µl of kinase buffer containing 1 µM ERK2 IMAP substrate peptide (0.9 µM unlabeled IPTTPITTTY-FFFK-$CONH_2$ and 100 nM IPTTPITTTYFFFK(5-carboxyfluorescein)-$CONH_2$) and 30 µM ATP. Reactions proceeded for 30 minutes before termination by addition of 600 IMAP detection beads in binding buffer. Plates were read as above after 30 minute binding equilibration. Active compounds were reconfirmed in an independent assay.

Ki values for representative compounds of this invention are shown in Table 1 below. Table 2 contains a list of additional compounds. Compounds with Ki values less than 20 nM are designated as A class compounds. Compounds with Ki values between 21 nM and 100 nM are designated as B class compounds. Compounds with Ki values between 101 nM and 1000 nM are designated as C class compounds. Finally, compounds with Ki values between 1001 and 100,000 nM are designated as D class compounds.

TABLE 1

| Cmpd ID No. | Kd TdF nM | ERK2 IC50 nM |
|---|---|---|
| 1 | C | N/A |
| 2 | D | D |
| 3 | D | D |
| 4 | C | C |
| 5 | D | D |
| 6 | D | D |
| 7 | D | D |
| 8 | C | C |
| 9 | C | C |
| 10 | D | D |
| 11 | D | D |
| 12 | C | C |
| 13 | A | B |
| 14 | D | D |
| 15 | D | D |
| 16 | D | D |
| 17 | D | D |
| 18 | D | D |
| 19 | D | D |
| 20 | D | D |
| 21 | D | D |
| 22 | D | C |
| 23 | D | C |
| 24 | D | C |
| 25 | D | C |
| 26 | D | C |
| 27 | D | C |
| 28 | D | C |
| 29 | D | C |
| 30 | D | C |
| 31 | D | C |
| 32 | D | C |
| 33 | D | C |
| 34 | D | N/A |
| 35 | D | N/A |
| 36 | D | N/A |
| 38 | D | D |
| 39 | D | D |
| 40 | D | D |
| 41 | D | D |
| 42 | D | D |
| 43 | D | D |
| 44 | D | D |
| 45 | D | N/A |
| 47 | A | A |
| 49 | A | A |
| 50 | C | C |
| 51 | D | C |
| 52 | N/A | B |
| 53 | A | A |
| 55 | A | B |
| 56 | A | A |
| 63 | B | C |
| 64 | C | C |
| 65 | B | C |
| 66 | A | A |
| 67 | A | B |
| 68 | A | B |
| 70 | A | B |
| 72 | A | B |
| 73 | A | C |
| 74 | A | C |
| 77 | A | B |
| 78 | B | C |
| 79 | A | C |
| 81 | A | B |
| 82 | C | C |
| 83 | A | C |
| 85 | A | A |
| 86 | A | B |
| 87 | D | C |
| 88 | C | C |
| 89 | A | B |
| 90 | A | B |
| 91 | A | A |
| 92 | D | C |
| 93 | D | C |
| 94 | A | B |
| 95 | A | C |
| 96 | C | C |
| 97 | A | B |
| 98 | A | C |
| 99 | A | B |
| 101 | A | B |
| 102 | A | B |
| 103 | A | B |
| 104 | A | B |
| 105 | C | C |
| 106 | A | C |
| 107 | C | C |
| 108 | D | C |

TABLE 1-continued

| Cmpd ID No. | Kd TdF nM | ERK2 IC50 nM |
|---|---|---|
| 111 | A | A |
| 114 | A | A |
| 115 | A | C |
| 116 | A | B |
| 117 | A | B |
| 118 | A | B |
| 119 | A | B |
| 120 | A | A |
| 121 | A | B |
| 122 | A | C |
| 124 | A | B |
| 125 | A | B |
| 126 | A | A |
| 127 | A | A |
| 128 | C | C |
| 129 | A | C |
| 130 | A | B |
| 131 | A | B |
| 132 | A | B |
| 133 | A | B |
| 134 | A | B |
| 135 | A | A |
| 136 | A | C |
| 137 | A | C |
| 138 | A | C |
| 139 | A | C |
| 140 | N/A | A |
| 141 | N/A | A |
| 142 | N/A | C |
| 143 | N/A | A |
| 144 | N/A | C |
| 146 | N/A | B |
| 148 | N/A | B |
| 149 | N/A | A |
| 150 | N/A | A |
| 151 | N/A | A |
| 152 | N/A | A |
| 153 | N/A | A |
| 154 | N/A | A |
| 155 | N/A | A |
| 156 | N/A | C |
| 157 | N/A | A |
| 158 | N/A | C |
| 159 | N/A | A |
| 160 | N/A | C |
| 161 | N/A | A |
| 162 | N/A | B |
| 163 | N/A | A |
| 164 | N/A | C |
| 165 | N/A | C |
| 166 | N/A | C |
| 167 | N/A | A |
| 168 | N/A | A |
| 169 | N/A | A |
| 170 | N/A | A |
| 171 | N/A | C |
| 172 | N/A | A |
| 173 | N/A | B |
| 174 | N/A | A |
| 175 | N/A | A |
| 176 | N/A | A |
| 177 | N/A | A |
| 178 | N/A | A |
| 179 | N/A | B |
| 180 | N/A | B |
| 181 | N/A | A |
| 182 | N/A | C |
| 183 | N/A | A |
| 184 | N/A | B |
| 185 | N/A | B |
| 186 | N/A | B |
| 187 | N/A | C |
| 188 | N/A | C |
| 189 | N/A | A |
| 190 | N/A | C |
| 191 | N/A | A |

Table 2 contains a list of compounds that exhibit Ki activities for the KdF assay in the range of 0.03 to 6.0 nM, and for the coupled ERK2 or Active ERK2 assays in the range of 0.3 to 6.3 nM.

TABLE 2

| Cmpd ID No. | Kd TdF nM | ERK2 IC50 nM |
|---|---|---|
| 37 | 6.0 | 1.16 |
| 46 | 0.7 | 0.89 |
| 48 | 0.37 | 0.65 |
| 53 | 0.15 | 3.8 |
| 54 | 0.51 | 1.97 |
| 57 | 0.3 | 0.5 |
| 58 | 0.25 | 1.98 |
| 59 | 1.51 | 1.78 |
| 60 | 1.12 | 1.24 |
| 61 | 0.47 | 0.3 |
| 62 | 2.1 | 2.01 |
| 69 | 0.31 | 2.4 |
| 71 | 0.15 | 2.07 |
| 75 | 1.36 | N/A |
| 76 | 1.55 | N/A |
| 80 | 0.51 | 4.83 |
| 84 | 0.13 | 6.3 |
| 100 | 0.4 | 3.7 |
| 109 | 0.14 | 3.0 |
| 110 | 0.03 | 5.3 |
| 112 | 0.12 | 3.1 |
| 113 | 0.03 | 4.2 |
| 123 | 0.06 | 4.3 |
| 145 | N/A | 1.52 |
| 147 | N/A | 1.9 |

What is claimed is:

1. A compound which is selected from the group consisting of:

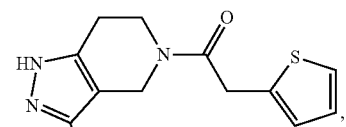

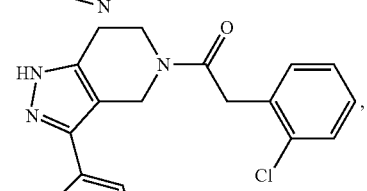

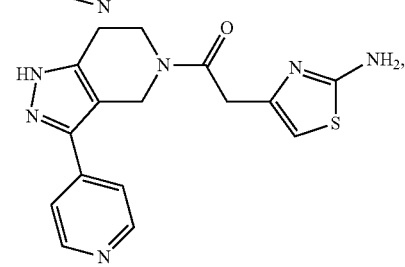

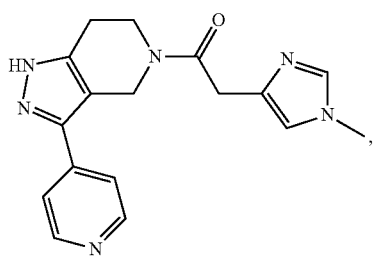
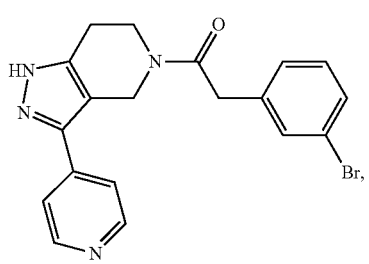
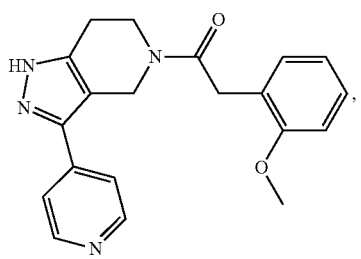
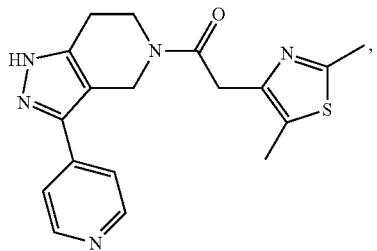
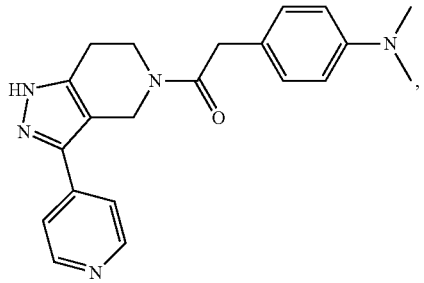
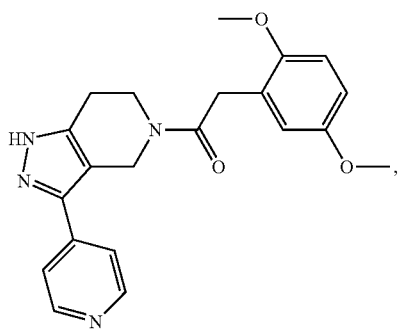
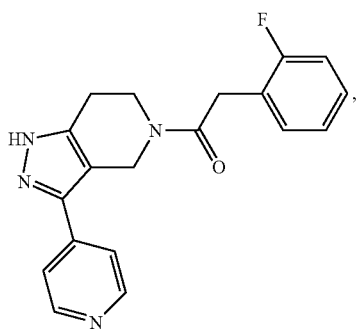
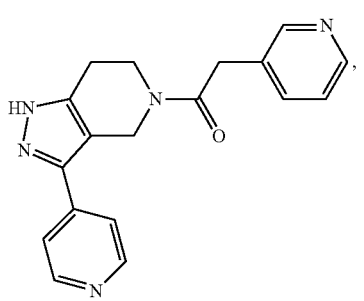
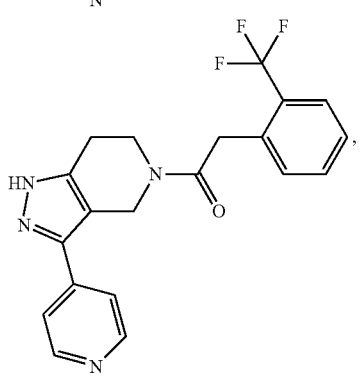
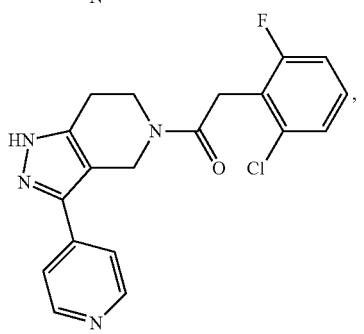
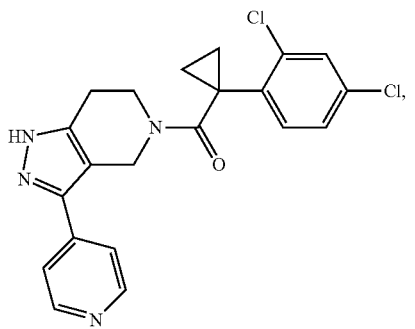

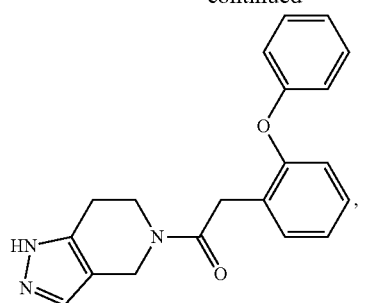
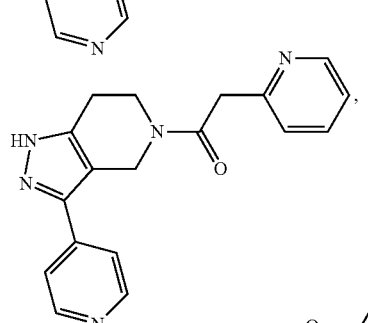
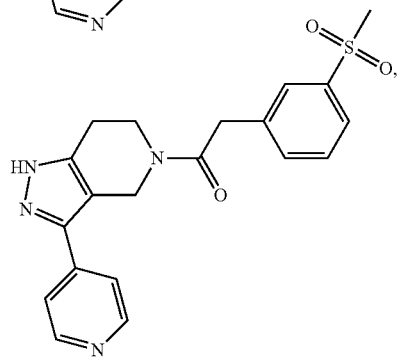
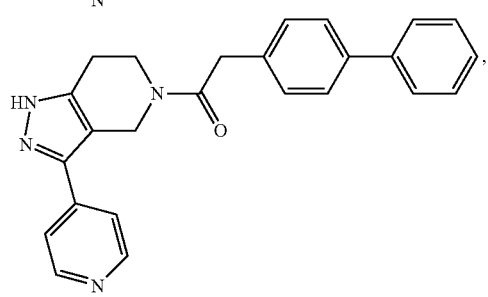
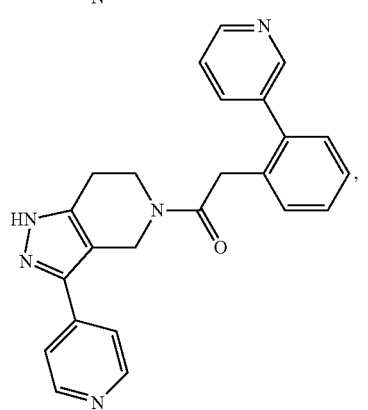
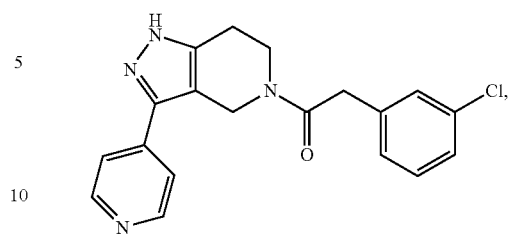
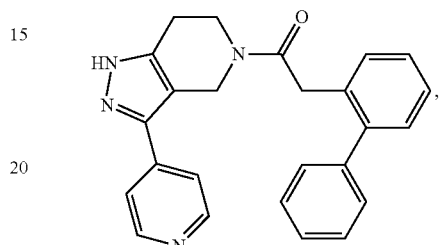
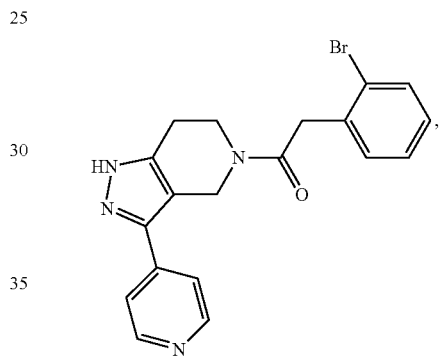
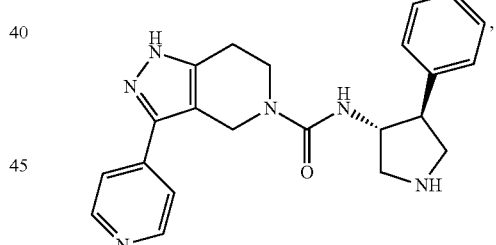
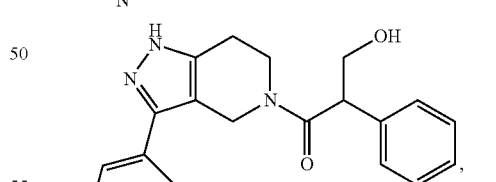
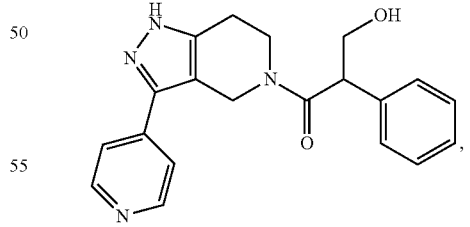
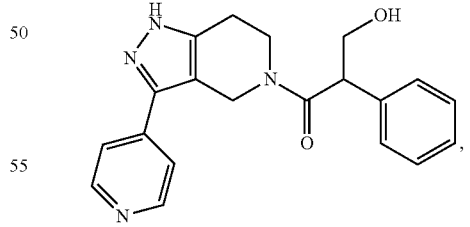

197
-continued
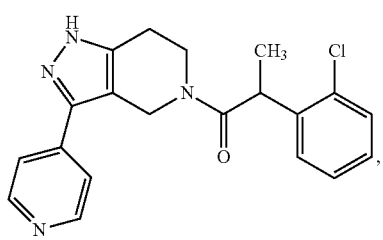
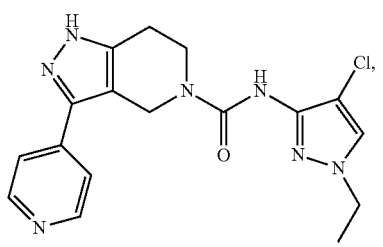
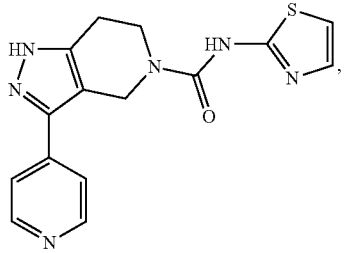
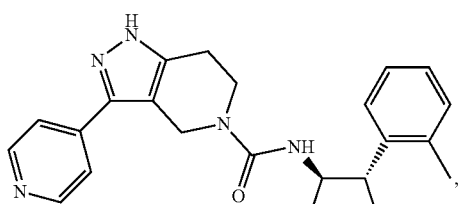
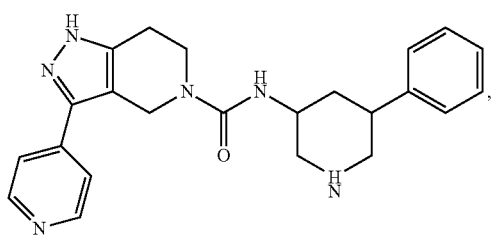
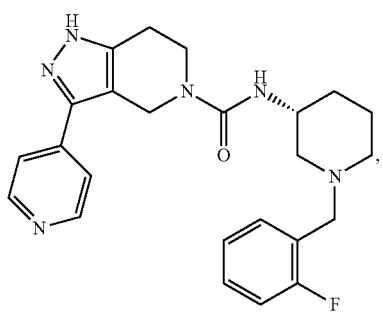
198
-continued
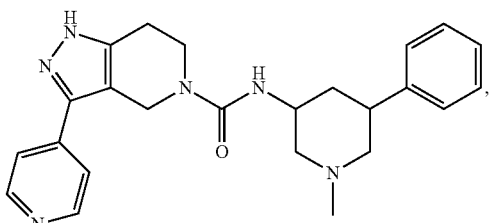
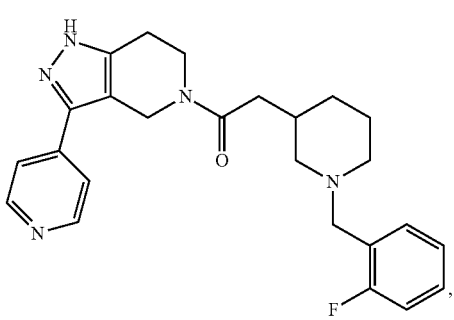
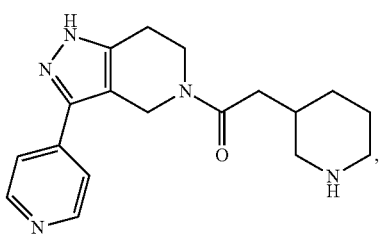
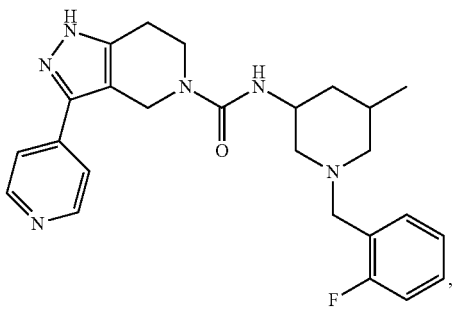
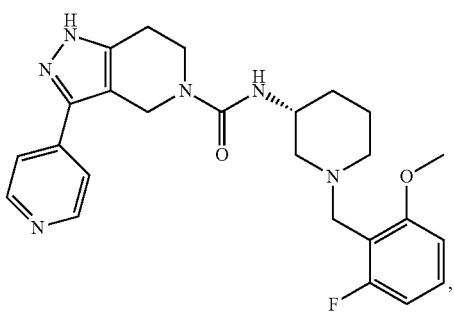
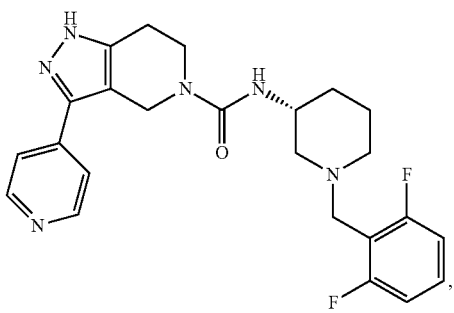

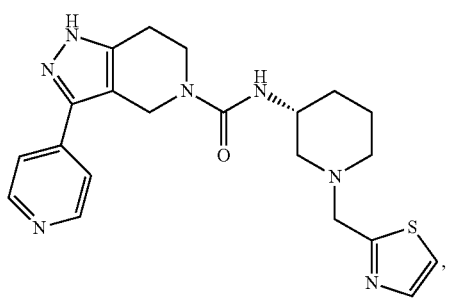
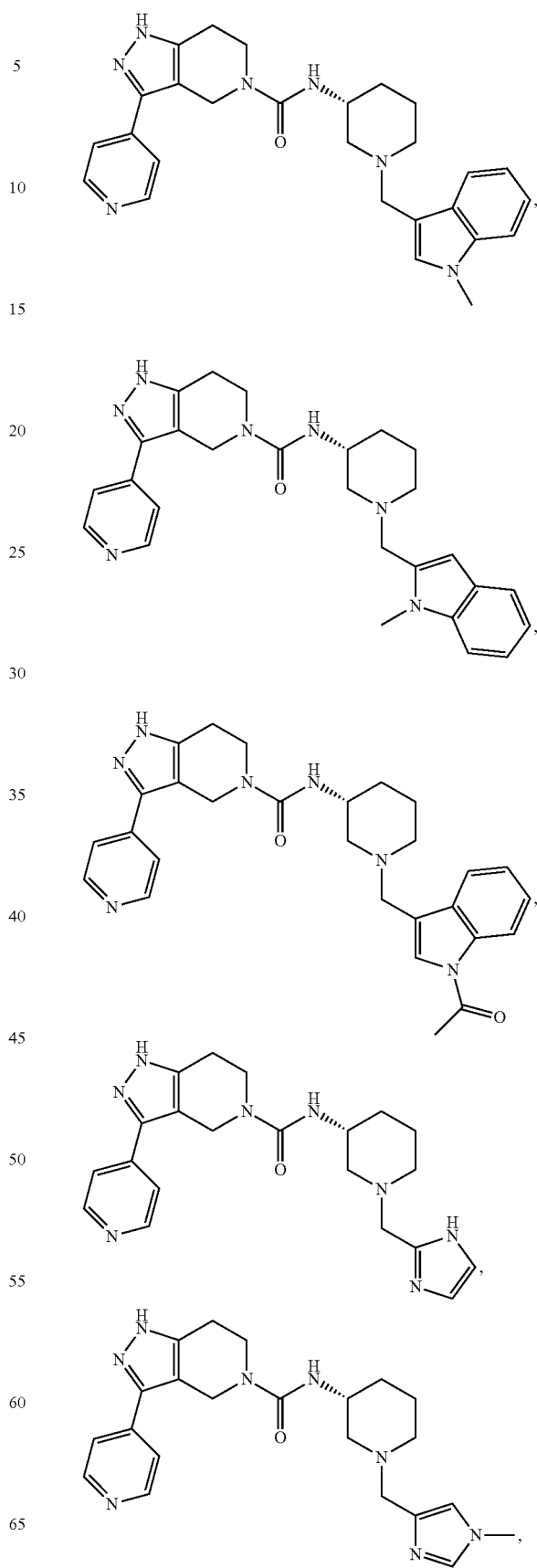

201
-continued
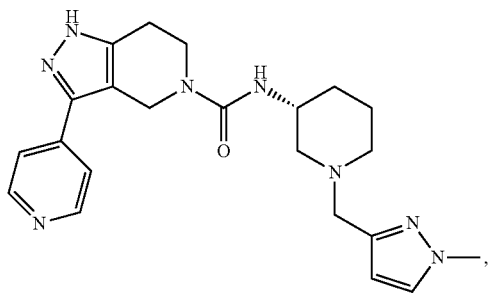
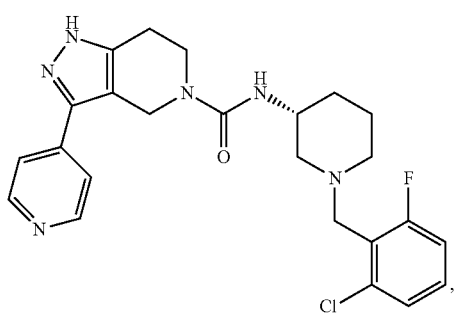
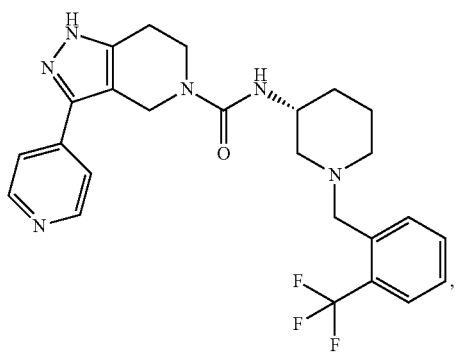
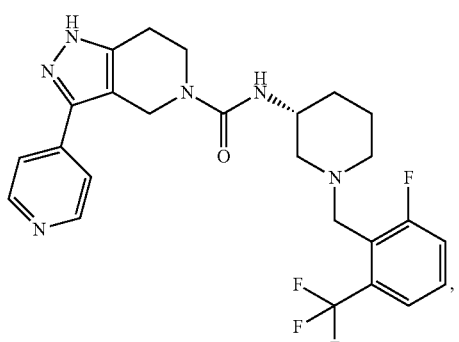
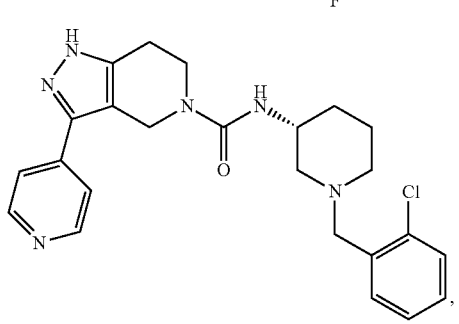
202
-continued
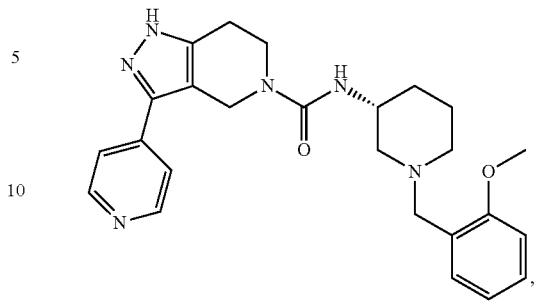
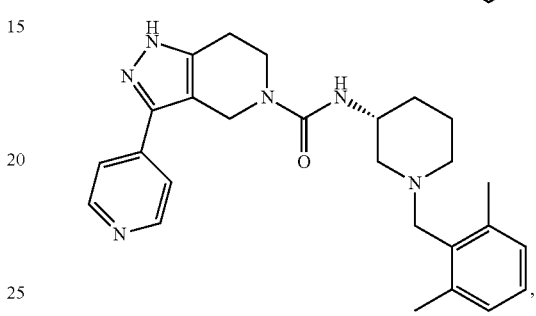
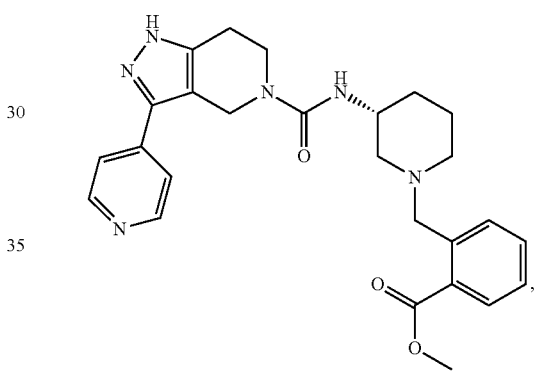
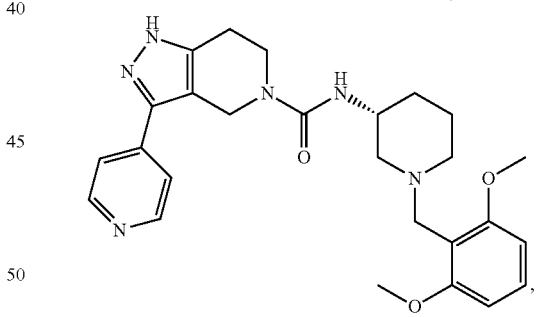
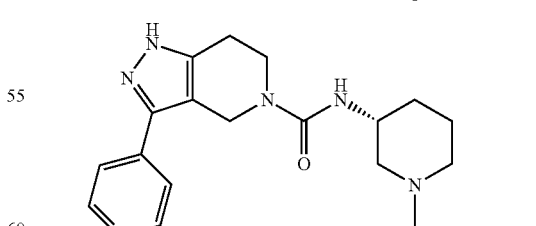

203
-continued
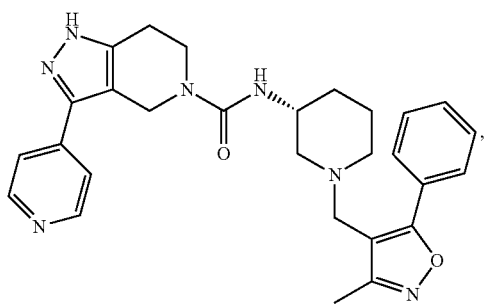
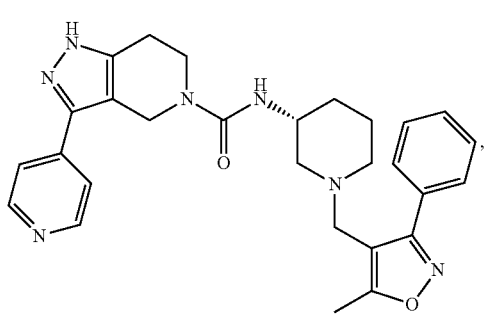
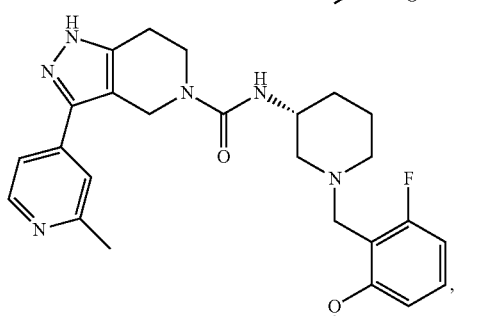
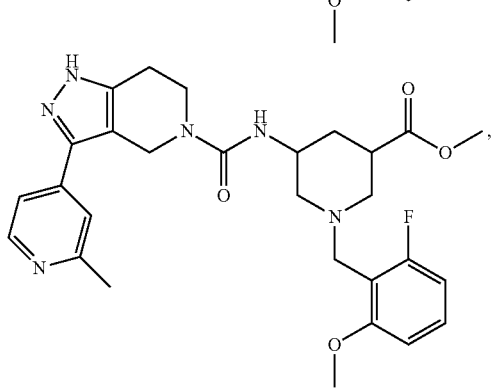
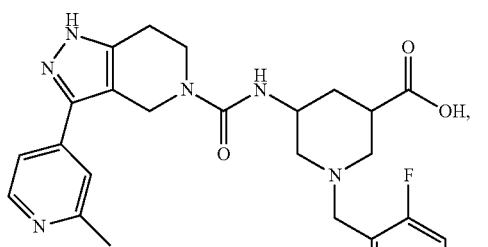
204
-continued
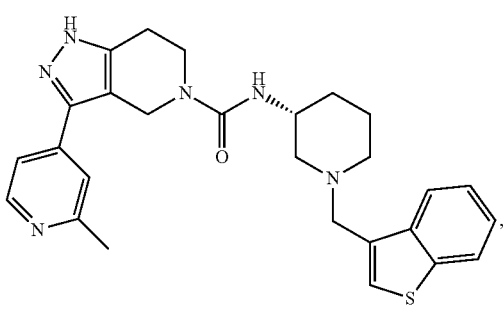
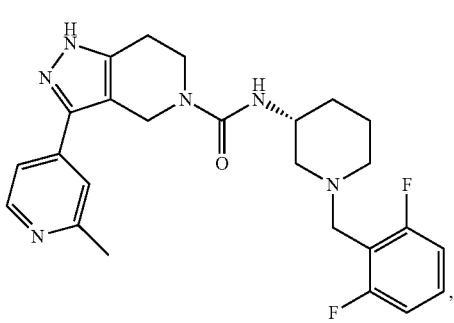
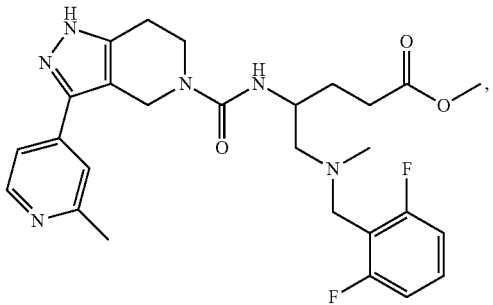
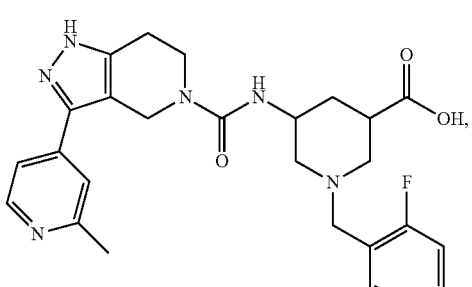
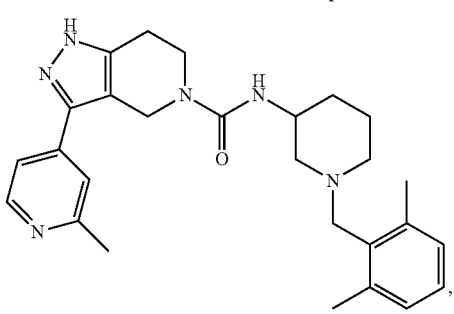

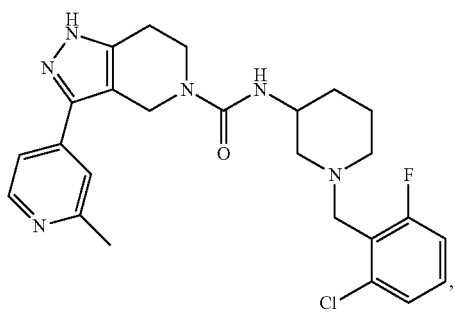
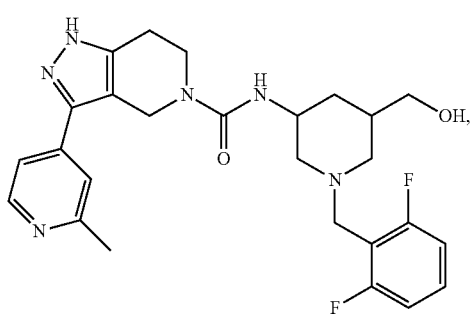
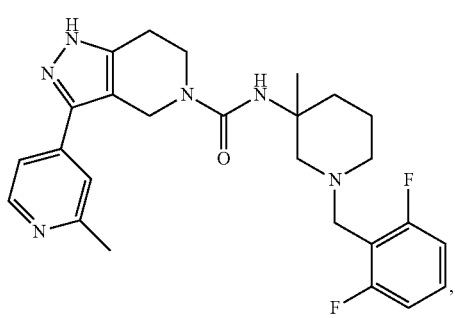
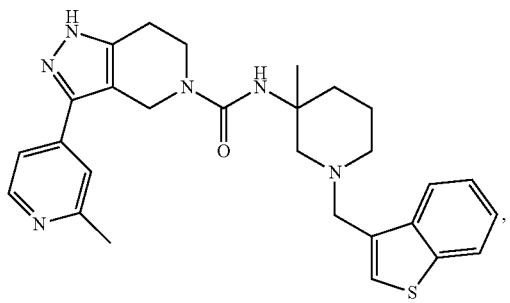
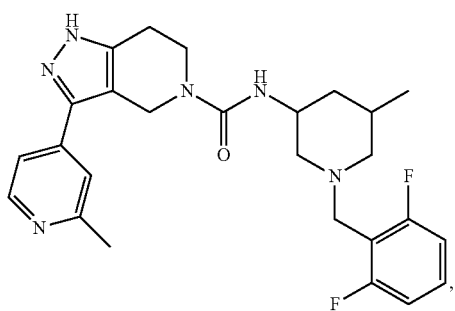
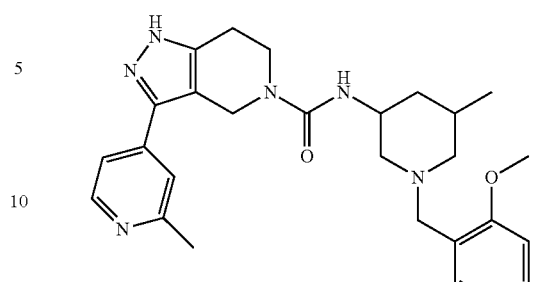
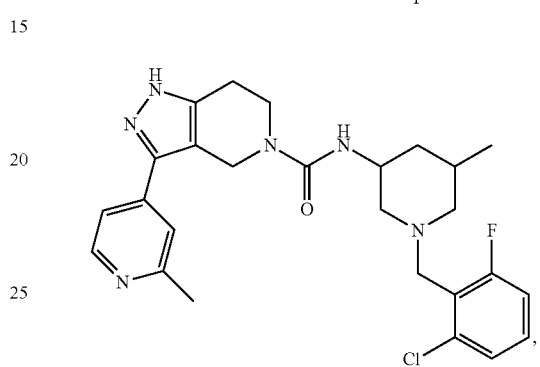
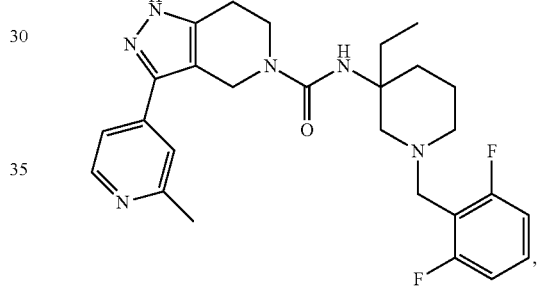
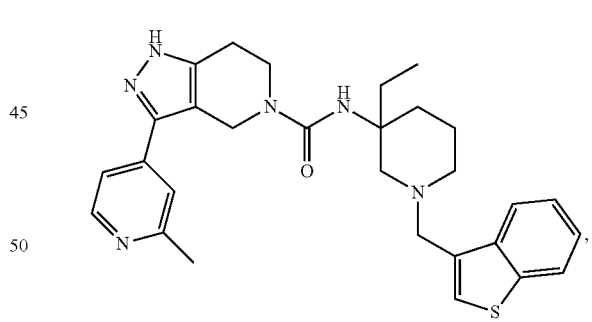
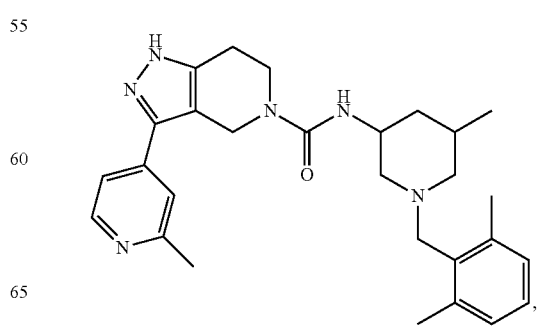

207
-continued
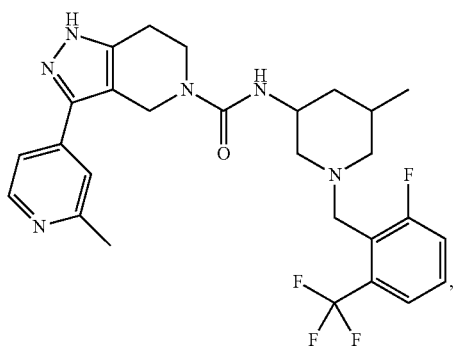
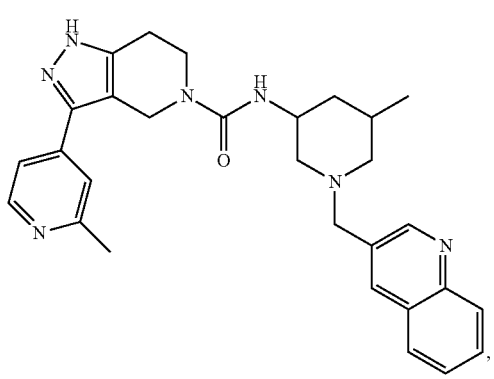
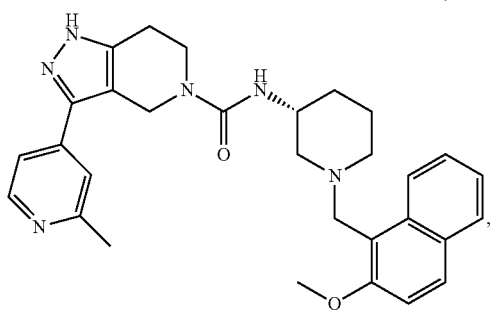
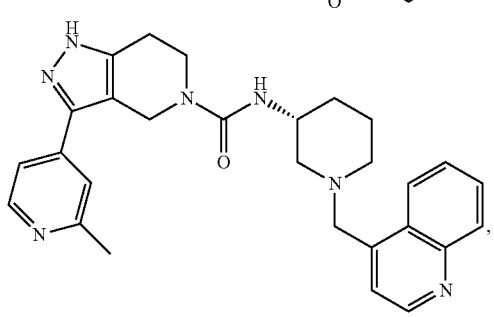
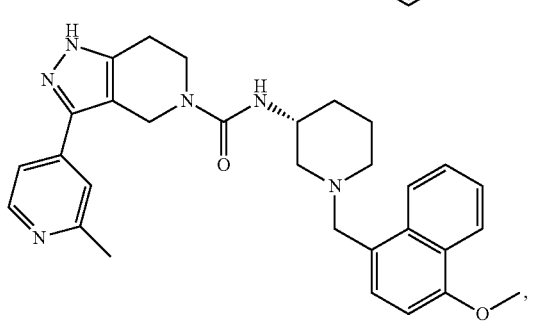
208
-continued
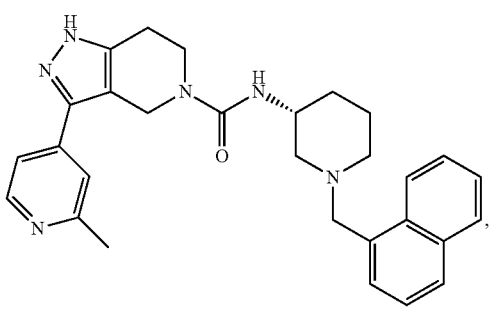
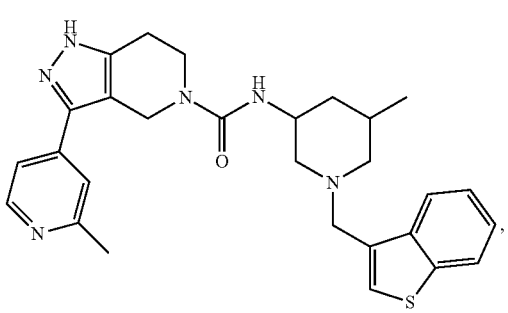
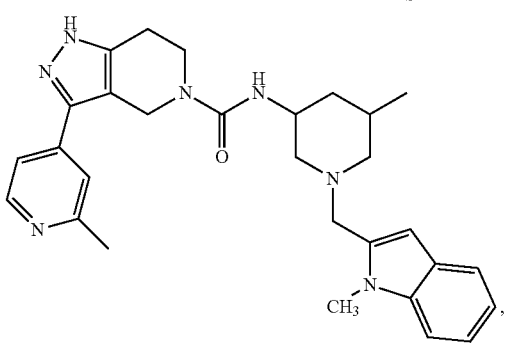
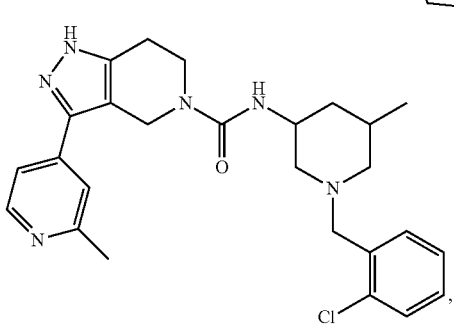
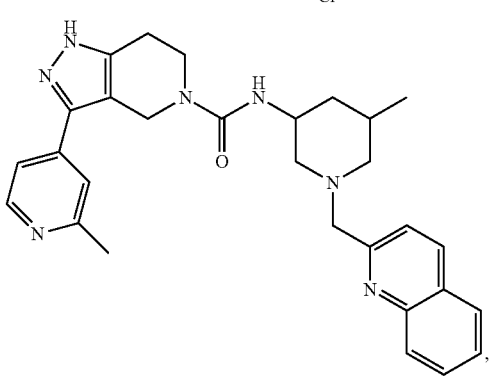

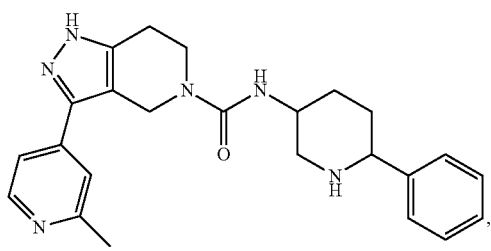
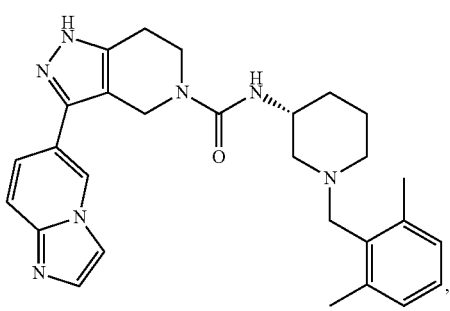
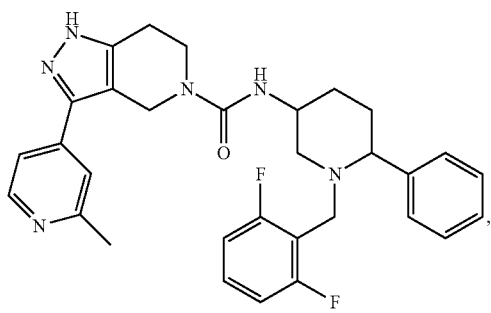
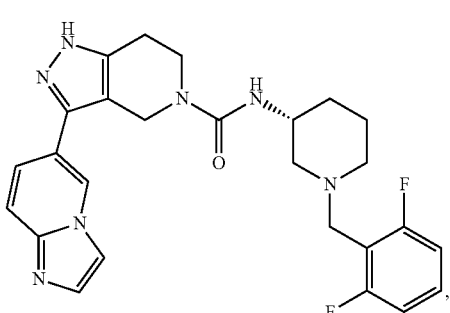
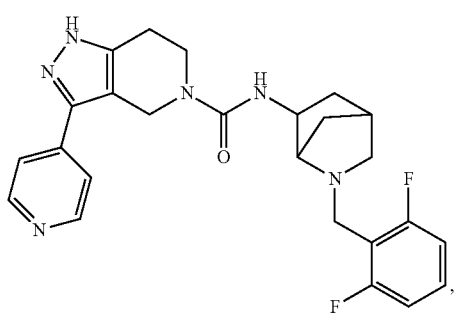
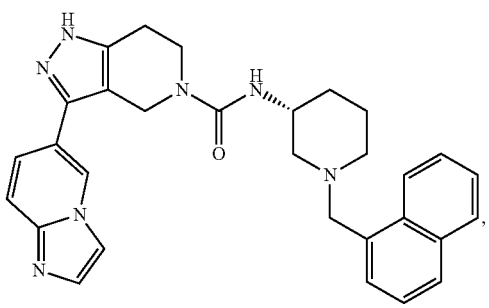
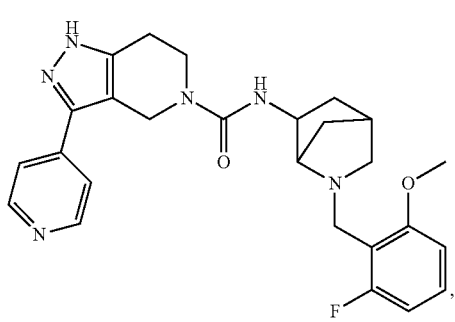
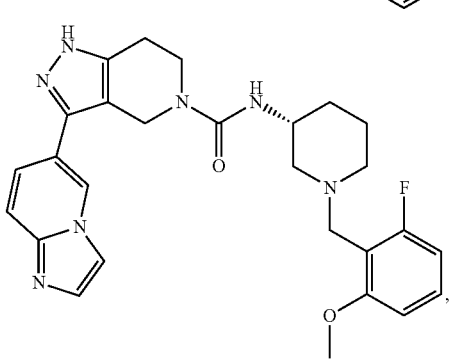
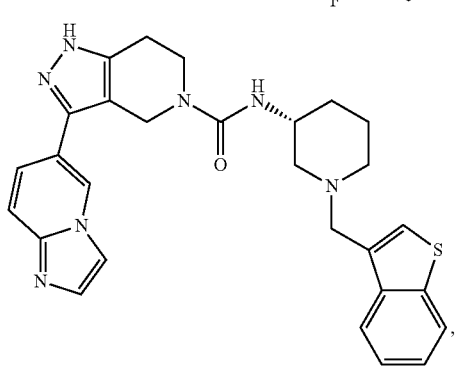
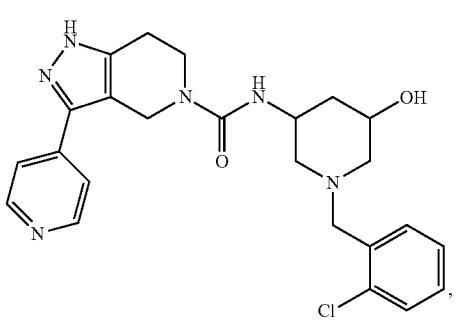

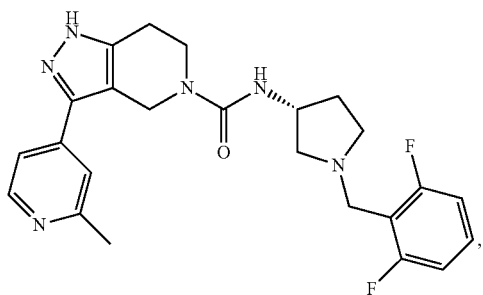
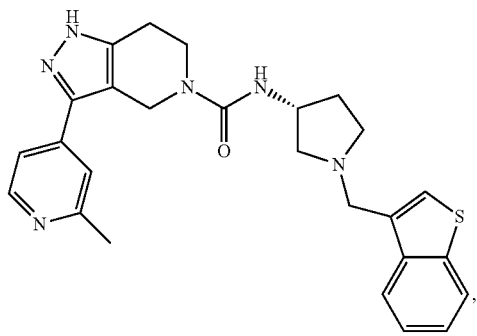
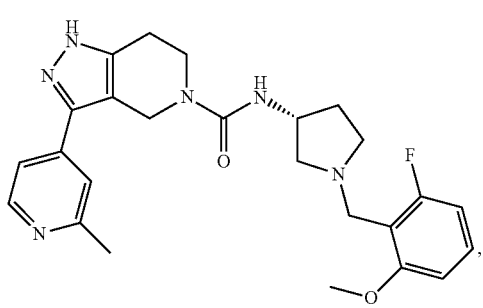
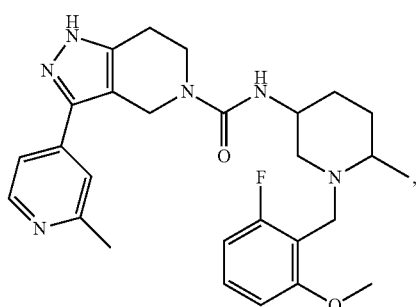
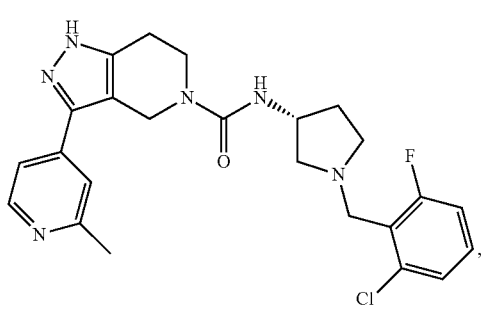
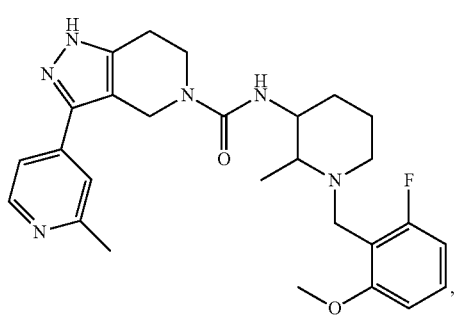
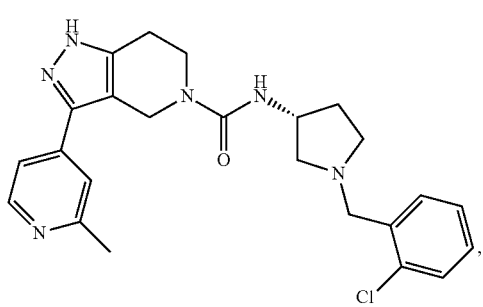
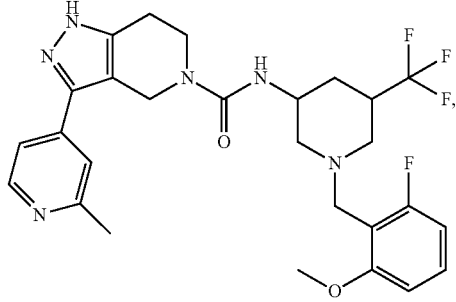
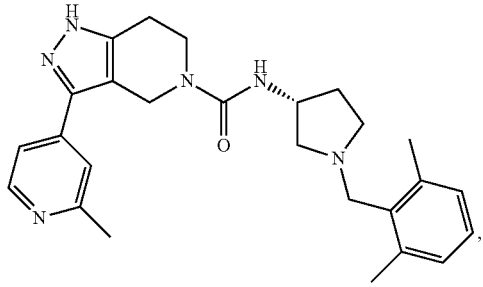
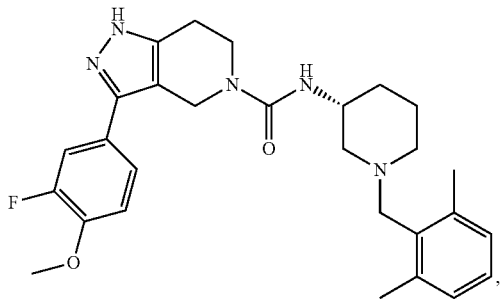

213
-continued
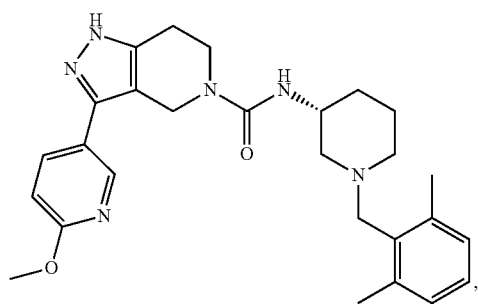
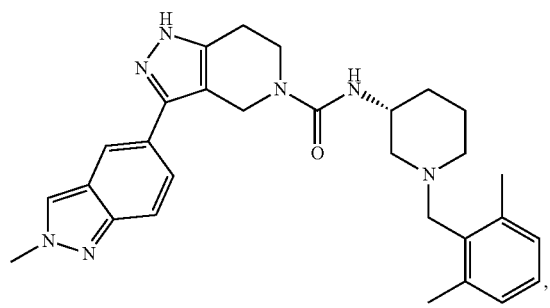
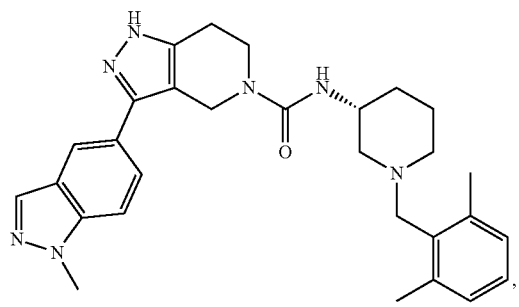
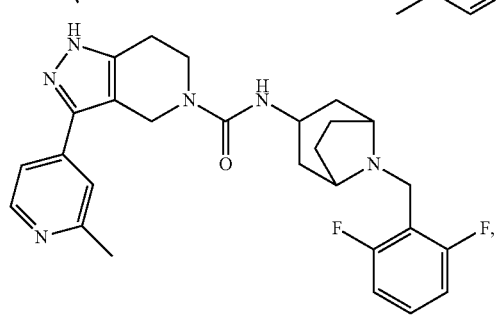
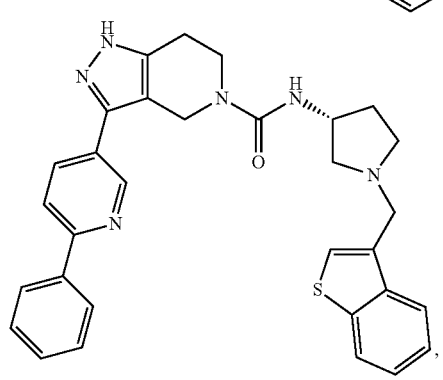
214
-continued
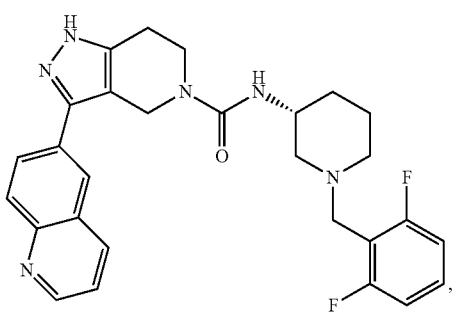
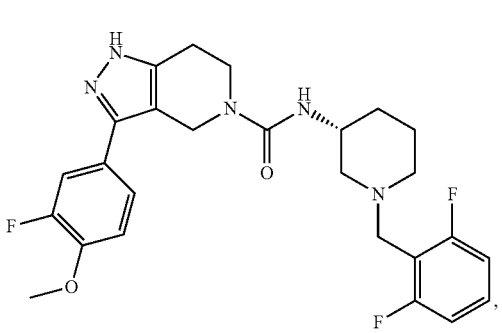
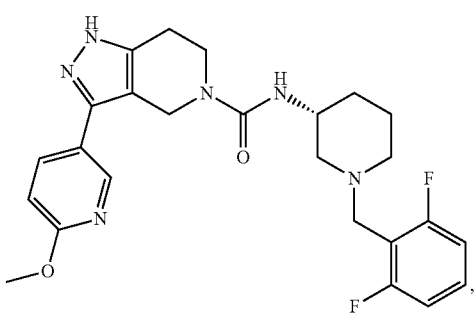
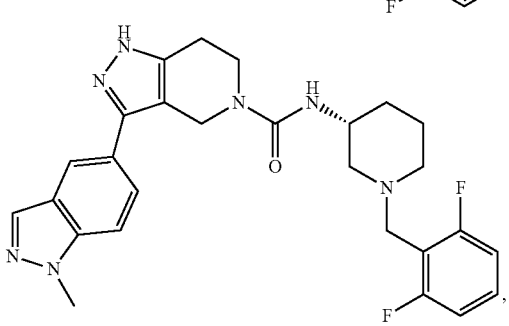

215
-continued
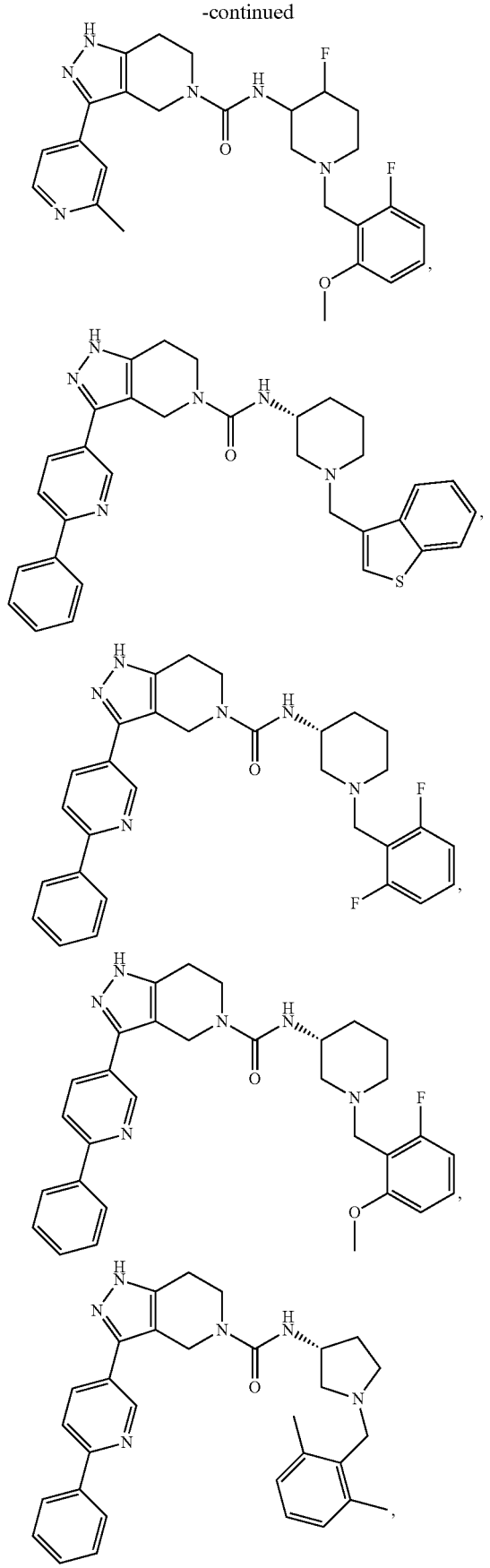
216
-continued
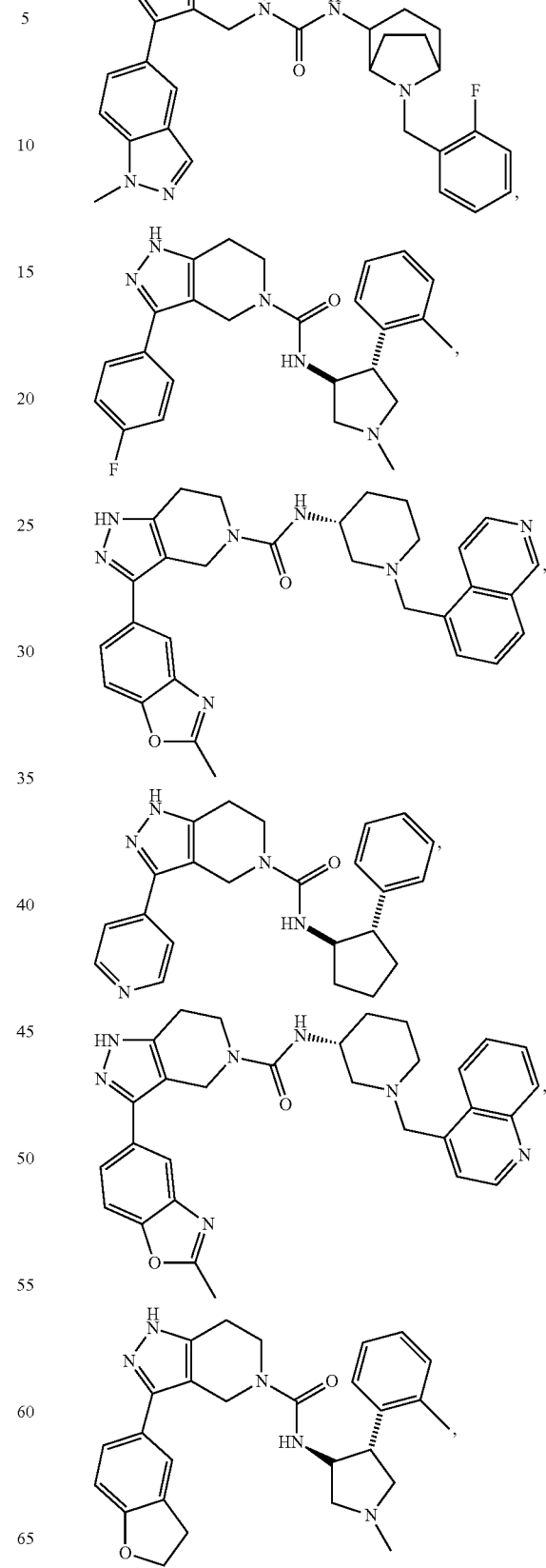

217
-continued
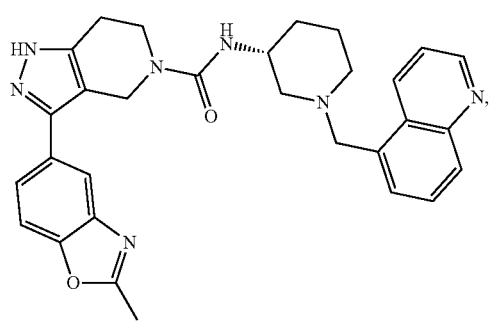
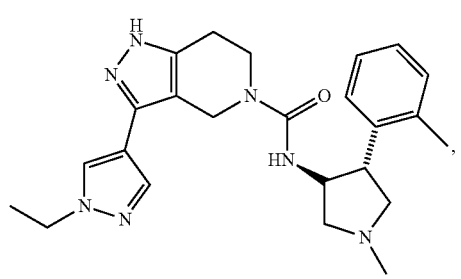
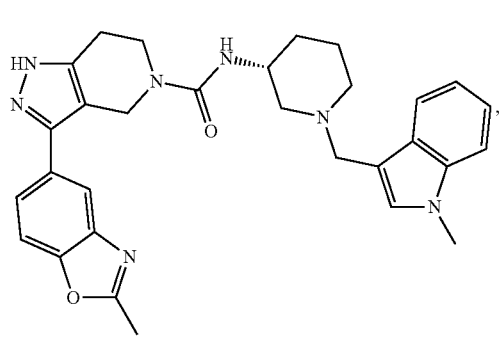
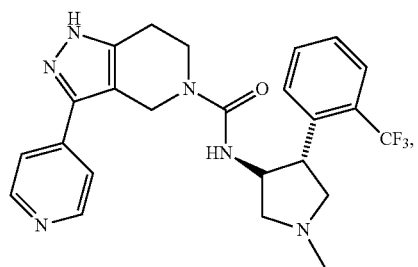
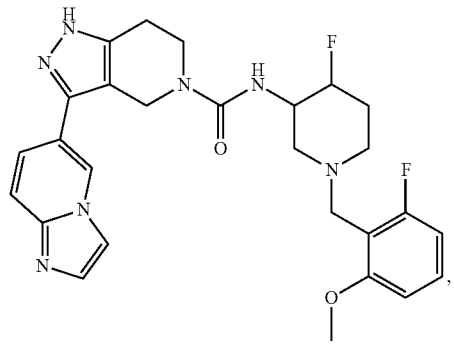
218
-continued
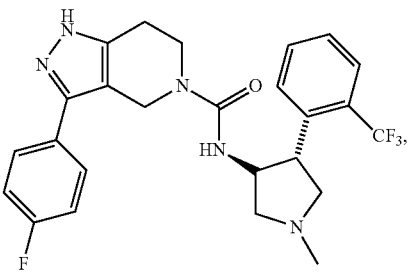
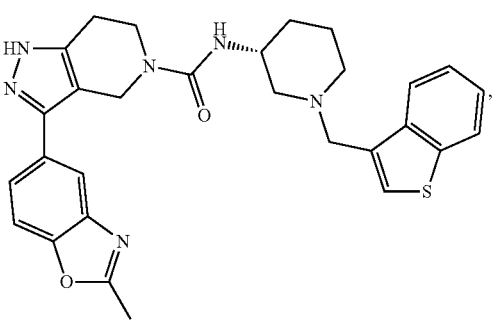
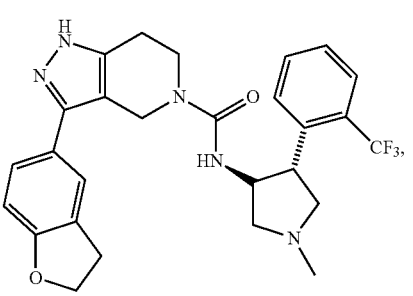
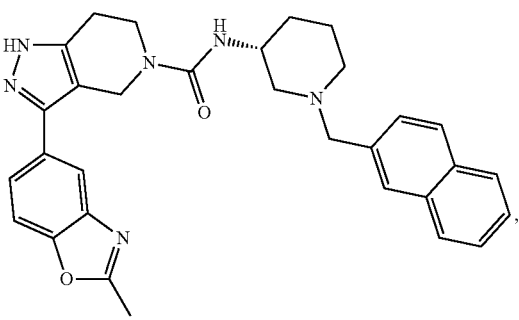
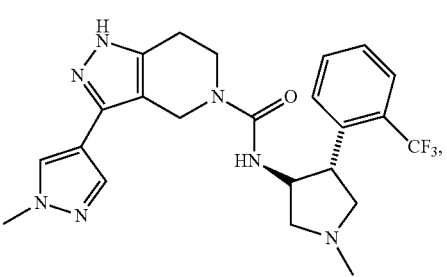

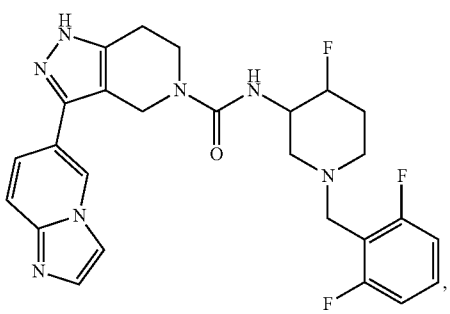
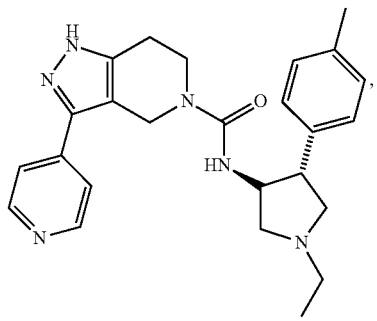
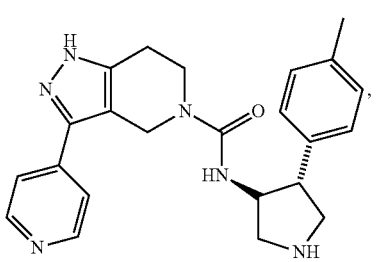
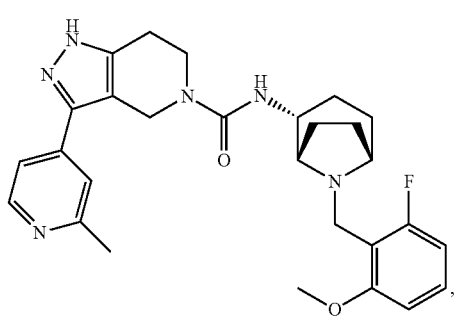
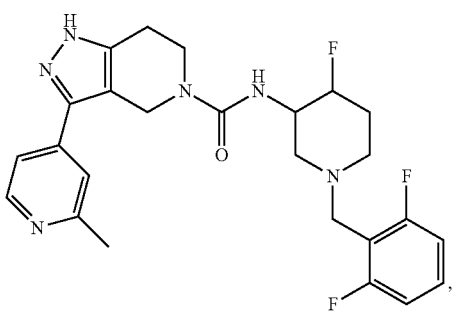
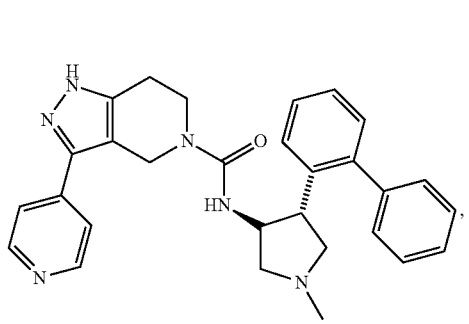
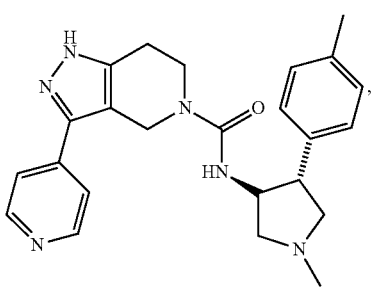
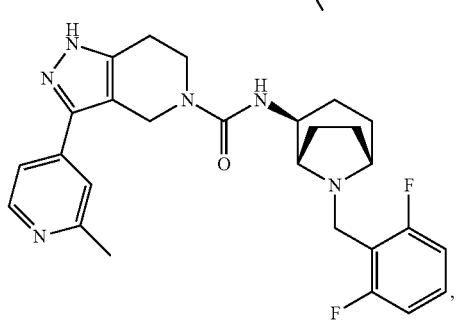
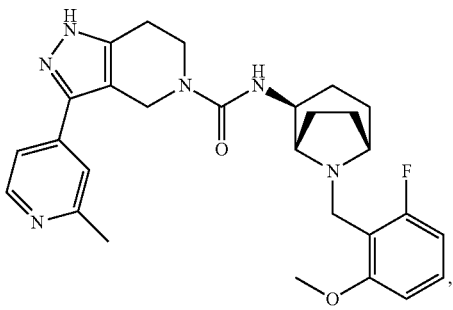
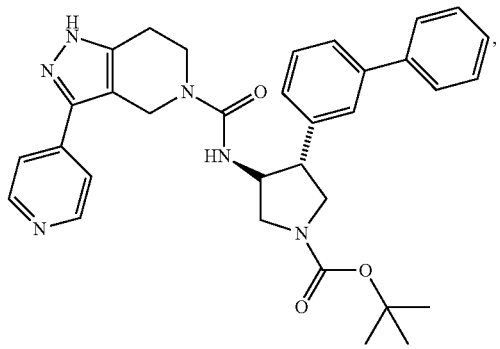

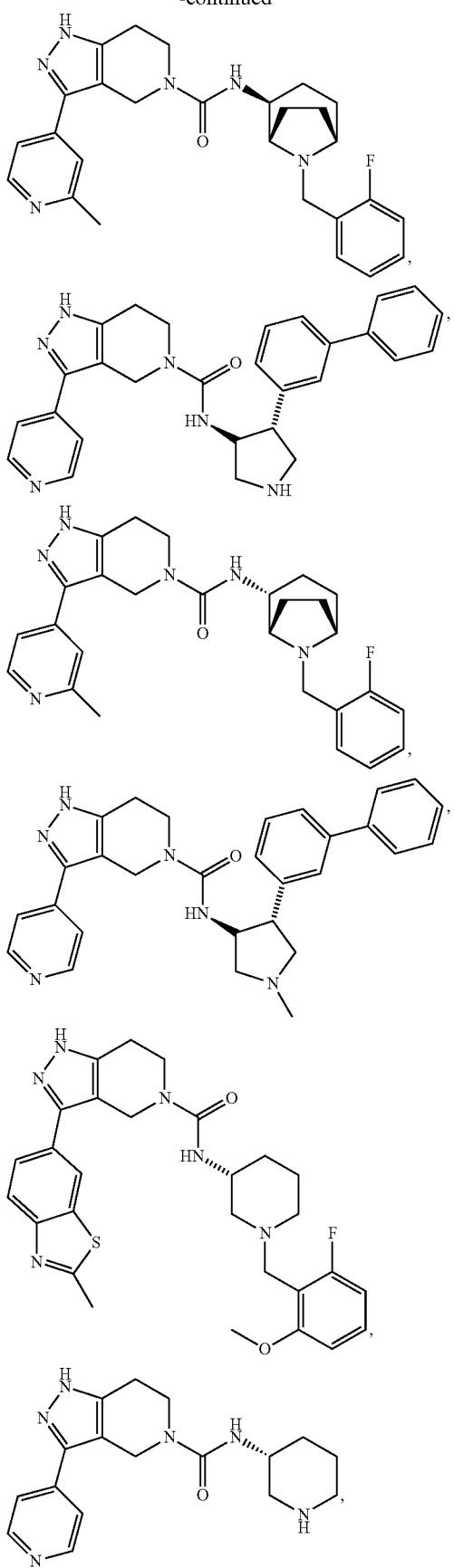
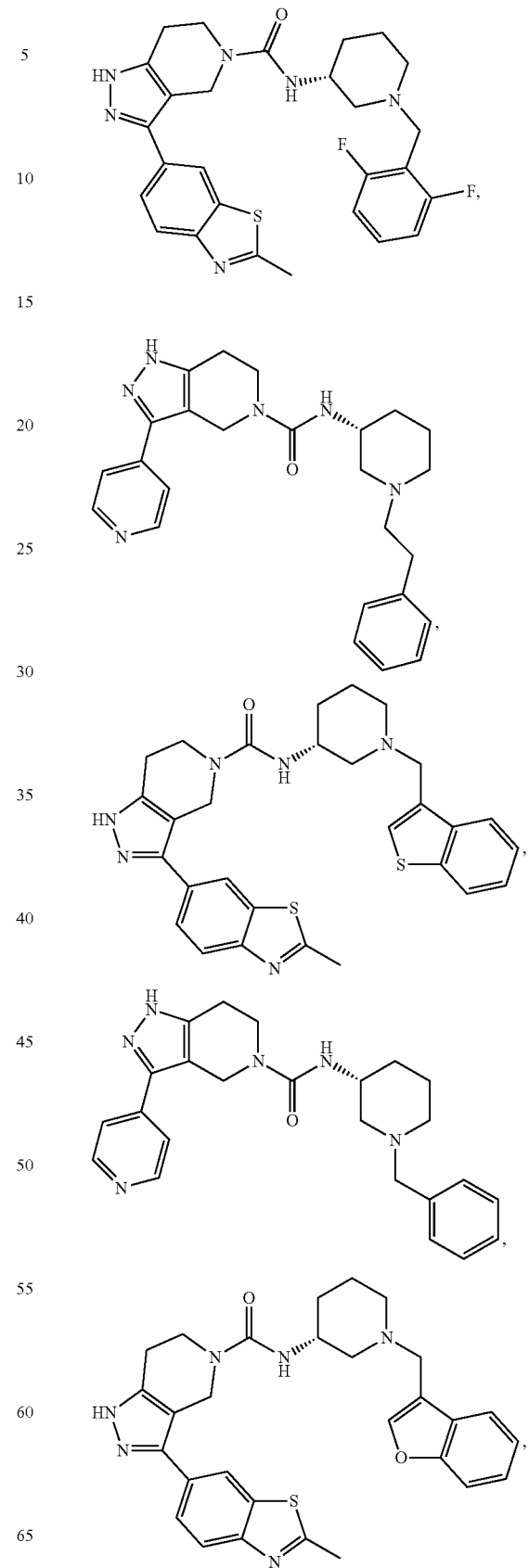

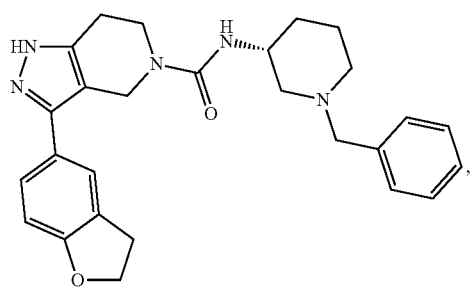
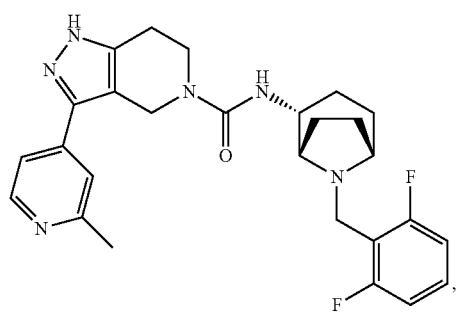
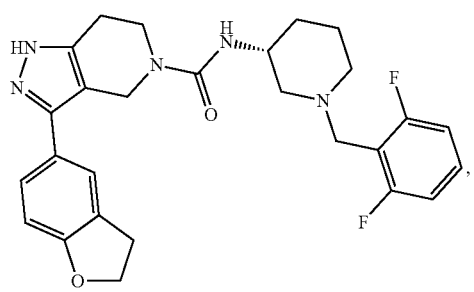
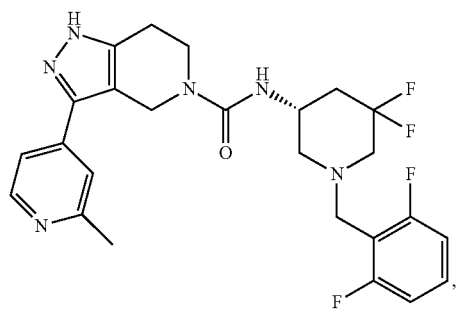
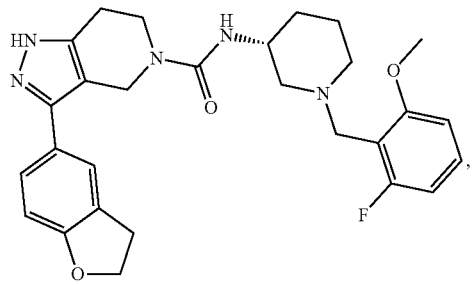
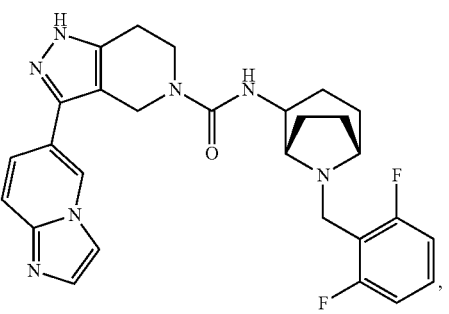
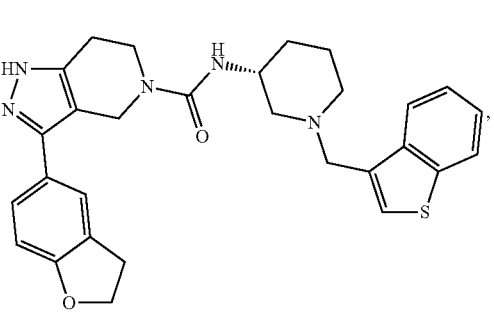
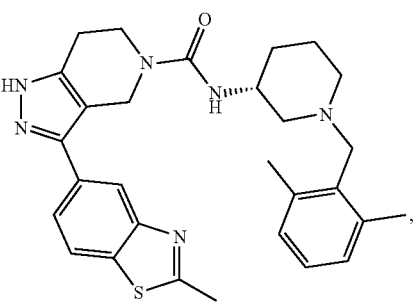
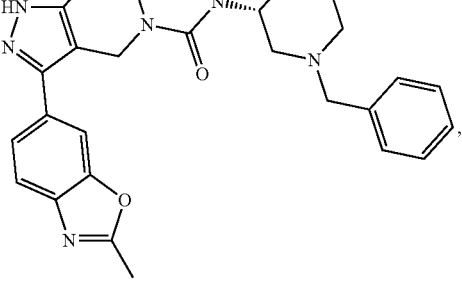
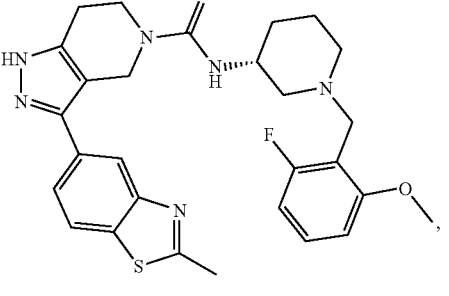

225
-continued
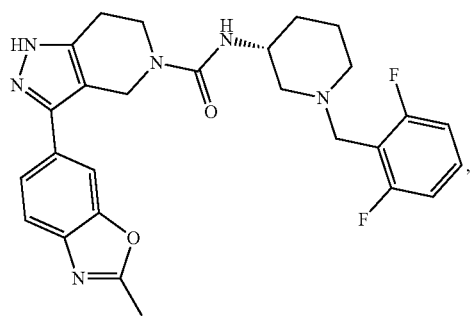
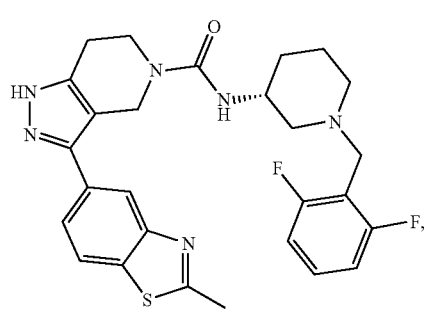
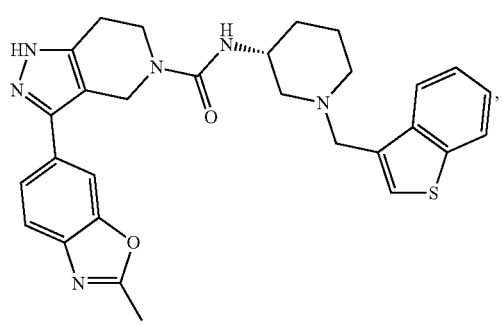
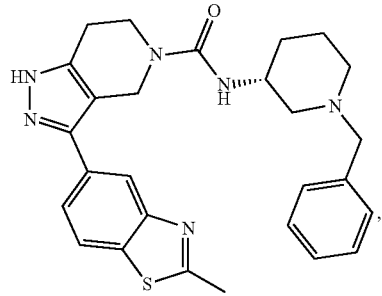
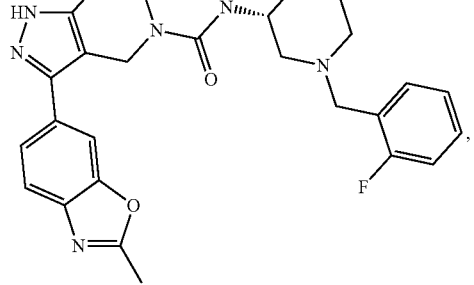
226
-continued
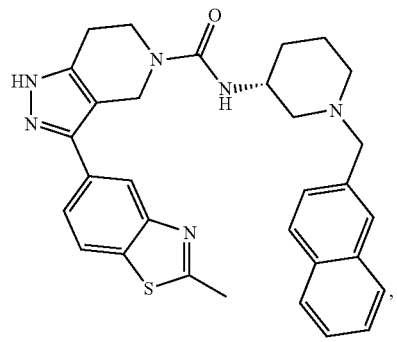
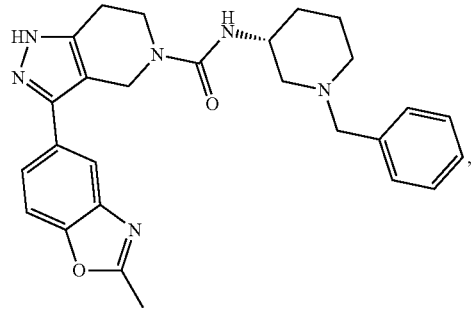
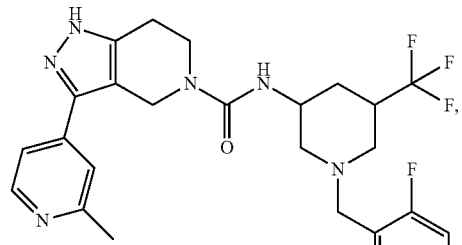
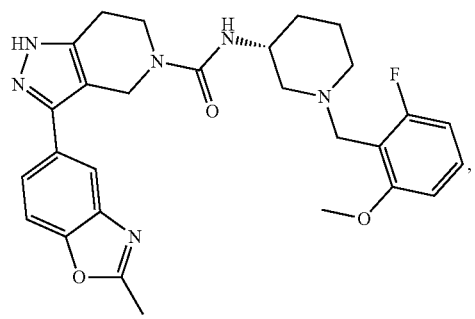
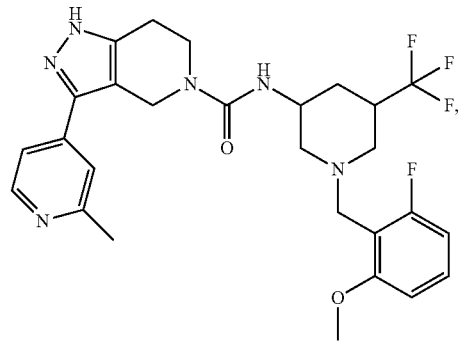

-continued
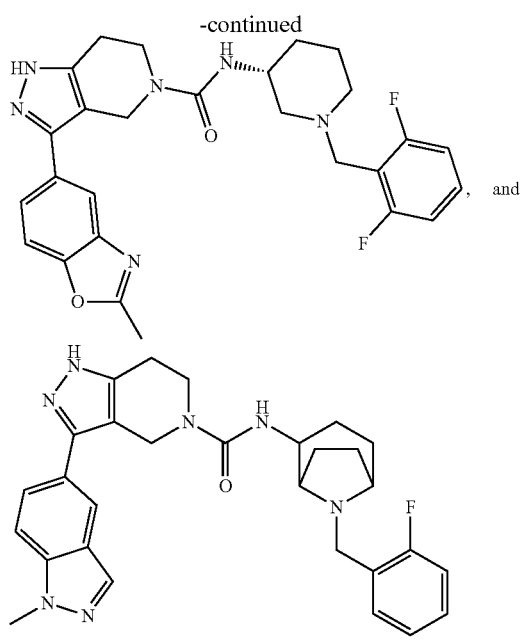
, and
or a pharmaceutically acceptable salt thereof.
2. A pharmaceutical composition comprising at least one compound of claim 1 and a pharmaceutically acceptable carrier.
* * * * *

UNITED STATES PATENT AND TRADEMARK OFFICE
CERTIFICATE OF CORRECTION

| | | |
|---|---|---|
| PATENT NO. | : 9,242,981 B2 | Page 1 of 1 |
| APPLICATION NO. | : 13/821149 | |
| DATED | : January 26, 2016 | |
| INVENTOR(S) | : Shipps, Jr. et al. | |

It is certified that error appears in the above-identified patent and that said Letters Patent is hereby corrected as shown below:

On the title page item (75),

Please replace "Binyuam Sun" with

--Binyuan Sun--

Signed and Sealed this
Twenty-third Day of August, 2016

Michelle K. Lee
*Director of the United States Patent and Trademark Office*